(12) United States Patent
Lapointe et al.

(10) Patent No.: US 10,221,142 B2
(45) Date of Patent: Mar. 5, 2019

(54) SUBSTITUTED PYRAZOLE COMPOUNDS AS RORGAMMAT INHIBITORS AND USES THEREOF

(71) Applicant: Merck Sharp & Dohme Corp., Rahway, NJ (US)

(72) Inventors: Blair T. Lapointe, Boston, MA (US); Peter H. Fuller, Boston, MA (US); Hakan Gunaydin, Boston, MA (US); Kun Liu, Boston, MA (US); Nunzio Sciammetta, Boston, MA (US); Benjamin Wesley Trotter, Boston, MA (US); Hongjun Zhang, Boston, MA (US); Kenneth J. Barr, Boston, MA (US); John K. F. Maclean, Kilmarnock (GB); Danielle F. Molinari, Brookline, MA (US); Vladimir Simov, South Boston, MA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/549,465

(22) PCT Filed: Feb. 11, 2016

(86) PCT No.: PCT/US2016/017566
§ 371 (c)(1),
(2) Date: Aug. 8, 2017

(87) PCT Pub. No.: WO2016/130818
PCT Pub. Date: Aug. 18, 2016

(65) Prior Publication Data
US 2018/0016239 A1    Jan. 18, 2018

Related U.S. Application Data

(60) Provisional application No. 62/114,854, filed on Feb. 11, 2015.

(51) Int. Cl.
| | | |
|---|---|---|
| C07D 231/56 | (2006.01) | |
| C07D 487/04 | (2006.01) | |
| A61K 45/06 | (2006.01) | |
| A61K 31/416 | (2006.01) | |
| C07D 471/04 | (2006.01) | |
| C07D 491/052 | (2006.01) | |
| C07D 491/107 | (2006.01) | |
| C07D 495/04 | (2006.01) | |
| C07D 403/12 | (2006.01) | |
| C07D 487/14 | (2006.01) | |
| C07D 405/12 | (2006.01) | |
| C07D 413/06 | (2006.01) | |
| C07D 487/06 | (2006.01) | |
| C07D 513/04 | (2006.01) | |

(52) U.S. Cl.
CPC .......... *C07D 231/56* (2013.01); *A61K 31/416* (2013.01); *A61K 45/06* (2013.01); *C07D 403/12* (2013.01); *C07D 405/12* (2013.01); *C07D 413/06* (2013.01); *C07D 471/04* (2013.01); *C07D 487/04* (2013.01); *C07D 487/06* (2013.01); *C07D 487/14* (2013.01); *C07D 491/052* (2013.01); *C07D 491/107* (2013.01); *C07D 495/04* (2013.01); *C07D 513/04* (2013.01); *A61K 2300/00* (2013.01)

(58) Field of Classification Search
None
See application file for complete search history.

(56) References Cited

U.S. PATENT DOCUMENTS

| | | | |
|---|---|---|---|
| 4,670,447 | A | 6/1987 | Strupczewski |
| 5,583,152 | A | 12/1996 | Bernstein et al. |
| 5,639,780 | A | 6/1997 | Lau et al. |
| 5,985,903 | A | 11/1999 | Assmann et al. |
| 6,020,354 | A | 2/2000 | Assmann et al. |
| 6,037,367 | A | 3/2000 | Christensen, IV et al. |

(Continued)

FOREIGN PATENT DOCUMENTS

| | | |
|---|---|---|
| EP | 0429257 A2 | 5/1991 |
| EP | 0882718 A1 | 12/1998 |

(Continued)

OTHER PUBLICATIONS

U.S. Appl. No. 15/463,371, RORgammaT Inhibitors, filed Mar. 20, 2017.

(Continued)

*Primary Examiner* — Kamal A Saeed
(74) *Attorney, Agent, or Firm* — Dechert LLP

(57) ABSTRACT

The present invention relates to compounds according to Formula (I-1) and pharmaceutically acceptable salts thereof. Such compounds can be used in the treatment of RORgammaT-mediated diseases or conditions.

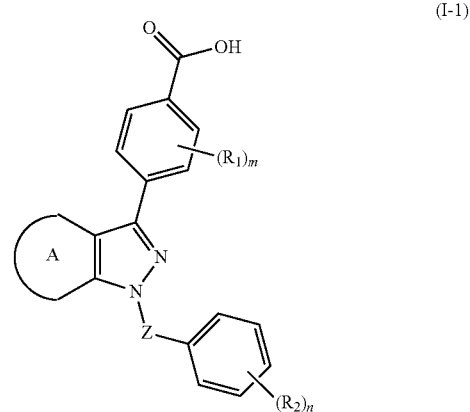

29 Claims, No Drawings

(56) References Cited

U.S. PATENT DOCUMENTS

| | | | |
|---|---|---|---|
| 6,133,290 A | 10/2000 | Krushinski, Jr. et al. |
| 6,160,001 A | 12/2000 | Assmann et al. |
| 6,172,092 B1 | 1/2001 | Assmann et al. |
| 6,180,643 B1 | 1/2001 | Zablocki et al. |
| 6,348,032 B1 | 2/2002 | Sperl et al. |
| 6,352,985 B1 | 3/2002 | Yamasaki et al. |
| 6,387,939 B1 | 5/2002 | Assmann et al. |
| 6,440,973 B1 | 8/2002 | Zablocki et al. |
| 6,534,535 B1 | 3/2003 | Zhu et al. |
| 6,605,634 B2 | 8/2003 | Zablocki et al. |
| 6,638,960 B2 | 10/2003 | Assmann et al. |
| 6,683,091 B2 | 1/2004 | Asberom et al. |
| 6,828,344 B1 | 12/2004 | Seehra et al. |
| 7,084,176 B2 | 8/2006 | Morie et al. |
| 7,115,750 B1 | 10/2006 | Kato et al. |
| 7,138,401 B2 | 11/2006 | Kasibhatla et al. |
| 7,329,675 B2 | 2/2008 | Cox et al. |
| 7,355,042 B2 | 4/2008 | Edgar et al. |
| 7,420,059 B2 | 9/2008 | O'Connor et al. |
| 7,482,342 B2 | 1/2009 | D'Orchymont et al. |
| 7,514,465 B2 | 4/2009 | Kuo et al. |
| 7,569,571 B2 | 8/2009 | Dong et al. |
| 7,696,200 B2 | 4/2010 | Ackermann et al. |
| 7,696,229 B2 | 4/2010 | Dunn et al. |
| 7,713,996 B2 | 5/2010 | Ackermann et al. |
| 7,741,495 B2 | 6/2010 | Liou et al. |
| 7,772,252 B2 | 8/2010 | Hendrix et al. |
| 7,799,933 B2 | 9/2010 | Ceccarelli et al. |
| 9,095,583 B2 * | 8/2015 | Karstens | C07D 231/56 |
| 9,266,827 B2 | 2/2016 | Aicher et al. |
| 9,273,070 B2 | 3/2016 | Knochel et al. |
| 9,487,490 B2 | 11/2016 | Barr et al. |
| 9,512,111 B2 | 12/2016 | Glick et al. |
| 9,556,168 B2 | 1/2017 | Barr et al. |
| 9,603,838 B2 * | 3/2017 | Karstens | C07D 231/56 |
| 9,657,033 B2 | 5/2017 | Aicher et al. |
| 9,663,522 B2 | 5/2017 | Barr et al. |
| 9,745,265 B2 | 8/2017 | Barr et al. |
| 2006/0004000 A1 | 1/2006 | D'Orchymont et al. |
| 2006/0030612 A1 | 2/2006 | Steffan et al. |
| 2006/0100218 A1 | 5/2006 | Ibrahim et al. |
| 2006/0100230 A1 | 5/2006 | Bischoff et al. |
| 2007/0010537 A1 | 1/2007 | Hamamura et al. |
| 2007/0010670 A1 | 1/2007 | Hirata et al. |
| 2007/0049556 A1 | 3/2007 | Zhang et al. |
| 2007/0060567 A1 | 3/2007 | Ackermann et al. |
| 2007/0154487 A1 | 7/2007 | Littman et al. |
| 2007/0191603 A1 | 8/2007 | Ackermann et al. |
| 2007/0197782 A1 | 8/2007 | Clough et al. |
| 2007/0281922 A1 | 12/2007 | Liu et al. |
| 2008/0027100 A1 | 1/2008 | McCormick et al. |
| 2008/0058386 A1 | 3/2008 | Liou et al. |
| 2008/0153805 A1 | 6/2008 | Ceccarelli et al. |
| 2008/0305169 A1 | 12/2008 | Miki et al. |
| 2009/0005410 A1 | 1/2009 | Charvat et al. |
| 2009/0075973 A1 | 3/2009 | Newcom et al. |
| 2009/0124616 A1 | 5/2009 | Song et al. |
| 2009/0233955 A1 | 9/2009 | Frazee et al. |
| 2009/0247502 A1 | 10/2009 | Newcom et al. |
| 2009/0275586 A1 | 11/2009 | Govek et al. |
| 2010/0022515 A1 | 1/2010 | Alper et al. |
| 2010/0130484 A1 | 5/2010 | Ackermann et al. |
| 2010/0234340 A1 | 9/2010 | Schunk et al. |
| 2010/0317863 A1 | 12/2010 | Kuzmich et al. |
| 2011/0053915 A1 | 3/2011 | Ivaschenko et al. |
| 2011/0112070 A1 | 5/2011 | Baldwin et al. |
| 2011/0118246 A1 | 5/2011 | Baldwin et al. |
| 2011/0130384 A1 | 6/2011 | Setoh et al. |
| 2011/0150864 A1 | 6/2011 | Bignan et al. |
| 2011/0178063 A1 | 7/2011 | Baldwin et al. |
| 2011/0263046 A1 | 10/2011 | Deuschle et al. |
| 2014/0088094 A1 | 3/2014 | Glick et al. |
| 2015/0111877 A1 | 4/2015 | Aicher et al. |
| 2015/0126493 A1 | 5/2015 | Aicher et al. |
| 2015/0191434 A1 | 7/2015 | Barr et al. |
| 2015/0210687 A1 | 7/2015 | Barr et al. |
| 2015/0218096 A1 | 8/2015 | Barr et al. |
| 2015/0218169 A1 | 8/2015 | Barr et al. |
| 2015/0297566 A1 | 10/2015 | Karstens et al. |
| 2016/0304476 A1 | 10/2016 | Aicher et al. |
| 2016/0304505 A1 | 10/2016 | Aicher et al. |
| 2016/0311787 A1 | 10/2016 | Aicher et al. |

FOREIGN PATENT DOCUMENTS

| | | |
|---|---|---|
| EP | 1820515 A1 | 8/2007 |
| EP | 2181710 A1 | 5/2010 |
| EP | 2487159 A1 | 8/2012 |
| JP | 6-250441 A | 9/1994 |
| JP | 2004307487 A | 11/2004 |
| JP | 2007238463 A | 9/2007 |
| JP | 2016-141632 A | 8/2016 |
| WO | WO-92/13856 A1 | 8/1992 |
| WO | WO-1996/37467 A1 | 11/1996 |
| WO | WO-97/01561 A1 | 1/1997 |
| WO | WO-97/48697 A1 | 12/1997 |
| WO | WO-98/22457 A1 | 5/1998 |
| WO | WO-00/17202 A1 | 3/2000 |
| WO | WO-01/012600 A1 | 2/2001 |
| WO | WO-02/100819 A1 | 12/2002 |
| WO | WO-03/014075 A2 | 2/2003 |
| WO | WO-2004/056830 A1 | 7/2004 |
| WO | WO-05/028434 A2 | 3/2005 |
| WO | WO-2005/037834 A1 | 4/2005 |
| WO | WO-2006/007486 A2 | 1/2006 |
| WO | WO-2006/052190 A1 | 5/2006 |
| WO | WO-2006/057460 A1 | 6/2006 |
| WO | WO-2006/063167 A1 | 6/2006 |
| WO | WO-2007/024944 A1 | 3/2007 |
| WO | WO-2007/031429 A1 | 3/2007 |
| WO | WO-2007/093507 A1 | 8/2007 |
| WO | WO-2007/103308 A2 | 9/2007 |
| WO | WO-2007/125405 A2 | 11/2007 |
| WO | WO-2007/138998 A1 | 12/2007 |
| WO | WO-2007/144327 A2 | 12/2007 |
| WO | WO-2008/003703 A1 | 1/2008 |
| WO | WO-2008/045664 A2 | 4/2008 |
| WO | WO-2008/062740 A1 | 5/2008 |
| WO | WO-2008/074692 A1 | 6/2008 |
| WO | WO-2008/097428 A2 | 8/2008 |
| WO | WO-2008/132434 A2 | 11/2008 |
| WO | WO-2008/138889 A2 | 11/2008 |
| WO | WO-2008/150827 A1 | 12/2008 |
| WO | WO-2008/153858 A1 | 12/2008 |
| WO | WO-2009/015067 A2 | 1/2009 |
| WO | WO-2009/032667 A1 | 3/2009 |
| WO | WO-2009/035997 A1 | 3/2009 |
| WO | WO-2009/077956 A2 | 6/2009 |
| WO | WO-2009/147187 A1 | 12/2009 |
| WO | WO-2009/149819 A1 | 12/2009 |
| WO | WO-2009/149820 A1 | 12/2009 |
| WO | WO-2009/157196 A1 | 12/2009 |
| WO | WO-2010/017827 A1 | 2/2010 |
| WO | WO-2010/038901 A1 | 4/2010 |
| WO | WO-2010/50837 A1 | 5/2010 |
| WO | WO-2010/057101 A2 | 5/2010 |
| WO | WO-2010/059602 A2 | 5/2010 |
| WO | WO-2010/068483 A2 | 6/2010 |
| WO | WO-2010/071853 A1 | 6/2010 |
| WO | WO-2010/102958 A1 | 9/2010 |
| WO | WO-2010/117425 A1 | 10/2010 |
| WO | WO-2010/123139 A1 | 10/2010 |
| WO | WO-2010/125082 A1 | 11/2010 |
| WO | WO-2010/150837 A1 | 12/2010 |
| WO | WO-2011/14775 A1 | 2/2011 |
| WO | WO-2011/019634 A2 | 2/2011 |
| WO | WO-2011/059839 A1 | 5/2011 |
| WO | WO-2011/067364 A1 | 6/2011 |
| WO | WO-2011/067365 A1 | 6/2011 |
| WO | WO-2011/067366 A1 | 6/2011 |
| WO | WO-2011/103189 A1 | 8/2011 |
| WO | WO-2011/109059 A1 | 9/2011 |
| WO | WO-2011/146313 A1 | 11/2011 |

| WO | WO-2012/032065 A1 | 3/2012 |
| WO | WO-2012/032067 A1 | 3/2012 |
| WO | WO-2012/037108 A1 | 3/2012 |
| WO | WO-2012/064744 A2 | 5/2012 |
| WO | WO-2012/077932 A2 | 6/2012 |
| WO | WO-2012/106995 A1 | 8/2012 |
| WO | WO-2012/139775 A1 | 10/2012 |
| WO | WO-2012/176763 A1 | 12/2012 |
| WO | WO-2013/169704 A2 | 11/2013 |
| WO | WO-2014/026327 | 2/2014 |
| WO | WO-2014/026327 A1 | 2/2014 |
| WO | WO-2014/026329 A1 | 2/2014 |
| WO | WO-2014/028589 A2 | 2/2014 |
| WO | WO-2014/028591 A2 | 2/2014 |
| WO | WO-2014/028597 A2 | 2/2014 |
| WO | WO-2014/028600 A2 | 2/2014 |
| WO | WO-2015/008234 A1 | 1/2015 |
| WO | WO-2015/087234 A1 | 6/2015 |
| WO | WO-2015/139621 | 9/2015 |
| WO | WO-2016/128908 A1 | 8/2016 |
| WO | WO-2016/130818 A1 | 8/2016 |

OTHER PUBLICATIONS

U.S. Appl. No. 15/647,437, 4-Heteroaryl Substituted Benzoic Acid Compounds as RORgammaT Inhibitors and Uses Thereof, filed Jul. 12, 2017.
International Search Report from PCT/CN2012/071017, dated May 24, 2012.
Bundgaard (ed.). Design of Prodrugs, Elsevier (1985).
Buonocore et al., "Innate lymphoid cells drive interleukin-23-dependent innate intestinal pathology," 464 Nature 1371-75 (2010).
Cheng et al., "Design and synthesis of heterocyclic malonyl-CoA decarboxylase inhibitors," 16 Bioorg. Med. Chem. Lett. 695-700 (2006).
Figueroa-Vega et al., "Increased Circulating Pro-Inflammatory Cytokines and Th17 Lymphocytes in Hashimoto's Thyroiditis," 95(2) J. Clin. Endocrinol. Metab. 953-62 (2010).
Gennaro (ed.), Remington: The Science and Practice of Pharmacy, 20th edition (2000).
Higuchi et al. (eds.), Pro-drugs as Novel Delivery Systems, 14 A.C.S. Symposium Series (1975).
Hueber et al., "Cutting Edge: Mast Cells Express IL-17A in Rheumatoid Arthritis Synovium," 184 J. Immunol. 3336-40 (2010).
Jia et al., "The T helper type 17/regulatory T cell imbalance in patients with acute Kawasaki disease," 162 Clin. Exp. Immunol. 131-37 (2010).
Kastelein et al., "Discovery and Biology of IL-23 and IL-27: Related but Functionally Distinct Regulators of Inflammation," 25 Annu. Rev. Immunol. 221-42 (2007).
Louten et al., "Development and function of TH17 cells in health and disease," 123(5) J. Allergy Clin. Immunol. 1004-11 (2009).
Roche (ed.), Biorevesible Carriers in Drug Design, Pergamon Press (1987).
Zhou et al., "Use of Homogeneous Time-Resolved Fluorescence Energy Transfer in the Measurement of Nuclear Receptor Activation," 25 Methods 54-61 (2001).
Extended European Search Report, EP Application No. 12744370.3, dated Sep. 9, 2014.
Ciattini et al., "An Efficient Synthesis of 3-Substituted Indoles by Palladium-Catalyzed Coupling Reaction of 3-Tributylstannylindoles with Organic Triflates and Halides," 35(15) Tetrahedron Letters 2405-08 (1994).
Inamoto et al., "Palladium-Catalyzed C-H Activation/Intramolecular Amination Reaction: A New Route to 3-Aryl/Alkylindazoles," 9(15) Org. Letts. 2931-34 (2007).
Larhed et al., "Rapid Microwave-Assisted Suzuki Coupling on Solid-Phase," 37(45) Tetrahedron Letters 8219-22 (1996).
Reckenbeil et al., "Supramolekulare Phosphorylierung kationischer Alkohole mit 3-Arylindol-4- carboxamidin-Struktur," Liebigs Ann. Chem. 1219-29 (1994).
Chen, Hua-Sin et al., "Synthesis and antiplatelet activity of ethyl 4-(1-benzyl-1H-indazol-3-yl)benzoate (YD-3) derivatives," *Bioorganic & Medicinal Chemistry*, vol. 16, pp. 1262-1278, (2008).

Annunziato et al., "Type 17 T helper cells-origins, features and possible roles in rheumatic disease," 5 Nat. Rev. Rheumatol. 325-31 (2009).
Boaventura et al., "Human mucosal leishmaniasis: Neutrophils infiltrate areas of tissue damage that express high levels of Th17-related cytokines," 40 Eur. J. Immunol. 2830-36 (2010).
Eberl et al., "An essential function for the nuclear receptor RORγt in the generation of fetal lymphoid tissue inducer cells," 5(1) Nat. Immunol. 64-73 (2004).
He et al., "RORγt, a Novel Isoform of an Orphan Receptor, Negatively Regulates Fas Ligand Expression and IL-2 Production in T Cells," 9 Immunity 797-806 (1998).
Hirose et al., "RORγ: the third member of ROR/RZR orphan receptor subfamily that is highly expressed in skeletal muscle," 205 Biochem. Biophys. Res. Comm. 1976-83 (1994).
Ivanov et al., "The Orphan Nuclear Receptor RORγt Directs the Differentiation Program of Proinflammatory IL-17+ T Helper Cells," 126 *Cell* 1121-33 (2006).
Jin et al., "Structural Basis for Hydroxycholesterols as Natural Ligands of Orphan Nuclear Receptor RORγ," *Mol. Endocrinol.* (2010) vol. 24, No. 5, pp. 923-929.
Kurebayashi et al., "Selective LXXLL peptides antagonize transcriptional activation by the retinoid-related orphan receptor RORγ," 315 Biochem. Biophys. Res. Comm. 919-27 (2004).
Miossec et al., "Interleukin-17 and Type 17 Helper T Cells," 361(9) New Eng. J. Med. 888-98 (2009).
Sun et al., "Requirement for RORγ in Thymocyte Survival and Lymphoid Organ Development," 288 Science 2369-72 (2000).
Sutton et al., "Interleukin-1 and IL-23 Induce Innate IL-17 Production from γδ T Cells, Amplifying Th17 Responses and Autoimmunity," 31 Immunity 331-41 (2009).
Varnavas et al., "Anthranilic acid based CCK1 receptor antagonists: preliminary investigation on their second 'touch point,'" 40(6) Euro. J. Med. Chem. 563-81 (2005).
Wang et al., "Identification of SR1078, a Synthetic Agonist for the Orphan Nuclear Receptors RORα and RORγ," 5(11) ACS Chem. Biol. 1029-34 (2010).
Wang et al., "Modulation of Retinoic Acid Receptor-related Orphan Receptor α and γ Activity by 7-Oxygenated Sterol Ligands," *J. Biol. Chem.* (2010) vol. 285, No. 7, pp. 5013-5025.
Xie et al., "RORγt Recruits Steroid Receptor Coactivators to Ensure Thymocyte Survival," 175(6) J. Immunol. 3800-09 (2005).
Yang et al., "T Helper 17 Lineage Differentiation is programmed by Orphan Nuclear Receptors RORα and RORγ," 28 Immunity 29-39 (2008).
International Search Report and Written Opinion for PCT/US2013/054893, dated Feb. 14, 2014 (5 pages).
Lee et al., "Synthesis of 1-Benzyl-3-(5'-hydroxymethy1-2'-furyl)indazole Analogues as Novel Antiplatelet Agents," 44 J. Med. Chem. 3746-49 (2001).
André et al., "Disruption of retinoid-related orphan receptor B changes circadian behaviour, causes retinal degeneration and leads to vacillans phenotype in mice," 17(14) The EMBO J. 3867-77 (1998).
Becker-André et al., "Identification of nuclear receptor mRNAs by RT-PCR amplification of conserved zinc-finger motif sequences," 194(3) Biochem. Biophys. Res. Comm. 1371-79 (1993).
Bernhardt et al., "Preparation of Solid Salt-Stabilized Functionalized Organozinc Compounds and their Application to Cross-Coupling and Carbonyl Addition Reactions," 50(39) Angew. Chem. Int. Ed. 9205-9209 (2011).
Boltze et al., "Chemische Struktur and antiphlogistische Wirkung in der Reihe der substituierten Indol-3-essigsauren," 30(8A) Arzneimittel-Forschung 1314-25 (1980).
Burris et al., "Targeting Orphan Nuclear Receptors for Treatment of Metabolic Diseases and Autoimmunity," 19(1) Chem. Biol. 51-59 (2012).
Cai, et al., "Pivotal Role of Dermal IL-17-Producing γδ T Cells in Skin Inflammation", Immunity (2011) vol. 35, pp. 596-610.
Carlberg et al., "RZRs, a new family of retinoid-related orphan receptors that function as both monomers and homodimers," 8 Mol. Endocrinol. 757-70 (1994).

D. van der Heijde, et al., "Secukinumab Provides Significant and Sustained Inhibition of Joint Structural Damage in a Phase III Study of Active Psoriatic Arthritis" Arthritis & Rheumatology Brief Report, Accepted Article DOI: 10.1002/art.39685, American College of Rheumatology, (2016) pp. 1-27.

Baeten, et al., "Secukinumab, an Interleukin-17A Inhibitor, in Ankylosing Spondylitis", The New England Journal of Medicine, (2015) vol. 373, pp. 2534-2548.

Dussault et al., "Orphan nuclear receptor RORα-deficient mice display the cerebellar defects of staggerer," 70 Mech. Develop. 147-53 (1998).

El-Sawy et al., "Synthesis, antimicrobial and anti-cancer activities of some new N-ethyl, N-benzyl and N-benzoyl-3-indolyl heterocycles," 62 Acta Pharm. 157-179 (2012).

Giguère et al., "Isoform-specific amino-terminal domains dictate DNA-binding properties of RORα, a novel family of orphan hormone nuclear receptors," 8 Genes & Develop. 538-53 (1994).

Guo et al., "Stereospecific microbial reduction of ethyl 1-benzyl-3-oxo-piperidine-4-carboxylate," 17(13) Tetrahedron: Asymmetry 2015-2020 (2006).

Hirose et al., "Benzoheterocyclic derivatives. XI. Synthesis and pharmacological actions of indoline derivatives. 2," CA76:46035 (1971).

Huh et al., "Small molecule inhibitors of RORγt: Targeting Th17 cells and other applications," 42 Eur. J. Immunol. 2232-2237 (2012).

Julia et al., "Research in the indole series. IX. Certain 3-indolylsuccinic acids and the corresponding succinimides and pyrrolidines," CA61:92261 (1964).

Krueger, "A welcome surprise in psoriasis", Nature Medicine, (2012) vol. 18, No. 12, pp. 1750-1751.

Leonardi, et al., "Anti-Interleukin-17 Monoclonal Antibody Ixekizumab in Chronic Plaque Psoriasis", The New England Journal of Medicine, (2012) vol. 366, Iss. 13, pp. 1-10.

Martinez, "Th17-biased RORγt transgenic mice become susceptible to a viral model for multiple sclerosis", Brain, Behavior, and Immunity, (2014) vol. 43, pp. 86-97.

Medvedev et al., "Cloning of a cDNA encoding the murine orphan receptor RZR/RORγ and characterization of its response element," 181 Gene 199-206 (1996).

Nakajima, et al., "IL-17A as an Inducer for Th2 Immune Responses in Murine Atopic Dermatitis Models", Journal of Investigative Dermatology, (2014) vol. 134, pp. 2122-2130.

Ortiz et al., "TOR: a new orphan receptor expressed in the thymus that can modulate retinoid and thyroid hormone signals," 9 Mol. Endocrinol. 1679-91 (1995).

Papp, et al. "Brodalumab, an Anti-Interleukin-17-Receptor Antibody for Psoriasis", The New England Journal of Medicine, (2012) vol. 366, Iss. 13, 9 pgs.

Skepner, J. et al. "Pharmacologic Inhibition of RORγt Regulates Th17 Signature Gene Expression and Suppresses Cutaneous Inflammation In Vivo," downloaded from the Internet at http://www.jimmunol.org/cgi/doi/10.4049/jimmunol.1302190 on Feb. 17, 2014, published in final edited form in *J. Immunol.* (2014) vol. 192, No. 6, pp. 2564-2575.

Smith, "The Bench-to-Bedside Story of IL-17 and the Therapeutic Efficacy of its Targeting in Spondyloarthritis", Curr Rheumatol Rep. (2016) vol. 18, pp. 1-10.

Solt et al., "Action of RORs and their ligands in (patho)physiology," 23(12) Trends in Endocrinology and Metabolism. 619-627 (2012).

Tlustochowicz, et al. "Efficacy and Safety of Subcutaneous and Intravenous Loading Dose Regimens of Secukinumab in Patients with Active Rheumatoid Arthritis: Results from a Randomized Phase II Study" The Journal of Rheumatology, (2016) vol. 43, No. 3, pp. 495-503.

Villey et al., "RORγT, a thymus-specific isoform of the orphan nuclear receptor RORγ/TOR, is up-regulated by signaling through the pre-T cell receptor and binds to the TEA promoter," 29 Eur. J. Immunol. 4072-80 (1999).

Whelligan et al., "Aminopyrazine Inhibitors Binding to an Unusual Inactive Conformation of the Mitotic Kinase Nek2: SAR and Structural Characterization," 53 J. Med. Chem. 7682-98 (2010).

Wiesenberg et al., "Transcriptional activation of the nuclear receptor RZRα by the pineal gland hormone melatonin and identification of CGP 52608 as a synthetic ligand," 23(3) Nucl. Acids Res. 327-33 (1995).

Xiao, et al., "Small-Molecule RORγt Antagonists Inhibit T Helper 17 Cell Transcriptional Network by Divergent Mechanisms", Immunity (2014) vol. 40, pp. 477-489.

International Search Report and Written Opinion for PCT/US2013/054887, dated Mar. 18, 2014 (5 pages).

International Search Report and Written Opinion for PCT/US2013/054902, dated Feb. 28, 2014 (5 pages).

International Search Report and Written Opinion for PCT/US2013/054911 dated Mar. 4, 2014 (9 pages).

Database Caplus [Online] Chemical Abstracts Service, Columbus, Ohio, US; Kusakabe, Kanekazu et al: "Preparation of condensed pyrazole compounds as TTK protein kinase inhibitors", retrieved from STN Database accession No. 2011:1578140 ; & Kusakabe, Kanekazu et al: "Preparation of condensed pyrazole compounds as TTK protein kinase inhibitors", Jpn. Kokai Tokkyo Koho, 134PP. CODEN: JKXXAF.

Arisawa et al., "Development of Isomerization and Cycloisomerization with Use of a Ruthenium Hydride with N-Heterocyclic Carbene and Its Application to the Synthesis of Heterocycles," 71 J. Org. Chem. 4255-61 (2006).

Berge et al., "Pharmaceutical salts," 66(1) J. Pharm. Sci. 1-19 (1977).

Bhagawanth et al., "Room-Temperature Pd-Catalyzed Amidation of Aryl Bromides Using tert-Butyl Carbamate," 74 J. Org. Chem. 4634-37 (2009).

Boger et al., "Regiocontrolled Nucleophilic Addition to Selectively Activated p-Quinone Diimines: Alternative Preparation of a Key Intermediate Employed in the Preparation of the CC-1065 Left-Hand Subunit," 55 J. Org. Chem. 1379-90 (1990).

Carroll et al., "Synthesis, Nicotinic Acetylcholine Receptor Binding, and Antinociceptive Properties of 2-exo-2-(2',3'-Disubstituted 5'-pyridinyI)-y-azabicyclo[2.2.1]heptanes: Epibatidine Analogues," 45 J. Med. Chem. 4755-61 (2002).

Chang et al., "7-Aroyl-aminoindoline-1-sulfonamides as a Novel Class of Potent Antitubulin Agents," 49 J. Med. Chem. 6656-59 (2006).

Colbon et al., "Double Arylation of Allyl Alcohol via a One-Pot Heck Arylation—Isomerization—Acylation Cascade," 13 Org. Lett. 5456-59 (2011).

De et al., Methods in Molecular Biology 1184, second edition, Human Press (2014).

Gould, "Salt selection for basic drugs," 33 Intl J. Pharmaceutics 201-217 (1986).

Grasa et al., "Amination Reactions of Aryl Halides with Nitrogen-Containing Reagents Mediated by Palladium/Imidazolium Salt Systems," 66 J. Org. Chem. 7729-37 (2001).

Greene & Wuts, Protective Groups in Organic Synthesis, 2d Edition (1991).

Guimond et al., "Rhodium(III)-Catalyzed Isoquinolone Synthesis: The N-O Bond as a Handle for C-N Bond Formation and Catalyst Turnover," 132(20) J. Am. Chem. Soc. 6908-09 (2010).

Hanessian et al., "A versatile protocol for the stereocontrolled elaboration of vicinal secondary and tertiary centers of relevance to natural product synthesis," 52(6) J. Org. Chem. 1170-72 (1987).

Hauser et al., "Relative Ease of Cyclization of 2-, 3-, and 4-Aminopyridine Derivatives. Synthesis of Naphthyridines," 15 J. Org. Chem. 1224-32 (1950).

International Search Report and Written Opinion for PCT/US2011/059788 dated May 23, 2012 (23 pages).

International Search Report and Written Opinion for PCT/US2013/039422 dated Oct. 11, 2013 (9 pages).

International Search Report and Written Opinion for PCT/US2013/039839 dated Oct. 18, 2013 (8 pages).

International Search Report and Written Opinion for PCT/US2013/040085 dated Oct. 23, 2013 (9 pages).

Ishikura et al., "An Efficient Synthesis of 3-Heteroarylpyridines via Diethyl-(3-pyridyl)-borane," Synthesis 936-38 (1984).

Jayashree et al., "Design and synthesis of 2-quinolones as antioxidants and antimicrobials: a rational approach," 19 Med. Chem. Res. 193-209 (2010).

Jiang et al., "Synthesis and Cytotoxicity Evaluation of Novel Indolylpyrimidines and Indolylpyrazines as Potential Antitumor Agents," 9 Bioorg. Med. Chem. 1149-54 (2001).

Li et al., "Chemical Libraries via Sequential C-H Functionalization of Phenols," 10 J. Comb. Chem. 170-74 (2008).

Li et al., "Synthesis and Resolution of a Novel Chiral Diamine Ligand and Application to Asymmetric Lithiation-Substitution," 2 Org. Lett. 875-78 (2000).

Liu et al., "1-Sulfonylindazoles as potent and selective 5-HT6 ligands," 19 Bioorg. Med. Chem. Lett. 2413-15 (2009).

Murase et al., "A New Concise Synthesis of Arcyriacyanin A and Its Unique Inhibitory Activity against a Panel of Human Cancer Cell Line," 48(1) Chem. Pharm. Bull. 81-84 (2000).

Ninomiya et al., "Phosphorous in Organic Synthesis—VII: Diphenyl Phosphorazidate (DPPA). A New Convenient Reagent for a Modified Curtius Reaction," 30 Tetrahedron 2151-57 (1975).

Nyrkova et al., "Synthesis of a New Heterocyclic System—3,4-Diazaphenoxazine," 1(9) J. Org. Chem. USSR, 1711-14, translating 1(9) Zh. Org. Chem. Khimii, 1688-91 (1965).

Santilli et al., "Synthesis of 5,6,7,8-Tetrahydro-5-oxopyrido[2,3-d]pyrimidine-6-carbonitriles and -6-carboxylic Acid Esters," 12 J. Het. Chem. 311-16 (1975).

Skraup, "Eine Synthese des Chinolins," 13 Berichte 2086-87 (1880).

Stefko et al., "General and Modular Synthesis of Isomeric 5-Substituted Pyridin-2-yl and 6Substituted Pyridin-3-yl C-Ribonucleosides Bearing Diverse Alkyl, Aryl, Hetaryl, Amino, Carbamoyl, and Hydroxy Groups," 76 J. Org. Chem. 6619-35 (2011).

STN Columbus, pp. 1-40 (2011).

Takano et al., "A new synthesis of a steroid side chain via stereocontrolled protonation: synthesis of (-)-desmosterol," 14 J. Chem. Soc., Chem. Commun. 760-61 (1983).

van Heerden et al., "Dibutylboron triflate promoted conjugate addition of benzylic and allylic organocopper reagents to chiral α,β-unsaturated N-acyl imidazolidinones" 38(10) Tet. Lett. 182-124 (1997).

Wang et al., "Synthesis of new carbon-11-labeled 7-aroyl-aminoindoline-1-sulfonamides as potential PET agents for imaging of tubulin polymerization in cancers," 51(1) J. Label. Compd. Radiopharm. 6-11 (2008).

Yeh et al., "Practical Cu-catalyzed amination of functionalized heteroaryl halides," 47(34) Tetrahedron Lett. 6011-16 (2006).

Zhu et al., "The Direct Formulation of Functionalized Alkyl(aryl)zinc halides by Oxidative Addition of Highly Reactive Zinc with Organic Halides and Their Reactions with Acid Chlorides, α,β-Unsaturated Ketones, and Allylic, Aryl, and Vinyl Halides," 56 J. Org. Chem. 1445-53 (1991).

International Search Report and Written Opinion for PCT/US2014/071671 dated Apr. 28, 2015 (10 pages).

International Search Report and Written Opinion for PCT/US2014/071663 dated Apr. 17, 2015 (6 pages).

International Search Report and Written Opinion for PCT/US2014/071656 dated Mar. 12, 2015 (8 pages).

International Search Report and Written Opinion for PCT/US2016/017566 dated May 6, 2016 (12 pages).

Fauber Benjamin P. "Modulators of the Nuclear Receptor Retinoic Acid Receptor-Related Orphan Receptor-[gamma] (ROR[gamma] or RORc," *Journal of Medicinal Chemistry*, vol. 57, No. 14, Jul. 24, 2014 (Jul. 24, 2014), pp. 5871-5892, XP055242989.

Fauber Benjamin P. "Discovery of imidazo[1,5-a]pyridines and —pyrimidines as potent and selective RORc inverse agonists," *Bioorganic & Medicinal Chemistry Letters*, vol. 25, No. 15, May 28, 2015 (May 28, 2015), pp. 2907-2912, XP029160601.

* cited by examiner

SUBSTITUTED PYRAZOLE COMPOUNDS AS RORGAMMAT INHIBITORS AND USES THEREOF

CROSS-REFERENCE TO RELATED APPLICATIONS

This application is the national stage of International (PCT) Patent Application Serial No. PCT/US2016/017566, filed Feb. 11, 2016, which claims the benefit of and priority to U.S. Provisional Patent Application Ser. No. 62/114,854, filed Feb. 11, 2015, the contents of each of which are hereby incorporated by reference.

BACKGROUND OF THE INVENTION

Upon activation by antigen-presenting cells naïve T helper cells undergo clonal expansion and will ultimately differentiate into cytokine secreting effector T cells, such as Th1 and Th2 subtypes. A third and distinct effector subset has been identified, which plays a key role in providing immunity to bacteria and fungi at mucosal surfaces (Kastelein et al., *Annu. Rev. Immunol.* 25: 221-242, 2007). This effector T helper cell subset can be distinguished based on its ability to produce large quantities of IL-17/F, IL-21 and IL-22, and is named Th17 (Miossec et al., *New Eng. J. Med.* 2361: 888-898, 2009).

Different T helper subsets are characterized by the expression of lineage specific master transcription factors. Th1 and Th2 effector cells express Tbet and GATA3, respectively. A Thymocyte/T cell specific variant of Retinoic Acid Receptor-related Orphan Receptor (ROR), RORgammaT, is highly expressed in Th17 cells (He et al., *Immunity* 9: 797-806, 1998). RORgammaT belongs to the nuclear hormone receptor superfamily (Hirose et al., *Biochem. Biophys. Res. Comm.* 205: 1976-1983, 1994). RORgammaT is a truncated form of RORgamma, lacking the first N-terminal 21 amino acids and is, in contrast to RORgamma which is expressed in multiple tissues (heart, brain, kidney, lung, liver, and muscle), exclusively expressed in cells of the lymphoid lineage and embryonic lymphoid tissue inducers (Sun et al., *Science* 288: 2369-2372, 2000; Eberl et al., *Nat. Immunol.* 5: 64-73, 2004).

Studies using heterozygous knock-in mice replacing the RORgammaT open reading frame with GFP (green fluorescent protein), revealed a constitutive expression of GFP in approximately 10% of the CD4+ T cells in the small intestinal lamina propria (LP), co-expressing the Th17 cytokines IL-17/F and IL-22 (Ivanov et al., *Cell* 126: 1121-1133, 2006). In mice deficient for RORgammaT, the number of Th17 cells was markedly decreased in the LP; and in vitro stimulation of CD4+ T cells under Th17 polarizing conditions resulted in a drastic decrease of IL-17 expression. These results were further substantiated via forced expression of RORgammaT in naïve CD4+ T cells, which resulted in an induction of IL-17/F and IL-22 (Ivanov et al., *Cell* 126: 1121-1133, 2006). The foregoing studies demonstrate the importance of RORgammaT in differentiation and stabilization of the Th17 lineage. In addition, a ROR family member, RORalpha, has been demonstrated to be involved in Th17 differentiation and stabilization (Yang et al., *Immunity* 28: 29-39, 2008).

Recently, RORgammaT was shown to play a crucial role in non-Th17 lymphoid cells. In these studies, RORgammaT was critically important in innate lymphoid cells expressing Thy1, SCA-1, and IL-23R proteins. Genetic disruption of RORgamma in a mouse colitis model dependent on these innate lymphoid cells prevented colitis development (Buonocore et al., *Nature* 464: 1371-1375, 2010). In addition, RORgammaT was shown to play a crucial role in other non-Th17 cells, such as mast cells (Hueber et al., *J. Immunol.* 184: 3336-3340, 2010). Finally, RORgammaT expression and secretion of Th17-type of cytokines was reported for Lymphoid Tissue Inducer cells, NK T-cells, NK cells (Eberl et al., *Nat. Immunol.* 5: 64-73, 2004), and gammadelta T-cells (Sutton et al., *Nat. Immunol.* 31: 331-341, 2009; Louten et al., *J. Allergy Clin. Immunol.* 123: 1004-1011, 2009), suggesting an important function for RORgammaT in these subtypes of cells.

Based on the role of IL-17 producing cells (either Th17 or non-Th17 cells), RORgammaT has been identified as a key mediator in the pathogenesis of several diseases (Louten et al., *J. Allergy Clin. Immunol.* 123: 1004-1011, 2009; Annuziato et al., *Nat. Rev. Rheumatol.* 5: 325-331, 2009). This was confirmed using several disease models representative of autoimmune diseases. Genetic ablation of the RORgamma gene in mice prevented the development of experimental autoimmune diseases, such as experimental autoimmune encephalomyelitis (EAE) and colitis (Ivanov et al., *Cell* 126:1121-33, 2006; Buonocore et al., *Nature* 464: 1371-1375, 2010).

With RORgammaT being a critical mediator in Th17 cells and non-Th17 cells, antagonism of the transcriptional activity of RORgammaT is expected to have a beneficial effect on autoimmune diseases such as, but not limited to, rheumatoid arthritis, psoriasis, multiple sclerosis, inflammatory bowel disease, Crohn's disease, and asthma (Annunziato et al., *Nat. Rev. Immunol.* 5: 325-331, 2009; Louten et al., *J. Allergy Clin. Immunol.* 123: 1004-1011, 2009). Antagonism of RORgammaT may also be beneficial in other diseases that are characterized by increased levels of Th17 cells and/or elevated levels of Th17 hallmark cytokines such as IL-17, IL-22 and IL-23. Examples of such diseases are Kawasaki Disease (Jia et al., *Clin. Exp. Immunol.* 162: 131-137, 2010) and Hashimoto's thyroiditis (Figueroa-Vega et al., *J. Clin. Endocrinol. Metab.* 95: 953-962, 2010). Other examples include various infectious diseases such as, but not limited to, mucosal leishmaniasis (Boaventura et al., *Eur. J. Immunol.* 40: 2830-2836, 2010). In each of the above examples the inhibition may be enhanced by simultaneous inhibition of RORalpha.

Compounds modulating RORgammaT have been reported. Examples of agonists include T0901317 and SR1078 (Wang et al., *ACS Chem. Biol.* 5:1029-1034, 2010). In addition, antagonists have been reported such as 7-oxygenated sterols (Wang et al., *J. Biol. Chem.* 285: 5013-5025, 2009) and compounds described in EP2181710 A1.

Numerous immune and inflammatory disorders continue to afflict millions of patients worldwide. Although significant advances have been made in treating these disorders, current therapies do not provide satisfactory results for all patients due to, for example, detrimental side effects or insufficient efficacy. One exemplary immune disorder in need of better therapy is psoriasis. Various therapeutics have been developed in an attempt to treat psoriasis. However, the traditional therapies for psoriasis often have toxic adverse effects. An exemplary inflammatory disorder in need of better treatment is rheumatoid arthritis. Numerous therapeutics have been developed in an attempt to treat this disorder. However, some patients develop resistance to current therapies. Another exemplary disorder in need of better therapy is cancer.

Accordingly, a need exists for improved treatments for immune disorders and inflammatory disorders. The present invention addresses this need and provides other related advantages.

SUMMARY OF THE INVENTION

The present invention provides compounds that alter the interaction of coregulator proteins with RORgammaT (and thereby, as commonly observed for nuclear hormone receptors, antagonize RORgammaT-mediated transcriptional activity; see e.g. "Differential Biochemical and Cellular Actions of Premarin Estrogens: Distinct Pharmacology of Bazedoxifene-Conjugate Estrogens Combination". Berrodin, T. J., Chang, K. C. N., Komm, B. S., Freedman, L. P., Nagpal, S. Molecular Endocrinology, January 2009, 23(1): 74-85) and are useful for the treatment of RORgammaT-mediated diseases or conditions, in particular autoimmune diseases and inflammatory diseases, as well as pharmaceutical compositions comprising such compounds and pharmaceutical carriers.

DETAILED DESCRIPTION OF THE INVENTION

Definitions

The terms used herein have their ordinary meaning and the meaning of such terms is independent at each occurrence thereof. That notwithstanding, and except where stated otherwise, the following definitions apply throughout the specification and claims. Chemical names, common names, and chemical structures may be used interchangeably to describe the same structure.

As used herein, and throughout this disclosure, the following terms, unless otherwise indicated, shall be understood to have the following meanings:

The term "alkyl," as used herein, refers to an aliphatic hydrocarbon group having one of its hydrogen atoms replaced with a bond having the specified number of carbon atoms. In an embodiment, an alkyl group contains, for example, from 1 to 4 carbon atoms ($C_{1-4}$)alkyl. In another embodiment, an alkyl group contains, for example, from 3 to 4 carbon atoms and is cyclic ($C_{3-4}$)cycloalkyl. Non-limiting examples of alkyl groups include methyl, ethyl, n-propyl, isopropyl, n-butyl, sec-butyl, isobutyl, tert-butyl, cyclopropyl and cyclobutyl. In one embodiment, an alkyl group is linear. In another embodiment, an alkyl group is branched. In another embodiment, an alkyl group is cyclic.

The term "($C_{0-4}$)alkyl" as used herein refers to a branched or unbranched alkyl group having 0-4 carbon atoms, for example, methyl, ethyl, n-propyl, isopropyl, n-butyl, isobutyl, sec-butyl and tert-butyl. ($C_0$)alkyl refers to hydrogen.

The term "cycloalkyl" as used herein refers to a monovalent saturated cyclic hydrocarbon group of 3-12, 3-8, 4-8, or 4-6 carbons, referred to herein, e.g., as "$C_3$-$C_6$ cycloalkyl," derived from a cycloalkane. Exemplary cycloalkyl groups include cyclohexyl, cyclopentyl, cyclobutyl, and cyclopropyl.

The term "carbocyclyl" as used herein refers to a monovalent cyclic hydrocarbon group, such as carbon ring having 3-12, 3-8, 4-8, or 4-6 carbons. The carbocyclyl may be saturated or unsaturated (e.g., an aromatic carbocyclyl).

The term "alkoxy", as used herein, refers to a linear or branched alkyl group of indicated number of carbon atoms attached via its oxygen atom to the rest of the molecule, i.e. —O-alkyl, wherein an alkyl group is defined above; for example "($C_{1-4}$)alkoxy" includes, but is not limited to, —OCH$_3$, —OCH$_2$CH$_3$, —OCH(CH$_3$)$_2$, —OC(CH$_3$)$_3$.

The term "halogen" (or "halo") refers to fluorine, chlorine, bromine and iodine (alternatively referred to as fluoro (F), chloro (Cl), bromo (Br), and iodo (I)). In one embodiment, a halogen is F or Cl. In another embodiment, halogen is F.

The term "alkylene" refers to a diradical of a linear or branched alkyl group having at least one carbon atom. An exemplary alkylene group is —CH$_2$CH$_2$—.

The term "haloalkyl" refers to an alkyl group having at least one carbon atom that is substituted with at least one halogen. For example, —CH$_2$F, —CHF$_2$, —CF$_3$, —CH$_2$CF$_3$, —CF$_2$CF$_3$, and the like.

The term "heteroalkyl" as used herein refers to a linear or branched $C_{2-10}$ alkyl group in which at least one carbon atom has been replaced with an O or S atom. The heteroalkyl may be, for example, an —O—$C_1$-$C_{10}$alkyl group, an —$C_1$-$C_6$alkylene-O—$C_1$-$C_6$alkyl group, or a $C_1$-$C_6$ alkylene-OH group. In certain embodiments, the "heteroalkyl" may be 2-8 membered heteroalkyl, indicating that the heteroalkyl contains from 2 to 8 atoms selected from the group consisting of carbon, oxygen, nitrogen, and sulfur. In yet other embodiments, the heteroalkyl may be a 2-6 membered, 4-8 membered, or a 5-8 membered heteroalkyl group (which may contain for example 1 or 2 heteroatoms selected from the group oxygen and nitrogen). In certain embodiments, the heteroalkyl is an "alkyl" group in which 1-3 carbon atoms have been replaced with oxygen atoms. One type of heteroalkyl group is an "alkoxyl" group.

The term "aryl" is art-recognized and refers to a carbocyclic aromatic group. Representative aryl groups include phenyl, naphthyl, anthracenyl, and the like. The term "aryl" includes polycyclic ring systems having two or more carbocyclic rings in which two or more carbons are common to two adjoining rings (the rings are "fused rings") wherein at least one of the rings is aromatic and, e.g., the other ring(s) may be cycloalkyls, cycloalkenyls, cycloalkynyls, and/or aryls. Unless specified otherwise, the aromatic ring may be substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —CO$_2$alkyl, carbonyl, carboxyl, alkylthio, sulfonyl, sulfonamido, sulfonamide, ketone, aldehyde, ester, heterocyclyl, aryl or heteroaryl moieties, —CF$_3$, —CN, or the like. In certain embodiments, the aromatic ring is substituted at one or more ring positions with halogen, alkyl, hydroxyl, or alkoxyl. In certain other embodiments, the aromatic ring is not substituted, i.e., it is unsubstituted. In certain embodiments, the aryl group is a 6-10 membered ring structure.

The term "aralkyl" refers to a $C_{1-10}$ alkyl group substituted with an aryl group.

The terms "heterocyclyl" and "heterocyclic group" are art-recognized and refer to saturated, partially unsaturated, or aromatic 3- to 10-membered ring structures, alternatively 3- to 7-membered rings, whose ring structures include one to four heteroatoms, such as nitrogen, oxygen, and sulfur. The number of ring atoms in the heterocyclyl group can be specified using $C_x$-$C_x$ nomenclature where x is an integer specifying the number of ring atoms. For example, a $C_3$-$C_7$heterocyclyl group refers to a saturated or partially unsaturated 3- to 7-membered ring structure containing one to four heteroatoms, such as nitrogen, oxygen, and sulfur. The designation "$C_3$-$C_7$" indicates that the heterocyclic ring contains a total of from 3 to 7 ring atoms, inclusive of any heteroatoms that occupy a ring atom position. One example of a $C_3$heterocyclyl is aziridinyl. Heterocycles may also be mono-, bi-, or other multi-cyclic ring systems including a spirocyclic ring system where at least one ring contains a ring heteroatom. A heterocycle may be fused to one or more aryl, partially unsaturated, or saturated rings. Heterocyclyl groups include, for example, biotinyl, chromenyl, dihydrofuryl, dihydroindolyl, dihydropyranyl, dihydrothienyl, dithiazolyl, homopiperidinyl, imidazolidinyl, isoquinolyl, isothiazolidinyl, isooxazolidinyl, morpholinyl, oxolanyl, oxazolidinyl, phenoxanthenyl, piperazinyl, piperidinyl, pyranyl, pyrazolidinyl, pyrazolinyl, pyridyl, pyrimidinyl, pyrrolidinyl, pyrrolidin-2-onyl, pyrrolinyl, tetrahydrofuryl, tetrahydroisoquinolyl, tetrahydropyranyl, tetrahydroquinolyl, thiazolidinyl, thiolanyl, thiomorpholinyl, thiopyranyl, xanthenyl, lactones, lactams such as azetidinones and pyrrolidinones, sultams, sultones, and the like. Unless specified otherwise, the heterocyclic ring is optionally substituted at one or more positions with substituents such as alkanoyl, alkoxy, alkyl, alkenyl, alkynyl, amido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, oxo, phosphate, phosphonato, phosphinato, sulfate, sulfide, sulfonamido, sulfonyl and thiocarbonyl. In certain embodiments, the heterocyclyl group is not substituted, i.e., it is unsubstituted.

The term "heterocycloalkyl" is art-recognized and refers to a saturated heterocyclyl group as defined above. In certain embodiments, the "heterocycloalkyl" is a 3- to 10-membered ring structures, alternatively a 3- to 7-membered rings, whose ring structures include one to four heteroatoms, such as nitrogen, oxygen, and sulfur.

The term "heterocycloalkylene" refers to a diradical of a heterocycloalkyl.

The term "heteroaryl" is art-recognized and refers to aromatic groups that include at least one ring heteroatom. In certain instances, a heteroaryl group contains 1, 2, 3, or 4 ring heteroatoms. Representative examples of heteroaryl groups include pyrrolyl, furanyl, thiophenyl, imidazolyl, oxazolyl, thiazolyl, triazolyl, pyrazolyl, pyridinyl, pyrazinyl, pyridazinyl and pyrimidinyl, and the like. Unless specified otherwise, the heteroaryl ring may be substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —CO$_2$alkyl, carbonyl, carboxyl, alkylthio, sulfonyl, sulfonamido, sulfonamide, ketone, aldehyde, ester, heterocyclyl, aryl or heteroaryl moieties, —CF$_3$, —CN, or the like. The term "heteroaryl" also includes polycyclic ring systems having two or more rings in which two or more carbons are common to two adjoining rings (the rings are "fused rings") wherein at least one of the rings is heteroaromatic, e.g., the other cyclic rings may be cycloalkyls, cycloalkenyls, cycloalkynyls, and/or aryls. In certain embodiments, the heteroaryl ring is substituted at one or more ring positions with halogen, alkyl, hydroxyl, or alkoxyl. In certain other embodiments, the heteroaryl ring is not substituted, i.e., it is unsubstituted. In certain embodiments, the heteroaryl group is a 5- to 10-membered ring structure, alternatively a 5- to 6-membered ring structure, whose ring structure includes 1, 2, 3, or 4 heteroatoms, such as nitrogen, oxygen, and sulfur.

The term "heteroaralkyl" refers to an linear or branched $C_{1-10}$ alkyl group substituted with a heteroaryl group.

The symbol "⁓" indicates a point of attachment.

When any variable occurs more than one time in any constituent or in any formula depicting and describing compounds of the invention, its definition on each occurrence is independent of its definition at every other occurrence. Also, combinations of substituents and/or variables are permissible only if such combinations result in stable compounds.

The term "substituted" means that one or more hydrogens on the designated atom/atoms is/are replaced with a selection from the indicated group, provided that the designated atom's normal valency under the existing circumstances is not exceeded, and that the substitution results in a stable compound. Combinations of substituents and/or variables are permissible only if such combinations result in stable compounds. "Stable compound" or "stable structure" is defined as a compound or structure that is sufficiently robust to survive isolation to a useful degree of purity from a reaction mixture, and formulation into an efficacious therapeutic agent.

The term "optionally substituted" means that a substitution with the specified groups, radicals, or moieties may or may not be made on the specified group.

When, in the definition of a substituent, it is indicated that "all of the alkyl groups" of said substituent are optionally substituted, this also includes the alkyl moiety of an alkoxy group.

When any substituent or variable occurs more than one time in any constituent or in the compound of Formulas (I-III), its definition on each occurrence is independent of its definition at every other occurrence, unless otherwise indicated.

The term "purified" as used herein, refers to the physical state of a compound after the compound has been isolated through a synthetic process (e.g., from a reaction mixture), from a natural source, or a combination thereof. The term "purified" also refers to the physical state of a compound after the compound has been obtained from a purification process or processes described herein or well-known to the skilled artisan (e.g., chromatography, recrystallization, and the like), in sufficient purity to be characterizable by standard analytical techniques described herein or well-known to the skilled artisan.

The term "amount" or "effective amount" as used herein refers to an amount of the compound of Formulas (I-III) and/or an additional therapeutic agent, or a composition thereof, that is effective in producing the desired therapeutic, ameliorative, inhibitory or preventative effect when administered to a subject suffering from an RORgammaT-mediated disease or disorder. In the combination therapies of the present invention, as effective amount can refer to each individual agent or to the combination as a whole, wherein the amounts of all agents administered are together effective, but wherein the component agent of the combination may not be present individually in an effective amount.

A "subject" is a human or non-human mammal. In one embodiment, a subject is a human. In another embodiment, a subject is a chimpanzee.

It should be noted that any carbon as well as heteroatom with unsatisfied valences in the text, schemes, examples and tables herein is assumed to have the sufficient number of hydrogen atom(s) to satisfy the valences.

Compounds of the Invention

The present invention provides a compound according to Formula I-1:

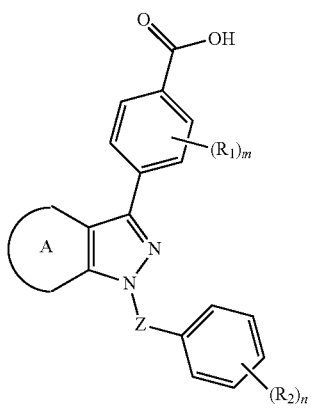

(I-1)

wherein:
Ring A is a monocyclic ring formed by an alkylene group taken together with the C=C of the pyrazolyl to which Ring A is fused, wherein 1, 2, or 3 carbon atoms of the alkylene group are optionally replaced with a heteroatom selected from O, N or S, and Ring A is optionally substituted with one to three substituents independently selected from $R_3$, wherein $R_3$ is selected from the group consisting of OH, oxo, $(C_{1-4})$alkyl, —$(C_{1-4})$alkylene-$N(R_a)_2$, —$(C_{1-4})$alkylene$(C_{3-6}$ cycloalkyl), $(C_{1-4})$ alkoxy, $N(R_a)_2$, $N(R_6)CO_2R_7$, $N(R_6)C(O)R_8$, $C(O)R_8$, $C(O)N(R_8)_2$,

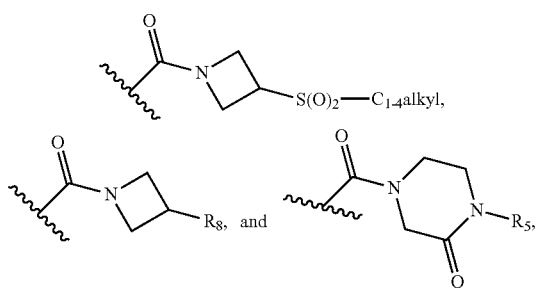

wherein said alkyl is optionally substituted with one or more halogen or hydroxyl;
Z is C(O) or $CH_2$;
m is 0, 1, or 2;
n is 1, 2 or 3;
$R_1$ is independently OH, halogen, $(C_{1-4})$alkyl, CN, $CF_3$, or $CHF_2$, wherein said alkyl is optionally substituted with one or more halogen;
$R_2$ is independently halogen, $(C_{1-4})$alkyl, $CF_3$, $CHF_2$, or $(C_{3-4})$cycloalkyl, wherein said alkyl and cycloalkyl are optionally substituted with one or more substituents independently selected from the group consisting of CN, $(C_{1-4})$haloalkyl, and halogen;
$R_5$ is independently OH, $(C_{0-4})$alkyl, or $S(O)_2R_b$;
$R_6$ is independently $(C_{0-4})$alkyl;
$R_7$ is independently $(C_{1-6})$alkyl;
$R_8$ is independently OH, $(C_{0-4})$alkyl, 2-8 membered heteroalkyl, or one of the following:
a heterocyclyl-containing group selected from 3-10 membered heterocyclyl, —$C_{1-6}$ alkylene-(5-6 membered heteroaryl), —O—$(C_{1-6}$ alkylene)-(5-6 membered heteroaryl), or -(3-10 membered heterocycloalkylene)-(3-10 membered heterocycloalkyl), each optionally substituted by one or more $R_9$);

a carbocyclyl-containing group selected from $C_{3-7}$ carbocyclyl, —$C_{1-6}$ alkylene-($C_{3-7}$ carbocyclyl), carbocyclyl, or —O—$(C_{1-6}$ alkylene)-$C_{3-7}$ carbocyclyl, each optionally substituted by one or more $R_9$;
$R_9$ is independently halogen, hydroxyl, $(C_{1-4})$alkyl, $(C_{1-4})$haloalkyl, $(C_{1-6})$alkoxyl, $N(R_a)_2$, $(C_{3-4})$cycloalkyl, or cyano, wherein said cycloalkyl is optionally substituted with one or more substituents independently selected from the group consisting of CN, $(C_{1-4})$haloalkyl, and halogen;
$R_a$ is independently $(C_{0-4})$alkyl, $(C_{1-4})$ haloalkyl, or 3-7 membered heterocycloalkyl; and
$R_b$ is $(C_{1-4})$alkyl;
or a pharmaceutically acceptable salt thereof.

In certain embodiments, Z is C(O).
In certain embodiments, $R_1$ is independently OH or halogen. In certain embodiments, $R_1$ is independently OH, chloro, or fluoro. In certain embodiments, $R_1$ is OH. In certain embodiments, $R_1$ is fluoro.
In certain embodiments, m is 1.
In certain embodiments, $R_1$ is located meta to the —$CO_2H$ group.
In certain embodiments, $R_2$ is independently halogen, $(C_{3-4})$cycloalkyl, or $(C_{3-4})$cycloalkyl substituted by $(C_{1-4}$ haloalkyl. In certain embodiments, $R_2$ is independently chloro, cyclopropyl, or cyclopropyl substituted by trifluoromethyl. In certain embodiments, a first occurrence of $R_2$ is chloro, and a second occurrence of $R^2$ is cyclopropyl. In certain embodiments, a first occurrence of $R_2$ is chloro, and a second occurrence of $R^2$ is cyclopropyl substituted by trifluoromethyl. In certain embodiments, a first occurrence of $R_2$ is chloro, and a second occurrence of $R^2$ is

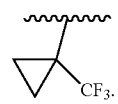

In certain embodiments, any $R_2$ is located at an ortho-position on the phenyl group to which $R_2$ is attached.
In certain embodiments, n is 2.
In certain embodiments, Ring A is a 6-membered monocyclic ring formed by an alkylene group taken together with the C=C of the pyrazolyl to which Ring A is fused, and Ring A is substituted with one $R_3$ group selected from $C(O)R_8$, $C(O)N(R_8)_2$, and

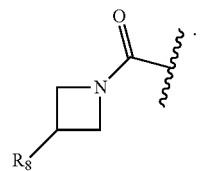

In certain embodiments, Ring A is

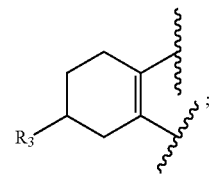

and $R_3$ is $C(O)R_8$, $C(O)N(R_8)_2$, or

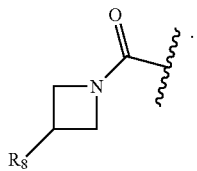

In certain embodiments, $R_8$ is independently $(C_{0-4})$alkyl, 2-8 membered heteroalkyl, or -(3-10 membered heterocyclyl optionally substituted by one or more $R_9$). In certain embodiments, $R_8$ is a 3-10 membered heterocyclyl optionally substituted by one or more $R_9$. In certain embodiments, $R_8$ is a 3-10 membered spirocyclic heterocyclyl optionally substituted by one or more $R_9$. In certain embodiments, $R_9$ is independently halogen, hydroxyl, or $(C_{1-4})$alkyl.

In certain embodiments, the compound is represented by Formula I-1A:

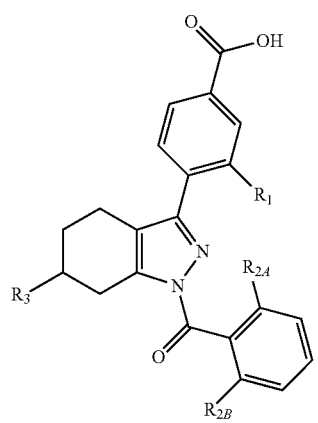

(I-1A)

wherein:
$R_1$ is halogen;
$R_{2A}$ is halogen;
$R_{2B}$ is independently halogen, $(C_{1-4})$alkyl, $CF_3$, $CHF_2$, or $(C_{3-4})$cycloalkyl, wherein said alkyl and cycloalkyl are optionally substituted with one or more substituents independently selected from the group consisting of CN, $(C_{1-4})$haloalkyl, and halogen;
$R_3$ is $N(R_a)_2$, $N(R_6)CO_2R_7$, $N(R_6)C(O)R_8$, $C(O)R_8$, $C(O)N(R_8)_2$, or

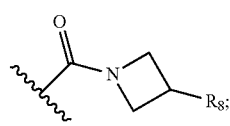

$R_6$ is independently $(C_{0-4})$alkyl;
$R_7$ is independently $(C_{1-6})$alkyl;
$R_8$ is independently $(C_{0-4})$alkyl, 2-8 membered heteroalkyl, or -(3-10 membered heterocyclyl optionally substituted by one or more $R_9$);
$R_9$ is independently halogen, hydroxyl, $(C_{1-4})$alkyl, or $(C_{1-4})$haloalkyl; and
$R_a$ is independently $(C_{0-4})$alkyl;
or a pharmaceutically acceptable salt thereof.

In certain embodiments, $R_8$ is a 3-10 membered heterocyclyl optionally substituted by one or more $R_9$. In certain embodiments, $R_8$ is a 3-10 membered spirocyclic heterocyclyl optionally substituted by one or more $R_9$. In certain embodiments, $R_9$ is independently halogen, hydroxyl, or $(C_{1-4})$alkyl.

In another embodiment, the present invention provides a compound according to Formula I-2:

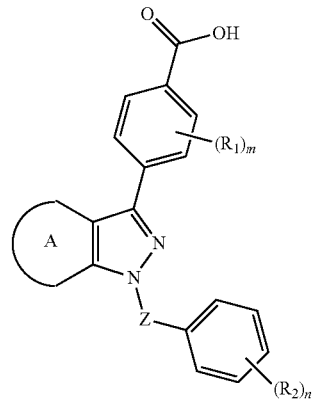

(I-2)

wherein:
Ring A is a saturated monocyclic ring optionally containing 1, 2, or 3 heteroatoms selected from O, N or S and optionally substituted with one to three substituents independently selected from $R_3$, wherein $R_3$ is selected from the group consisting of OH, oxo, $(C_{1-4})$alkyl, $(C_{1-4})$alkyl-$N(R_a)_2$, $(C_{1-4})$alkoxy, $N(R_a)_2$, $C(O)R_5$, $C(O)N(R_5)_2$,

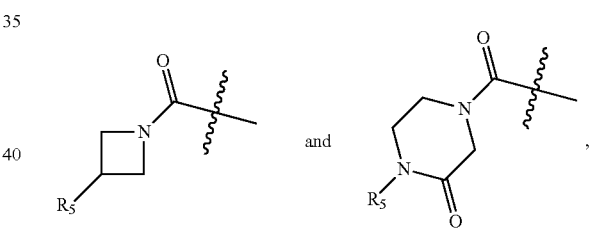

wherein said alkyl is optionally substituted with one or more halogen;
Z is $CH_2$ or $C(O)$;
m is 0, 1, or 2;
n is 1, 2 or 3;
$R_1$ is independently OH, $(C_{1-4})$alkyl, CN, $CF_3$, $CHF_2$ or halogen, wherein said alkyl is optionally substituted with one or more halogen;
$R_2$ is independently selected from halogen, $(C_{1-4})$alkyl, $CF_3$, $CHF_2$ and $(C_{3-4})$cycloalkyl, wherein said alkyl may optionally be substituted with CN and one to three halogen;
$R_5$ is independently selected from OH, $(C_{0-4})$alkyl, $(C_{1-4})$alkoxy and $S(O)_2R_b$;
$R_a$ is independently selected from $(C_{0-4})$alkyl; and
$R_b$ is $(C_{0-4})$alkyl;
or a pharmaceutically acceptable salt thereof.

As appreciated, Ring A is fused to the pyrazolyl group in Formula I-2 and accordingly the description of Ring A as a saturated monocyclic ring optionally containing 1, 2, or 3 heteroatoms selected from O, N or S means that bonds between ring atoms in Ring A are a single bond except for the C—C double bond of the pyrazolyl group to which Ring A is fused.

In another embodiment, the present invention provides a compound according to Formula II:

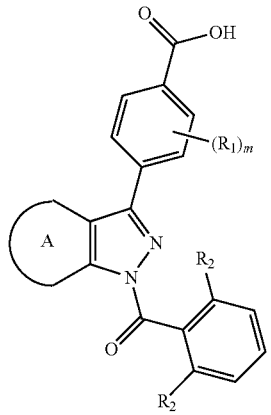

II wherein:

Ring A is a saturated monocyclic ring optionally containing 1, 2, or 3 heteroatoms selected from O, N or S and optionally substituted with one to three substituents independently selected from $R_3$, wherein $R_3$ is selected from the group consisting of OH, oxo, $(C_{1-4})$alkyl, $(C_{1-4})$alkyl-$N(R_a)_2$, $(C_{1-4})$alkoxy, $N(R_a)_2$, $C(O)R_5$, $C(O)N(R_5)_2$,

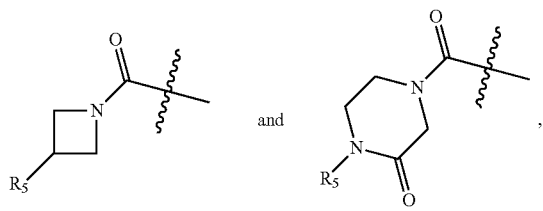

wherein said alkyl is optionally substituted with one or more halogen;

Z is $CH_2$ or $C(O)$;

m is 0, 1, or 2;

$R_1$ is independently OH, $(C_{1-4})$alkyl, CN, $CF_3$, $CHF_2$ or halogen, wherein said alkyl is optionally substituted with one or more halogen;

$R_2$ is independently selected from halogen, $(C_{1-4})$alkyl, $CF_3$, $CHF_2$ and $(C_{3-4})$cycloalkyl, wherein said alkyl may optionally be substituted with CN and one to three halogen;

$R_5$ is independently selected from OH, $(C_{0-4})$alkyl, $(C_{1-4})$alkoxy and $S(O)_2R_b$;

$R_a$ is independently selected from $(C_{0-4})$alkyl; and $R_b$ is $(C_{0-4})$alkyl;

or a pharmaceutically acceptable salt thereof.

As appreciated, Ring A is fused to the pyrazolyl group in Formula II and accordingly the description of Ring A as a saturated monocyclic ring optionally containing 1, 2, or 3 heteroatoms selected from O, N or S means that bonds between ring atoms in Ring A are a single bond except for the C—C double bond of the pyrazolyl group to which Ring A is fused.

In a third embodiment, the present invention provides a compound according to Formula III:

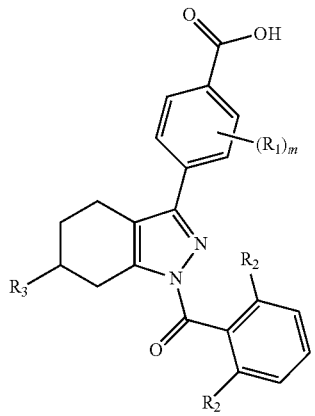

III wherein:

m is 0, 1, or 2;

$R_1$ is independently OH, methyl or F;

$R_2$ is independently selected from Cl, $CF_3$ and $(C_{3-4})$cycloalkyl, wherein the cycloalkyl may optionally be substituted with CN; and $R_3$ is selected from the group consisting of OH, oxo, $(C_{1-4})$alkoxy, $C(O)R_5$, $C(O)N(R_5)_2$,

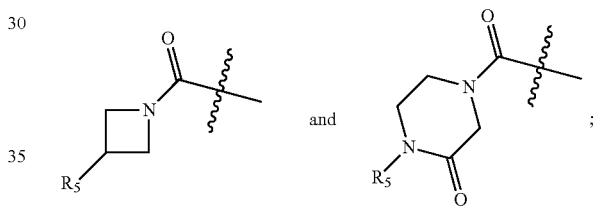

$R_5$ is independently selected from OH, $(C_{0-4})$alkyl, $(C_{1-4})$alkoxy and $S(O)_2R_b$; and $R_b$ is methyl;

or a pharmaceutically acceptable salt thereof.

In certain embodiments, compounds according to the instant invention are selected from: 4-(1-(2-chloro-6-(trifluoromethyl)benzoyl)-4,5,6,7-tetrahydro-1H-indazol-3-yl)-3-fluorobenzoic acid; 4-(1-(2-chloro-6-(trifluoromethyl)benzoyl)-1,4,5,6-tetrahydrocyclopenta[c]pyrazol-3-yl)-3-fluorobenzoic acid; 4-(6-(tert-butoxycarbonyl)-1-(2-chloro-6-(trifluoromethyl)benzoyl)-1,4,5,6,7,8-hexahydropyrazolo[3,4-d]azepin-3-yl)-3-fluorobenzoic acid; 4-(1-(2-chloro-6-cyclopropylbenzoyl)-4,5,6,7-tetrahydro-1H-indazol-3-yl)-2-hydroxybenzoic acid; 4-(1-(2-chloro-6-cyclopropylbenzoyl)-4,5,6,7-tetrahydro-1H-indazol-3-yl)-3-fluorobenzoic acid; 4-(1-(2-chloro-6-cyclopropylbenzoyl)-6-hydroxy-4,5,6,7-tetrahydro-1H-indazol-3-yl)-3-fluorobenzoic acid; 4-(6-(tert-butoxycarbonyl)-1-(2-chloro-6-cyclopropylbenzoyl)-4,5,6,7-tetrahydro-1H-pyrazolo[3,4-c]pyridin-3-yl)-3-fluorobenzoic acid; 4-(1-(2-chloro-6-cyclopropylbenzoyl)-4-oxo-4,5,6,7-tetrahydro-1H-indazol-3-yl)-3-fluorobenzoic acid; 4-(1-(2-chloro-6-cyclopropylbenzoyl)-6-methoxy-4,5,6,7-tetrahydro-1H-indazol-3-yl)-3-fluorobenzoic acid; 4-(1-(2-chloro-6-cyclopropylbenzoyl)-6-oxo-4,5,6,7-tetrahydro-1H-indazol-3-yl)-3-fluorobenzoic acid; 4-(1-(2-chloro-6-cyclopropylbenzoyl)-1,4,5,6,7,8-hexahydrocyclohepta[c]pyrazol-3-yl)-3-fluorobenzoic acid; 4-(1-(2-chloro-6-cyclobutylbenzoyl)-4,5,6,7-tetrahydro-1H-indazol-3-yl)-3- fluorobenzoic acid; 4-(1-(2,6-dichlorobenzoyl)-4,5,6,7-tetrahydro-1H-indazol-3-yl)benzoic acid; 4-(1-(2-chloro-6-cyclopropylbenzoyl)-4,5,6,7-tetrahydro-1H-indazol-3-yl)-5-fluoro-2-hydroxybenzoic acid; 4-(1-(2-chloro-6-(trifluoromethyl)benzoyl)-1,4,5,6,7,8-hexahydropyrazolo[3,4-d]azepin-3-yl)-3-fluorobenzoic acid; 4-(1-(2-chloro-6-(trifluoromethyObenzyl)-4,5,6,7-tetrahydro-1H-indazol-3-yl)-3-fluorobenzoic acid; 3-(4-carboxy-2-fluorophenyl)-1-(2-chloro-6-cyclopropylbenzoyl)-4,5,6,7-tetrahydro-1H-indazole-6-carboxylic acid; 4-(1-(2-chloro-6-cyclopropylbenzoyl)-6-(dimethylcarbamoyl)-4,5,6,7-tetrahydro-1H-indazol-3-yl)-3-fluorobenzoic acid; 4-(6-(azetidine-1-carbonyl)-1-(2-chloro-6-cyclopropylbenzoyl)-4,5,6,7-tetrahydro-1H-indazol-3-yl)-3-fluorobenzoic acid; 4-(1-(2-chloro-6-cyclopropylbenzoyl)-6-(methylcarbamoyl)-4,5,6,7-tetrahydro-1H-indazol-3-yl)-3-fluorobenzoic acid; 4-(4-(tert-butoxycarbonyl)-1-(2-chloro-6-cyclopropylbenzoyl)-4,5,6,7-tetrahydro-1H-pyrazolo[4,3-b]pyridin-3-yl)-3-fluorobenzoic acid; 4-(1-(2-chloro-6-cyclopropylbenzoyl)-1,4,6,7-tetrahydropyrano[4,3-c]pyrazol-3-yl)benzoic acid; 4-(1-(2-chloro-6-cyclopropylbenzoyl)-1,4,5,7-tetrahydropyrano[3,4-c]pyrazol-3-yl)-3-fluorobenzoic acid; 4-(6-acetyl-1-(2-chloro-6-cyclopropylbenzoyl)-4,5,6,7-tetrahydro-1H-pyrazolo[3,4-c]pyridin-3-yl)-3-fluorobenzoic acid; 4-(1-(2-chloro-6-cyclopropylbenzoyl)-6-(methoxycarbonyl)-4,5,6,7-tetrahydro-1H-pyrazolo[3,4-c]pyridin-3-yl)-3-fluorobenzoic acid; 4-(1-(2-chloro-6-cyclopropylbenzoyl)-6-(3-methoxyazetidine-1-carbonyl)-4,5,6,7-tetrahydro-1H-indazol-3-yl)-3-fluorobenzoic acid; 4-(1-(2-chloro-6-cyclopropylbenzoyl)-6-(3-methoxyazetidine-1-carbonyl)-4,5,6,7-tetrahydro-1H-indazol-3-yl)-3-fluorobenzoic acid; 4-(1-(2-chloro-6-(1-cyanocyclopropyl)benzoyl)-6-(3-methoxyazetidine-1-carbonyl)-4,5,6,7-tetrahydro-1H-indazol-3-yl)-3-fluorobenzoic acid; 4-(1-(2-chloro-6-(1-cyanocyclopropyl)benzoyl)-6-(3-methoxyazetidine-1-carbonyl)-4,5,6,7-tetrahydro-1H-indazol-3-yl)-3-fluorobenzoic acid; 4-(1-(2-chloro-6-(1-cyanocyclobutyl)benzoyl)-6-(3-(methylsulfonyl)azetidine-1-carbonyl)-4,5,6,7-tetrahydro-1H-indazol-3-yl)-3-fluorobenzoic acid;
4-(1-(2-chloro-6-(1-cyanocyclobutyl)benzoyl)-6-(3-(methylsulfonyl)azetidine-1-carbonyl)-4,5,6,7-tetrahydro-1H-indazol-3-yl)-3-fluorobenzoic acid; 4-(1-(2-chloro-6-(1-cyanocyclobutyl)benzoyl)-6-(4-methyl-3-oxopiperazine-1-carbonyl)-4,5,6,7-tetrahydro-1H-indazol-3-yl)-3-fluorobenzoic acid; 4-(1-(2-chloro-6-(1-cyanocyclobutyl)benzoyl)-6-(4-methyl-3-oxopiperazine-1-carbonyl)-4,5,6,7-tetrahydro-1H-indazol-3-yl)-3-fluorobenzoic acid; and 4-(1-(2-chloro-6-cyclopropylbenzoyl)-6-(3-methoxyazetidine-1-carbonyl)-4,5,6,7-tetrahydro-1H-indazol-3-yl)-2-methylbenzoic acid; or a pharmaceutically acceptable salt thereof.

In an embodiment of Formula I-2 or II:
Ring A is a saturated monocyclic ring optionally containing 1, 2, or 3 heteroatoms selected from O, N or S and optionally substituted with one to three substituents independently selected from $R_3$, wherein $R_3$ is selected from the group consisting of OH, oxo, $(C_{1-4})$alkoxy, $C(O)R_5$, $C(O)N(R_5)_2$,

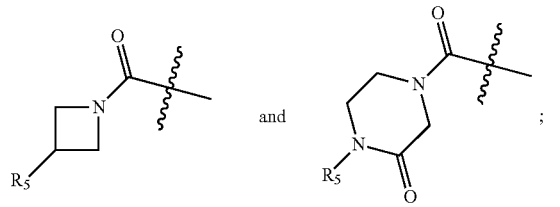

Z is $CH_2$ or $C(O)$;
m is 0, 1, or 2;
$R_1$ is independently OH, $(C_{1-4})$alkyl or halogen;
$R_2$ is independently selected from halogen and $(C_{3-4})$cycloalkyl;
$R_5$ is independently selected from OH, $(C_{0-4})$alkyl, $(C_{1-4})$alkoxy and $S(O)_2R_b$; and
$R_b$ is methyl;

In an embodiment, Ring A is selected from:

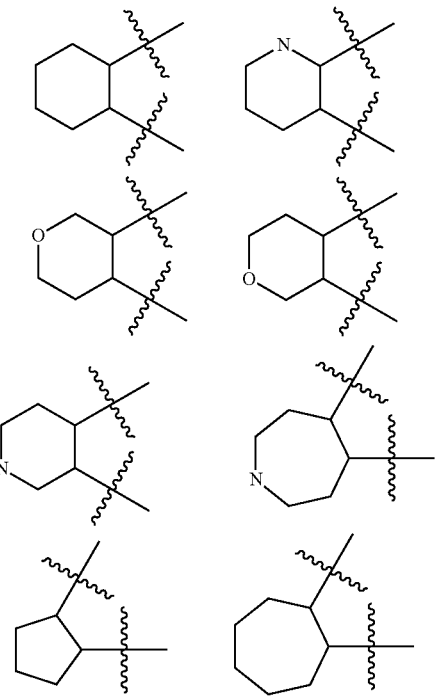

optionally substituted with one to three $R_3$, wherein $R_3$ is selected from the group consisting of OH, oxo, $(C_{1-4})$alkyl, $(C_{1-4})$alkyl-$N(R_a)_2$, $(C_{1-4})$alkoxy, $N(R_a)_2$, $C(O)R_5$, $C(O)N(R_5)_2$,

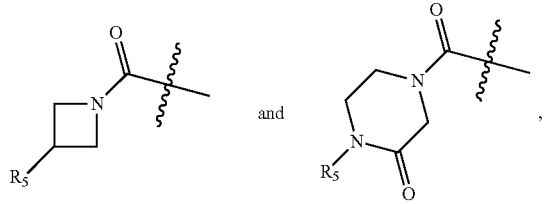

wherein said alkyl is optionally substituted with one or more halogen; and it is understood that the bond between carbon atoms in Ring A shared with the pyrazolyl group is a C—C double bond. This may be more specifically depicted as wherein Ring A is selected from:

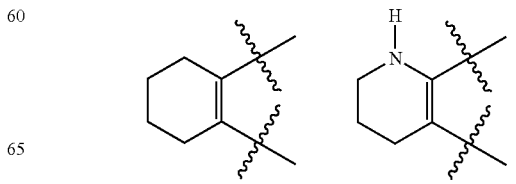

-continued

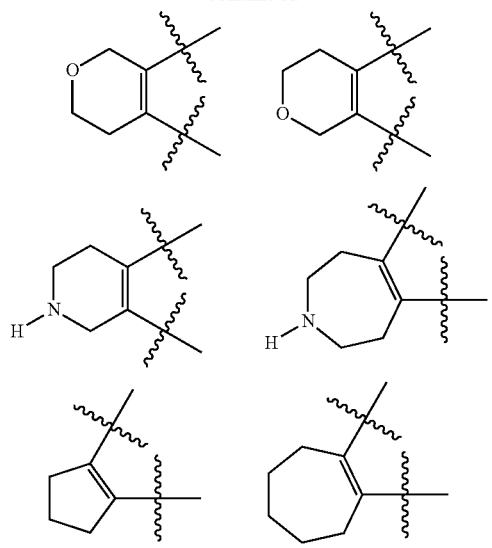

optionally substituted with one to three R$_3$, wherein R$_3$ is selected from the group consisting of OH, oxo, (C$_{1-4}$)alkyl, (C$_{1-4}$)alkyl-N(R$_a$)$_2$, (C$_{1-4}$)alkoxy, N(R$_a$)$_2$, C(O)R$_5$, C(O)N(R$_5$)$_2$,

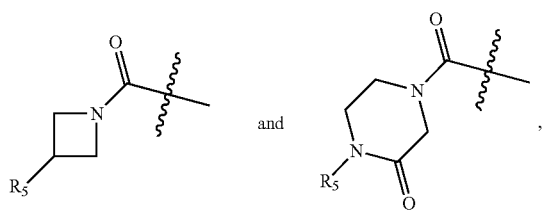

wherein said alkyl is optionally substituted with one or more halogen.

In another embodiment, Ring A is selected from:

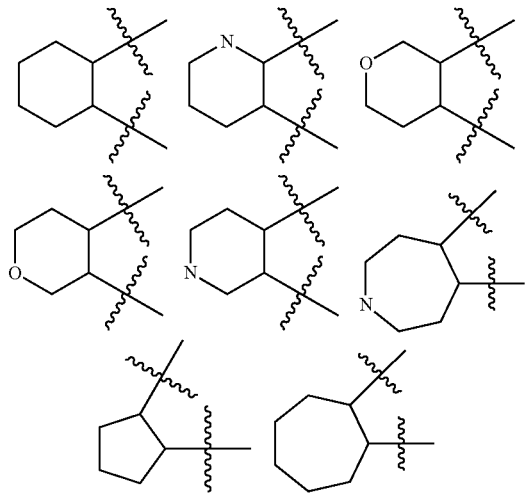

optionally substituted with one to three R$_3$, wherein R$_3$ is independently selected from the group consisting of OH, oxo, (C$_{1-4}$)alkoxy, C(O)R$^5$, C(O)N(R$^5$)$_2$,

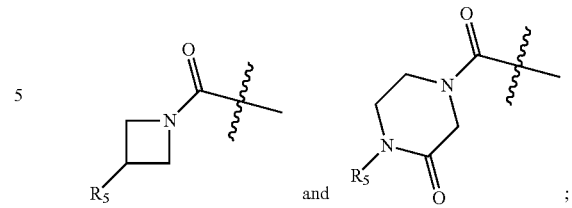

and it is understood that the bond between carbon atoms in Ring A shared with the pyrazolyl group is a C—C double bond. This may be more specifically depicted as wherein Ring A is selected from:

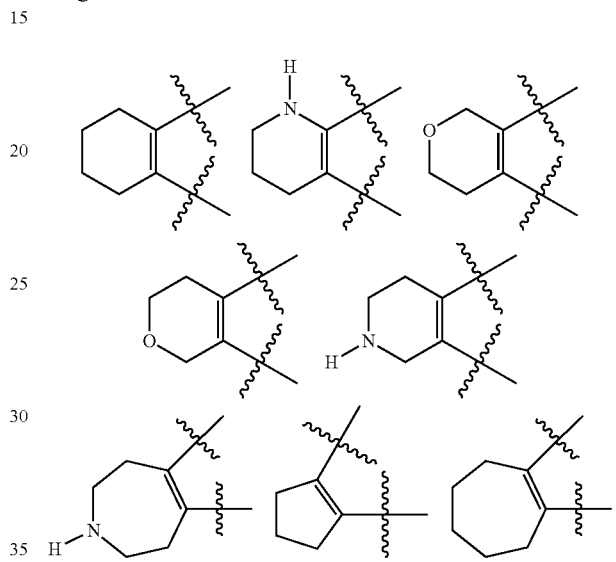

optionally substituted with one to three R$_3$, wherein R$_3$ is independently selected from the group consisting of OH, oxo, (C$_{1-4}$)alkoxy, C(O)R$^5$, C(O)N(R$^5$)$_2$,

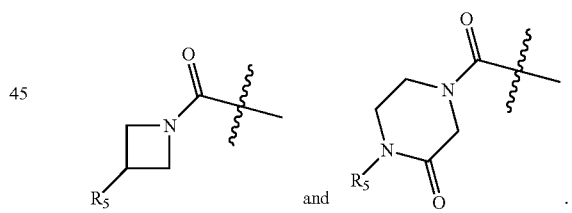

In another embodiment, Ring A is selected from:

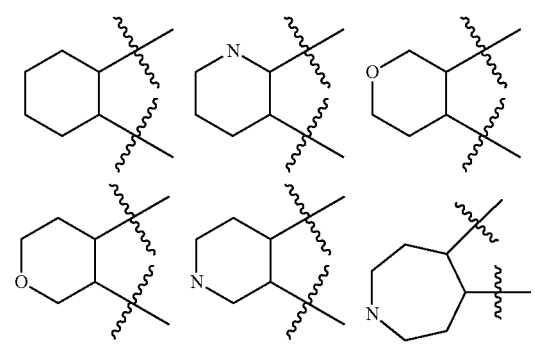

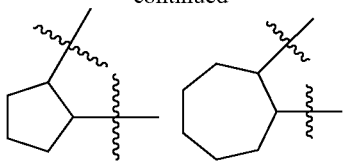

optionally substituted with one $R_3$, wherein $R_3$ is independently selected from the group consisting of OH, oxo, $(C_{1-4})$alkoxy, $C(O)R_5$, $C(O)N(R_5)_2$,

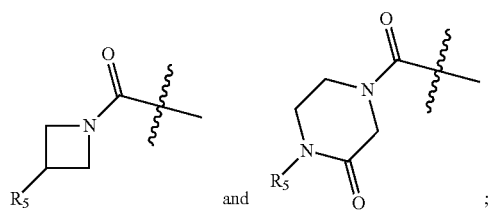

and it is understood that the bond between carbon atoms in Ring A shared with the pyrazolyl group is a C—C double bond. This may be more specifically depicted as wherein Ring A is selected from:

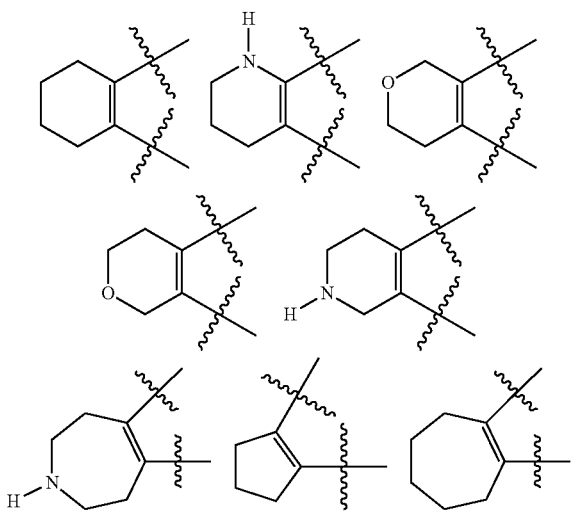

optionally substituted with one $R_3$, wherein $R_3$ is independently selected from the group consisting of OH, oxo, $(C_{1-4})$alkoxy, $C(O)R_5$, $C(O)N(R_5)_2$,

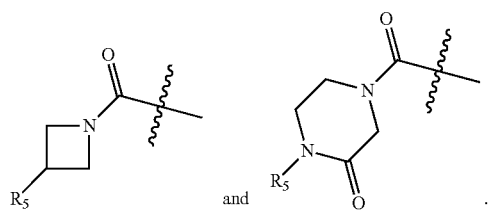

In an embodiment, m is 1 and $R_1$ is fluorine.

In an embodiment, n is 2 and $R_2$ is chlorine and cyclopropyl.

The invention also provides a compound of Formulas I (i.e., Formula I-1, I-1A, and I-2), II or III, or a pharmaceutically acceptable salt thereof in purified form.

The compounds of this invention include the prodrugs, hydrates or solvates of the compounds. The use of the terms "prodrug", "hydrate", "salt", "solvate", "ester", and the like is intended to equally apply to the salt, solvate, ester, and prodrug of enantiomers, stereoisomers, rotamers, tautomers, positional isomers, racemates, or prodrugs of the inventive compounds.

Optical Isomers-Diastereomers-Geometric Isomers-Tautomers

The compounds of Formulas (I-III) may contain asymmetric or chiral centers, and, therefore, exist in different stereoisomeric forms. It is intended that all stereoisomeric forms of the compounds of Formulas (I-III) as well as mixtures thereof, including racemic mixtures, form part of the present invention. In addition, the present invention embraces all geometric and positional isomers. For example, if a compound of Formulas (I-III) incorporates a double bond or a fused ring, both the cis- and trans-forms, as well as mixtures, are embraced within the scope of the invention.

Compounds described herein may contain an asymmetric center and may thus exist as enantiomers. Where the compounds according to the invention possess two or more asymmetric centers, they may additionally exist as diastereomers. The present invention includes all such possible stereoisomers as substantially pure resolved enantiomers, racemic mixtures thereof, as well as mixtures of diastereomers. The above Formulas (I-III) are shown without a definitive stereochemistry at certain positions. The present invention includes all stereoisomers of Formulas (I-III) and pharmaceutically acceptable salts thereof.

Diastereoisomeric pairs of enantiomers may be separated by, for example, fractional crystallization from a suitable solvent, and the pair of enantiomers thus obtained may be separated into individual stereoisomers by conventional means, for example by the use of an optically active acid or base as a resolving agent or on a chiral HPLC column. Further, any enantiomer or diastereomer of a compound of the general Formulas (I-III) may be obtained by stereospecific synthesis using optically pure starting materials or reagents of known configuration.

When compounds described herein contain olefinic double bonds, unless specified otherwise, such double bonds are meant to include both E and Z geometric isomers.

Some of the compounds described herein may exist with different points of attachment of hydrogen. Such compounds are referred to as tautomers. For example, compounds including carbonyl —$CH_2C(O)$— groups (keto forms) may undergo tautomerism to form hydroxyl —CH=C(OH)— groups (enol forms). Both keto and enol forms, individually as well as mixtures thereof, are included within the scope of the present invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g. chiral auxiliary such as a chiral alcohol or Mosher's acid chloride), separating the diastereomers and converting (e.g. hydrolyzing) the individual diastereomers to the corresponding pure enantiomers. Also, some of the compounds of Formulas (I-III) may be atropisomers (e.g. substituted biaryls) and are considered as part of this invention. Enantiomers can also be separated by use of chiral HPLC column.

It is also possible that the compounds of Formulas I-III may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters, and prodrugs of the compounds as well as the salts, solvates, and esters of the prodrugs), such as those that may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations.

Salts

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (-ic and -ous), potassium, sodium, zinc and the like salts. Preferred are the ammonium, calcium, magnesium, potassium and sodium salts. Salts prepared from pharmaceutically acceptable organic non-toxic bases include salts of primary, secondary, and tertiary amines derived from both naturally occurring and synthetic sources. Pharmaceutically acceptable organic non-toxic bases from which salts can be formed include, for example, arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, dicyclohexylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, its corresponding salt can be conveniently prepared from pharmaceutically acceptable non-toxic inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids.

The compounds of Formulas I-III can form salts which are also within the scope of this invention. Reference to a compound of Formulas I-III herein is understood to include reference to salts thereof, unless otherwise indicated.

The term pharmaceutically acceptable salt represents those salts that are, within the scope of medical judgment, suitable for use in contact for the tissues of humans and lower animals without undue toxicity, irritation, allergic response and the like, and are commensurate with a reasonable benefit/risk ratio. Pharmaceutically acceptable salts are well known in the art. They may be obtained during the final isolation and purification of the compounds of the invention, or separately by reacting the free base function with a suitable mineral acid such as hydrochloric acid, phosphoric acid, or sulfuric acid, or with an organic acid such as for example ascorbic acid, citric acid, tartaric acid, lactic acid, maleic acid, malonic acid, fumaric acid, glycolic acid, succinic acid, propionic acid, acetic acid, methanesulfonic acid, and the like. The acid function can be reacted with an organic or a mineral base, like sodium hydroxide, potassium hydroxide, calcium hydroxide, calcium carbonate, ammonium (e.g. diethylamine) or lithium hydroxide.

Solvates

The present invention includes within its scope solvates of compounds of Formulas (I-III). As used herein, the term "solvate" refers to a complex of variable stoichiometry formed by a solute (i.e., a compound of Formulas (I-III)) or a pharmaceutically acceptable salt thereof and a solvent that does not interfere with the biological activity of the solute. Examples of solvents include but are not limited to water, ethanol, and acetic acid. When the solvent is water, the solvate is known as hydrate; hydrate includes, but is not limited to, hemi-, mono, sesqui-, di- and trihydrates.

The compounds of the invention may form hydrates or solvates. It is known to those of skill in the art that charged compounds form hydrated species when lyophilized with water, or form solvated species when concentrated in a solution with an appropriate organic solvent. One or more compounds of the invention may exist in unsolvated as well as solvated forms with pharmaceutically acceptable solvents such as water, ethanol, and the like, and it is intended that the invention embrace both solvated and unsolvated forms. "Solvate" may also mean a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

Prodrugs

The present invention includes within its scope the use prodrugs of the compounds of this invention. In general, such prodrugs will be functional derivatives of the compounds of this invention which are readily convertible in vivo into the required compound. Thus, in the methods of treatment of the present invention, the term "administering" shall encompass the treatment of the various conditions described with a compound of Formulas I-III or with a compound that may not be a compound of Formulas I-III, but that converts to a compound of Formulas I-III in vivo after administration to the patient. Conventional procedures for the selection and preparation of suitable prodrug derivatives are described, for example, in "Design of Prodrugs," ed. H. Bundgaard, Elsevier, 1985.

The term "prodrug" means a compound (e.g., a drug precursor) that is transformed in vivo to yield a compound of Formulas I-III or a pharmaceutically acceptable salt, hydrate or solvate of the compound. The transformation may occur by various mechanisms (e.g., by metabolic or chemical processes), such as, for example, through hydrolysis in blood. A discussion of prodrugs and the use of prodrugs is provided by T. Higuchi and W. Stella, "Pro-drugs as Novel Delivery Systems," Vol. 14 of the A.C.S. Symposium Series, 1987; and in Bioreversible Carriers in Drug Design, ed. Edward B. Roche, American Pharmaceutical Association and Pergamon Press, 1987.

Isotopes

In the compounds of generic Formulas (I-III), the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formulas I-III. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. In light of the present disclosure, isotopically-enriched compounds within generic Formulas (I-III) can be prepared without undue experimentation by conventional techniques well known to those skilled in the art or by processes analogous to those described in the Schemes and Examples herein using appropriate isotopically-enriched reagents and/or intermediates.

Utilities

Compounds of the present invention alter the interaction of coregulator proteins with Retinoic Acid Receptor-related Orphan Receptor gamma t (RORgammaT) and thereby antagonize RORgammaT-mediated transcriptional activity, and as such are useful in the treatment of diseases and conditions in which inhibition of RORgammaT is desirable, such as autoimmune and inflammatory diseases and disorders.

Accordingly, another embodiment of the present invention provides a method for treating a disease or condition mediated by RORgammaT in a subject comprising administering to the subject an amount of a compound having Formulas I-III, or a pharmaceutically acceptable salt thereof, that is effective for treating the disease or condition mediated by RORgammaT in the subject.

The compounds according to the invention can be used in therapy.

A further aspect of the invention resides in the use of compounds according to the invention or a pharmaceutically acceptable salt thereof for the treatment of RORgammaT-mediated diseases or RORgammaT mediated conditions.

Another aspect of the invention resides in the use of compounds or a pharmaceutically acceptable salt thereof having the general Formulas (I-III) for the treatment of autoimmune diseases, in particular those diseases in which Th17 cells and non-Th17 cells, which express Th17 hallmark cytokines, play a prominent role. These include, but are not limited to, the treatment of rheumatoid arthritis, psoriasis, inflammatory bowel disease, Crohn's disease, ankylosing spondylitis and multiple sclerosis.

In another aspect, compounds or a pharmaceutically acceptable salt thereof having the general Formulas (I-III) can be used for treatment of inflammatory diseases in which Th17 cells and/or non-Th17 cells, which express Th17 hallmark cytokines, play a prominent role, such as but not limited to respiratory diseases, osteoarthritis and asthma. Also, compounds or a pharmaceutically acceptable salt thereof having the general Formulas (I-III) can be used for treatment of infectious diseases in which Th17 cells and/or non-Th17 cells, which express Th17 hallmark cytokines, play a prominent role, such as but not limited to mucosal leishmaniasis.

Compounds or a pharmaceutically acceptable salt thereof having the general Formulas (I-III) can also be used for treatment of other diseases in which Th17 cells and/or non-Th17 cells, which express Th17 hallmark cytokines, play a prominent role, such as but not limited to Kawasaki disease and Hashimoto's thyroiditis.

In one aspect the disease or condition is an autoimmune disease or an inflammatory disease. The disease or condition includes, but is not limited to, multiple sclerosis, inflammatory bowel disease, Crohn's disease, ankylosing spondylitis, psoriasis, rheumatoid arthritis, asthma, osteoarthritis, Kawasaki disease, Hashimoto's thyroiditis or mucosal leishmaniasis.

In another aspect, the compounds according to the invention can be used in therapies to treat or prevent multiple sclerosis, inflammatory bowel disease, Crohn's disease, psoriasis, rheumatoid arthritis, asthma, osteoarthritis, Kawasaki disease, Hashimoto's thyroiditis and mucosal leishmaniasis. In another aspect the compounds according to the invention can be used to treat or prevent psoriasis. In yet another aspect the compounds according to the invention can be used to treat inflammatory bowel disease.

In yet another aspect the compounds according to the invention can be used to treat cancer. The term cancer includes, but is not limited to, colorectal, lung, and pancreatic cancer. In another aspect the compounds according to the invention can be used to treat colorectal cancer. In another aspect the compounds according to the invention can be used to treat lung cancer. In another aspect the compounds according to the invention can be used to treat pancreatic cancer. In yet other embodiments, the cancer to be treated is a solid tumor or leukemia. In certain other embodiments, the cancer is colon cancer, pancreatic cancer, breast cancer, ovarian cancer, prostate cancer, squamous cell carcinoma, basal cell carcinoma, adenocarcinoma, sweat gland carcinoma, sebaceous gland carcinoma, lung cancer, leukemia, bladder cancer, stomach cancer, cervical cancer, testicular cancer, skin cancer, rectal cancer, thyroid cancer, kidney cancer, uterus cancer, espophagus cancer, liver cancer, an acoustic neuroma, oligodendroglioma, meningioma, neuroblastoma, or retinoblastoma. In certain other embodiments, the cancer is small cell lung cancer, non-small cell lung cancer, melanoma, cancer of the central nervous system tissue, brain cancer, Hodgkin's lymphoma, non-Hodgkin's lymphoma, cutaneous T-Cell lymphoma, cutaneous B-Cell lymphoma, or diffuse large B-Cell lymphoma. In certain other embodiments, the cancer is breast cancer, colon cancer, small-cell lung cancer, non-small cell lung cancer, prostate cancer, renal cancer, ovarian cancer, leukemia, melanoma, or cancer of the central nervous system tissue. In certain other embodiments, the cancer is colon cancer, small-cell lung cancer, non-small cell lung cancer, renal cancer, ovarian cancer, renal cancer, or melanoma.

Additional exemplary cancers include fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, Ewing's tumor, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, epithelial carcinoma, glioma, astrocytoma, medulloblastoma, and hemangioblastoma.

In certain embodiments, the cancer is a neuroblastoma, meningioma, hemangiopericytoma, multiple brain metastase, glioblastoma multiforms, glioblastoma, brain stem glioma, poor prognosis malignant brain tumor, malignant glioma, anaplastic astrocytoma, anaplastic oligodendroglioma, neuroendocrine tumor, rectal adeno carcinoma, Dukes C & D colorectal cancer, unresectable colorectal carcinoma, metastatic hepatocellular carcinoma, Kaposi's sarcoma, karotype acute myeloblastic leukemia, Hodgkin's lymphoma, non-Hodgkin's lymphoma, cutaneous T-Cell lymphoma, cutaneous B-Cell lymphoma, diffuse large B-Cell lymphoma, low grade follicular lymphoma, metastatic melanoma, localized melanoma, malignant mesothelioma, malignant pleural effusion mesothelioma syndrome, peritoneal carcinoma, papillary serous carcinoma, gynecologic sarcoma, soft tissue sarcoma, scleroderma, cutaneous vasculitis, Langerhans cell histiocytosis, leiomyosarcoma, fibrodysplasia ossificans progressive, hormone refractory prostate cancer, resected high-risk soft tissue sarcoma, unrescectable hepatocellular carcinoma, Waidenstrom's macroglobulinemia, smoldering myeloma, indolent myeloma, fallopian tube cancer, androgen independent prostate cancer, androgen dependent stage IV non-metastatic prostate cancer, hormone-insensitive prostate cancer, chemotherapy-insensitive prostate cancer, papillary thyroid carcinoma, follicular thyroid carcinoma, medullary thyroid carcinoma, or leiomyoma.

Another aspect of the present invention further includes the use of a compound of Formulas I-III, or a pharmaceutically acceptable salt thereof, in the manufacture of a medicament for the treatment of a disease or condition mediated by RORgammaT.

Route of Administration/Dosage

The compounds of this invention can be administered for the treatment or prevention of afflictions, diseases and illnesses according to the invention by any means that effects contact of the active ingredient compound with the site of action in the body of a warm-blooded animal. For example, administration can be oral, topical, including transdermal, ocular, buccal, intranasal, inhalation, intravaginal, rectal, intracisternal and parenteral. The term "parenteral" as used herein refers to modes of administration that include subcutaneous, intravenous, intramuscular, intraarticular injection or infusion, intrasternal and intraperitoneal. For the purpose of this disclosure, a warm-blooded animal is a member of the animal kingdom possessed of a homeostatic mechanism and includes mammals and birds.

The compounds can be administered by any conventional means available for use in conjunction with pharmaceuticals, either as individual therapeutic agents or in a combination of therapeutic agents. They can be administered alone, but are generally administered with a pharmaceutical carrier selected on the basis of the chosen route of administration and standard pharmaceutical practice.

The dosage administered will be dependent on the age, health and weight of the recipient, the extent of disease, kind of concurrent treatment, if any, frequency of treatment and the nature of the effect desired. Usually, a daily dosage of active ingredient compound will be from about 1.0-2000 milligrams per day. Ordinarily, from 10 to 500 milligrams per day in one or more applications is effective to obtain desired results. These dosages are the effective amounts for the treatment and prevention of afflictions, diseases and illnesses described above, e.g., autoimmune and inflammatory diseases and disorders.

Compositions include e.g. those suitable for oral, sublingual, subcutaneous, intravenous, intramuscular, nasal, local, or rectal administration, and the like, all in unit dosage forms for administration.

For oral administration, the active ingredient may be presented as discrete units, such as tablets, capsules, powders, granulates, solutions, suspensions, and the like. For parenteral administration, the pharmaceutical composition of the invention may be presented in unit-dose or multi-dose containers, e.g. injection liquids in predetermined amounts, for example in sealed vials and ampoules, and may also be stored in a freeze dried (lyophilized) condition requiring only the addition of sterile liquid carrier, e.g. water, prior to use.

Mixed with such pharmaceutically acceptable auxiliaries, e.g. as described in the standard reference, Gennaro, A. R. et al., Remington: *The Science and Practice of Pharmacy* (20th Edition, Lippincott Williams & Wilkins, 2000, see especially Part 5: Pharmaceutical Manufacturing), the active agent may be compressed into solid dosage units, such as pills, tablets, or be processed into capsules or suppositories. By means of pharmaceutically acceptable liquids the active agent can be applied as a fluid composition, e.g. as an injection preparation, in the form of a solution, suspension, emulsion, or as a spray, e.g. a nasal spray.

For making solid dosage units, the use of conventional additives such as fillers, colorants, polymeric binders and the like is contemplated. In general any pharmaceutically acceptable additive that does not interfere with the function of the active compounds can be used. Suitable carriers with which the active agent of the invention can be administered as solid compositions include lactose, starch, cellulose derivatives and the like, or mixtures thereof, used in suitable amounts. For parenteral administration, aqueous suspensions, isotonic saline solutions and sterile injectable solutions may be used, containing pharmaceutically acceptable dispersing agents and/or wetting agents, such as propylene glycol or butylene glycol.

Pharmaceutical Compositions

Another aspect of the present invention provides pharmaceutical compositions comprising a compound of Formulas (I-III), or a pharmaceutically acceptable salt thereof, and one or more pharmaceutically acceptable excipients or carriers. The term "excipient" and "carrier" may be used interchangeably. The term "composition", as in pharmaceutical composition, is intended to encompass a product comprising the active ingredient(s), and the inert ingredient(s) (pharmaceutically acceptable excipients) that make up the carrier, as well as any product that results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of Formulas I-III, additional active ingredient(s), and pharmaceutically acceptable excipients.

The pharmaceutical compositions of the present invention comprise a compound represented by Formulas I-III (or pharmaceutically acceptable salts thereof) as an active ingredient, a pharmaceutically acceptable carrier and optionally other therapeutic ingredients or adjuvants. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

The active ingredient can be administered orally in solid dosage forms, such as capsules, tablets, troches, dragees, granules and powders, or in liquid dosage forms, such as elixirs, syrups, emulsions, dispersions, and suspensions. The active ingredient can also be administered parenterally, in sterile liquid dosage forms, such as dispersions, suspensions or solutions. Other dosages forms that can also be used to administer the active ingredient as an ointment, cream, drops, transdermal patch or powder for topical administration, as an ophthalmic solution or suspension formation, i.e., eye drops, for ocular administration, as an aerosol spray or powder composition for inhalation or intranasal administration, or as a cream, ointment, spray or suppository for rectal or vaginal administration.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propylparaben, and chlorobutanol.

Suitable pharmaceutical carriers are described in *Remington's Pharmaceutical Sciences*, A. Osol, a standard reference text in this field.

For administration by inhalation, the compounds of the present invention may be conveniently delivered in the form of an aerosol spray presentation from pressurized packs or nebulizers. The compounds may also be delivered as powders which may be formulated and the powder composition may be inhaled with the aid of an insufflation powder inhaler device. The preferred delivery system for inhalation is a metered dose inhalation (MDI) aerosol, which may be formulated as a suspension or solution of a compound of Formulas I-III in suitable propellants, such as fluorocarbons or hydrocarbons.

For ocular administration, an ophthalmic preparation may be formulated with an appropriate weight percent solution or suspension of the compounds of Formulas in an appropriate ophthalmic vehicle, such that the compound is maintained in contact with the ocular surface for a sufficient time period to allow the compound to penetrate the corneal and internal regions of the eye.

Useful pharmaceutical dosage-forms for administration of the compounds of this invention include, but are not limited to, hard and soft gelatin capsules, tablets, parenteral injectables, and oral suspensions.

A large number of unit capsules are prepared by filling standard two-piece hard gelatin capsules each with 100 milligrams of powdered active ingredient, 150 milligrams of lactose, 50 milligrams of cellulose, and 6 milligrams magnesium stearate.

A mixture of active ingredient in a digestible oil such as soybean oil, cottonseed oil or olive oil is prepared and injected by means of a positive displacement pump into gelatin to form soft gelatin capsules containing 100 milligrams of the active ingredient. The capsules are washed and dried.

A large number of tablets are prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

A parenteral composition suitable for administration by injection is prepared by stirring 1.5% by weight of active ingredient in 10% by volume propylene glycol. The solution is made to volume with water for injection and sterilized.

An aqueous suspension is prepared for oral administration so that each 5 milliliters contain 100 milligrams of finely divided active ingredient, 100 milligrams of sodium carboxymethyl cellulose, 5 milligrams of sodium benzoate, 1.0 grams of sorbitol solution, U.S.P., and 0.025 milliliters of vanillin.

The same dosage forms can generally be used when the compounds of this invention are administered stepwise or in conjunction with another therapeutic agent. When drugs are administered in physical combination, the dosage form and administration route should be selected depending on the compatibility of the combined drugs. Thus the term coadministration is understood to include the administration of the two agents concomitantly or sequentially, or alternatively as a fixed dose combination of the two active components.

The present invention also relates to a pharmaceutical composition comprising compounds or pharmaceutically acceptable salts thereof having the general Formulas I-III in admixture with pharmaceutically acceptable auxiliaries and optionally other therapeutic agents. The auxiliaries must be "acceptable" in the sense of being compatible with the other ingredients of the composition and not deleterious to the recipients thereof.

The invention further includes a pharmaceutical composition, as hereinbefore described, in combination with packaging material suitable for said composition, said packaging material including instructions for the use of the composition for the use as hereinbefore described.

The exact dose and regimen of administration of the active ingredient, or a pharmaceutical composition thereof, may vary with the particular compound, the route of administration, and the age and condition of the individual subject to whom the medicament is to be administered.

In general parenteral administration requires lower dosages than other methods of administration which are more dependent upon absorption. However, a dosage for humans preferably contains 0.0001-100 mg per kg body weight. The desired dose may be presented as one dose or as multiple subdoses administered at appropriate intervals throughout the day. The dosage as well as the regimen of administration may differ between a female and a male recipient.

Combination Therapy

Compounds of the present invention, and their salts and solvates, and physiologically functional derivatives thereof, may be employed alone or in combination with other therapeutic agents for the treatment of diseases and conditions associated with inappropriate IL-17 pathway activity. Combination therapies according to the present invention thus comprise the administration of at least one compound of formulas (I-III) or a pharmaceutically acceptable salt thereof, or a physiologically functional derivative thereof, and the use of at least one other pharmaceutically active agent. The compound(s) of formulas (I-III) and the other pharmaceutically active agent(s) may be administered together or separately and, when administered separately this may occur simultaneously or sequentially in any order. The amounts of the compound(s) of formulas (I-III) and the other pharmaceutically active agent(s) and the relative timings of administration will be selected in order to achieve the desired combined therapeutic effect. For the treatment of the inflammatory and autoimmune diseases, rheumatoid arthritis, psoriasis, inflammatory bowel disease, ankylosing spondylitis, SLE, uveitis, atopic dermatitis, COPD, asthma and allergic rhinitis a compound of Formulas (I-III) may be combined with one or more other active agents such as: (1) TNF-α inhibitors; (2) non-selective COX-I/COX-2 inhibitors; (3) COX-2 inhibitors; (4) other agents for treatment of inflammatory and autoimmune diseases including glucocorticoids, methotrexate, leflunomide, sulfasalazine, azathioprine, cyclosporin, tacrolimus, penicillamine, bucillamine, actarit, mizoribine, lobenzarit, ciclesonide, hydroxychloroquine, d-penicillamine, aurothiomalate, auranofin or parenteral or oral gold, cyclophosphamide, Lymphostat-B, BAFF/APRIL inhibitors and CTLA-4-Ig or mimetics thereof; (5) leukotriene biosynthesis inhibitor, 5-lipoxygenase (5-LO) inhibitor or 5-lipoxygenase activating protein (FLAP) antagonist; (6) LTD4 receptor antagonist; (7) PDE4 inhibitor; (8) antihistamine HI receptor antagonists; (9) al- and a2-adrenoceptor agonist; (10) anticholinergic agents; (11) β-adrenoceptor agonists; (12) insulin-like growth factor type I (IGF-1) mimetic; (13) glucocorticosteroids; (14) kinase inhibitors such as inhibitors of the Janus Kinases (JAK 1 and/or JAK2 and/or JAK 3 and/or TYK2), p38 MAPK and IKK2; (15) B-cell targeting biologies such as rituximab; (16) selective costimulation modulators such as abatacept; (17) interleukin inhibitors, such as IL-1 inhibitor anakinra, IL-6 inhibitor tocilizumab, and IL12/IL-23 inhibitor ustekinumab. It could also be combined with anti-IL17 antibodies to obtain additive/synergistic responses for the treatment of inflammatory and autoimmune diseases.

Compounds of the present invention, and their salts and solvates, and physiologically functional derivatives thereof, may be employed alone or in combination with other anti-cancer agents for the treatment of cancer.

It will be clear to a person skilled in the art that, where appropriate, the other therapeutic ingredient(s) may be used in the form of salts, for example as alkali metal or amine salts or as acid addition salts, or prodrugs, or as esters, for example lower alkyl esters, or as solvates, for example hydrates, to optimize the activity and/or stability and/or physical characteristics, such as solubility, of the therapeutic ingredient. It will be clear also that, where appropriate, the therapeutic ingredients may be used in optically pure form.

The combinations referred to above may conveniently be presented for use in the form of a pharmaceutical composition and thus pharmaceutical compositions comprising a combination as defined above together with a pharmaceutically acceptable diluent or carrier represent a further aspect of the invention. These combinations are of particular interest in respiratory diseases and are conveniently adapted for inhaled or intranasal delivery.

The individual compounds of such combinations may be administered either sequentially or simultaneously in separate or combined pharmaceutical compositions. Preferably, the individual compounds will be administered simultaneously in a combined pharmaceutical composition. Appropriate doses of known therapeutic agents will be readily appreciated by those skilled in the art.

Accordingly, the pharmaceutical compositions of the present invention include those that also comprise at least one additional therapeutically active agent, in addition to the compound of Formulas I-III.

The invention further includes a compound of Formulas I-III in combination with one or more other drug(s).

Methods of Preparing the Compounds of Formulas (I-III)

Methods for preparing the compounds of this invention are illustrated in the following schemes and examples. Other synthetic protocols will be readily apparent to those skilled in the art in light of the present disclosure. The examples illustrate the preparation of the compounds of Formulas (I-III) and as such are not to be considered as limiting the invention set forth in the claims appended hereto. Unless otherwise indicated, all variables are as previously defined.

All the end products of the Formulas (I-III) were analyzed by NMR and/or LCMS. Intermediates were analyzed by NMR and/or TLC and/or LCMS. Most compounds were purified by reverse phase HPLC, MPLC on silica gel, recrystallization and/or swish (suspension in a solvent followed by filtration of the solid). The course of the reactions was followed by thin layer chromatography (TLC) and/or LCMS and/or NMR and reaction times are given for illustration only.

Abbreviations used herein are as follows: EtOAc: Ethyl acetate; PE: Petroleum ether; EA: Ethyl acetate; DCM: Dichloro methane; Dppf: 1,1'-Bis(diphenylphosphino) ferrocene; AcOH: Acetic acid; DMAC: N,N-Dimethylacetamide; $Pd(PPh_3)_4$: Tetrakis(Triphenylphosphine)Palladium (0); $Pd(dppf)Cl_2$: [1,1'-Bis(diphenylphosphino) ferrocene] dichloropalladium (II); $Ac_2O$: Acetic anhydride; LiHMDS: Lithium bis(trimethylsilyl)amide; $PhNTf_2$: N-Phenyl-bis(trifluoromethanesulfonimide); S-Phos: 2-Dicyclohexylphosphino-2',6'-dimethoxybiphenyl; X-Phos: 2-Dicyclohexylphosphino-2',4',6'-triisopropylbiphenyl; CPME: Cyclopentyl methyl ether; DMAP: 4-Dimethylaminopyridine; TEA: Triethylamine; THF: Tetrahydrofuran; PYAOP: (7-Azabenzotriazol-1-yloxy)tripyrrolidinophosphonium hexafluorophosphate.

Schemes

Scheme 1 illustrates a general method toward the preparation of compounds of formula I. Starting with the halogenation of compound A followed by N-acylation with either carboxylic acids or acid chlorides in the presence of base led to the formation of compound C. Subsequent Suzuki coupling followed by ester hydrolysis afforded the final compound. In certain cases, ester hydrolysis occurred under the Suzuki coupling condition and led to the formation of final product within one pot.

Scheme 2 illustrates a general method toward the preparation of compounds of formula II. Starting with the halogenation of compound A followed by N-acylation with either carboxylic acids or acid chlorides in the presence of base led to the formation of compound C. Ester hydrolysis led to compound D. Standard amide coupling furnished intermediate E. Subsequent Suzuki coupling followed by ester hydrolysis led to the formation of the final product II.

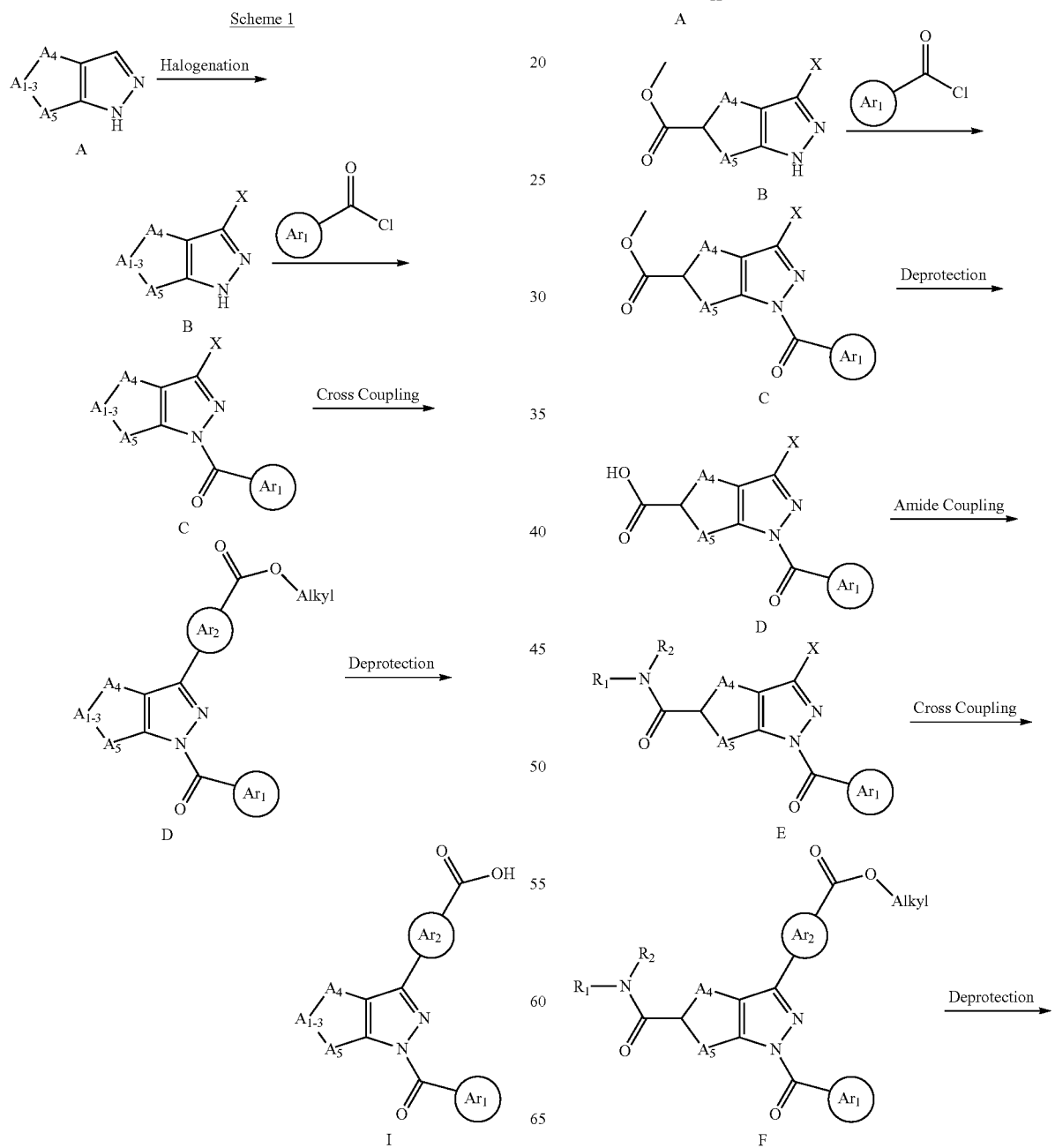

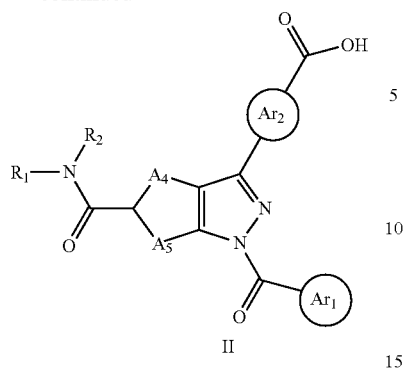

II

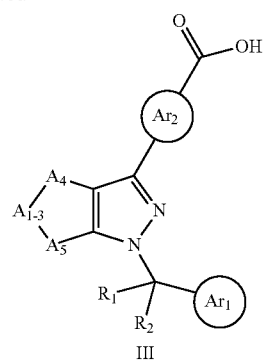

III

Scheme 3 illustrates a general method toward the preparation of compounds of formula III. After the halogenation of compound A, N-alkylation through benzyl halides or using standard Mitsunobu conditions with the respective benzyl alcohols yielded compound C. Subsequent Suzuki coupling followed by ester hydrolysis led to the formation of the final product III.

Scheme 4 illustrates a general method for the preparation of compounds of formula IV, which are not easily accessible by following the general methods described previously. Compound A is treated with base and coupled with the respective acid chloride followed by condensation with hydrazine to yield fused pyrazole intermediate B. N-acylation with either carboxylic acids or acid chlorides in the presence of base leads to the formation of compound C. Carbonylation under palladium conditions in the presence of alcohol yields ester D. Subsequent ester hydrolysis leads to the formation of the final product IV.

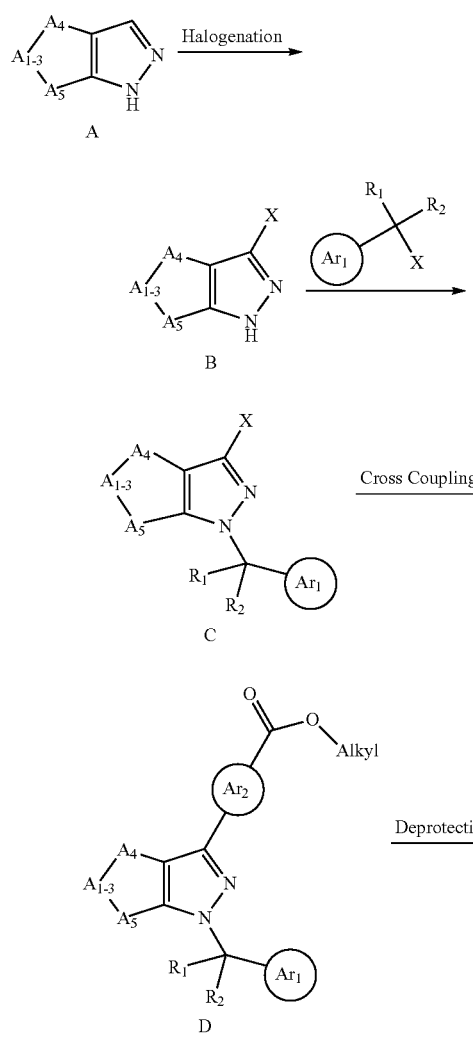

Scheme 3

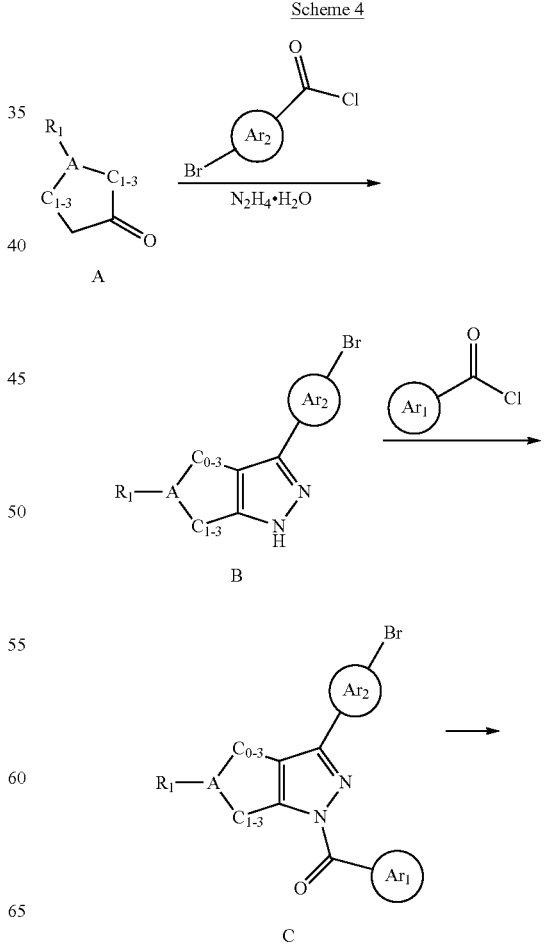

Scheme 4

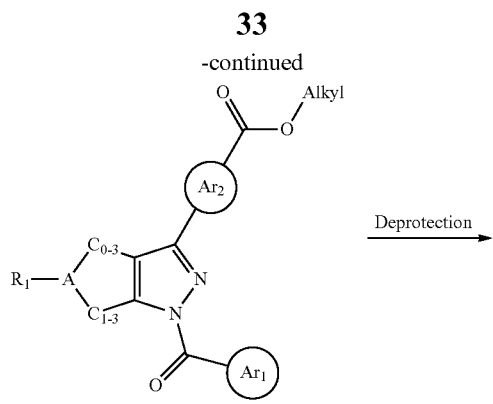

D

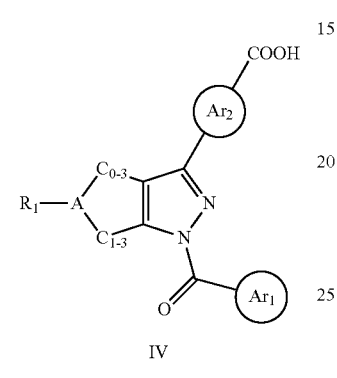

IV

Commercially Available/Previously Described Materials

The following table lists commercial sources, and previously disclosed synthetic routes for chemical materials employed in the synthesis of intermediates, and examples of the instant invention. The list is not intended to be exhaustive, exclusive, or limiting in any way.

| Structure | Source |
|---|---|
| 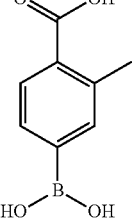 | Acros Organics |
| 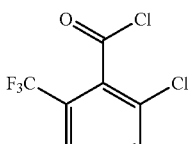 | Alfa Aesar |
| 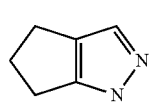 | Syntech Solutions |
| 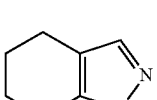 | Alfa Aesar |
| 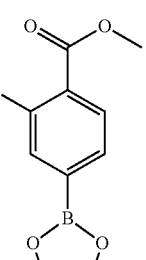 | Chembridge Corporation |
| 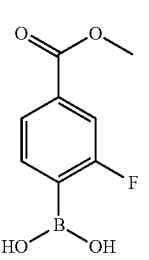 | Sigma-Aldrich |
| 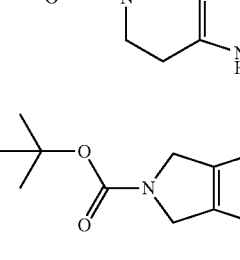 | WuXi App Tec Co. Ltd. |
| 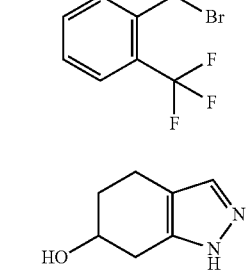 | Synthonix Corporation |
| 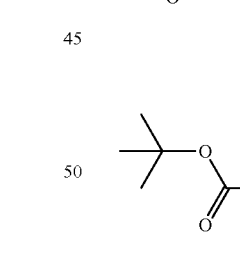 | Matrix Scientific |
| 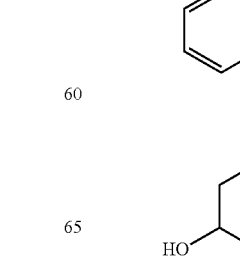 | Alfa Aesar |
| 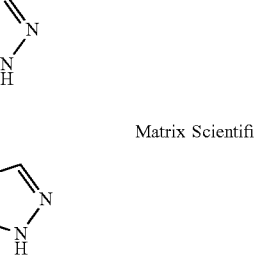 | Enamine |

-continued

| Structure | Source |
|---|---|
| (methyl 4,5,6,7-tetrahydro-1H-indazole-6-carboxylate) | Enamine |
| (tert-butyl 4,5,6,7-tetrahydro-pyrazolo[3,4-c]pyridine-6-carboxylate) | DL Chiral Chemicals |
| (6,7-dihydro-1H-indazol-4(5H)-one) | Chembridge Corporation |

INTERMEDIATES

Intermediate i-1a

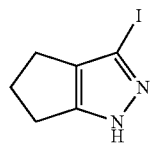

3-iodo-1,4,5,6-tetrahydrocyclopenta[c]pyrazole

A mixture of 1,4,5,6-tetrahydrocyclopenta[c]pyrazole (200 mg, 1.85 mmol) and NIS (416 mg, 1.85 mmol) in DMF (2.3 ml) was stirred at room temperature overnight. The reaction mixture was diluted with water and EtOAc. The organic layer was separated and washed twice with aqueous $NaHCO_3$ and once with brine. Aqueous layers were back extracted once with EtOAc, combined organic layers were dried with $Na_2SO_4$, filtered and the solvent was evaporated under reduced pressure. The residue was purified by silica gel chromatography for Intermediate i-1a which (EtOAc/Hexane 25-90%) to afford the title compound. LCMS (ESI) calc'd for $C_6H_7IN_2$ $[M+H]^+$: 235, found: 235.

The following examples shown in Table 1 were prepared following similar procedures described can be achieved by those of ordinary skill in the art of organic synthesis.

TABLE 1

| Intermediate | Structure | IUPAC Name | MS (M + 1) |
|---|---|---|---|
| i-1b | (3-iodo-4,5,6,7-tetrahydro-1H-indazole structure) | 3-iodo-4,5,6,7-tetrahydro-1H-indazole | 249 |
| i-1c | (tert-butyl 3-iodo-4,6-dihydropyrrolo[3,4-c]pyrazole-5(1H)-carboxylate structure) | tert-butyl 3-iodo-4,6-dihydropyrrolo[3,4-c]pyrazole-5(1H)-carboxylate | 336 |
| i-1d | (tert-butyl 3-iodo-6,7-dihydro-1H-pyrazolo[4,3-c]pyridine-5(4H)-carboxylate structure) | tert-butyl 3-iodo-6,7-dihydro-1H-pyrazolo[4,3-c]pyridine-5(4H)-carboxylate | 350 |
| i-1e | (3-iodo-4,5,6,7-tetrahydro-1H-indazol-6-ol structure) | 3-iodo-4,5,6,7-tetrahydro-1H-indazol-6-ol | 264 |

TABLE 1-continued

| Intermediate | Structure | IUPAC Name | MS (M + 1) |
|---|---|---|---|
| i-1f | 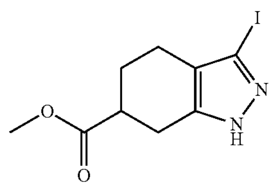 | methyl 3-iodo-4,5,6,7-tetrahydro-1H-indazole-6-carboxylate | 307 |
| i-1g | 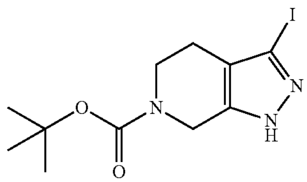 [SMILES: CC(C)(C)OC(=O)N1CCc2c(I)n[nH]c2C1] | tert-butyl 3-iodo-1,4,5,7-tetrahydro-6H-pyrazolo[3,4-c]pyridine-6-carboxylate | 350 |
| i-1h | 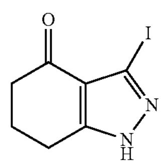 [SMILES: O=C1CCCc2[nH]nc(I)c21] | 3-iodo-6,7-dihydro-1H-indazol-4(5H)-one | 262 |
| i-1i | 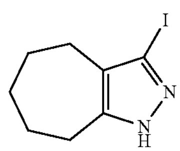 [SMILES: Ic1n[nH]c2c1CCCCC2] | 3-iodo-1,4,5,6,7,8-hexahydrocyclohepta[c]pyrazole | 263 |

Intermediate i-2a

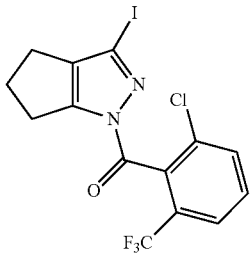 [SMILES: O=C(c1c(Cl)cccc1C(F)(F)F)n1nc(I)c2c1CCC2]

(2-chloro-6-(trifluoromethyl)phenyl)(3-iodo-5,6-dihydrocyclopenta[c]pyrazol-1(4H)-yl)methanone To a mixture of i-1a (90 mg, 0.39 mmol), DIPEA (134 µl, 0.77 mmol) and DMAP (71 mg, 0.58 mmol) in DMF (1.9 ml) was added 2-chloro-6-(trifluoromethyl)benzoyl chloride (140 mg, 0.58 mmol) drop wise and the reaction was allowed to stir at room temperature overnight. The reaction mixture was diluted with EtOAc. The organic layer was separated and washed twice with aqueous $NaHCO_3$ and once with brine. The combined organic layers were dried with $Na_2SO_4$, filtered and the solvent was evaporated under reduced pressure. The residue was purified by silica gel chromatography (EtOAc/Hexane 0-65%) to afford the title compound. LCMS (ESI) calc'd for $C_{14}H_9ClF_3IN_2O$ $[M+H]^+$: 440, found: 440.

The following examples shown in Table 2 were prepared following similar procedures described for Intermediate i-2a which can be achieved by those of ordinary skill in the art of organic synthesis.

TABLE 2

| Intermediate | Structure | IUPAC Name | MS (M + 1) |
|---|---|---|---|
| i-2b | 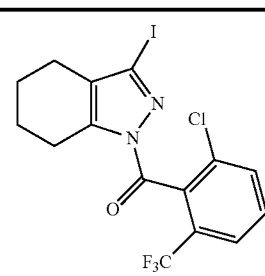 | (2-chloro-6-(trifluoromethyl)phenyl)(3-iodo-4,5,6,7-tetrahydro-1H-indazol-1-yl)methanone | 454 |

TABLE 2-continued

| Intermediate | Structure | IUPAC Name | MS (M + 1) |
|---|---|---|---|
| i-2c | 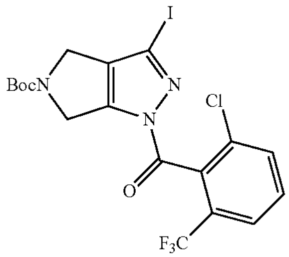 [SMILES: CC(C)(C)OC(=O)N1Cc2c(I)nn(C(=O)c3c(Cl)cccc3C(F)(F)F)c2C1] | tert-butyl 1-(2-chloro-6-(trifluoromethyl)benzoyl)-3-iodo-4,6-dihydropyrrolo[3,4-c]pyrazole-5(1H)-carboxylate | 541 |
| i-2d | 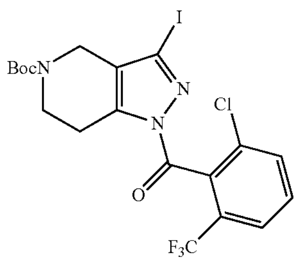 [SMILES: CC(C)(C)OC(=O)N1CCc2c(c(I)nn2C(=O)c2c(Cl)cccc2C(F)(F)F)C1] | tert-butyl 1-(2-chloro-6-(trifluoromethyl)benzoyl)-3-iodo-6,7-dihydro-1H-pyrazolo[4,3-c]pyridine-5(4H)-carboxylate | 556 |
| i-2e | 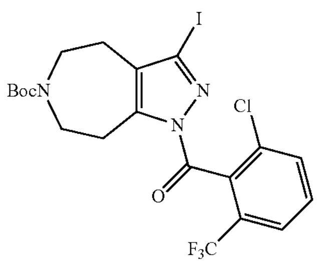 [SMILES: CC(C)(C)OC(=O)N1CCc2c(I)nn(C(=O)c3c(Cl)cccc3C(F)(F)F)c2CC1] | tert-butyl 1-(2-chloro-6-(trifluoromethyl)benzoyl)-3-iodo-4,5,7,8-tetrahydropyrazolo[3,4-d]azepine-6(1H)-carboxylate | 570 |

Intermediate i-3

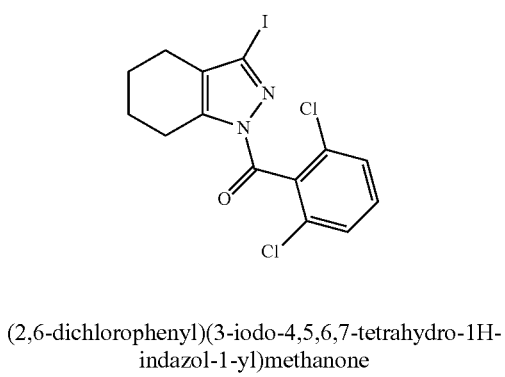

(2,6-dichlorophenyl)(3-iodo-4,5,6,7-tetrahydro-1H-indazol-1-yl)methanone

To a mixture of i-1b (200 mg, 0.8 mmol), TEA (1124 μl, 8.0 mmol), and DMAP (98 mg, 0.8 mmol) in DMF (2.6 ml) was added 2,6-dichlorobenzoyl chloride (253 mg, 1.2 mmol) drop wise. The reaction was allowed to stir overnight at room temperature. The mixture was diluted with EtOAc. The organic layer was separated and washed twice with aqueous $NaHCO_3$ and once with brine. The combined organic layers were dried with $Na_2SO_4$, filtered and the solvent was evaporated under reduced pressure. The residue was purified by silica gel chromatography (EtOAc/Hexane 5-75%) to afford the title compound. LCMS (ESI) calc'd for $C_{14}H_{11}Cl_2IN_2O$ [M+H]$^+$: 420, found: 420.

Intermediate i-4

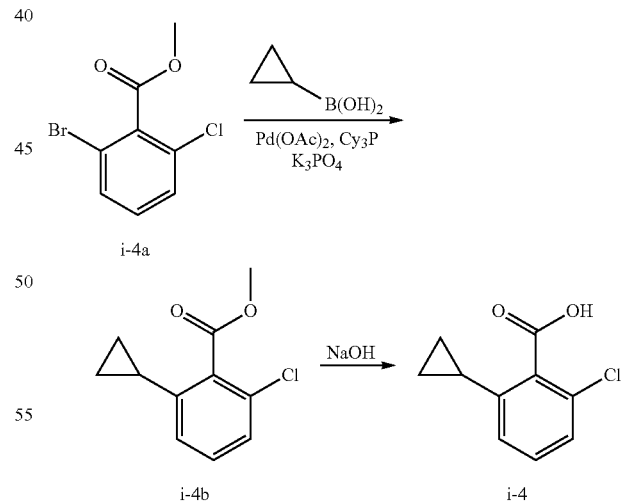

2-chloro-6-cyclopropylbenzoic acid

Step 1. Preparation of methyl 2-chloro-6-cyclopropylbenzoate (i-4b)

Methyl 2-bromo-6-chlorobenzoate (1.0 g, 4.0 mmol), cyclopropylboronic acid (516 mg, 6.0 mmol), Pd(OAc)$_2$ (90 mg, 0.4 mmol), Cy$_3$P (224 mg, 0.8 mmol) and K$_3$PO$_4$ (2.5 g, 12.0 mmol) were mixed in toluene (20 ml) and H$_2$O (2.5 ml). The mixture was stirred at 100° C. for 14 h under N$_2$ atmosphere. The mixture was cooled down and poured into water. The mixture was extracted with EtOAc and the organic layer was dried over Na$_2$SO$_4$ and concentrated. The residue was purified by flash chromatography (Petroleum/EtOAc 15/1) to give title compound. LCMS (ESI) calc'd for C$_H$H$_H$ClO$_2$ [M+H]$^+$: 211, found: 211.

Step 2. Preparation of
2-chloro-6-cyclopropylbenzoic acid (i-4)

NaOH (380 mg, 9.5 mmol) was added to a solution of methyl 2-chloro-6-cyclopropylbenzoate (i-4b) (200 mg, 0.95 mmol) in EtOH (15 ml) and H$_2$O (6 ml). The resulted solution was stirred at 80° C. overnight. The mixture was cooled down and acidified with 2N HCl to pH=2~3. Then the mixture was extracted with EtOAc. The organic layer was dried over Na$_2$SO$_4$ and concentrated to afford the title compound. LCMS (ESI) calc'd for C$_{10}$H$_9$ClO$_2$ [M+H]$^+$: 197, found: 197.

Intermediate i-5a

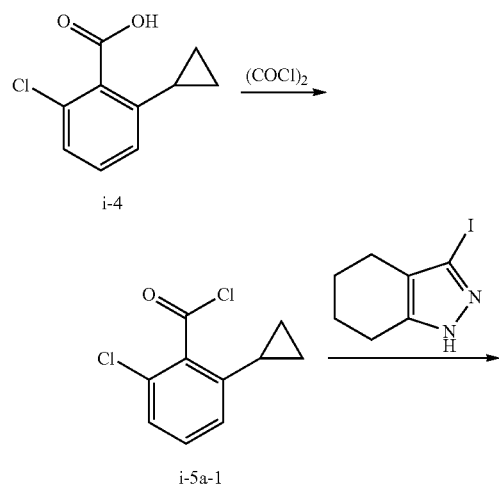

(2-chloro-6-cyclopropylphenyl)(3-iodo-4,5,6,7-tetrahydro-1H-indazol-1-yl)methanone Step 1: 2-chloro-6-cyclopropylbenzoyl chloride
(i-5a-1)

A mixture of i-4 (1.0 g 5.1 mmol), oxalyl chloride (1.1 mL, 12.7 mmol) and DMF (0.039 mL, 0.51 mmol) in DCM (10.2 mL) was allowed to stir at room temperature for 30 minutes. The mixture was concentrated in vacuum to give the crude title compound, which was directly used to next step without further purification.

Step 2: (2-chloro-6-cyclopropylphenyl)(3-iodo-4,5, 6,7-tetrahydro-1H-indazol-1-yl)methanone (i-5a)

To a stirred solution of i-1b (950 mg, 3.83 mmol), DMAP (468 mg, 3.83 mmol) and TEA (5.3 ml, 38.3 mmol) in DMF (5 ml) was added i-5a-1 (1318 mg, 6.13 mmol) drop wise. The solution was allowed to stir at room temperature overnight. The reaction mixture was diluted with ethyl acetate. The organic layer was separated and washed twice with aqueous sodium hydrogen carbonate and once with brine. The combined organic layers were dried with Na$_2$SO$_4$, filtered and the solvent was evaporated under reduced pressure. The residue was purified by silica gel chromatography (EtOAc/Hexane 5-50%) to afford the title compound. LCMS (ESI) calc'd for C$_{17}$H$_{16}$ClIN$_2$O [M+H]$^+$: 427 found: 427.

The following examples shown in Table 3 were prepared following similar procedures described for Intermediate i-5a which can be achieved by those of ordinary skill in the art of organic synthesis.

TABLE 3

| Intermediate | Structure | IUPAC Name | MS (M + 1) |
|---|---|---|---|
| i-5b | ![structure] | (2-chloro-6-cyclopropylphenyl)(6-hydroxy-3-iodo-4,5,6,7-tetrahydro-1H-indazol-1-yl)methanone | 443 |

TABLE 3-continued

| Intermediate | Structure | IUPAC Name | MS (M + 1) |
|---|---|---|---|
| i-5c | 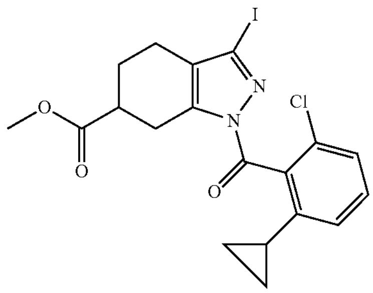 [SMILES: COC(=O)C1CCc2c(I)nn(C(=O)c3c(Cl)cccc3C3CC3)c2C1] | methyl 1-(2-chloro-6-cyclopropylbenzoyl)-3-iodo-4,5,6,7-tetrahydro-1H-indazole-6-carboxylate | 485 |
| i-5d | 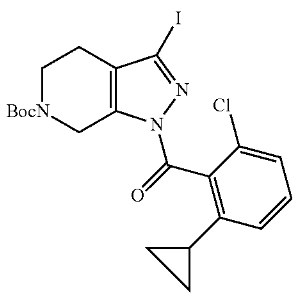 [SMILES: CC(C)(C)OC(=O)N1CCc2c(I)nn(C(=O)c3c(Cl)cccc3C3CC3)c2C1] | tert-butyl 1-(2-chloro-6-cyclopropylbenzoyl)-3-iodo-4,5-dihydro-1H-pyrazolo[3,4-c]pyridine-6(7H)-carboxylate | 528 |
| i-5e | 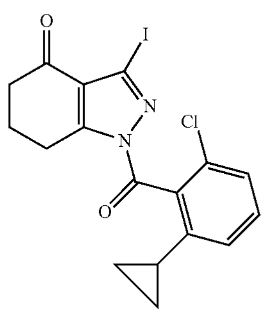 [SMILES: O=C1CCCc2c1c(I)nn2C(=O)c1c(Cl)cccc1C1CC1] | 1-(2-chloro-6-cyclopropylbenzoyl)-3-iodo-6,7-dihydro-1H-indazol-4(5H)-on | 440 |
| i-5f | 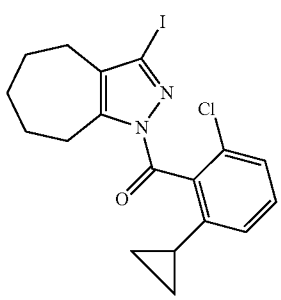 [SMILES: O=C(c1c(Cl)cccc1C1CC1)n1nc(I)c2c1CCCCC2] | (2-chloro-6-cyclopropylphenyl)(3-iodo-5,6,7,8-tetrahydrocyclohepta[c]pyrazol-1(4H)-yl)methanone | 441 |
| i-5g | 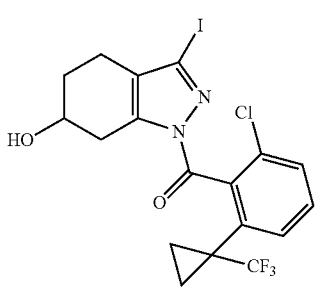 [SMILES: O=C(c1c(Cl)cccc1C1(C(F)(F)F)CC1)n1nc(I)c2c1CC(O)CC2] | (2-chloro-6-(1-(trifluoromethyl)cyclopropyl)phenyl)(6-hydroxy-3-iodo-4,5,6,7-tetrahydro-1H-indazol-1-yl)methanone | 511 |

Intermediate i-6

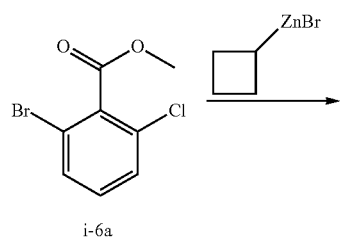

i-6a

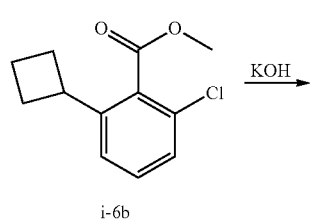

i-6b

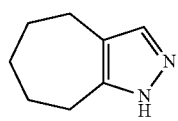

i-6

Step 1. Preparation of methyl 2-chloro-6-cyclobutylbenzoate (i-6b)

A mixture of methyl 2-bromo-6-chlorobenzoate (i-6a) (750 mg, 3 mmol), $(PPh_3)_4Pd$ (345 mg, 0.3 mmol) and cyclobutylzinc bromide (0.5M in THF, 12 ml) were mixed under $N_2$ protection. The mixture was stirred at 70° C. for 12 h under $N_2$. The mixture was extracted with EtOAc and water. The organic phase was washed with brine, dried over $Na_2SO_4$, filtered, and concentrated. The residue was purified with flash chromatography (PE:EtOAc=50:1) to give the title compound. LCMS (ESI) calc'd for $C_{12}H_{13}ClO_2$ $[M+H]^+$: 225, found: 225.

Step 2. Preparation of 2-chloro-6-cyclobutylbenzoic acid (i-6)

To a solution of methyl 2-chloro-6-cyclobutylbenzoate (i-6b) (350 mg, 1 mmol) in EtOH (2 ml), was added 0.2M KOH (1.5 ml, 3 mmol). The mixture was stirred at 100° C. for 12 h, acidified with 3N HCl and extracted with EtOAc. The organic phase was washed with brine, dried over $Na_2SO_4$, filtered and concentrated. The residue was purified with prep-HPLC (ACN: $H_2O$) to give the title compound. LCMS (ESI) calc'd for $C_{11}H_{11}ClO_2$ $[M+H]^+$: 211, found: 211.

Intermediate i-7

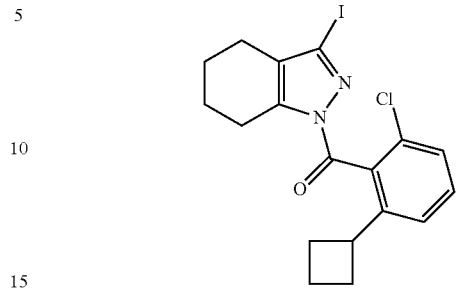

(2-chloro-6-cyclobutylphenyl)(3-iodo-4,5,6,7-tetrahydro-1H-indazol-1-yl)methanone To a mixture of i-6 (208 mg, 0.99 mmol), and DMF (7.7 µl, 0.1 mmol) in DCM (3.2 ml) was added oxalyl chloride (216 µl, 2.47 mmol) dropwise and the resulting solution was stirred at room temperature for 30 minutes. The reaction was concentrated, brought up in DCM (2.5 ml). The resulting solution was added to a mixture of i-1b (125 mg, 0.5 mmol), DMAP (61.6 mg, 0.5 mmol) and TEA (702 µl, 5.0 mmol) in DMF (2.5 ml). The solution was allowed to stir at room temperature overnight. The mixture was diluted with EtOAc, washed twice with $NaHCO_3$ and once with brine. The combined organic layers were dried with $Na_2SO_4$, filtered and the solvent was evaporated under reduced pressure. The residue was purified by silica gel chromatography (EtOAc/Hexane 5-60%) to afford the title compound. LCMS (ESI) calc'd for $C_{18}H_{18}ClIN_2O$ $[M+H]^+$: 441 found: 441.

Intermediate i-8

1,4,5,6,7,8-hexahydrocyclohepta[c]pyrazole

Step 1: (Z)-2-(hydroxymethylene)cycloheptanone (i-8a)

To a mixture of sodium hydride (60% in mineral oil, 178 mg, 4.46 mmol) in diethyl ether (14.9 mL) at 0° C. was added ethanol (0.02 mL, 0.36 mmol) drop wise and the resulting mixture was allowed to stir at 0° C. for 30 minutes. A solution of cycloheptanone (500 mg, 4.46 mmol) and ethyl formate (0.58 mL, 7.13 mmol) in diethyl ether (3 mL) was then added drop wise to the cooled solution over 10 mins. The resulting mixture was allowed to stir at 0° C. for an hour and then warmed to room temperature and allowed to stir for additional 4 h. The reaction was quenched with 1 mL of ethanol and then 10 mL of water. The layers were separated and the aqueous layer was washed twice with diethyl ether. The combined aqueous layer were acidified with 2N HCl to a pH of ~2. The aqueous layer was then washed twice with diethyl ether. The resulting organic layers

Step 2: 1,4,5,6,7,8-hexahydrocyclohepta[c]pyrazole (i-8)

To a mixture of i-8a (490 mg, 3.50 mmol) in MeOH (3.5 ml) at 0° C. was added hydrazine (313 µl, 3.50 mmol) drop wise and the then the solution was allowed to stir at room temperature for 30 min. The reaction was concentrated and the residue was brought up in DCM and washed with water and brine. The organic layer was dried over $Na_2SO_4$, filtered, and concentrated to afford the title compound. LCMS (ESI) calc'd for $C_8H_{12}N_2$ [M+H]$^+$: 137 found: 137.

Intermediate i-9

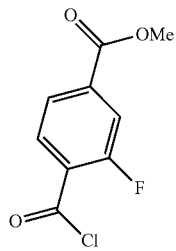 [SMILES: COC(=O)c1ccc(C(=O)Cl)c(F)c1]

methyl 4-(chlorocarbonyl)-3-fluorobenzoate

A mixture of 2-fluoro-4-(methoxycarbonyl)benzoic acid (400 mg, 2.02 mmol) in thionyl chloride (7 mL) was stirred at 80° C. for 2 hours. After the reaction was completed, the mixture was concentrated in vacuum to give the crude title compound, which was directly used to next step without further purification.

Intermediate i-10

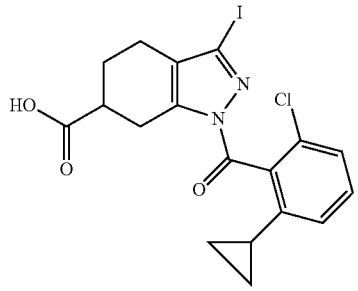 [SMILES: O=C(O)C1CCc2c(I)nn(C(=O)c3c(Cl)cccc3C3CC3)c2C1]

1-(2-chloro-6-cyclopropylbenzoyl)-3-iodo-4,5,6,7-tetrahydro-1H-indazole-6-carboxylic acid A mixture of i-5c (577 mg, 1.19 mmol) and LiOH (285 mg, 11.9 mmol) in THF (2.9 ml), and water (2.9 ml) was allowed to stir at room temperature overnight. The reaction was acidified with 2N HCl and the resulting solution was extracted twice with ethyl acetate. The combined organic layers were dried with $Na_2SO_4$, filtered and the solvent was evaporated under reduced pressure to afford title compound. LCMS (ESI) calc'd for $C_{18}H_{16}ClIN_2O_3$ [M+H]$^+$: 471 found: 471.

Intermediate i-11

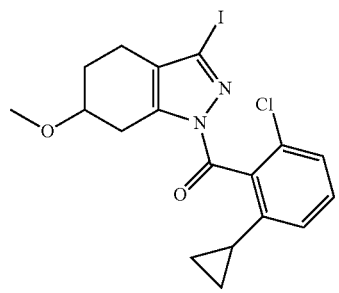 [SMILES: COC1CCc2c(I)nn(C(=O)c3c(Cl)cccc3C3CC3)c2C1]

(2-chloro-6-cyclopropylphenyl)(3-iodo-6-methoxy-4,5,6,7-tetrahydro-1H-indazol-1-yl)methanone To a mixture of i-5b (50 mg, 0.11 mmol) in THF (1.1 ml) was added sodium hydride (9.04 mg, 0.23 mmol) and the solution was allowed to stir at room temperature for 30 minutes. Methyl iodide (7.77 µl, 0.12 mmol) was then added drop wise and the resulting solution was allowed to stir overnight at room temperature. The reaction was quenched with water and then diluted with ethyl acetate. The organic layer was separated and washed twice with aqueous $NaHCO_3$ and once with brine. The combined organic layers were dried with $Na_2SO_4$, filtered and the solvent was evaporated under reduced pressure. The residue was purified by silica gel chromatography (EtOAc/Hexane 5-75%) to afford the title compound. LCMS (ESI) calc'd for $C_{18}H_{18}ClIN_2O_2$ [M+H]$^+$: 457 found: 457.

Intermediate i-12

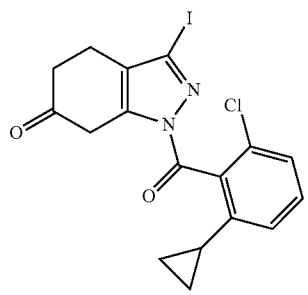 [SMILES: O=C1CCc2c(I)nn(C(=O)c3c(Cl)cccc3C3CC3)c2C1]

1-(2-chloro-6-cyclopropylbenzoyl)-3-iodo-1,4,5,7-tetrahydro-6H-indazol-6-one

To a mixture of i-5b (126 mg, 0.29 mmol) in DCM (2.8 ml) was added Dess-Martin Periodinane (181 mg, 0.43 mmol) and the resulting solution was allowed to stir at room temperature overnight. The mixture was diluted with ethyl acetate, washed twice with aqueous $NaHCO_3$ and once with brine. The combined organic layers were dried with $Na_2SO_4$, filtered and the solvent was evaporated under reduced pressure. The residue was purified by silica gel chromatography (EtOAc/Hexane 10-75%) to afford the title compound. LCMS (ESI) calc'd for $C_{17}H_{14}ClIN_2O_2$ [M+H]$^+$: 440 found: 440.

Intermediate i-13

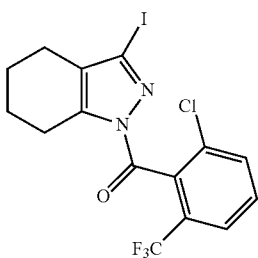 [SMILES: O=C(c1c(Cl)cccc1C(F)(F)F)n1nc(I)c2c1CCCC2]

1-(2-chloro-6-(trifluoromethyl)benzyl)-3-iodo-4,5,6,7-tetrahydro-1H-indazole

A mixture of i-1b (260 mg, 1.05 mmol), 2-chloro-6-(trifluoromethyl)benzyl bromide (344 mg, 1.26 mmol) and $Cs_2CO_3$ (683 mg, 2.1 mmol) in DMF (5.2 ml) was stirred at room temperature overnight. The mixture was diluted with ethyl acetate, washed twice with aqueous $NaHCO_3$ and once with brine. The combined organic layers were dried with $Na_2SO_4$, filtered and the solvent was evaporated under reduced pressure. The residue was purified by silica gel chromatography (EtOAc/Hexane 10-100%) to afford the title compound. LCMS (ESI) calc'd for $C_{15}H_{13}ClF_3IN_2$ $[M+H]^+$: 440 found: 440.

Intermediate i-14

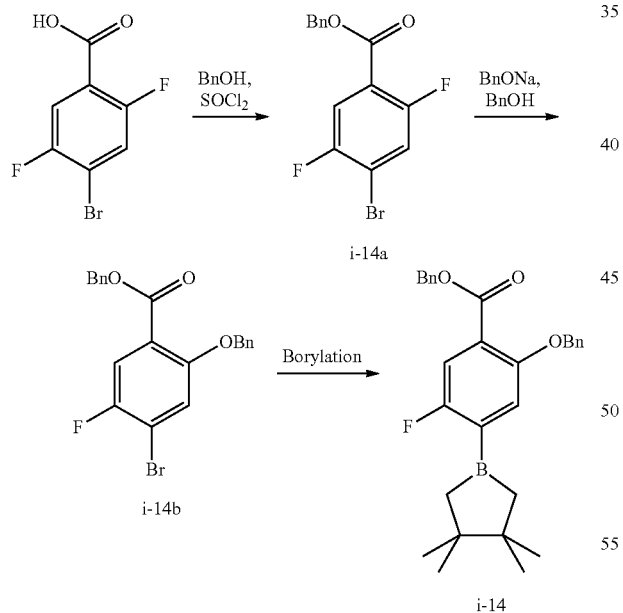

benzyl 2-(benzyloxy)-5-fluoro-4-(4,4,5,5-tetramethyl-1,3,2-dioxaborolan-2-yl)benzoate Step 1: benzyl 4-bromo-2,5-difluorobenzoate (i-14a)

To a mixture of 4-bromo-2,5-difluorobenzoic acid (1 g, 4.2 mmol) in benzyl alcohol (3 mL) was added an excess amount of thionyl chloride. The reaction mixture was stirred at room temperature overnight. LCMS indicated partial conversion, an additional aliquot of thionyl chloride was added and the mixture was heated to 70° C. overnight. The reaction mixture was cooled and concentrated. The residue was purified by silica gel chromatography (5% EtOAc in Hexane) to afford the title compound.

Step 2: benzyl 2-(benzyloxy)-4-bromo-5-fluorobenzoate (i-14b)

To a solution of i-14a (560 mg, 1.71 mmol) in DMF (0.5 ml) at 0° C. was added drop wise a solution of 1M sodium phenylmethanolate in benzyl alcohol (1.71 ml, 1.71 mmol). The resulting reaction mixture was stirred at 0° C. and allowed to warm to room temperature overnight. The reaction was quenched with water and EtOAc. The organic layer was separated, dried over $Na_2SO_4$, filtered and the solvent was evaporated under reduced pressure. The residue was purified by silica gel chromatography (15% EtOAc in Hexane) to afford the title compound.

Step 3: benzyl 2-(benzyloxy)-5-fluoro-4-(4,4,5,5-tetramethyl-1,3,2-dioxaborolan-2-yl)benzoate (i-14)

To a reaction vessel was added a mixture of i-14b (170 mg, 0.41 mmol), Xphos G2 biphenyl precatalyst (32.2 mg, 0.04 mmol), potassium acetate (80 mg, 0.82 mmol) and bispinacolatodiboron (208 mg, 0.82 mmol). The flask was evacuated and backfilled with nitrogen three times. Dry cyclopentylmethyl ether (2.0 ml) was then introduced to the reaction flask and the mixture was heated at 80° C. overnight. The mixture was cooled, diluted with ethyl acetate, filtered through celite and concentrated. The residue was purified by silica gel chromatography (30% EtOAc in Hexane) to afford the title compound. LCMS (ESI) calc'd for $C_{27}H_{28}BFO_5$ $[M+H]^+$: 463, found: 463.

Intermediate i-15

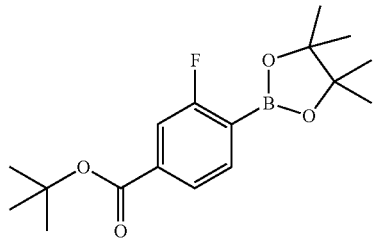 [SMILES: CC(C)(C)OC(=O)c1ccc(B2OC(C)(C)C(C)(C)O2)c(F)c1]

tert-butyl 3-fluoro-4-(4,4,5,5-tetramethyl-1,3,2-dioxaborolan-2-yl)benzoate

Step 1: Preparation of tert-butyl 3-fluoro-4-(4,4,5,5-tetramethyl-1,3,2-dioxaborolan-2-yl)benzoate To a flask was added tert-butyl 4-bromo-3-fluorobenzoate (6.1 g, 22.17 mmol), bis(pinacolato)diboron (6.19 g, 24.39 mmol), potassium acetate (6.53 g, 66.5 mmol) and dichloro [1,1'-bis (diphenylphosphino) ferrocene] palladium II dichloromethane adduct (0.543 g, 0.665 mmol) and the reaction was thoroughly degassed with argon for 5 minutes. DMSO (44.3 ml) was then added and the solution was further degassed with Argon. Reaction was then heated to 80° C. overnight. The reaction was cooled poured into Water (100 mL) and extracted with diethyl ether (3×50 mL). The combined organic layers were washed with brine, dried with $Na_2SO_4$, filtered, and concentrated in vacuo. The residue was purified by silica gel chromatography (0-100% EtOAc/Hexane) to afford the title compound. MS: 267 (M-56). $^1$H NMR (600 MHz, $CDCl_3$) δ 7.76-7.73 (m, 1H), 7.72-7.69 (m, 1H), 7.57 (d, J=9.8 Hz, 1H), 1.57 (s, 9H), 1.35 (s, 12H).

Intermediate i-16

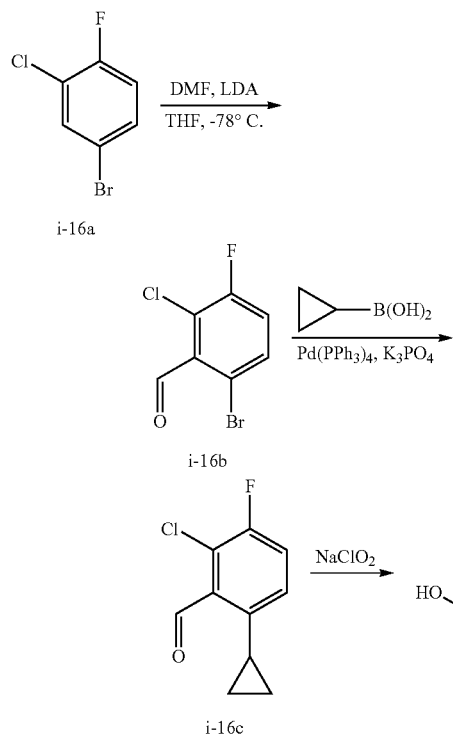

2-chloro-6-cyclopropyl-3-fluorobenzoic acid

Step 1. Preparation of 6-bromo-2-chloro-3-fluorobenzaldehyde (i-16b)

To a solution of 4-bromo-2-chloro-1-fluorobenzene (5.00 g, 23.9 mmol) in THF (40 mL) was added lithium diisopropylamide (14.3 mL, 28.6 mmol) dropwise at −78° C. The resultant mixture was stirred at −78° C. for 2 h and then DMF (2.70 mL, 35.8 mmol) was added. The reaction mixture was warmed to room temperature, quenched with aq. $NH_4Cl$, and extracted with EtOAc (3×100 mL). The combined organic layers were concentrated and purified by chromatography (0-10% EtOAc in petroleum ether) to give the title compound. $^1$H NMR (400 MHz, $CDCl_3$) δ 10.27-10.33 (m, 1H), 7.56 (dd, J=8.6 Hz, 4.3 Hz, 1H), 7.18-7.26 (m, 1H).

Step 2. Preparation of 2-chloro-6-cyclopropyl-3-fluorobenzaldehyde (i-16c)

To a mixture of 6-bromo-2-chloro-3-fluorobenzaldehyde (2.00 g, 8.42 mmol) and cyclopropylboronic acid (1.09 g, 12.7 mmol) in toluene (20 mL) and water (2 mL) was added $K_3PO_4$ (3.58 g, 16.8 mmol) and tetrakis(triphenylphosphine)palladium (0.97 g, 0.84 mmol). The resultant mixture was stirred at 100° C. for 3 h under $N_2$. The reaction mixture was cooled to room temperature and concentrated in vacuo. The residue was purified by chromatography (0-10% EtOAc in petroleum ether) to give the title compound. $^1$H NMR (400 MHz, $CDCl_3$) δ 10.63-10.74 (m, 1H), 7.23 (t, J=8.4 Hz, 1H), 7.00 (dd, J=8.6 Hz, 4.7 Hz, 1H), 2.53-2.65 (m, 1H), 1.02-1.09 (m, 3H), 0.66 (q, J=5.5 Hz, 3H).

Step 3. Preparation of 2-chloro-6-cyclopropyl-3-fluorobenzoic acid (i-16)

2-Methylbut-2-ene (2.54 g, 36.2 mmol) was added to the solution of 2-chloro-6-cyclopropyl-3-fluorobenzaldehyde (800 mg, 4.03 mmol) in t-BuOH (3 mL). Then an aqueous solution of sodium chlorite (474 mg, 5.24 mmol) and sodium dihydrogen phosphate (628 mg, 5.24 mmol) was added slowly to the reaction mixture. The resultant mixture was stirred at room temperature for 16 h. The solution was concentrated in vacuo and acidified to pH 2 with 1 M HCl aq., and extracted with EtOAc (3×20 mL). The combined organic layers were concentrated to give the title compound. $^1$H NMR (400 MHz, MeOD) δ 7.16 (t, J=8.8 Hz, 1H), 6.98 (dd, J=8.6 Hz, 4.7 Hz, 1H), 1.89-1.96 (m, 1H), 0.91-0.97 (m, 2H), 0.68 (q, J=5.2 Hz, 2H).

Intermediate i-17

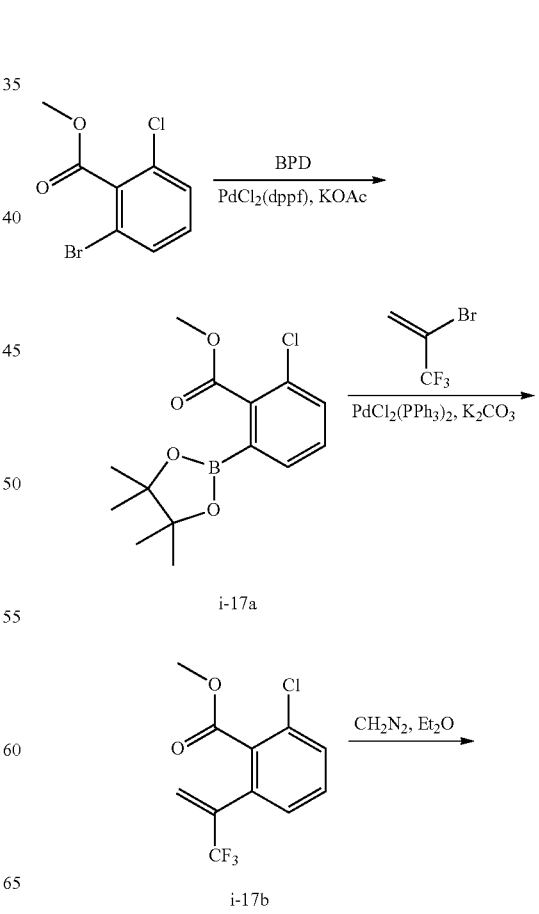

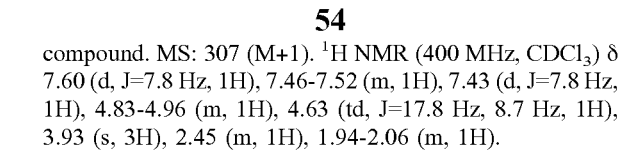

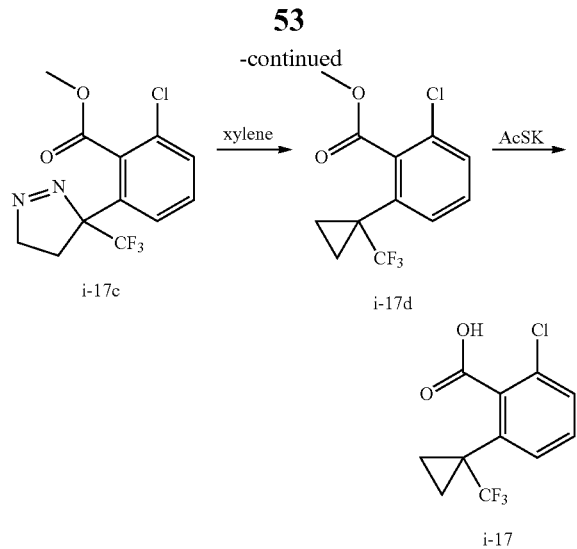

2-chloro-6-(1-(trifluoromethyl)cyclopropyl)benzoic acid

Step 1. Preparation of methyl 2-chloro-6-(4,4,5,5-tetramethyl-1,3,2-dioxaborolan-2-yl)benzoate (i-17a)

To a solution of methyl 2-bromo-6-chlorobenzoate (7.50 g, 30.1 mmol) in dioxane (65 mL) was added Bis(pinacolato)diboron (15.3 g, 60.3 mmol), AcOK (3.54 g, 36.1 mmol) and PdCl$_2$(dppf) (0.66 g, 0.90 mmol) under N$_2$ atmosphere, then the resulting mixture was stirred at 100° C. for 18 h, cooled to room temperature, filtered and concentrated, the residue was purified by chromatography (0-3% EtOAc in petroleum ether) to give the title compound. MS: 297 (M+1). $^1$H NMR (400 MHz, CDCl$_3$) δ 7.67 (d, J=7.4 Hz, 1H), 7.46 (d, J=7.8 Hz, 1H), 7.29-7.39 (m, 1H), 3.92 (s, 3H), 1.32 (s, 12H).

Step 2. Preparation of methyl 2-chloro-6-(3,3,3-trifluoroprop-1-en-2-yl)benzoate (i-17b)

Bis(triphenylphosphine)palladium(ii) dichloride (120 mg, 0.171 mmol) was added to a solution of methyl 2-chloro-6-(4,4,5,5-tetramethyl-1,3,2-dioxaborolan-2-yl)benzoate (2.00 g, 6.74 mmol), 2-bromo-3,3,3-trifluoroprop-1-ene (3.54 g, 20.23 mmol) and K$_2$CO$_3$ (1.86 g, 13.49 mmol) in THF (25 mL) and water (2 mL). The resultant mixture was stirred at 70° C. for 5 h. The mixture was concentrated in vacuo and purified by chromatography (0-5% EtOAc in petroleum ether) to give the title compound. $^1$H NMR (400 MHz, CDCl$_3$) δ 7.43-7.49 (m, 1H), 7.37 (t, J=7.8 Hz, 1H), 7.27-7.32 (m, 1H), 6.08 (s, 1H), 5.66 (s, 1H), 3.86 (s, 3H).

Step 3. Preparation of methyl 2-chloro-6-(3-(trifluoromethyl)-4,5-dihydro-3H-pyrazol-3-yl)benzoate (i-17c)

Diazomethane (300 mL, 75.0 mmol in Et$_2$O) was added to a solution of methyl 2-chloro-6-(3,3,3-trifluoroprop-1-en-2-yl)benzoate (1.03 g, 3.89 mmol) in DCM (10 mL). The resultant mixture was stirred at 0° C. for 24 h, and quenched with AcOH (1 mL). Then the reaction mixture was concentrated in vacuo and purified by column chromatography on silica gel (0-10% EtOAc in petroleum ether) to give the title compound. MS: 307 (M+1). $^1$H NMR (400 MHz, CDCl$_3$) δ 7.60 (d, J=7.8 Hz, 1H), 7.46-7.52 (m, 1H), 7.43 (d, J=7.8 Hz, 1H), 4.83-4.96 (m, 1H), 4.63 (td, J=17.8 Hz, 8.7 Hz, 1H), 3.93 (s, 3H), 2.45 (m, 1H), 1.94-2.06 (m, 1H).

Step 4. Preparation of methyl 2-chloro-6-(1-(trifluoromethyl)cyclopropyl)benzoate (i-17d)

A solution of methyl 2-chloro-6-(3-(trifluoromethyl)-4,5-dihydro-3H-pyrazol-3-yl)benzoate (900 mg, 2.93 mmol) in xylene (5.0 mL) was heated at 130° C. for 6 h, then cooled to room temperature, purified by chromatography on silica gel (petroleum ether:EtOAc=10:1) to give the title compound. $^1$H NMR (400 MHz, CDCl$_3$) δ 7.45 (d, J=7.8 Hz, 1H), 7.38-7.43 (m, 1H), 7.35 (d, J=7.8 Hz, 1H), 3.95 (s, 3H), 1.33-1.40 (m, 2H), 1.11-1.19 (m, 2H).

Step 5. Preparation of 2-chloro-6-(1-(trifluoromethyl)cyclopropyl)benzoic acid (i-17)

To a solution of methyl 2-chloro-6-(1-(trifluoromethyl)cyclopropyl)benzoate (600 mg, 2.15 mmol) in DMF (1 mL) was added potassium thioacetate (984 mg, 8.61 mmol), followed by Polyethylene glycol-tert-octylphenyl ether (111 mg, 0.22 mmol). The resulting mixture was heated at 130° C. for 2 h, and then cooled to room temperature. The mixture was purified by Prep-HPLC to give the title compound. $^1$H NMR (400 MHz, CDCl$_3$) δ 7.36-7.48 (m, 2H), 7.28-7.36 (m, 1H), 1.32-1.41 (m, 2H), 1.15-1.19 (m, 2H).

Intermediate i-18

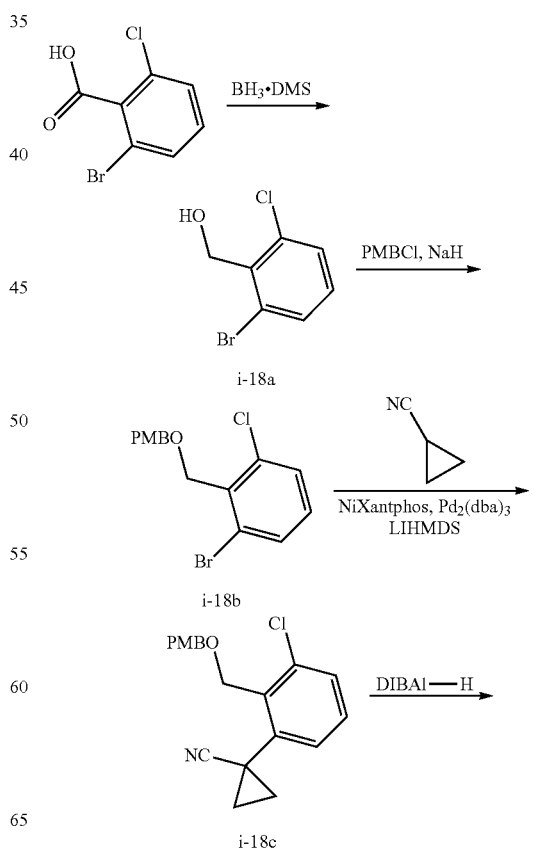

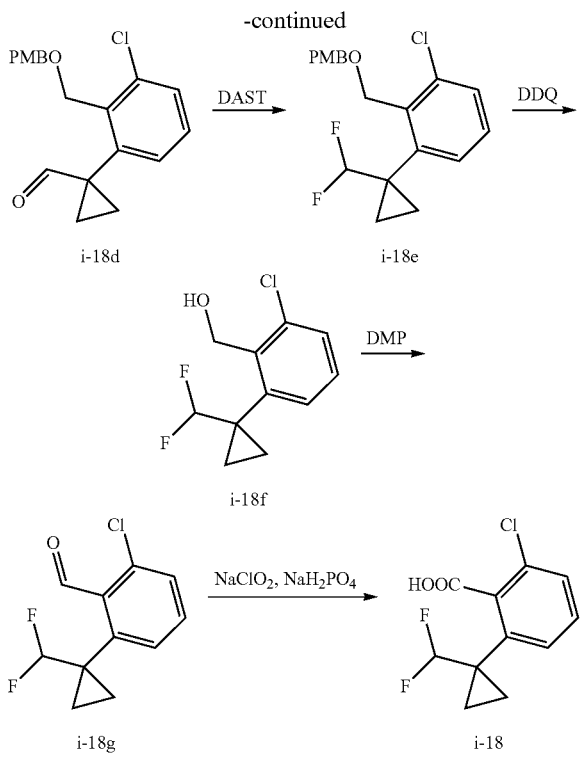

2-chloro-6-(1-(difluoromethyl)cyclopropyl)benzoic acid

Step 1. Preparation of (2-bromo-6-chlorophenyl)methanol (i-18a)

To a solution of 2-bromo-6-chlorobenzoic acid (20 g, 85 mmol) in THF (200 mL) was added BH$_3$·DMS (42.5 mL, 425 mmol) slowly at 0° C. The resulting solution was heated at 80° C. for 17 h. The reaction was cooled and quenched with MeOH (100 mL) and NaClO (aq., 100 mL) carefully, then most of THF and MeOH were removed under reduced pressure and the remaining aqueous phase was filtered. The filtrate was extracted with EtOAc (4×30 mL). The combined organic layers were washed with brine (50 mL), dried over Na$_2$SO$_4$, filtered and concentrated in vacuo. The residue was purified by silica gel column chromatography (petroleum ether:EtOAc=50:1-20:1) to give the title compound. $^1$H NMR (400 MHz, CDCl$_3$) δ 7.52 (d, J=8.0 Hz, 1H), 7.38 (d, J=8.0 Hz, 1H), 7.12 (t, J=8.0 Hz, 1H), 4.99 (d, J=3.5 Hz, 2H), 2.08-2.29 (m, 1H).

Step 2. Preparation of 1-bromo-3-chloro-2-(((4-methoxybenzyl)oxy)methyl)benzene (i-18b)

To a solution of (2-bromo-6-chlorophenyl)methanol (18.41 g, 83 mmol) in THF (200 mL) was added NaH (60%, 4.99 g, 125 mmol) at 0° C. After the mixture was stirred for 0.5 h, 1-(chloromethyl)-4-methoxybenzene (15.62 g, 100 mmol) was added. The mixture was stirred at 0° C. for 3 h and then at room temperature for 17 h. The mixture was quenched with H$_2$O (80 mL), extracted with EtOAc (3×100 mL). The combined organic layers were washed with brine (80 mL), dried over Na$_2$SO$_4$, filtered and concentrated in vacuo. The residue was purified by silica gel column chromatography (petroleum ether:EtOAc=100:1-50:1) to give the title compound. $^1$H NMR (400 MHz, CDCl$_3$) δ 7.51 (d, J=8.0 Hz, 1H), 7.30-7.43 (m, 3H), 7.07-7.15 (m, 1H), 6.89 (d, J=8.6 Hz, 2H), 4.80 (s, 2H), 4.58 (s, 2H), 3.81 (s, 3H).

Step 3. Preparation of 1-(3-chloro-2-(((4-methoxybenzyl)oxy)methyl)phenyl)-cyclopropanecarbonitrile (i-18c)

4, 6-Bis(diphenylphosphino)-10H-phenoxazine (1.94 g, 3.51 mmol) and Pd$_2$(dba)$_3$ (1.61 g, 1.76 mmol) was dissolved in THF (100 mL). The mixture was stirred at room temperature for 30 min under N$_2$. 1-bromo-3-chloro-2-(((4-methoxybenzyl)oxy)methyl)benzene (12 g, 35.13 mmol) and cyclopropanecarbonitrile (2.88 g, 42.85 mmol) was added. Then LHMDS (52.8 mL, 52.8 mmol) (1.0 M in THF) was added immediately. The mixture was stirred at 80° C. for 18 h under N$_2$. The mixture was cooled and quenched with sat. NH$_4$Cl (100 mL) and the mixture was extracted with ethyl acetate (4×60 mL). The combined organic fractions were washed with brine (50 mL), dried over Na$_2$SO$_4$, filtered and the solvent was evaporated under reduced pressure. The residue was purified by silica gel column flash chromatography, eluting with EtOAc/petroleum ether=0-20% to give the title compound. $^1$H NMR (400 MHz, CDCl$_3$) δ 7.35-7.42 (m, 3H), 7.27-7.32 (m, 1H), 7.21-7.26 (m, 1H), 6.92 (d, J=8.6 Hz, 2H), 4.80-4.91 (m, 2H), 4.65 (s, 2H), 3.77-3.91 (m, 3H), 1.57-1.60 (m, 2H), 1.38-1.45 (m, 2H).

Step 4. Preparation of 1-(3-chloro-2-(((4-methoxybenzyl)oxy)methyl)phenyl)-cyclopropanecarbaldehyde (i-18d)

Diisobutylaluminum hydride (55 mL, 55.0 mmol) (1.0 M in toluene) was added to a stirred mixture of 1-(3-chloro-2-(((4-methoxybenzyl)oxy)methyl)phenyl)-cyclopropanecarbonitrile (9 g, 27.5 mmol) in toluene (60 mL) at room temperature and the mixture was stirred at room temperature for 2 h. The mixture was cooled to 0° C., i-PrOH (12 mL) was added. After stirring at 0° C. for 30 min, hydrochloric acid (1M, 60 mL) was added and the mixture was extracted with ethyl acetate (4×50 mL). The combined organic fractions were washed with brine (saturated, 50 mL), dried (Na$_2$SO$_4$), filtered and the solvent was evaporated under reduced pressure. The residue was purified by silica gel column flash chromatography, (EtOAc/petroleum ether=0-10%) to give the title compound. $^1$H NMR (400 MHz, CDCl$_3$) δ 9.16 (s, 1H), 7.39 (d, J=7.5 Hz, 1H), 7.31 (d, J=8.4 Hz, 2H), 7.23 (d, J=7.9 Hz, 1H), 7.16-7.22 (m, 1H), 6.89 (d, J=8.6 Hz, 2H), 4.61 (s, 2H), 4.52 (s, 2H), 3.82 (s, 3H), 1.58 (d, J=2.9 Hz, 2H), 1.38-1.47 (m, 2H).

Step 5. Preparation of methyl 1-chloro-3-(1-(difluoromethyl)cyclopropyl)-2-(((4-methoxybenzyl)oxy)methyl)benzene (i-18e)

DAST (2.80 mL, 21.16 mmol) was added to a stirred mixture of 1-(3-chloro-2-(((4-methoxybenzyl)oxy)methyl)phenyl)cyclopropanecarbaldehyde (3.5 g, 10.58 mmol) in DCM (40 mL) at room temperature and the mixture was stirred at 30° C. for 18 h. The mixture was concentrated to dryness. The residue was purified by silica gel column flash chromatography, (EtOAc/petroleum ether=0-5%) to give the title compound. $^1$H NMR (400 MHz, CDCl$_3$) δ 7.29-7.40 (m, 4H), 7.19-7.25 (m, 1H), 6.89-6.93 (m, 2H), 5.57-5.91 (m, 1H), 4.71-4.82 (m, 2H), 4.61 (s, 2H), 3.82 (s, 3H), 1.17 (s, 2H), 1.04 (d, J=2.3 Hz, 2H).

Step 6. Preparation of (2-chloro-6-(1-(difluoromethyl)cyclopropyl)phenyl)methanol (i-18f)

DDQ (1.930 g, 8.50 mmol) was added to a stirred mixture of 1-chloro-3-(1-(difluoromethyl)cyclopropyl)-2-(((4-methoxybenzyl)oxy)methyl)benzene (2 g, 5.67 mmol) in DCM (12 mL) and water (2 mL) at room temperature and the mixture was stirred at room temperature for 18 h. The mixture was filtered and the filter cake was washed with dichloromethane (30 mL), the combined organic fractions were washed with Na$_2$SO$_3$ (Saturated, 2×20 mL), dried (Na$_2$SO$_4$), filtered and concentrated. The residue was dissolved in MeOH (10 mL), added NaBH$_4$ (0.643 g, 17.01 mmol) at 0° C. After the mixture was stirred at 0° C. for 2 h, water (5 mL) was added. The mixture was concentrated in vacuo to remove the most of MeOH, and then extracted with ethyl acetate (3×15 mL). The combined organic fractions were washed with brine (20 mL), dried over Na$_2$SO$_4$, filtered and the solvent was evaporated under reduced pressure. The residue was purified by silica gel column flash chromatography, (EtOAc/petroleum ether=0-15%) to give the title compound. $^1$H NMR (400 MHz, CDCl$_3$) δ 7.38 (dd, J=14.0 Hz, 7.8 Hz, 2H), 7.22-7.27 (m, 1H), 5.52-5.87 (m, 1H), 4.93-5.13 (m, 2H), 2.10-2.21 (m, 1H), 1.30 (s, 2H), 1.09 (brs, 2H).

Step 7. Preparation of 2-chloro-6-(1-(difluoromethyl)cyclopropyl)benzaldehyde (i-18g)

DMP (3.10 g, 7.31 mmol) was added to a stirred mixture of (2-chloro-6-(1-(difluoromethyl)cyclopropyl)phenyl) methanol (0.85 g, 3.65 mmol) in DCM (10 mL) at room temperature and the mixture was stirred at room temperature for 5 h. The mixture was diluted with DCM (20 mL), filtered and the filter cake was washed with dichloromethane (20 mL). The filtrate was concentrated and purified by silica gel column flash chromatography, (EtOAc/petroleum ether=0-10%) to give the title compound. $^1$H NMR (400 MHz, CDCl$_3$) δ 10.61 (s, 1H), 7.41-7.55 (m, 3H), 5.97-6.28 (m, 1H), 1.33-1.39 (m, 2H), 0.80 (brs, 2H).

Step 8. Preparation of 2-chloro-6-(1-(difluoromethyl)cyclopropyl)benzoic acid (i-18)

2-Methylbut-2-ene (1.672 g, 23.85 mmol) was added to a stirred mixture of 2-chloro-6-(1-(difluoromethyl)cyclopropyl)benzaldehyde (0.55 g, 2.385 mmol) in t-BuOH (10 mL) at room temperature. Then sodium dihydrogenphosphate (0.515 g, 4.29 mmol) in H$_2$O (3 mL) and sodium chlorite (0.324 g, 3.58 mmol) in H$_2$O (2 mL) was added. The mixture was stirred at room temperature for 18 h, diluted with ethyl acetate (20 mL) and hydrochloric acid (1 M, 3 mL). The mixture was extracted with ethyl acetate (4×15 mL), washed with brine (20 mL), dried over Na$_2$SO$_4$, filtered and the solvent was evaporated under reduced pressure. The residue was purified by preparative HPLC (reverse phase C-18 column), eluting with Acetonitrile/Water+0.1% HCOOH to give the title compound. $^1$H NMR (400 MHz, CDCl$_3$) δ 7.29-7.72 (m, 3H), 5.96-6.32 (m, 1H), 1.30 (brs, 2H), 1.02 (brs, 2H).

Intermediate i-19A and i-19B

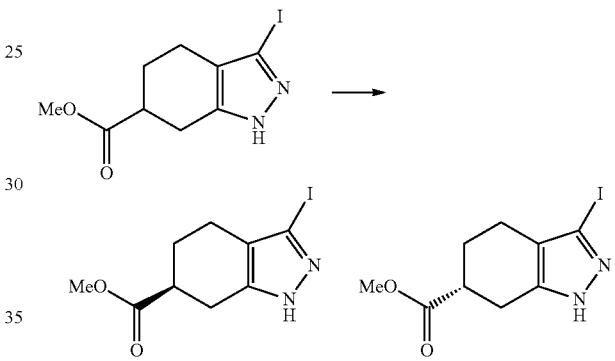

methyl (6R)-3-iodo-4,5,6,7-tetrahydro-1H-indazole-6-carboxylate and methyl (6S)-3-iodo-4,5,6,7-tetrahydro-1H-indazole-6-carboxylate The mixture of the two stereoisomers was purified by chiral SFC (AD-H column, 30%/70% Methanol/CO$_2$) to afford i-19A (faster eluting): MS: 307 (M+1). i-19B (slower eluting): MS: 307 (M+1).

The following examples shown in Table 4 were prepared using i-19A and following similar procedures described in i-5a can be achieved by those of ordinary skill in the art of organic synthesis.

TABLE 4

| Intermediate | Structure | IUPAC Name | MS (M + 1) |
|---|---|---|---|
| i-20A | 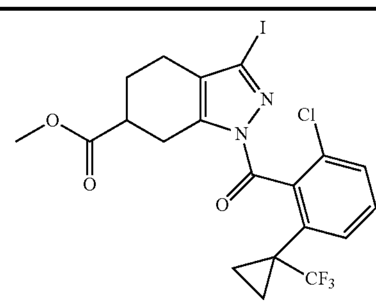 | methyl (R or S)-1-(2-chloro-6-(1-(trifluoromethyl)cyclopropyl)benzoyl)-3-iodo-4,5,6,7-tetrahydro-1H-indazole-6-carboxylate | 553 |

TABLE 4-continued

| Intermediate | Structure | IUPAC Name | MS (M + 1) |
|---|---|---|---|
| i-21A | 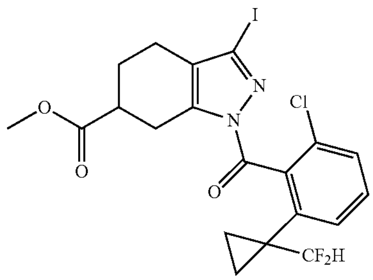 [SMILES: COC(=O)C1CCc2c(I)nn(C(=O)c3c(Cl)cccc3C3(C(F)F)CC3)c2C1] | methyl (R or S)-1-(2-chloro-6-(1-(difluoromethyl)cyclopropyl)benzoyl)-3-iodo-4,5,6,7-tetrahydro-1H-indazole-6-carboxylate | 535 |
| i-22A | 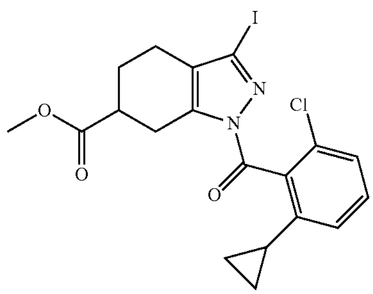 [SMILES: COC(=O)C1CCc2c(I)nn(C(=O)c3c(Cl)cccc3C3CC3)c2C1] | methyl (R or S)-1-(2-chloro-6-cyclopropylbenzoyl)-3-iodo-4,5,6,7-tetrahydro-1H-indazole-6-carboxylate | 485 |

Intermediate i-23A and i-23B

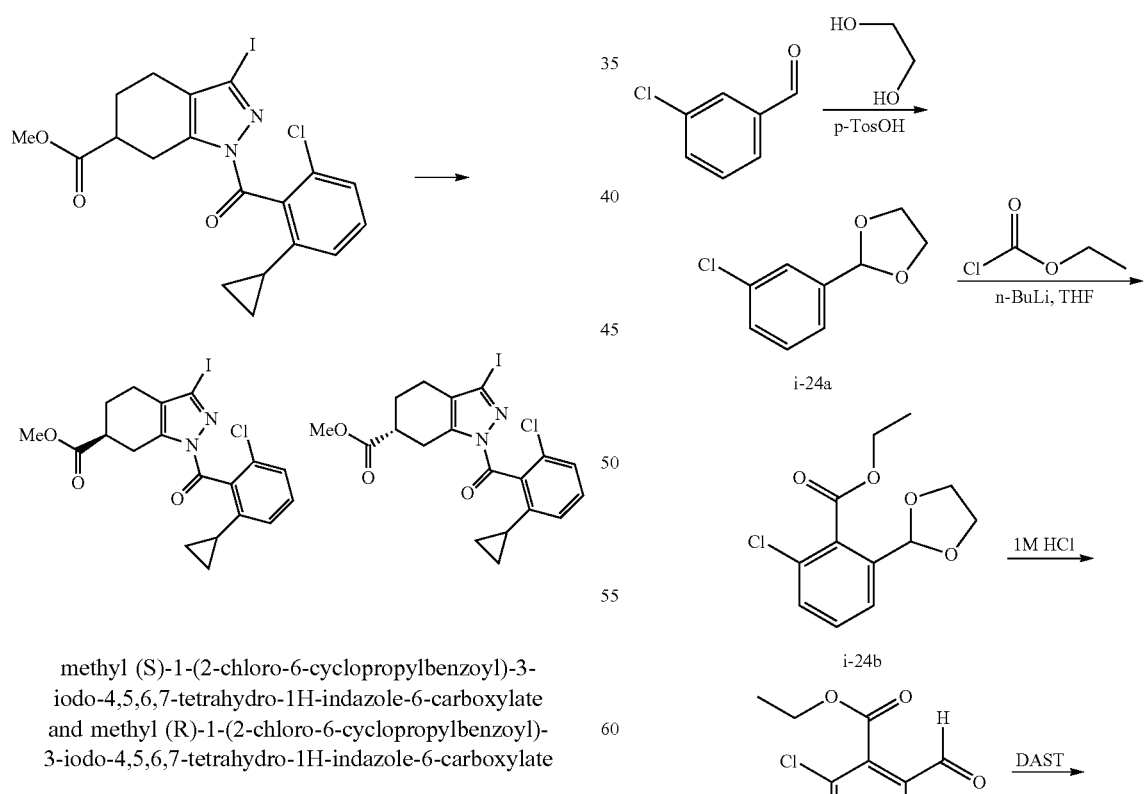

methyl (S)-1-(2-chloro-6-cyclopropylbenzoyl)-3-iodo-4,5,6,7-tetrahydro-1H-indazole-6-carboxylate and methyl (R)-1-(2-chloro-6-cyclopropylbenzoyl)-3-iodo-4,5,6,7-tetrahydro-1H-indazole-6-carboxylate The mixture of the two stereoisomers was purified by chiral SFC (OJ-H column, 20%/80% Methanol with 0.25% DME/CO$_2$) to afford i-23A (faster eluting): MS: 485 (M+1). 23B (slower eluting): MS: 485 (M+1).

Intermediate i-24

-continued

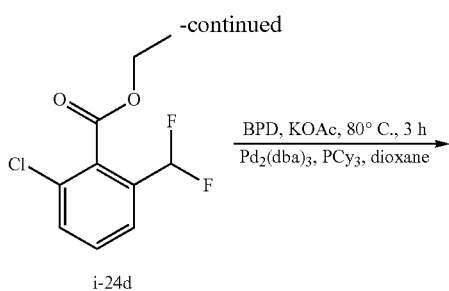

i-24d

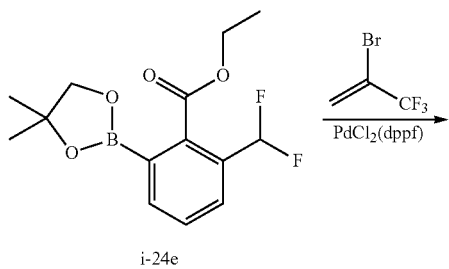

i-24e

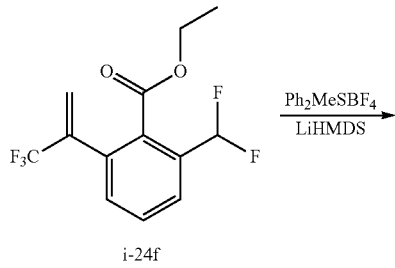

i-24f

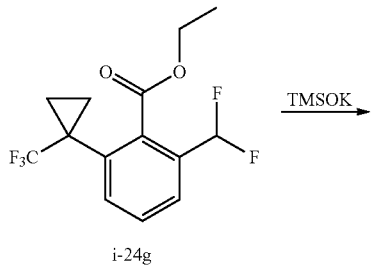

i-24g

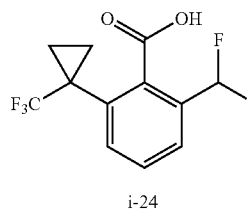

i-24

2-(difluoromethyl)-6-(1-(trifluoromethyl)cyclopropyl)benzoic acid

Step 1: Preparation of 2-(3-chlorophenyl)-1,3-dioxolane (i-24a)

A mixture of 3-chlorobenzaldehyde (100 g, 711 mmol), ethane-1,2-diol (64 mL, 1145 mmol) and P-TosOH (100 mg, 0.581 mmol) in toluene (200 mL) was stirred in a Dean-Stark apparatus at 110° C. for 15 hours. TLC showed no starting material remained and one major new spot formed. The reaction mixture was cooled to 20° C., diluted with EtOAc (300 mL) and water (500 mL). The aqueous layer was extracted with EtOAc (3×200 mL). The combined organic phase was dried over $Na_2SO_4$, filtered and concentrated in vacuo to afford 2-(3-chlorophenyl)-1,3-dioxolane.

$^1$H NMR (400 MHz, chloroform-d) δ 7.47 (s, 1H), 7.36-7.28 (m, 3H), 5.77 (s, 1H), 4.11-4.01 (m, 4H).

Step 2: Preparation of ethyl 2-chloro-6-(1,3-dioxolan-2-yl)benzoate (i-24b)

To a solution of 2-(3-chlorophenyl)-1,3-dioxolane (33 g, 179 mmol) in THF (130 mL) cooled to −78° C. was added n-BuLi (107 mL, 268 mmol). The reaction mixture was stirred at −78° C. for 1 hour. Ethyl carbonochloridate (97 g, 894 mmol) was added to the above mixture and the resulting mixture was warmed to 20° C. and stirred for 2 hours. TLC showed no starting material remained and one major new spot formed. The reaction was then diluted with EtOAc (100 mL) and water (500 mL). The aqueous layer was extracted with EtOAc (3×200 mL). The combined organic phase was dried over $Na_2SO_4$, filtered and concentrated in vacuo. The residue was purified by column chromatography ($SiO_2$, PE:EtOAc=100:1 to 8:1) to give ethyl 2-chloro-6-(1,3-dioxolan-2-yl)benzoate. MS: 256.9 (M+1). $^1$H NMR (400 MHz, chloroform-d) δ 7.49 (d, J=7.4 Hz, 1H), 7.43-7.32 (m, 2H), 6.04 (s, 1H), 4.44 (q, J=7.0 Hz, 2H), 3.98-3.97 (m, 1H), 4.01 (s, 4H), 1.41 (t, J=7.0 Hz, 3H).

Step 3: Preparation of ethyl 2-chloro-6-formylbenzoate (i-24c)

To a solution of ethyl 2-chloro-6-(1,3-dioxolan-2-yl)benzoate (15.6 g, 60.8 mmol) in THF (60 mL) was added 1N HCl (60 mL, 60.0 mmol). The reaction mixture was stirred at 60° C. for 1 hour. LC-MS showed the reaction was finished. After cooled to 20° C., the mixture was neutralized with sat. aq $NaHCO_3$ till pH=9. To the mixture was added EtOAc (100 mL) and water (200 mL). The aqueous layer was extracted with EtOAc (3×50 mL). The combined organic phase was dried over $Na_2SO_4$, filtered and concentrated in vacuo. The residue was purified by column chromatography ($SiO_2$, PE:EtOAc=100:1 to 6:1) to give ethyl 2-chloro-6-formyl benzoate. MS: 212.9 (M+1). $^1$H NMR (400 MHz, chloroform-d) δ 9.98 (s, 1H), 7.80 (d, J=7.4 Hz, 1H), 7.67 (d, J=7.8 Hz, 1H), 7.58-7.51 (m, 1H), 4.51 (q, J=7.2 Hz, 2H), 1.42 (t, J=7.0 Hz, 3H).

Step 4: Preparation of ethyl 2-chloro-6-(difluoromethyl)benzoate (i-24d)

To a solution of ethyl 2-chloro-6-formylbenzoate (12.35 g, 58.1 mmol) in DCM (150 ml) was added DAST (23.02 mL, 174 mmol). The reaction mixture was stirred at 40° C. for 2 hours. TLC showed no starting material remained and one major new spot formed. After cooled to 20° C., the reaction mixture was diluted with DCM (100 mL) and water (500 mL).

The aqueous layer was extracted with DCM (3×200 mL). The combined organic phase was dried over $Na_2SO_4$, filtered and concentrated in vacuo. The residue was purified by column chromatography ($SiO_2$, PE:EtOAc=100:1 to 10:1) to give ethyl 2-chloro-6-(difluoromethyl)benzoate. MS: 276 (M+1). $^1$H NMR (400 MHz, chloroform-d) δ 7.59-7.51 (m, 2H), 7.50-7.43 (m, 1H), 6.98-6.67 (m, 1H), 4.47 (q, J=7.0 Hz, 2H), 1.42 (t, J=7.0 Hz, 3H).

Step 5: Preparation of ethyl 2-(difluoromethyl)-6-(4,4,5,5-tetramethyl-1,3,2-dioxaborolan-2-yl)benzoate (i-24e)

To a mixture of ethyl 2-chloro-6-(difluoromethyl)benzoate (8.95 g, 38.1 mmol) and 4,4,4',4',5,5,5',5'-octamethyl-2,2'-bi(1,3,2-dioxaborolane) (14.53 g, 57.2 mmol) in dioxane (120 mL) were added $Pd_2(dba)_3$ (3.49 g, 3.81 mmol), $PCy_3$ (2.57 g, 9.15 mmol) and KOAc (11.23 g, 114 mmol) under N$_2$. The reaction mixture was stirred at 80° C. under N$_2$ for 12 hours. LC-MS showed the reaction was finished. The reaction was then diluted with EtOAc (100 mL) and water (200 mL). The aqueous layer was extracted with EtOAc (3×100 mL). The combined organic phase was dried over Na$_2$SO$_4$, filtered and concentrated in vacuo. The residue was purified by column chromatography (SiO$_2$, PE:EtOAc=100:1 to 10:1) to give ethyl 2-(difluoromethyl)-6-(4,4,5,5-tetramethyl-1,3,2-dioxaborolan-2-yl)benzoate. MS: 327 (M+1). $^1$H NMR (400 MHz, chloroform-d) δ 7.77 (dd, J=7.6, 16.4 Hz, 2H), 7.56 (d, J=7.7 Hz, 1H), 7.10-6.89 (m, 1H), 4.41 (q, J=7.1 Hz, 2H), 1.43-1.32 (m, 15H).

Step 6: Preparation of ethyl 2-(difluoromethyl)-6-(3,3,3-trifluoroprop-1-en-2-yl)benzoate (i-24f)

To a mixture of ethyl 2-(difluoromethyl)-6-(4,4,5,5-tetramethyl-1,3,2-dioxaborolan-2-yl)benzoate (4.97 g, 9.14 mmol) and 2-bromo-3,3,3-trifluoroprop-1-ene (6.40 g, 36.6 mmol) in dioxane (50 mL) and water (5.0 mL) were added PdCl$_2$(dppf) (0.669 g, 0.914 mmol) and K$_2$CO$_3$ (2.53 g, 18.29 mmol) under N$_2$. The reaction mixture was stirred at 70° C. under N$_2$ for 12 hours. LC-MS showed the reaction was finished. The reaction was then diluted with EtOAc (30 mL) and water (50 mL). The aqueous layer was extracted with EtOAc (3×20 mL). The combined organic phase was dried over Na$_2$SO$_4$, filtered and concentrated in vacuo. The residue was purified by column chromatography (SiO$_2$, PE:EtOAc=100:1 to 20:1) to give ethyl 2-(difluoro methyl)-6-(3,3,3-trifluoroprop-1-en-2-yl)benzoate. MS: 336 (M+1). $^1$H NMR (400 MHz, chloroform-d) δ 7.72 (d, J=7.8 Hz, 1H), 7.58-7.51 (m, 1H), 7.49-7.43 (m, 1H), 7.11-6.80 (m, 1H), 6.05 (d, J=0.8 Hz, 1H), 5.58 (d, J=0.8 Hz, 1H), 4.30 (q, J=7.2 Hz, 2H), 1.30 (t, J=7.2 Hz, 3H).

Step 7: Preparation of ethyl 2-(difluoromethyl)-6-(1-(trifluoromethyl)cyclopropyl)benzoate (i-24g)

To a mixture of ethyl 2-(difluoromethyl)-6-(3,3,3-trifluoroprop-1-en-2-yl)benzoate (2.08 g, 7.07 mmol) and Ph$_2$MeSBF$_4$ (4.07 g, 14.14 mmol) in THF (30 mL) at −78° C. under N$_2$ was added LiHMDS (28.3 mL, 28.3 mmol). The reaction mixture was stirred at 20° C. for 2 hours. LC-MS showed the reaction was finished. The reaction was then diluted with EtOAc (50 mL) and saturated aqueous NH$_4$Cl (50 mL). The aqueous layer was extracted with EtOAc (3×30 mL). The combined organic phase was dried over Na$_2$SO$_4$, filtered and concentrated in vacuo. The residue was purified by column chromatography (SiO$_2$, PE:EtOAc=100:1 to 20:1) to give ethyl 2-(difluoromethyl)-6-(1-(trifluoromethyl)cyclopropyl)benzoate. MS: 309 (M+1). $^1$H NMR (400 MHz, chloroform-d) δ 7.68 (d, J=7.8 Hz, 2H), 7.57-7.50 (m, 1H), 7.03-6.72 (m, 1H), 4.43 (q, J=7.0 Hz, 2H), 1.44-1.38 (m, 5H), 1.16 (br. s., 2H).

Step 8: Preparation 2-(difluoromethyl)-6-(1-(trifluoromethyl)cyclopropyl)benzoic acid (i-24)

To a mixture of ethyl 2-(difluoromethyl)-6-(1-(trifluoromethyl)cyclopropyl)benzoate (1.12 g, 3.63 mmol) in dioxane (15 mL) was added potassium trimethylsilanolate (1.398 g, 10.90 mmol). The reaction mixture was stirred at 90° C. for 18 hours. LCMS showed no starting material remained. The reaction was cooled to 20° C., diluted with EtOAc (30 mL) and water (20 mL). The aqueous layer was acidified with 2N HCl to PH<1, extracted with EtOAc (3×20 mL). The combined organic phase was dried over Na$_2$SO$_4$, filtered and concentrated in vacuo to afford 2-(difluoromethyl)-6-(1-(trifluoromethyl)cyclopropyl)benzoic acid, which was used directly for next step without purification. MS: 303 (M+Na). $^1$H NMR (400 MHz, chloroform-d) δ 7.77-7.66 (m, 2H), 7.63-7.55 (m, 1H), 7.17-6.87 (m, 1H), 1.52-1.41 (m, 2H), 1.30-1.19 (m, 2H).

EXAMPLES

Example 1A

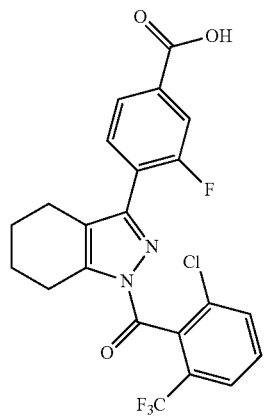 [SMILES: O=C(O)c1ccc(-c2nn(C(=O)c3c(Cl)cccc3C(F)(F)F)c3c2CCCC3)c(F)c1]

4-(1-(2-chloro-6-(trifluoromethyl)benzoyl)-4,5,6,7-tetrahydro-1H-indazol-3-yl)-3-fluorobenzoic acid Step 1: methyl 4-(1-(2-chloro-6-(trifluoromethyl)benzoyl)-4,5,6,7-tetrahydro-1H-indazol-3-yl)-3-fluorobenzoate (1A-1)

A mixture of i-2b (50 mg, 0.11 mmol), (2-fluoro-4-(methoxycarbonyl)phenyl)boronic acid (33 mg, 0.17 mmol), PdCl$_2$(dppf)-CH$_2$Cl$_2$ (18 mg, 0.02 mmol), potassium acetate (32 mg, 0.33 mmol) in THF (880 μl) and water (220 μl) was purged with argon for 5 minutes. Reaction was then heated to 80° C. overnight. The reaction was cooled and diluted with EtOAc. The organic layer was separated and washed twice with aqueous NaHCO$_3$ and once with brine. The combined organic layers were dried with Na$_2$SO$_4$, filtered and the solvent was evaporated under reduced pressure. The residue was purified by silica gel chromatography (EtOAc/Hexane 5-65%) to afford the title compound. LCMS (ESI) calc'd for C$_{23}$H$_{17}$ClF$_4$N$_2$O$_3$ [M+H]$^+$: 481, found: 481.

Step 2: 4-(1-(2-chloro-6-(trifluoromethyl)benzoyl)-4,5,6,7-tetrahydro-1H-indazol-3-yl)-3-fluorobenzoic acid (1A)

A mixture of 1A-1 (37 mg, 0.08 mmol) and LiOH (37 mg, 1.54 mmol) in THF (769 μl) and water (769 μl) was allowed to stir at room temperature for 3 hours. The reaction mixture was acidified with 2N HCl and then extracted with EtOAc. The organic layer was dried with Na$_2$SO$_4$, filtered and the solvent was evaporated under reduced pressure. The residue was purified by Prep-HPLC, eluting with acetonitrile/water+0.10% TFA 45-95% to give the title compound. LCMS (ESI) calc'd for C$_{22}$H$_{15}$ClF$_4$N$_2$O$_3$ [M+H]+: 467, found: 467. $^1$H NMR (600 MHz, DMSO-d$_6$) δ 13.37 (s, 1H), 7.92 (br s, 1H), 7.87 (br s, 1H), 7.76 (br s, 2H), 7.70 (d, J=10.0, 1H), 7.45 (br s, 1H), 3.07 (s, 2H), 2.44 (s, 2H), 1.84 (s, 2H), 1.69 (s, 2H).

The following examples shown in Table 5 were prepared following similar procedures described for Example 1A which can be achieved by those of ordinary skill in the art of organic synthesis.

TABLE 5

| Example No. | Structure | Name | MS (M + 1) |
|---|---|---|---|
| 1B | 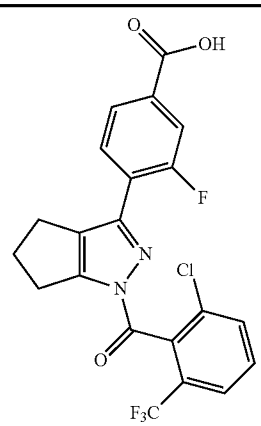 | 4-(1-(2-chloro-6-(trifluoromethyl)benzoyl)-1,4,5,6-tetrahydrocyclopenta[c]pyrazol-3-yl)-3-fluorobenzoic acid | 453 |
| 1C | 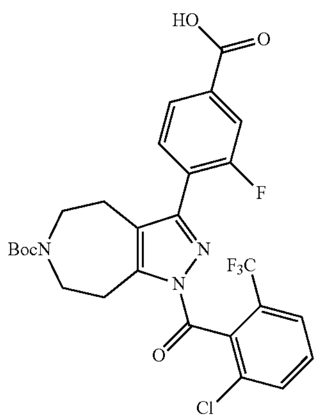 [SMILES: CC(C)(C)OC(=O)N1CCc2c(-c3ccc(C(=O)O)cc3F)nn(C(=O)c3c(Cl)cccc3C(F)(F)F)c2CC1] | 4-(6-(tert-butoxycarbonyl)-1-(2-chloro-6-(trifluoromethyl)benzoyl)-1,4,5,6,7,8-hexahydropyrazolo[3,4-d]azepin-3-yl)-3-fluorobenzoic acid | 582 |
| 1D | 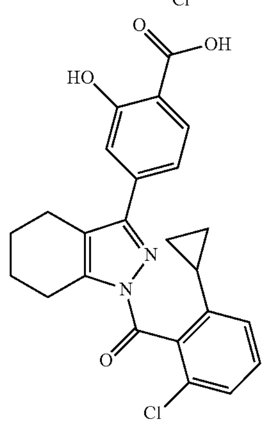 | 4-(1-(2-chloro-6-cyclopropylbenzoyl)-4,5,6,7-tetrahydro-1H-indazol-3-yl)-2-hydroxybenzoic acid | 437 |
| 1E | 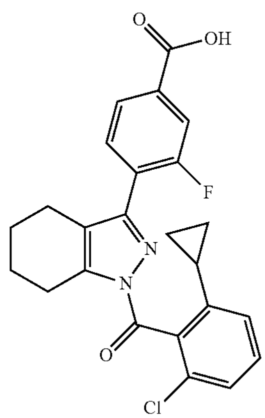 [SMILES: O=C(O)c1ccc(-c2nn(C(=O)c3c(Cl)cccc3C3CC3)c3c2CCCC3)c(F)c1] | 4-(1-(2-chloro-6-cyclopropylbenzoyl)-4,5,6,7-tetrahydro-1H-indazol-3-yl)-3-fluorobenzoic acid | 439 |

TABLE 5-continued

| Example No. | Structure | Name | MS (M + 1) |
| --- | --- | --- | --- |
| 1F | 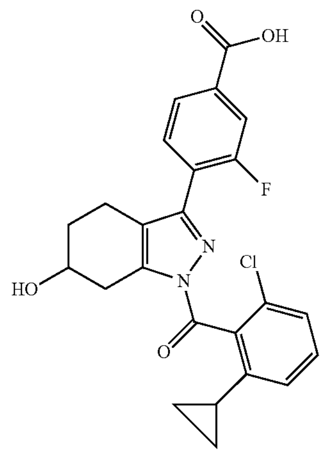 [SMILES: O=C(O)c1ccc(-c2nn(C(=O)c3c(Cl)cccc3C3CC3)c3c2CCC(O)C3)c(F)c1] | 4-(1-(2-chloro-6-cyclopropylbenzoyl)-6-hydroxy-4,5,6,7-tetrahydro-1H-indazol-3-yl)-3-fluorobenzoic acid | 455 |
| 1G | 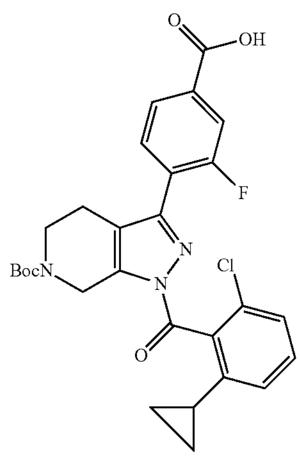 [SMILES: CC(C)(C)OC(=O)N1CCc2c(-c3ccc(C(=O)O)cc3F)nn(C(=O)c3c(Cl)cccc3C3CC3)c2C1] | 4-(6-(tert-butoxycarbonyl)-1-(2-chloro-6-cyclopropylbenzoyl)-4,5,6,7-tetrahydro-1H-pyrazolo[3,4-c]pyridin-3-yl)-3-fluorobenzoic acid | 540 |
| 1H | 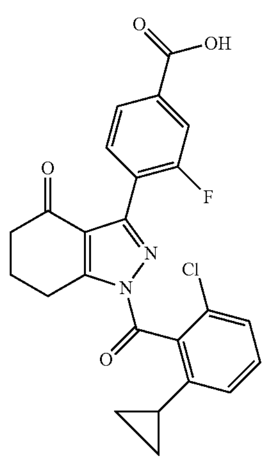 [SMILES: O=C(O)c1ccc(-c2nn(C(=O)c3c(Cl)cccc3C3CC3)c3c2C(=O)CCC3)c(F)c1] | 4-(1-(2-chloro-6-cyclopropylbenzoyl)-4-oxo-4,5,6,7-tetrahydro-1H-indazol-3-yl)-3-fluorobenzoic acid | 453 |

TABLE 5-continued

| Example No. | Structure | Name | MS (M + 1) |
| --- | --- | --- | --- |
| 1I | 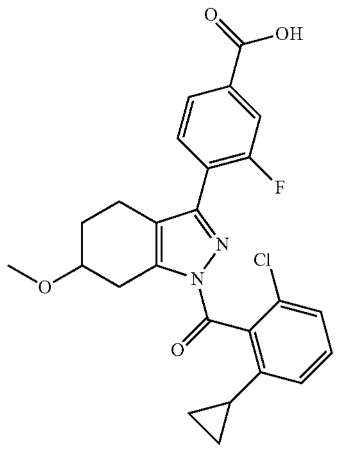 [SMILES: COC1CCc2c(-c3ccc(C(=O)O)cc3F)nn(C(=O)c3c(Cl)cccc3C3CC3)c2C1] | 4-(1-(2-chloro-6-cyclopropylbenzoyl)-6-methoxy-4,5,6,7-tetrahydro-1H-indazol-3-yl)-3-fluorobenzoic acid | 469 |
| 1J | 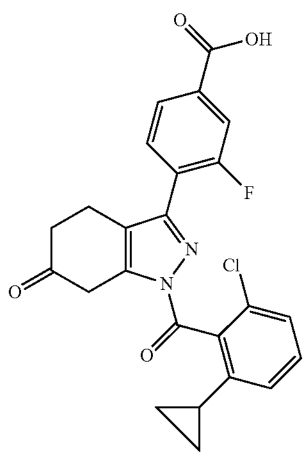 [SMILES: O=C1CCc2c(-c3ccc(C(=O)O)cc3F)nn(C(=O)c3c(Cl)cccc3C3CC3)c2C1] | 4-(1-(2-chloro-6-cyclopropylbenzoyl)-6-oxo-4,5,6,7-tetrahydro-1H-indazol-3-yl)-3-fluorobenzoic acid | 453 |
| 1K | 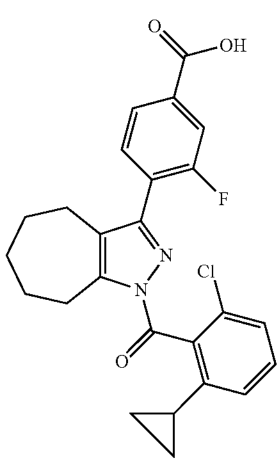 [SMILES: O=C(O)c1ccc(-c2nn(C(=O)c3c(Cl)cccc3C3CC3)c3c2CCCCC3)c(F)c1] | 4-(1-(2-chloro-6-cyclopropylbenzoyl)-1,4,5,6,7,8-hexahydrocyclohepta[c]pyrazol-3-yl)-3-fluorobenzoic acid | 453 |

TABLE 5-continued

| Example No. | Structure | Name | MS (M + 1) |
|---|---|---|---|
| 1L | 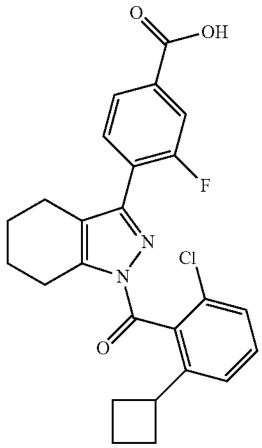 [SMILES: O=C(O)c1ccc(-c2nn(C(=O)c3c(Cl)cccc3C3CCC3)c3c2CCCC3)c(F)c1] | 4-(1-(2-chloro-6-cyclobutylbenzoyl)-4,5,6,7-tetrahydro-1H-indazol-3-yl)-3-fluorobenzoic acid | 453 |
| 1M | 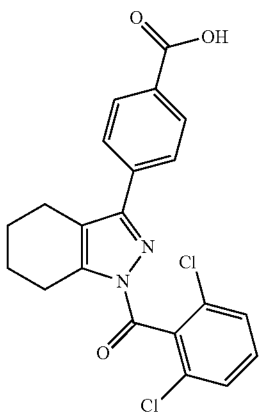 [SMILES: O=C(O)c1ccc(-c2nn(C(=O)c3c(Cl)cccc3Cl)c3c2CCCC3)cc1] | 4-(1-(2,6-dichlorobenzoyl)-4,5,6,7-tetrahydro-1H-indazol-3-yl)benzoic acid | 415 |

Example 2A

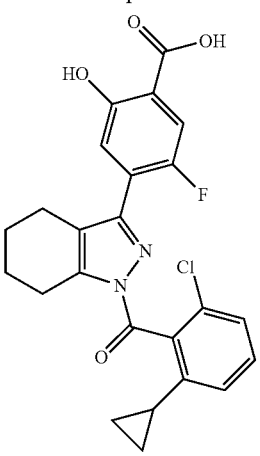

4-(1-(2-chloro-6-cyclopropylbenzoyl)-4,5,6,7-tetrahydro-1H-indazol-3-yl)-5-fluoro-2-hydroxybenzoic acid Step 1: benzyl 2-(benzyloxy)-4-(1-(2-chloro-6-cyclopropylbenzoyl)-4,5,6,7-tetrahydro-1H-indazol-3-yl)-5-fluorobenzoate (2A-1)

A mixture of i-5a (184 mg, 0.43 mmol), i-14 (299 mg, 0.65 mmol), PdCl$_2$(dppf)-CH$_2$Cl$_2$ (70.4 mg, 0.09 mmol), potassium acetate (127 mg, 1.29 mmol) in water (0.86 ml) and THF (3.4 ml) was purged with argon. The reaction was then heated to 80° C. overnight. The mixture was cooled and diluted with EtOAc. The organic layer was separated and washed twice with aqueous NaHCO$_3$ and once with brine. The combined organic layers were dried with Na$_2$SO$_4$, filtered and the solvent was evaporated under reduced pressure. The residue was purified by silica gel chromatography (EtOAc/hexane 5-75%) to afford the title compound. LCMS (ESI) calc'd for C$_{38}$H$_{32}$ClFN$_2$O$_4$ [M+H]$^+$: 635, found: 635.

Step 1: 4-(1-(2-chloro-6-cyclopropylbenzoyl)-4,5,6,7-tetrahydro-1H-indazol-3-yl)-5-fluoro-2-hydroxybenzoic acid (2A)

To a flask was added Pd/C (3.8 mg, 0.036 mmol) and the flask thoroughly degassed with argon. A solution of 2A-1 (231 mg, 0.36 mmol) in MeOH (1.8 ml) and EtOAc (1.8 ml) was then introduced to the reaction flask and the resulting mixture was further purged with argon. A H$_2$ (0.7 mg, 0.36 mmol) balloon was then affixed to the reaction flask and the flask was sequentially vacuumed and refilled with hydrogen three times. The reaction was allowed to stir at room temperature overnight with a positive pressure of hydrogen (H$_2$ balloon). The reaction mixture was filtered through celite and concentrated. The residue was purified by Prep-HPLC, eluting with acetonitrile/water+0.10% TFA 50-100% to give the title compound. LCMS (ESI) calc'd for C$_{24}$H$_{20}$ClFN$_2$O$_4$ [M+H]+: 455, found: 455. $^1$H NMR (600 MHz, DMSO-d$_6$) δ 7.56 (d, J=10.1, 1H), 7.41-7.30 (m, 2H), 7.02 (d, J=7.2, 1H), 6.87 (d, J=5.4, 1H), 3.10 (s, 2H), 2.45-2.38 (m, 2H), 1.89-1.78 (m, 2H), 1.76-1.59 (m, 3H), 0.91-0.81 (m, 1H), 0.79-0.71 (m, 1H), 0.71-0.64 (m, 1H), 0.63-0.55 (m, 1H).

Example 3A

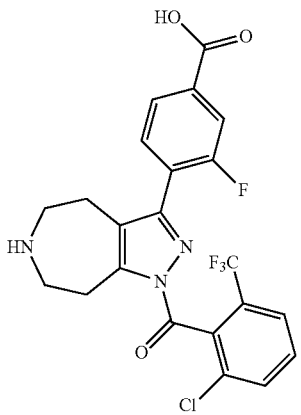 [SMILES: O=C(O)c1ccc(-c2nn(C(=O)c3c(Cl)cccc3C(F)(F)F)c3c2CCNCC3)c(F)c1]

4-(1-(2-chloro-6-(trifluoromethyl)benzoyl)-1,4,5,6,7, 8-hexahydropyrazolo[3,4-d]azepin-3-yl)-3-fluorobenzoic acid A mixture of 1C (21 mg, 0.04 mmol) in TFA (72 µl) and CH$_2$Cl$_2$ (289 µl) was allowed to stir at room temperature overnight. The reaction mixture was concentrated and the residue was purified by Prep-HPLC, eluting with acetonitrile/water+0.10% TFA 30-90%, to afford the title compound as the TFA salt. LCMS (ESI) calc'd for C$_{22}$H$_{16}$ClF$_4$N$_3$O$_3$ [M+H]+: 482, found: 482. $^1$H NMR (500 MHz, DMSO-d$_6$) δ 13.50 (s, 1H), 8.99 (br s, 2H), 7.97 (d, J=8.0, 1H), 7.93 (d, J=8.0, 1H), 7.86-7.75 (m, 3H), 7.44 (t, J=7.5, 1H), 3.74 (s, 2H), 3.52 (s, 2H), 2.82 (s, 2H), 2.56-2.48 (bs, 2H).

Example 4A

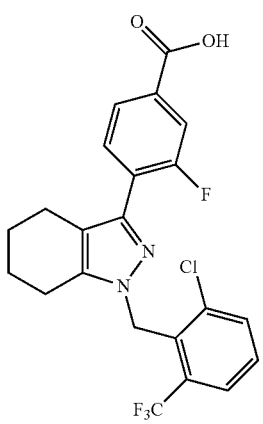 [SMILES: O=C(O)c1ccc(-c2nn(Cc3c(Cl)cccc3C(F)(F)F)c3c2CCCC3)c(F)c1]

4-(1-(2-chloro-6-(trifluoromethyl)benzyl)-4,5,6,7-tetrahydro-1H-indazol-3-yl)-3-fluorobenzoic acid Step 1: methyl 4-(1-(2-chloro-6-(trifluoromethyl)benzyl)-4,5,6,7-tetrahydro-1H-indazol-3-yl)-3-fluorobenzoate (4A-1)

A mixture of i-13 (190 mg, 0.43 mmol), (2-fluoro-4-(methoxycarbonyl)phenyl)boronic acid (128 mg, 0.65 mmol), PdCl$_2$(dppf)-CH$_2$Cl$_2$ (70 mg, 0.09 mmol) and potassium acetate (127 mg, 1.29 mmol) in THF (1.7 ml) and water (0.43 ml) was purged with argon for 5 minutes. The reaction was then heated to 80° C. overnight. The mixture was cooled and diluted with EtOAc. The organic layer was separated and washed twice with aqueous NaHCO$_3$ and once with brine. The combined organic layers were dried with Na$_2$SO$_4$, filtered and the solvent was evaporated under reduced pressure. The residue was purified by silica gel chromatography (EtOAc/Hexanes 5-65%) to afford the title compound. LCMS (ESI) calc'd for C$_{23}$H$_{19}$ClF$_4$N$_2$O$_2$ [M+H]+: 467, found: 467.

Step 2: 4-(1-(2-chloro-6-(trifluoromethyl)benzyl)-4, 5,6,7-tetrahydro-1H-indazol-3-yl)-3-fluorobenzoic acid (4A)

A mixture of 4A-1 (165 mg, 0.35 mmol) and lithium hydroxide (85 mg, 3.5 mmol) in THF (1.7 ml) and water (1.7 ml) was allowed to stir overnight at room temperature. The reaction mixture was acidified with 2N HCl and extracted twice with ethyl acetate. The combined organic layers were dried with Na$_2$SO$_4$, filtered and the solvent was evaporated under reduced pressure. The residue was purified by Prep-HPLC, eluting with acetonitrile/water+0.10% TFA 45-100%, to afford the title compound. LCMS (ESI) calc'd for C$_{22}$H$_{17}$ClF$_4$N$_2$O$_2$ [M+H]+: 453, found: 453. $^1$H NMR (600 MHz, DMSO-d$_6$) δ 7.83-7.76 (m, 2H), 7.71-7.66 (m, 1H), 7.64-7.55 (m, 2H), 7.38 (t, J=7.2, 1H), 5.34 (s, 2H), 2.72 (t, J=6.0, 2H), 2.44-2.37 (m, 2H), 1.85-1.73 (m, 2H), 1.69-1.58 (m, 2H).

Example 5A

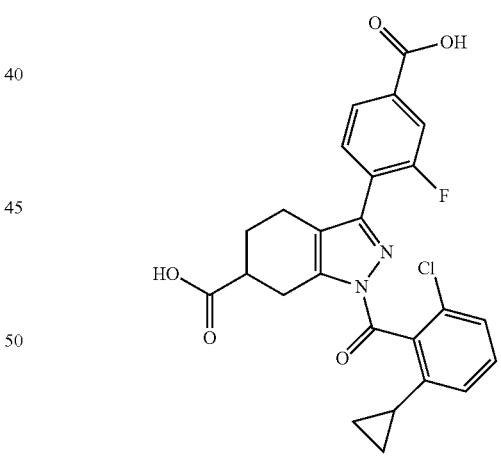

3-(4-carboxy-2-fluorophenyl)-1-(2-chloro-6-cyclopropylbenzoyl)-4,5,6,7-tetrahydro-1H-indazole-6-carboxylic acid Step 1: methyl 1-(2-chloro-6-cyclopropylbenzoyl)-3-(2-fluoro-4-(methoxycarbonyl)phenyl)-4,5,6,7-tetrahydro-1H-indazole-6-carboxylate (5A-1)

A mixture of i-5c (140 mg, 0.29 mmol), (2-fluoro-4-(methoxycarbonyl)phenyl)boronic acid (114 mg, 0.58 mmol), PdCl$_2$(dppf)-CH$_2$Cl$_2$ (47 mg, 0.06 mmol), and potassium acetate (85 mg, 0.87 mmol) in THF (1.1 ml) and water (0.28 ml) was purged with argon for 5 minutes. The reaction was then heated to 80° C. overnight. The mixture was cooled and diluted with ethyl acetate. The organic layer was separated and washed twice with aqueous NaHCO$_3$ and once with brine. The combined organic layers were dried with Na$_2$SO$_4$, filtered and the solvent was evaporated under reduced pressure. The residue was purified by silica gel chromatography (EtOAc/Hexanes 5-65%) to afford the title compound. LCMS (ESI) calc'd for C$_{27}$H$_{24}$ClFN$_2$O$_5$ [M+H]+: 511, found: 511.

Step 2: 3-(4-carboxy-2-fluorophenyl)-1-(2-chloro-6-cyclopropylbenzoyl)-4,5,6,7-tetrahydro-1H-indazole-6-carboxylic acid (5A)

A mixture of 5A-1 (25 mg, 0.05 mmol) and lithium hydroxide (11 mg, 0.49 mmol) in THF (489 µl) and water (489 µl) was allowed to stir at room temperature for 3 h. The reaction mixture was acidified with 2N HCl and concentrated. The residue was purified by Prep-HPLC, eluting with acetonitrile/water+0.10% TFA 50-95%, to afford the title compound. LCMS (ESI) calc'd for C$_{25}$H$_{20}$ClFN$_2$O$_5$ [M+H]+: 483, found: 483. $^1$H NMR (600 MHz, DMSO-d$_6$) δ 7.78 (d, J=7.8, 1H), 7.72 (d, J=10.2, 1H), 7.49 (t, J=7.2, 1H), 7.40-7.31 (m, 2H), 7.03 (dd, J=7.5, 19.0, 1H), 3.27-3.17 (m, 2H), 2.95-2.81 (m, 1H), 2.62-2.48 (m, 2H), 2.14-2.01 (m, 1H), 1.83-1.70 (m, 1H), 1.70-1.60 (m, 1H), 0.91-0.54 (m, 4H).

Example 6A

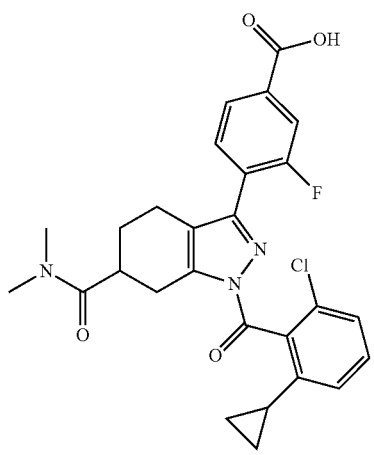

4-(1-(2-chloro-6-cyclopropylbenzoyl)-6-(dimethylcarbamoyl)-4,5,6,7-tetrahydro-1H-indazol-3-yl)-3-fluorobenzoic acid Step 1: 1-(2-chloro-6-cyclopropylbenzoyl)-3-iodo-N,N-dimethyl-4,5,6,7-tetrahydro-1H-indazole-6-carboxamide (6A-1)

A mixture of i-10 (80 mg, 0.17 mmol), dimethylamine (170 µl, 0.34 mmol), BOP (113 mg, 0.26 mmol) and Hunig's Base (89 µl, 0.51 mmol) in THF (1.7 ml) was allowed to stir at room temperature for 3 h. The reaction mixture was then diluted with ethyl acetate. The organic layer was separated and washed twice with aqueous NaHCO$_3$ and once with brine. The combined organic layers were dried with Na$_2$SO$_4$, filtered and the solvent was evaporated under reduced pressure. The residue was purified by silica gel chromatography (EtOAc/Hexanes 10-95%) to afford the title compound. LCMS (ESI) calc'd for C$_{20}$H$_{21}$ClIN$_3$O$_2$ [M+H]+: 498, found: 498.

Step 2: methyl 4-(1-(2-chloro-6-cyclopropylbenzoyl)-6-(dimethylcarbamoyl)-4,5,6,7-tetrahydro-1H-indazol-3-yl)-3-fluorobenzoate (6A-2)

A mixture of 6A-1 (66 mg, 0.13 mmol), (2-fluoro-4-(methoxycarbonyl)phenyl)boronic acid (39 mg, 0.2 mmol), PdCl$_2$(dppf)-CH$_2$Cl$_2$ (21 mg, 0.03 mmol) and potassium acetate (39 mg, 0.4 mmol) in THF (1.0 ml) and water (0.26 ml) was purged with argon for 5 minutes. The reaction was then heated to 80° C. overnight. The mixture was cooled and diluted with ethyl acetate. The organic layer was separated and washed twice with aqueous NaHCO$_3$ and once with brine. The combined organic layers were dried with Na$_2$SO$_4$, filtered and the solvent was evaporated under reduced pressure to give title compound. LCMS (ESI) calc'd for C$_{28}$H$_{27}$ClFN$_3$O$_4$ [M+H]+: 524, found: 524.

Step 3: 4-(1-(2-chloro-6-cyclopropylbenzoyl)-6-(dimethylcarbamoyl)-4,5,6,7-tetrahydro-1H-indazol-3-yl)-3-fluorobenzoic acid (6A)

A mixture of 6A-2 (70 mg, 0.13 mmol) and lithium hydroxide (3.2 mg, 0.13 mmol) in THF (0.66 ml) and water (0.66 ml) was allowed to stir at room temperature for 3 h. The reaction mixture was acidified with 2N HCl and then extracted twice with ethyl acetate. The combined organic layers were dried with Na$_2$SO$_4$, filtered and the solvent was evaporated under reduced pressure. The residue was purified by Prep-HPLC, eluting with acetonitrile/water+0.10% TFA 50-95%, to afford the title compound as the TFA salt. LCMS (ESI) calc'd for C$_{27}$H$_{25}$ClFN$_3$O$_4$ [M+H]+: 510, found: 510. $^1$H NMR (500 MHz, DMSO-d$_6$) δ 7.82 (d, J=8.0, 1H), 7.76 (d, J=10.6, 1H), 7.58-7.49 (m, 1H), 7.45-7.32 (m 2H), 7.06 (dd, J=7.3, 19.5, 1H), 3.45-3.14 (m, 2H), 3.11 (d, J=3.5, 3H), 2.88 (s, 3H), 2.74-2.57 (m, 2H), 2.48-2.41 (m, 1H), 1.96 (d, J=11.7, 1H), 1.79-1.52 (m, 2H), 0.95-0.57 (m, 4H).

The following examples shown in Table 6 were prepared following similar procedures described for Example 6A which can be achieved by those of ordinary skill in the art of organic synthesis.

TABLE 6
| Example No. | Structure | Name | MS (M + 1) |
|---|---|---|---|
| 6B | 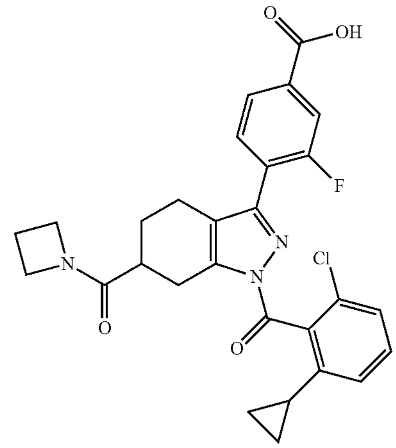 [SMILES: O=C(O)c1ccc(-c2nn(C(=O)c3c(Cl)cccc3C3CC3)c3c2CCC(C(=O)N2CCC2)C3)c(F)c1] | 4-(6-(azetidine-1-carbonyl)-1-(2-chloro-6-cyclopropylbenzoyl)-4,5,6,7-tetrahydro-1H-indazol-3-yl)-3-fluorobenzoic acid | 522 |
| 6C | 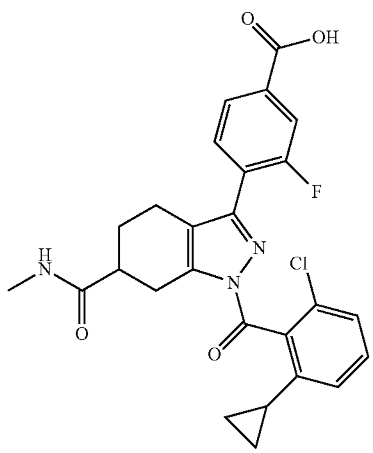 [SMILES: CNC(=O)C1CCc2c(-c3ccc(C(=O)O)cc3F)nn(C(=O)c3c(Cl)cccc3C3CC3)c2C1] | 4-(1-(2-chloro-6-cyclopropylbenzoyl)-6-(methylcarbamoyl)-4,5,6,7-tetrahydro-1H-indazol-3-yl)-3-fluorobenzoic acid | 496 |
Example 7A
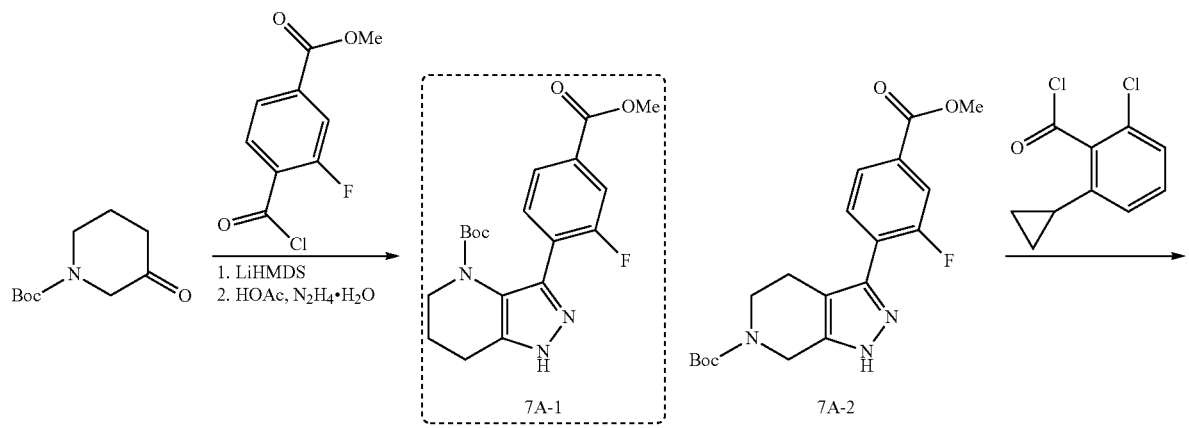

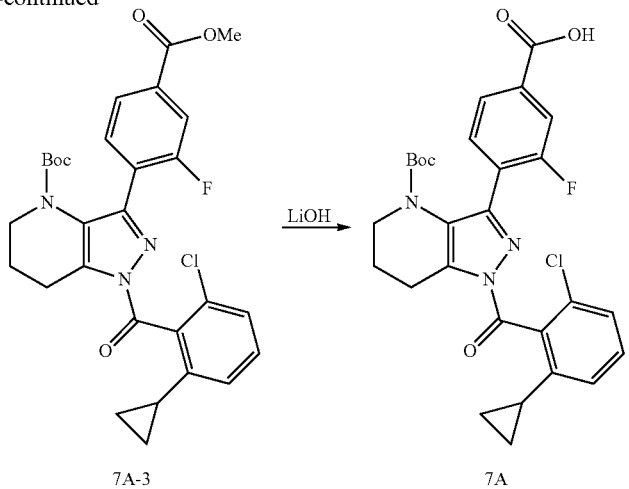

7A-3      7A

Step 1: tert-butyl 3-(2-fluoro-4-(methoxycarbonyl)phenyl)-6,7-dihydro-1H-pyrazolo[4,3-b]pyridine-4(5H)-carboxylate (7A-1)

To a solution of tert-butyl 3-oxopiperidine-1-carboxylate (221 mg, 1.11 mmol) in THF (10 mL) was added LiHMDS (185 mg, 1.11 mmol) at 0° C. After 15 min, i-9 (200 mg, 0.92 mmol) was added and the reaction mixture was stirred for 10 min. Acetic acid (1 mL) was added followed by addition of hydrazine (296 mg, 9.23 mmol). The reaction mixture was warmed slowly to 15° C. and further stirred for 1 hour. The reaction was quenched with aqueous NaHCO$_3$ and the mixture was extracted with ethyl acetate. The combined organic layers were washed with saturated brine dried over Na$_2$SO$_4$ and evaporated to give the crude product. The residue was purified prep-TLC (ethyl acetate/petroleum ether=2:3) to give two isomers:

tert-butyl 3-(2-fluoro-4-(methoxycarbonyl)phenyl)-6,7-dihydro-1H-pyrazolo[4,3-b]pyridine-4(5H)-carboxylate 7A-1. LCMS (ESI) calc'd for C$_9$H$_6$ClFO$_3$ [M+H]+: 376, found: 376. 1H NMR (400 MHz, CDCl$_3$) δ 7.64-7.82 (m, 3H), 6.37 (brs, 1H), 3.95 (s, 3H), 3.82 (brs, 2H), 2.86 (t, J=6.6 Hz, 2H), 1.97 (brs, 2H), 1.46 (s, 9H).

tert-butyl 3-(2-fluoro-4-(methoxycarbonyl)phenyl)-4,5-dihydro-1H-pyrazolo[3,4-c]pyridine-6(7H)-carboxylate 7A-2. LCMS (ESI) calc'd for C$_9$H$_6$ClFO$_3$ [M+H]+: 376, found: 376. 1H NMR (400 MHz, CDCl$_3$) 8.21 (t, J=8.0 Hz, 1H), 7.92 (t, J=9.4 Hz, 1H), 7.84 (t, J=12.4 Hz, 1H), 6.09 (brs, 1H), 4.66 (s, 1H), 3.96 (s, 4H), 3.56-3.86 (m, 2H), 2.77-2.88 (m, 2H), 1.46 (s, 9H).

Step 2: tert-butyl 1-(2-chloro-6-cyclopropylbenzoyl)-3-(2-fluoro-4-(methoxycarbonyl) phenyl)-6,7-dihydro-1H-pyrazolo[4,3-b]pyridine-4(5H)-carboxylate (7A-2)

To a solution of 7A-1 (20 mg, 0.05 mmol) in DMF (3 mL) was added sodium hydride (60% in mineral oil, 6.39 mg, 0.16 mmol) at 0° C. After stirring for 30 min, i-5a-1 (17 mg, 0.08 mmol) was added at 0° C. and the reaction mixture was warmed slowly to room temperature (~15° C.) and further stirred for 30 min. The reaction mixture was quenched by saturated aqueous NH$_4$Cl and extracted with EtOAc. The combined organic layers were washed by saturated brine, then dried over sodium sulfate and evaporated. The crude product was purified by prep-TLC (ethyl acetate/petroleum ether=4:1) to give the title compound. LCMS (ESI) calc'd for C$_{29}$H$_{29}$ClFN$_3$O$_5$ [M+H]+: 554, found: 554.

Step 3: 4-(4-(tert-butoxycarbonyl)-1-(2-chloro-6-cyclopropylbenzoyl)-4,5,6,7-tetrahydro-1H-pyrazolo[4,3-b]pyridin-3-yl)-3-fluorobenzoic acid (7A)

To a solution of 7A-2 (20 mg, 0.04 mmol) in acetonitrile (2 mL) and water (1 mL) was added lithium hydroxide (4.5 mg, 0.18 mmol) at 0° C. The mixture was warmed to room temperature and stirred for 18 h. The resulting mixture was acidified with 2N HCl and then extracted with EtOAc. The combined organic layers were dried with anhydrous Na$_2$SO$_4$, filtered and the solvent was evaporated under reduced pressure. The residue was purified by Prep-HPLC, eluting with acetonitrile/water+0.10% TFA 45-95% to give the title compound. LCMS (ESI) calc'd for C$_{28}$H$_{27}$ClFN$_3$O$_5$ [M+H]+: 540, found: 540. 1H NMR (400 MHz, Methanol-d$_4$) δ 7.80 (d, J=7.8 Hz, 1H), 7.70 (d, J=9.4 Hz, 1H), 7.59 (brs, 1H), 7.39 (t, J=7.8 Hz, 1H), 7.31 (d, J=8.0 Hz, 1H), 7.07 (d, J=7.4 Hz, 1H), 3.84 (brs, 2H), 3.36 (t, J=6.0 Hz, 2H), 2.04 (s, 2H), 1.79-1.80 (m, 1H), 1.08 (s, 9H), 0.88-0.93 (m, 1H), 0.73-0.82 (m, 2H), 0.61-0.62 (m, 1H).

Example 8A

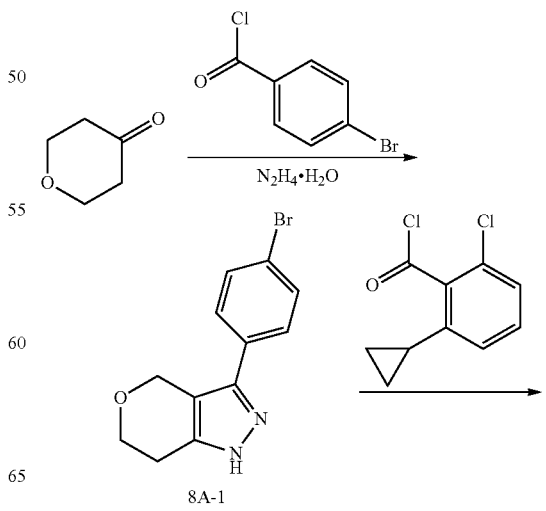

8A-1

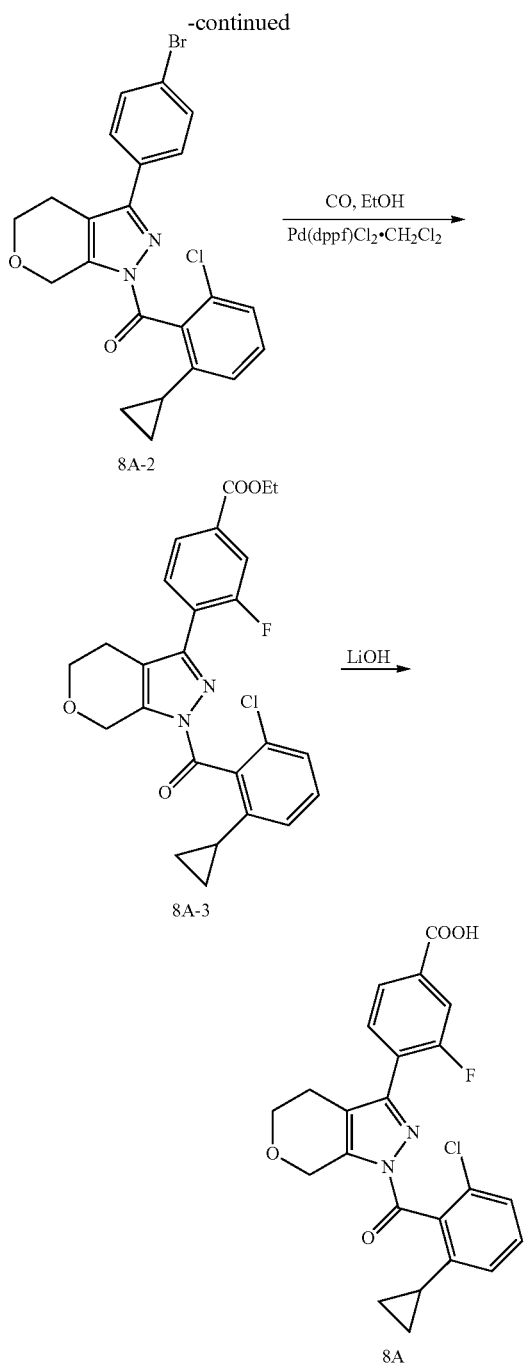

(25 mL) were added respectively. Then N₂H₄H₂O (8.58 g, 171.30 mmol) was added and the mixture was refluxed for 20 minutes. The resulting solution was poured into 1.0 M NaOH (a.q.) and extracted with EA. The organic phase was washed with brine, dried over Na₂SO₄ and concentrated. The residue was purified by column chromatography (DCM:EA=5:1) to afford the title compound. LCMS (ESI) calc'd for $C_{12}H_{11}BrN_2O$ [M+H]⁺: 279, found: 279.

Step 2: (3-(4-bromophenyl)-6,7-dihydropyrano[4,3-c]pyrazol-1(4H)-yl)(2-chloro-6-cyclopropylphenyl)methanone (8A-2)

A solution of 8A-1 (200 mg, 0.72 mmol) in DMF (1 mL) was added dropwise to a mixture of NaH (37.25 mg, 0.93 mmol, 60% in oil) in DMF (3 mL) at 0° C. After stirring for 0.5 h, i-5a-1 (185 mg, 0.86 mmol) in DMF (1 mL) was added drop wise. The resulting mixture was stirred at 0° C. for 2 hours. After diluted with water, the mixture was extracted with EtOAc. The organic layer was separated and dried over Na₂SO₄ and concentrated. The residue was purified by prep-TLC (PE:EA=5:1) to afford the title compound.

Step 3: ethyl 4-(1-(2-chloro-6-cyclopropylbenzoyl)-1,4,6,7-tetrahydropyrano[4,3-c]pyrazol-3-yl)benzoate (8A-3)

To a mixture of 8A-2 (87 mg, 0.19 mmol) and Et₃N (58 mg, 0.57 mmol) in EtOH (10 mL) was added Pd(dppf)Cl₂·CH₂Cl₂ (13 mg, 0.19 mmol). The resulting mixture was stirred at 60° C. under CO (50 Psi) atmosphere overnight. The resulting mixture was concentrated and purified by prep-TLC (PE:EA=10:1) to afford the title compound. LCMS (ESI) calc'd for $C_{25}H_{23}ClN_2O_4$ [M+H]⁺: 451, found: 451.

Step 4: 4-(1-(2-chloro-6-cyclopropylbenzoyl)-1,4,6,7-tetrahydropyrano[4,3-c]pyrazol-3-yl)benzoic acid (8A)

A mixture of 8A-3 (30 mg, 0.07 mmol) and LiOH.H₂O (12 mg, 0.27 mmol) in THF and H₂O (2 mL and 0.5 mL) was stirred at 0° C. to room temperature for 3 hours. After diluted with water, the mixture was extracted with EtOAc. The organic phase was dried over Na₂SO₄ and concentrated. The residue was purified by prep-TLC (DCM:MeOH=20:1) to afford title compound. LCMS (ESI) calc'd for $C_{23}H_{19}ClN_2O_4$ [M+H]+: 423, found: 423. ¹H NMR (Methanol-d₄, 400 MHz) δ 8.03 (d, J=7.8 Hz, 2H), 7.59 (d, J=7.8 Hz, 2H), 7.38-7.43 (m, 1H), 7.29-7.36 (m, 1H), 7.10 (d, J=7.8 Hz, 1H), 4.92 (brs, 2H), 4.04 (brs, 2H), 1.74-1.88 (m, 1H), 1.28 (brs, 1H), 0.89 (d, J=7.0 Hz, 2H), 0.76 (t, J=6.1 Hz, 2H), 0.59-0.64 (m, 1H).

Example 9A 4-(1-(2-chloro-6-cyclopropylbenzoyl)-1,4,6,7-tetrahydropyrano[4,3-c]pyrazol-3-yl)benzoic acid Step 1: 3-(4-bromophenyl)-1,4,6,7-tetrahydropyrano[4,3-c]pyrazole (8A-1)

A mixture of dihydro-2H-pyran-4(3H)-one (1 g, 10 mmol) in toluene (20 mL) was cooled to 0° C. under N₂ and then LiHMDS (10.5 mL, 1.0 M in THF, 10.5 mmol) was added quickly and the resulting mixture was stirred for 1 minute followed by addition of 4-bromobenzoyl chloride (1.10 g, 4.99 mmol) dissolved in toluene (5 mL). After stirred for 1 minute, AcOH (10 mL), EtOH (50 mL) and THF

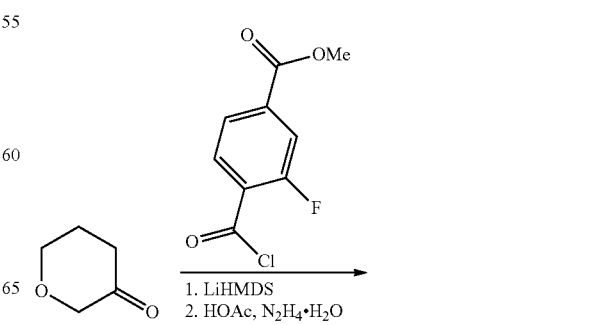

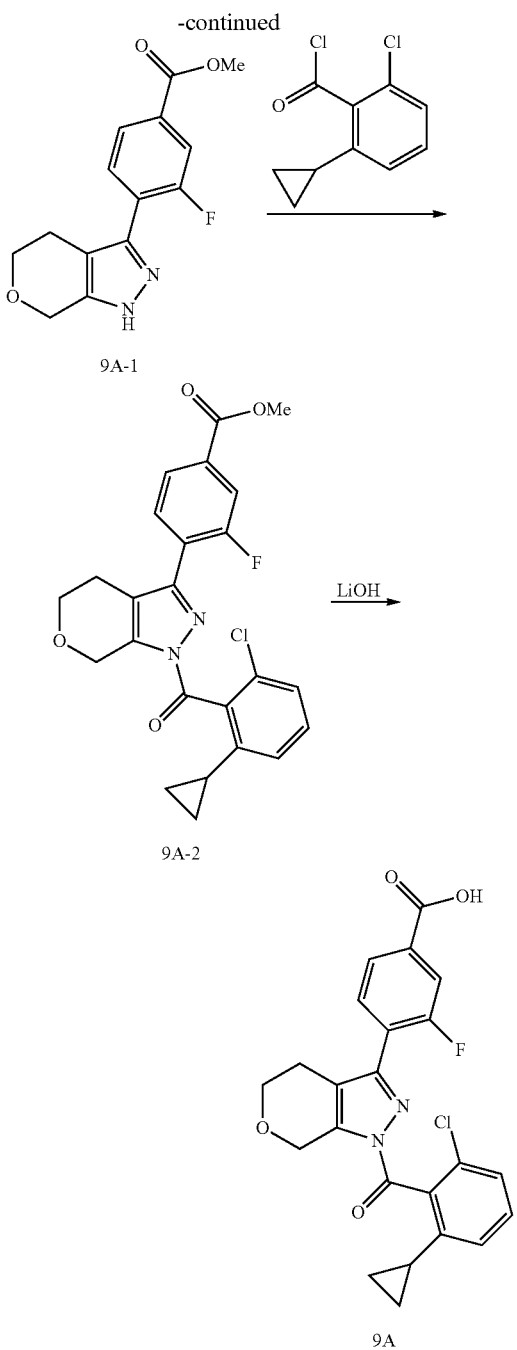

9A-1

9A-2

9A 4-(1-(2-chloro-6-cyclopropylbenzoyl)-1,4,5,7-tetrahydropyrano[3,4-c]pyrazol-3-yl)-3-fluorobenzoic acid Step 1: methyl 3-fluoro-4-(1,4,5,7-tetrahydropyrano[3,4-c]pyrazol-3-yl)benzoate (9A-1)

To a solution of dihydro-2H-pyran-3(4H)-one (100 mg, 1.0 mmol) in dry THF (10 mL) was added lithium bis(trimethylsilyl)amide (1.2 mL, 1.2 mmol, 1M in THF) at 0° C. After stirring for 5 min, i-9 (260 mg, 1.2 mmol) was added and stirred for additional 5 min. Acetic acid (1 mL) was added followed by addition of hydrazine monohydrate (1 mL, 85%). The reaction was quenched with aqueous NaHCO₃ and the mixture was extracted with EtOAc. The combined organic layers were washed with saturated brine, dried over Na₂SO₄ and concentrated. The residue was purified by prep TLC (EtOAc/PE=1:1) to give the title compound. LCMS (ESI) calc'd for C14H13FN2O3[M+H]+: 277, found: 277.

Step 2: methyl 4-(1-(2-chloro-6-cyclopropylbenzoyl)-1,4,5,7-tetrahydropyrano[3,4-c]pyrazol-3-yl)-3-fluorobenzoate (9A-2)

To a solution of 9A-1 (100 mg, 0.362 mmol) in dry N,N-Dimethylformamide (5 mL) was added sodium hydride (10.4 mg, 0.434 mmol, 60% in mineral oil) at 0° C. After stirring for 30 min at 0° C., i-5a-1 (78 mg, 0.362 mmol) was added and warmed slowly to room temperature and further stirred for 30 min. The reaction mixture was quenched by saturated aqueous NH₄Cl and extracted with EtOAc, the organic layers was washed by brine, then dried over sodium sulfate and evaporated to dryness. The crude product was purified by prep TLC (EtOAc/PE=1:2) to give the title compound. LCMS (ESI) calc'd for C24H20ClFN2O4 [M+H]+: 455, found: 455.

Step 3: 4-(1-(2-chloro-6-cyclopropylbenzoyl)-1,4,5,7-tetrahydropyrano[3,4-c]pyrazol-3-yl)-3-fluorobenzoic acid (9A)

To a solution of 9A-2 (30 mg, 0.066 mmol) in acetonitrile (2 mL) and water (2 mL) at 0° C. was added LiOH.H₂O (8 mg, 0.198 mmol), the mixture was warmed to room temperature and stirred for 1 h. The reaction mixture was concentrated and the residue was purified by the residue was purified by Prep-HPLC, eluting with acetonitrile/water+0.05% TFA 35-90%, to afford the title compound. LCMS (ESI) calc'd for C23H18ClFN2O4 [M+H]+: 441, found: 441. ¹H NMR (400 MHz, methanol-d4) δ 7.83 (1H, d, J=8.0 Hz), 7.78 (1H, d, J=11.2 Hz), 7.58 (1H, t, J=7.2 Hz), 7.37 (1H, t, J=8.0 Hz), 7.0 (1H, d, J=8.0 Hz), 7.07 (1H, d, J=7.6 Hz), 5.17 (2H, s), 3.92 (2H, t, J=5.2 Hz), 2.69 (2H, s), 1.75-1.82 (1H, m), 0.88-0.90 (1H, m), 0.73-0.78 (2H, m), 0.58-0.61 (1H, m).

The following example shown in Table 7 was prepared following similar procedures described for Example 9A which can be achieved by those of ordinary skill in the art of organic synthesis.

TABLE 7

| Example No. | Structure | IUPAC Name | Exact Mass [M + H]+ |
|---|---|---|---|
| 9B | (structure shown) | 4-[1-({2-chloro-6-[1-(trifluoromethyl)cyclopropyl]phenyl}carbonyl)-1,4,5,7-tetrahydropyrano[3,4-c]pyrazol-3-yl]-3-fluorobenzoic acid | 509 |

Example 10A

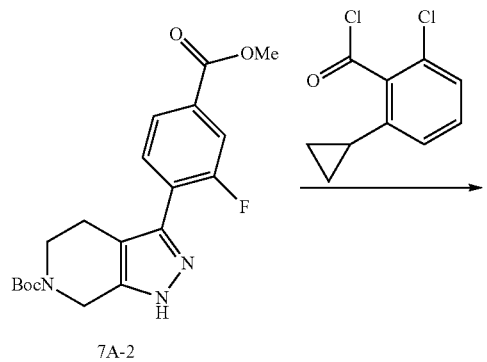

7A-2

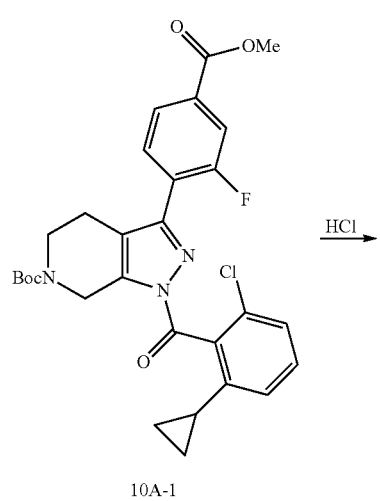

10A-1

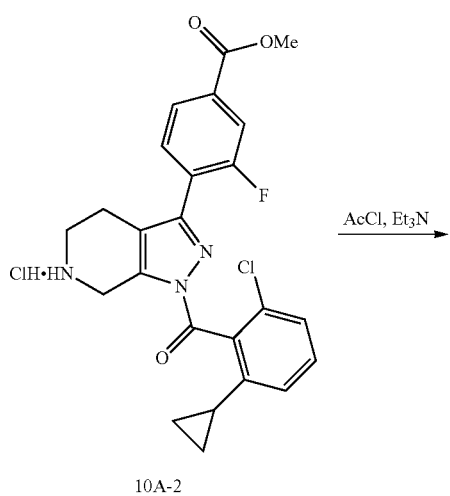

10A-2

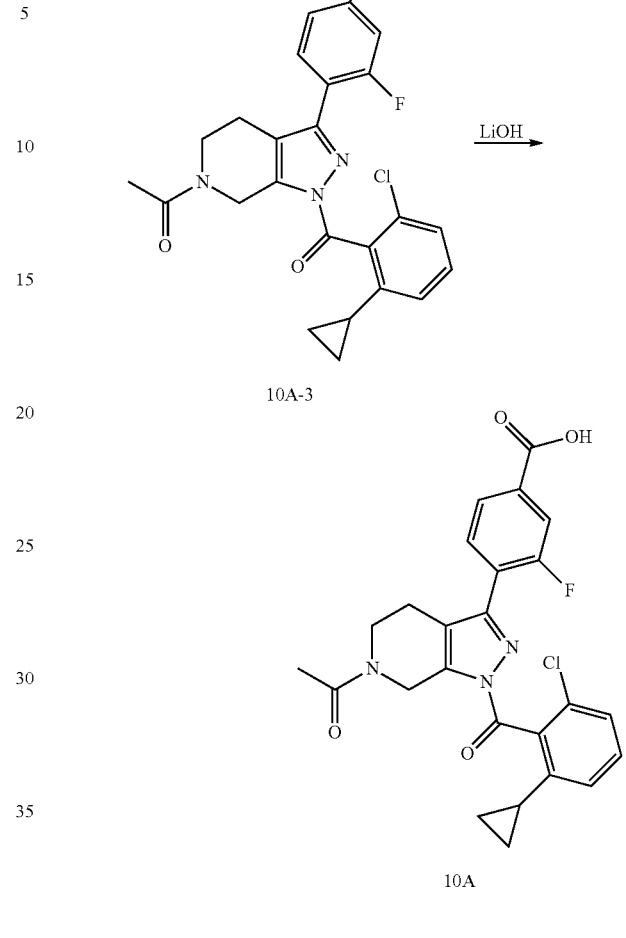

10A-3

10A 4-(6-acetyl-1-(2-chloro-6-cyclopropylbenzoyl)-4,5,6,7-tetrahydro-1H-pyrazolo[3,4-c]pyridin-3-yl)-3-fluorobenzoic acid Step 1: tert-butyl 1-(2-chloro-6-cyclopropylbenzoyl)-3-(2-fluoro-4-(methoxycarbonyl) phenyl)-4,5-dihydro-1H-pyrazolo[3,4-c]pyridine-6(7H)-carboxylate (10A-1)

To a solution of tert-butyl 3-(2-fluoro-4-(methoxycarbonyl)phenyl)-4,5-dihydro-1H-pyrazolo[3,4-c]pyridine-6(7H)-carboxylate (7A-2) (40 mg, 0.107 mmol) in dry DMF (5 mL) was added sodium hydride (60% in mineral oil, 8.5 mg, 0.214 mmol) at 0° C. After stirring for 30 min at 0° C., i-5a-1 (26 mg, 0.161 mmol) was added. The reaction was warmed slowly to 20° C. and further stirred for 30 min. The reaction mixture was quenched by saturated aqueous NH₄Cl and extracted with EtOAc, the combined organic layers were washed by brine, then dried over sodium sulfate and evaporated. The crude product was purified by prep-TLC (ethyl acetate/petroleum ether=4:1) to give the title compound. LCMS (ESI) calc'd for $C_{29}H_{29}ClFN_3O_5$ [M+H]⁺: 554, found: 554.

Step 2: methyl 4-(1-(2-chloro-6-cyclopropylbenzoyl)-4,5,6,7-tetrahydro-1H-pyrazolo[3,4-c]pyridin-3-yl)-3-fluorobenzoate hydrochloride (10A-2)

To a solution of 10A-1 (100 mg, 0.180 mml) in EtOAc (10 ml) was added hydrochloric acid ethyl acetate (4 mL, 4M) slowly at 0° C. The suspension was warmed to 20° C. and stirred for 30 minutes. The mixture was concentrated in vacuo to give crude product. LCMS (ESI) calc'd for $C_{24}H_{22}C_{12}FN_3O_3[M+H]^+$: 454.1, found: 454.1.

Step 3: methyl 4-(6-acetyl-1-(2-chloro-6-cyclopropylbenzoyl)-4,5,6,7-tetrahydro-1H-pyrazolo[3,4-c]pyridin-3-yl)-3-fluorobenzoate (10A-3)

To a solution of 10A-2 (30 mg, 0.061 mml) and triethylamine (24.6 mg, 0.244 mml) in DCM (5 ml) was added acetyl chloride (14.3 mg, 0.183 mml) slowly at 0° C. The suspension was warmed to 20° C. and stirred for 30 minutes. Then the mixture was concentrated in vacuo, diluted with water and extracted with EtOAc. The organic layers dried over $Na_2SO_4$, filtered and evaporated to dryness. The residue was purified by prep-TLC (ethyl acetate/petroleum ether=2:3) to give title compound. LCMS (ESI) calc'd for $C_{26}H_{23}ClFN_3O_4$ $[M+H]^+$: 496.1, found: 496.1.

Step 4: 4-(6-acetyl-1-(2-chloro-6-cyclopropylbenzoyl)-4,5,6,7-tetrahydro-1H-pyrazolo[3,4-c]pyridin-3-yl)-3-fluorobenzoic acid (10A)

At 0° C., to a solution of 10A-3 (15 mg, 0.030 mml) in acetonitrile (2 ml) and water (1 ml) was added lithium hydroxide (2.1 mg, 0.091 mmol). The mixture was warmed to room temperature and stirred for 12 hrs. Then the reaction mixture was diluted with water, acidified with acetic acid (1 mL) and extracted with EtOAc. The organic layers dried over $Na_2SO_4$ and evaporated to dryness. The residue was purified by prep-HPLC, eluting with Acetonitrile/Water+ 0.10% TFA 45-95% to afford the title compound. LCMS (ESI) calc'd for $C_{25}H_{21}ClFN_3O_4$ $[M+H]^+$: 482.1, found: 482.0; $^1$H NMR (400 MHz, Methanol-d$_4$) δ 7.76-7.84 (m, 2H), 7.54-7.56 (m, 1H), 7.35-7.37 (m, 1H), 7.29-7.31 (m, 1H), 7.06-7.08 (m, 1H), 5.16-5.20 (m, 2H), 3.80-3.86 (m, 2H), 2.64 (s, 2H), 2.24 (s, 3H), 1.74-1.80 (m, 1H), 0.86-0.89 (m, 1H), 0.74-0.75 (m, 2H), 0.57-0.60 (m, 1H).

Example 11A

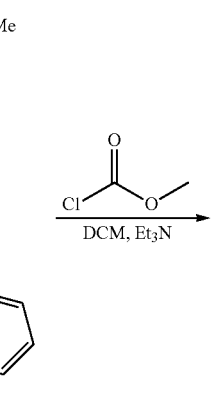

10A-2

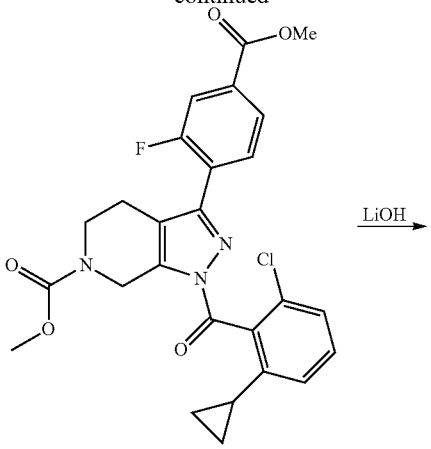

11A-1

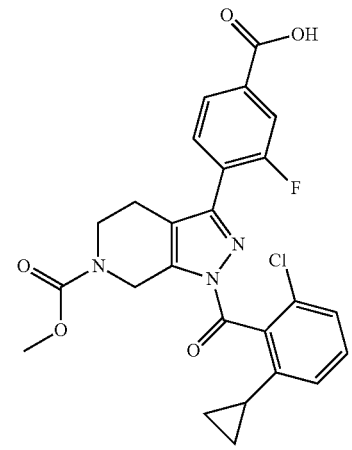

11A 4-(1-(2-chloro-6-cyclopropylbenzoyl)-6-(methoxycarbonyl)-4,5,6,7-tetrahydro-1H-pyrazolo[3,4-c]pyridin-3-yl)-3-fluorobenzoic acid

Step 1: methyl 1-(2-chloro-6-cyclopropylbenzoyl)-3-(2-fluoro-4-(methoxycarbonyl)phenyl)-4,5-dihydro-1H-pyrazolo[3,4-c]pyridine-6(7H)-carboxylate (11A-1)

To a solution of 10A-2 (30 mg, 0.066 mmol) in DCM (15 ml) was added Et3N (0.037 ml, 0.264 mmol) and methyl carbonochloridate (9.37 mg, 0.099 mmol) at 0° C. The mixture was stirred at 0° C. for 1 h. The mixture was concentrated under reduced pressure, and then purified by column chromatography on silica gel (PE:EA=5:1) to give title compound. LCMS (ESI) calc'd for $C_{26}H_{23}ClFN_3O_5$ $[M+H]^+$: 512.1, found: 512.1.

Step 2: 4-(1-(2-chloro-6-cyclopropylbenzoyl)-6-(methoxycarbonyl)-4,5,6,7-tetrahydro-1H-pyrazolo[3,4-c]pyridin-3-yl)-3-fluorobenzoic acid (11A)

At 0° C., to a solution of 11A-1 (20 mg, 0.039 mml) in ACN (3 ml) and water (1 ml) was added lithium hydroxide (2.8 mg, 0.117 mmol). The mixture was warmed to room temperature and stirred for 12 hrs. The reaction mixture was diluted with water, acidified with acetic acid (1 mL) and extracted with EtOAc. The organic layers dried over $Na_2SO_4$ and evaporated to dryness. The residue was purified by prep-HPLC, eluting with acetonitrile/water+0.10% TFA 45-95% to afford title compound. LCMS (ESI) calc'd for $C_{25}H_{21}ClFN_3O_5$ [M+H]$^+$: 498.1, found: 498.2; $^1$H NMR (400 MHz, Methanol-$d_4$) δ 7.76-7.83 (m, 2H), 7.53-7.54 (m, 1H), 7.35-7.37 (m, 1H), 7.28-7.30 (m, 1H), 7.05-7.07 (d, J=7.6 Hz, 1H), 5.09 (s, 2H), 3.74-3.85 (m, 5H), 2.65 (s, 2H), 1.75-1.80 (m, 1H), 0.86-0.90 (m, 1H), 0.74-0.76 (m, 2H), 0.58-0.59 (m, 1H).

Examples 12A-A/12A-B

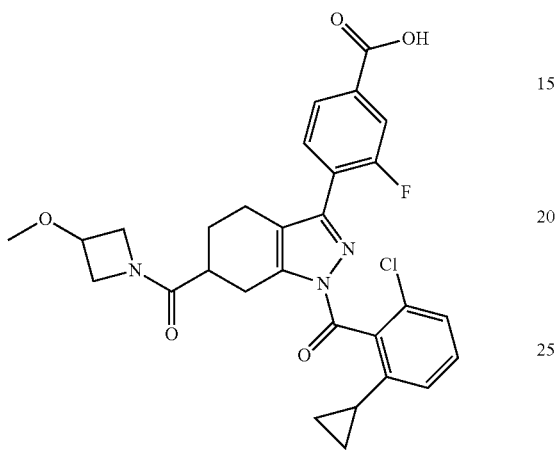

Examples 12A-A and 12A-B were synthesized in a similar fashion to example 6A with resolution of enantiomers achieved after amide coupling by SFC purification using a Chiralcel OJ-H, 21×250 (mm) column, at 70 mL/min with a 20% $CO_2$ in methanol (with +0.25 diemthyl ethylamine) acetonitrile solvent system. Retention times were 3.8 minutes for Peak 1 & 5.25 minutes for Peak 2. Peak 1 was advanced on to give title compound 12A-A. Peak 2 was advanced on to give title compound 12A-B.

The following examples shown in Table 8 were prepared following similar procedures described for Example 12A-A which can be achieved by those of ordinary skill in the art of organic synthesis.

TABLE 8

| Example No. | Structure | Name | MS (M + 1) |
| --- | --- | --- | --- |
| 12A-A | 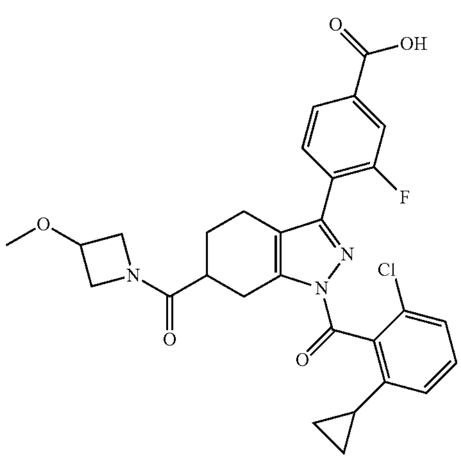 [SMILES: COC1CN(C(=O)C2CCc3c(-c4ccc(C(=O)O)cc4F)nn(C(=O)c4c(Cl)cccc4C4CC4)c3C2)C1] | 4-(1-(2-chloro-6-cyclopropylbenzoyl)-6-(3-methoxyazetidine-1-carbonyl)-4,5,6,7-tetrahydro-1H-indazol-3-yl)-3-fluorobenzoic acid | 552 |

TABLE 8-continued

| Example No. | Structure | Name | MS (M + 1) |
|---|---|---|---|
| 12A-B | 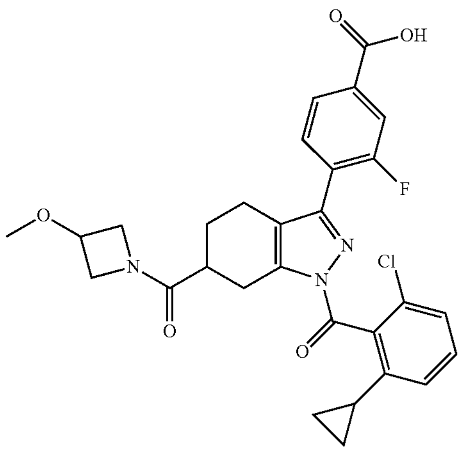 [SMILES: COC1CN(C(=O)C2CCc3c(-c4ccc(C(=O)O)cc4F)nn(C(=O)c4c(Cl)cccc4C4CC4)c3C2)C1] | 4-(1-(2-chloro-6-cyclopropylbenzoyl)-6-(3-methoxyazetidine-1-carbonyl)-4,5,6,7-tetrahydro-1H-indazol-3-yl)-3-fluorobenzoic acid | 552 |
| 13A-A | 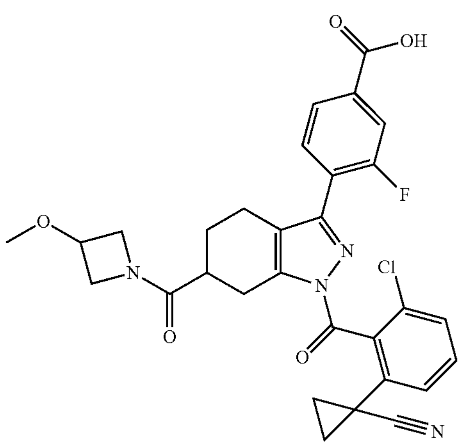 [SMILES: COC1CN(C(=O)C2CCc3c(-c4ccc(C(=O)O)cc4F)nn(C(=O)c4c(Cl)cccc4C4(C#N)CC4)c3C2)C1] | 4-(1-(2-chloro-6-(1-cyanocyclopropyl)benzoyl)-6-(3-methoxyazetidine-1-carbonyl)-4,5,6,7-tetrahydro-1H-indazol-3-yl)-3-fluorobenzoic acid | 577 |
| 13A-B | 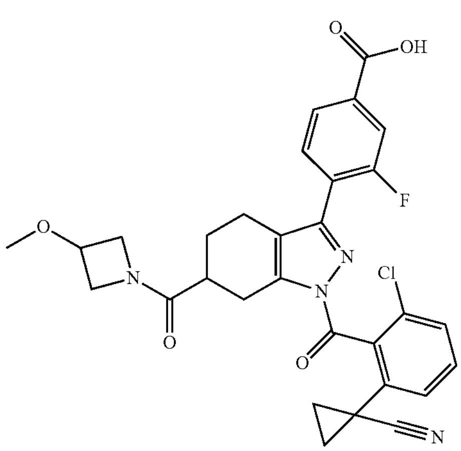 [SMILES: COC1CN(C(=O)C2CCc3c(-c4ccc(C(=O)O)cc4F)nn(C(=O)c4c(Cl)cccc4C4(C#N)CC4)c3C2)C1] | 4-(1-(2-chloro-6-(1-cyanocyclopropyl)benzoyl)-6-(3-methoxyazetidine-1-carbonyl)-4,5,6,7-tetrahydro-1H-indazol-3-yl)-3-fluorobenzoic acid | 577 |

TABLE 8-continued

| Example No. | Structure | Name | MS (M + 1) |
|---|---|---|---|
| 14A-A | 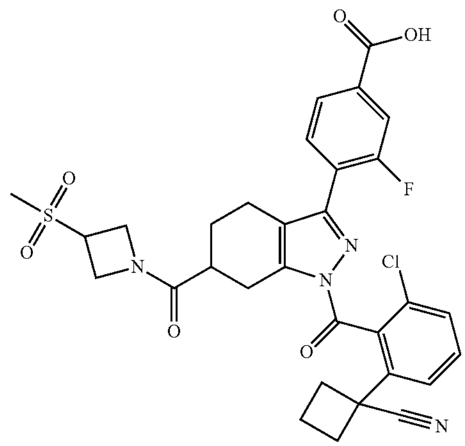 [SMILES: CS(=O)(=O)C1CN(C(=O)C2CCc3c(-c4ccc(C(=O)O)cc4F)nn(C(=O)c4c(Cl)cccc4C4(C#N)CCC4)c3C2)C1] | 4-(1-(2-chloro-6-(1-cyanocyclobutyl)benzoyl)-6-(3-(methylsulfonyl)azetidine-1-carbonyl)-4,5,6,7-tetrahydro-1H-indazol-3-yl)-3-fluorobenzoic acid | 639 |
| 14A-B | 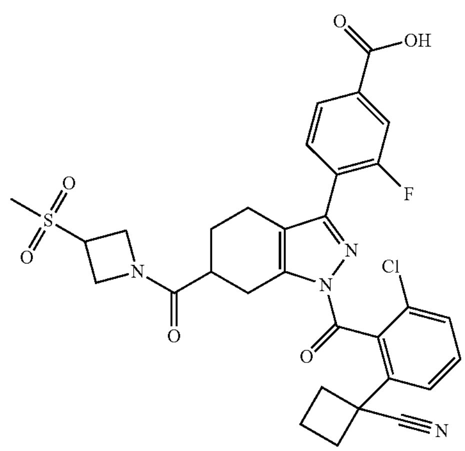 [SMILES: CS(=O)(=O)C1CN(C(=O)C2CCc3c(-c4ccc(C(=O)O)cc4F)nn(C(=O)c4c(Cl)cccc4C4(C#N)CCC4)c3C2)C1] | 4-(1-(2-chloro-6-(1-cyanocyclobutyl)benzoyl)-6-(3-(methylsulfonyl)azetidine-1-carbonyl)-4,5,6,7-tetrahydro-1H-indazol-3-yl)-3-fluorobenzoic acid | 639 |
| 15A-A | 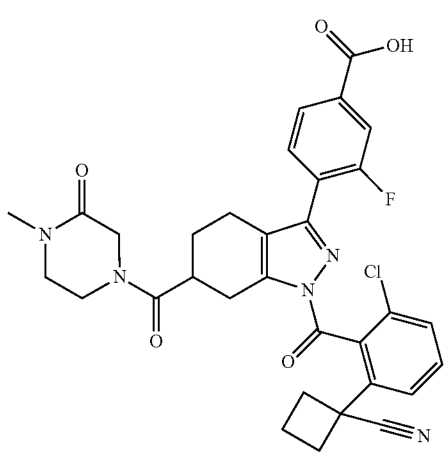 [SMILES: CN1CCN(C(=O)C2CCc3c(-c4ccc(C(=O)O)cc4F)nn(C(=O)c4c(Cl)cccc4C4(C#N)CCC4)c3C2)CC1=O] | 4-(1-(2-chloro-6-(1-cyanocyclobutyl)benzoyl)-6-(4-methyl-3-oxopiperazine-1-carbonyl)-4,5,6,7-tetrahydro-1H-indazol-3-yl)-3-fluorobenzoic acid | 618 |

TABLE 8-continued
| Example No. | Structure | Name | MS (M + 1) |
|---|---|---|---|
| 15A-B | 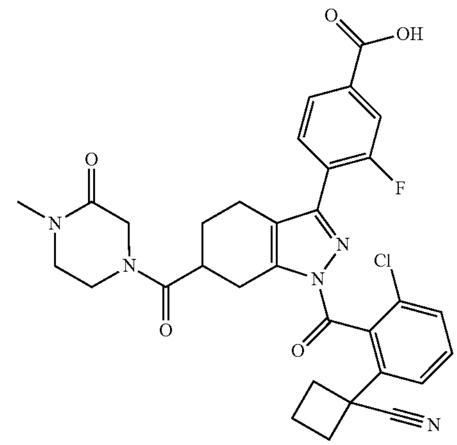 [SMILES: CN1CCN(C(=O)C2CCc3c(-c4ccc(C(=O)O)cc4F)nn(C(=O)c4c(Cl)cccc4C4(C#N)CCC4)c3C2)CC1=O] | 4-(1-(2-chloro-6-(1-cyanocyclobutyl)benzoyl)-6-(4-methyl-3-oxopiperazine-1-carbonyl)-4,5,6,7-tetrahydro-1H-indazol-3-yl)-3-fluorobenzoic acid | 618 |
| 16A-B | 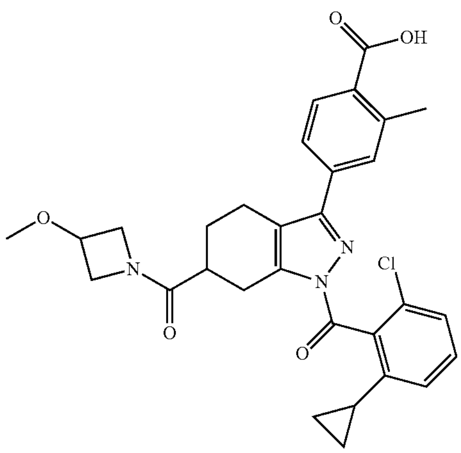 [SMILES: COC1CN(C(=O)C2CCc3c(-c4ccc(C(=O)O)c(C)c4)nn(C(=O)c4c(Cl)cccc4C4CC4)c3C2)C1] | 4-(1-(2-chloro-6-cyclopropylbenzoyl)-6-(3-methoxyazetidine-1-carbonyl)-4,5,6,7-tetrahydro-1H-indazol-3-yl)-2-methylbenzoic acid | 548 |
Example 17A
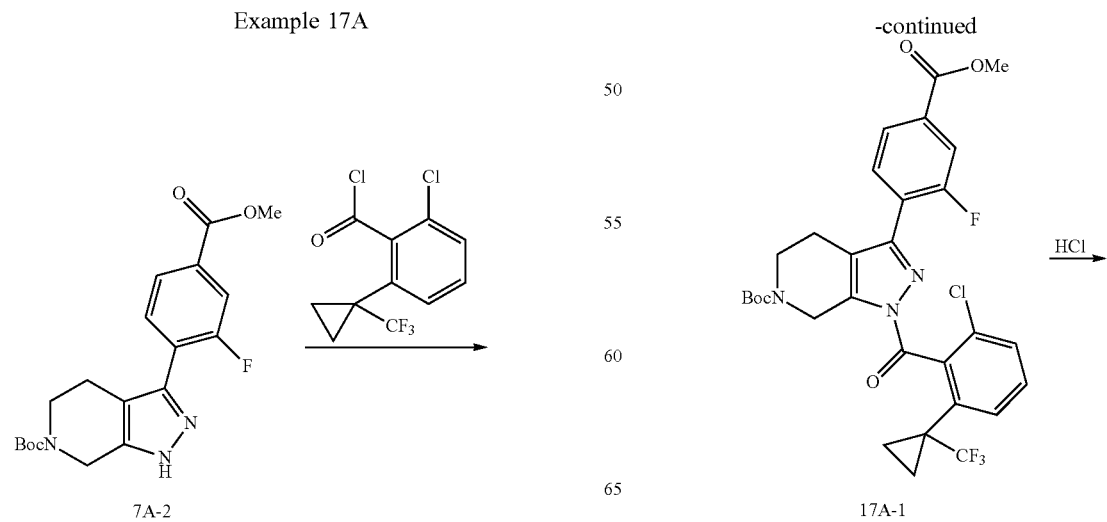

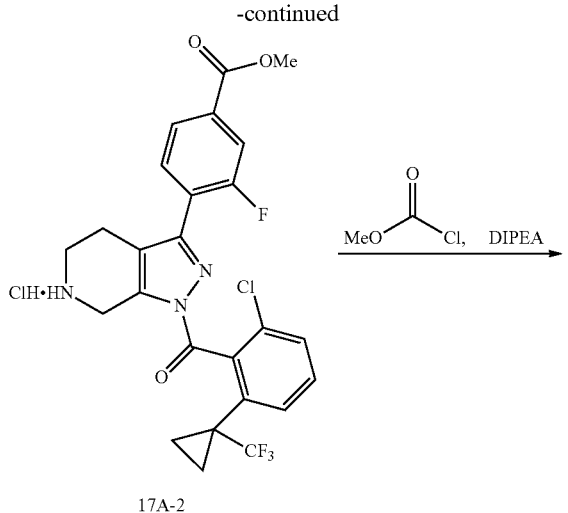

17A-2

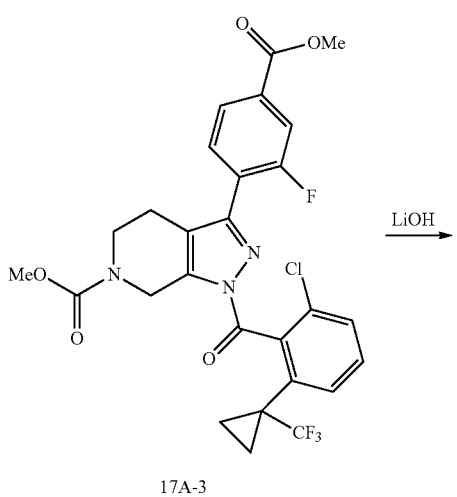

17A-3

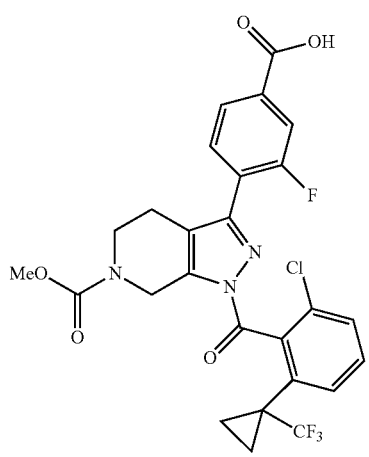

17A 4-(1-(2-chloro-6-(1-(trifluoromethyl)cyclopropyl)benzoyl)-6-(methoxycarbonyl)-4,5,6,7-tetrahydro-1H-pyrazolo[3,4-c]pyridin-3-yl)-3-fluorobenzoic acid Step 1: tert-butyl 1-(2-chloro-6-(1-(trifluoromethyl)cyclopropyl)benzoyl)-3-(2-fluoro-4-(methoxycarbonyl)phenyl)-1,4,5,7-tetrahydro-6H-pyrazolo[3,4-c]pyridine-6-carboxylate (17A-1)

To a solution of tert-butyl 3-(2-fluoro-4-(methoxycarbonyl)phenyl)-4,5-dihydro-1H-pyrazolo[3,4-c]pyridine-6(7H)-carboxylate (7A-2) (15 mg, 0.040 mmol) in DCM (80 µl) at room temperature was added 2-chloro-6-(1-(trifluoromethyl)cyclopropyl)benzoyl chloride (20.36 mg, 0.072 mmol), followed by Et$_3$N (16.71 µl, 0.120 mmol) and DMAP (9.76 mg, 0.080 mmol). The reaction mixture was stirred for 12 hours, then quenched and extracted with IPA/CHl$_3$ and saturated sodium bicarbonate. The separated organic layer was dried with sodium sulfate and concentrated. The crude product was purified by reverse phase HPLC (MeCN/water; TFA buffer) to afford the title compound as white solid. MS: 622 (M+1)

Step 2: methyl 4-(1-(2-chloro-6-(1-(trifluoromethyl)cyclopropyl)benzoyl)-4,5,6,7-tetrahydro-1H-pyrazolo[3,4-c]pyridin-3-yl)-3-fluorobenzoate hydrochloride (17A-2)

To a solution of 17A-1 (926 mg, 1.489 mmol) was added 4M HCl in dioxane (7444 µl, 29.8 mmol) and the reaction stirred at room temperature for 30 min. The mixture was concentrated in vacuo to give the crude product, which was taken forward without further purification. MS: 522 (M+1)

Step 3: methyl 1-(2-chloro-6-(1-(trifluoromethyl)cyclopropyl)benzoyl)-3-(2-fluoro-4-(methoxycarbonyl)phenyl)-1,4,5,7-tetrahydro-6H-pyrazolo[3,4-c]pyridine-6-carboxylate (17A-3)

To a solution of 17A-2 (20 mg, 0.036 mmol) was added methyl carbonochloridate (16.92 mg, 0.179 mmol) and DIPEA (0.063 mL, 0.358 mmol) in CH$_2$Cl$_2$ (1 mL). The mixture was stirred at room temperature for 1 h, then quenched with saturated NaHCO$_3$ and extracted 3× with IPA/CHCl$_3$. The organic layer was separated, dried over sodium sulfate and concentrated. The crude product was taken forward without further purification. MS: 580 (M+1)

Step 4: 4-(1-(2-chloro-6-(1-(trifluoromethyl)cyclopropyl)benzoyl)-6-(methoxycarbonyl)-4,5,6,7-tetrahydro-1H-pyrazolo[3,4-c]pyridin-3-yl)-3-fluorobenzoic acid (17A)

The crude methyl ester 17-A3 (21 mg, 0.036 mmol) was dissolved in 1,4-Dioxane (0.7 mL) and Water (0.3 mL), then treated with LiOH (4.29 mg, 0.179 mmol) for 30 min. Upon completion, the reaction was concentrated, dissolved in DMSO, filtered and purified by reverse phase HPLC (MeCN/water; TFA buffer) to afford the desired product as a white solid. MS: 566 (M+1); $^1$H NMR (400 MHz, DMSO-d$_6$) δ 7.82 (d, J=8.2 Hz, 1H), 7.76 (d, J=10.7 Hz, 1H), 7.65 (m, 3H), 7.53 (t, J=8.0 Hz, 1H), 5.02 (s, 2H), 3.71 (s, 3H), 3.40 (m, 2H), 2.62 (m, 2H), 1.38 (m, 1H), 1.29-1.18 (m, 2H), 0.82 (m, 1H).

The following carbamate examples shown in Table 9 were prepared following similar procedures described for Example 17-A which can be achieved by those of ordinary skill in the art of organic synthesis.

TABLE 9

| Example No. | Structure | Name | MS (M + 1) |
|---|---|---|---|
| 17-B | 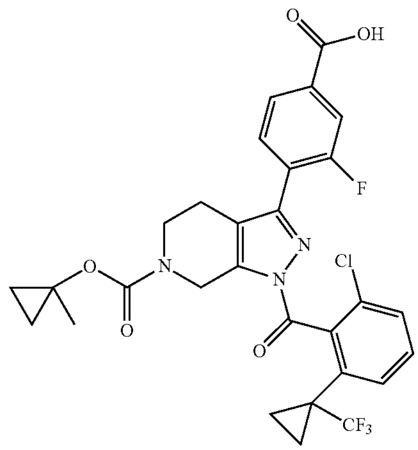 [SMILES: CC1(OC(=O)N2CCc3c(-c4ccc(C(=O)O)cc4F)nn(C(=O)c4c(Cl)cccc4C4(C(F)(F)F)CC4)c3C2)CC1] | 4-(1-(2-chloro-6-(1-(trifluoromethyl)cyclopropyl)benzoyl)-6-((1-methylcyclopropoxy)carbonyl)-4,5,6,7-tetrahydro-1H-pyrazolo[3,4-c]pyridin-3-yl)-3-fluorobenzoic acid | 606 |
| 17-C | 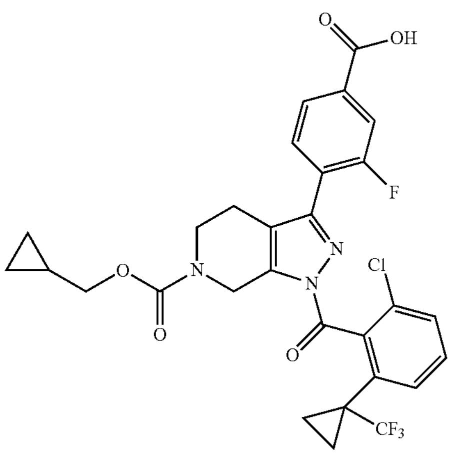 [SMILES: O=C(O)c1ccc(-c2nn(C(=O)c3c(Cl)cccc3C3(C(F)(F)F)CC3)c3c2CCN(C(=O)OCC2CC2)C3)c(F)c1] | 4-(1-(2-chloro-6-(1-(trifluoromethyl)cyclopropyl)benzoyl)-6-((cyclopropylmethoxy)carbonyl)-4,5,6,7-tetrahydro-1H-pyrazolo[3,4-c]pyridin-3-yl)-3-fluorobenzoic acid | 606 |
| 17-D | 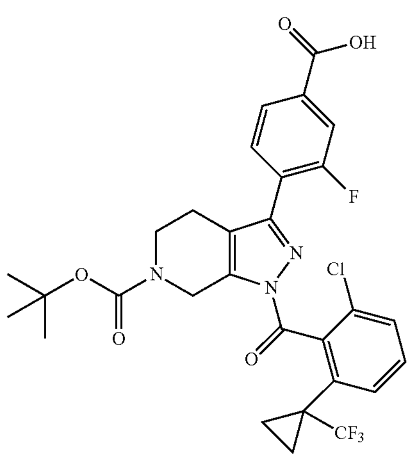 [SMILES: CC(C)(C)OC(=O)N1CCc2c(-c3ccc(C(=O)O)cc3F)nn(C(=O)c3c(Cl)cccc3C3(C(F)(F)F)CC3)c2C1] | 4-(6-(tert-butoxycarbonyl)-1-(2-chloro-6-(1-(trifluoromethyl)cyclopropyl)benzoyl)-4,5,6,7-tetrahydro-1H-pyrazolo[3,4-c]pyridin-3-yl)-3-fluorobenzoic acid | 577 |

The following urea examples shown in Table 10 were prepared using the corresponding carbamic chloride following similar procedures described for Example 17-A which can be achieved by those of ordinary skill in the art of organic synthesis.

TABLE 10

| Example No. | Structure | Name | MS (M + 1) |
|---|---|---|---|
| 18-A | 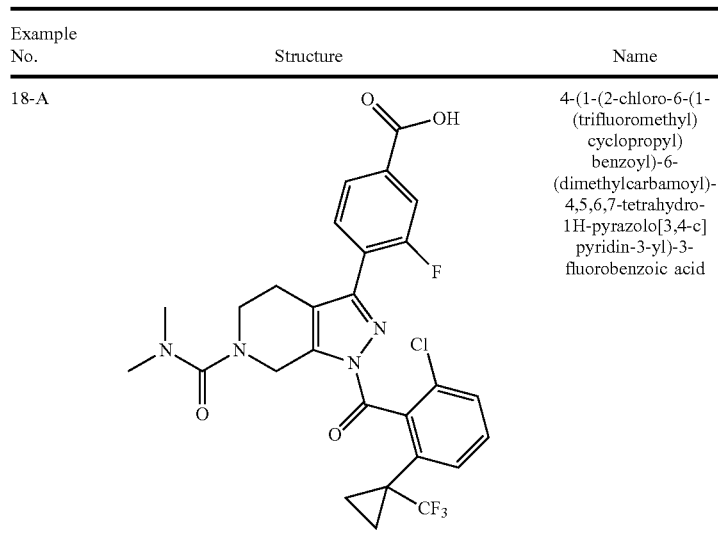 | 4-(1-(2-chloro-6-(1-(trifluoromethyl) cyclopropyl) benzoyl)-6-(dimethylcarbamoyl)-4,5,6,7-tetrahydro-1H-pyrazolo[3,4-c] pyridin-3-yl)-3-fluorobenzoic acid | 579 |
| 18-B | 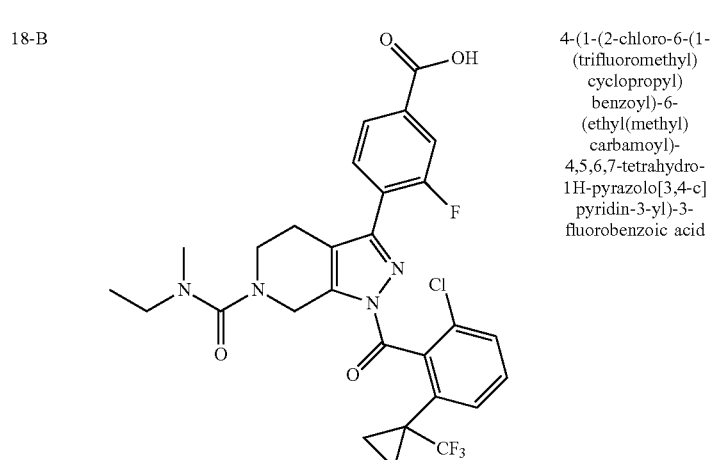 | 4-(1-(2-chloro-6-(1-(trifluoromethyl) cyclopropyl) benzoyl)-6-(ethyl(methyl) carbamoyl)-4,5,6,7-tetrahydro-1H-pyrazolo[3,4-c] pyridin-3-yl)-3-fluorobenzoic acid | 593 |
| 18-C | 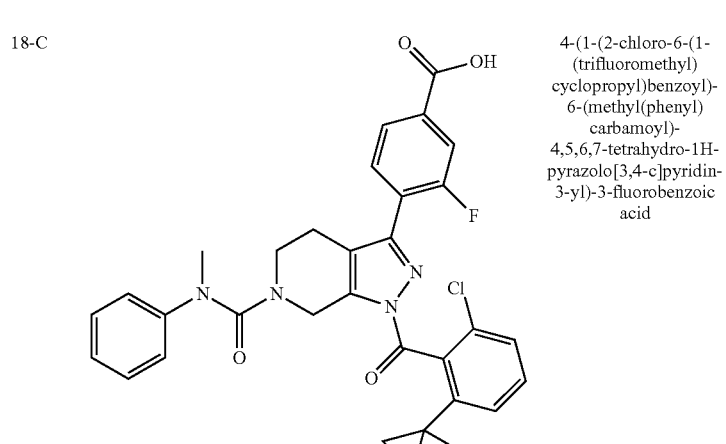 | 4-(1-(2-chloro-6-(1-(trifluoromethyl) cyclopropyl)benzoyl)-6-(methyl(phenyl) carbamoyl)-4,5,6,7-tetrahydro-1H-pyrazolo[3,4-c]pyridin-3-yl)-3-fluorobenzoic acid | 641 |

TABLE 10-continued

| Example No. | Structure | Name | MS (M + 1) |
| --- | --- | --- | --- |
| 18-D | 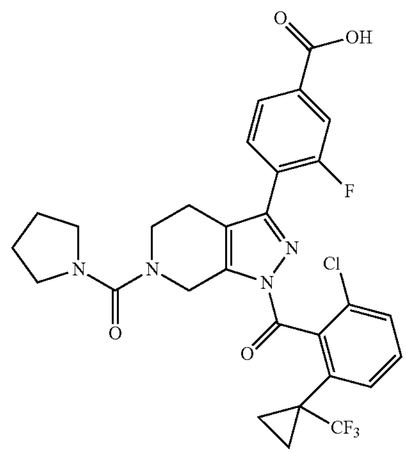 [SMILES: O=C(O)c1ccc(-c2nn(C(=O)c3c(Cl)cccc3C3(C(F)(F)F)CC3)c3c2CCN(C(=O)N2CCCC2)C3)c(F)c1] | 4-(1-(2-chloro-6-(1-(trifluoromethyl) cyclopropyl) benzoyl)-6-(pyrrolidine-1-carbonyl)-4,5,6,7-tetrahydro-1H-pyrazolo[3,4-c] pyridin-3-yl)-3-fluorobenzoic acid | 605 |
| 18-E | 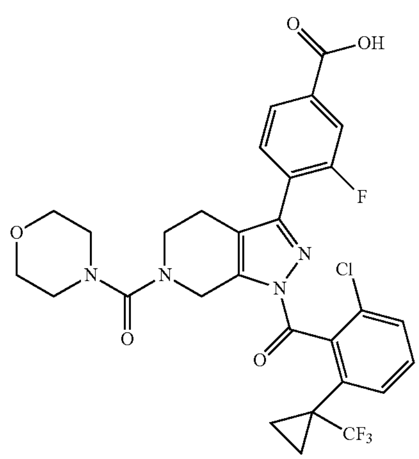 [SMILES: O=C(O)c1ccc(-c2nn(C(=O)c3c(Cl)cccc3C3(C(F)(F)F)CC3)c3c2CCN(C(=O)N2CCOCC2)C3)c(F)c1] | 4-(1-(2-chloro-6-(1-(trifluoromethyl) cyclopropyl) benzoyl)-6-(morpholine-4-carbonyl)-4,5,6,7-tetrahydro-1H-pyrazolo[3,4-c]pyridin-3-yl)-3-fluorobenzoic acid | 621 |
| 18-F | 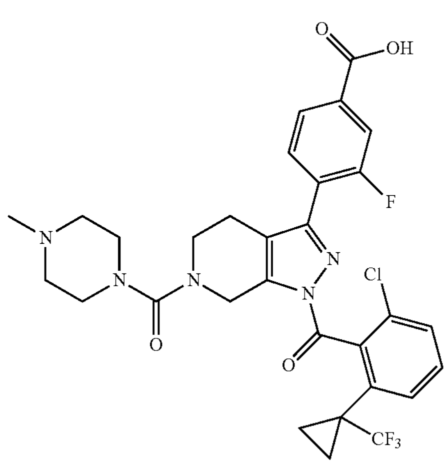 [SMILES: CN1CCN(C(=O)N2CCc3c(-c4ccc(C(=O)O)cc4F)nn(C(=O)c4c(Cl)cccc4C4(C(F)(F)F)CC4)c3C2)CC1] | 4-(1-(2-chloro-6-(1-(trifluoromethyl) cyclopropyl)benzoyl)-6-(4-methylpiperazine-1-carbonyl)-4,5,6,7-tetrahydro-1H-pyrazolo[3,4-c] pyridin-3-yl)-3-fluorobenzoic acid | 634 |

TABLE 10-continued

| Example No. | Structure | Name | MS (M + 1) |
|---|---|---|---|
| 18-G | 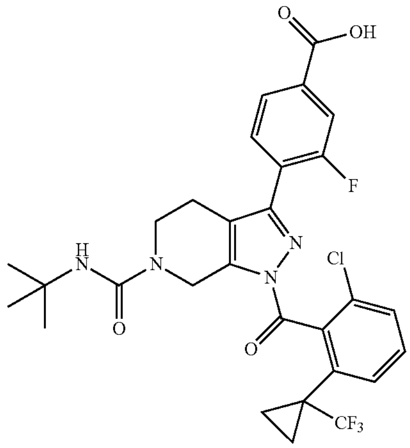 [SMILES: CC(C)(C)NC(=O)N1CCc2c(-c3ccc(C(=O)O)cc3F)nn(C(=O)c3c(Cl)cccc3C3(C(F)(F)F)CC3)c2C1] | 4-(6-(tert-butylcarbamoyl)-1-(2-chloro-6-(1-(trifluoromethyl)cyclopropyl)benzoyl)-4,5,6,7-tetrahydro-1H-pyrazolo[3,4-c]pyridin-3-yl)-3-fluorobenzoic acid | 607 |

The following alkyl amine examples shown in Table 11 were prepared using the corresponding alkyl halides following similar procedures described for Example 17-A which can be achieved by those of ordinary skill in the art of organic synthesis.

TABLE 11

| Example No. | Structure | Name | MS (M + 1) |
|---|---|---|---|
| 19-A | 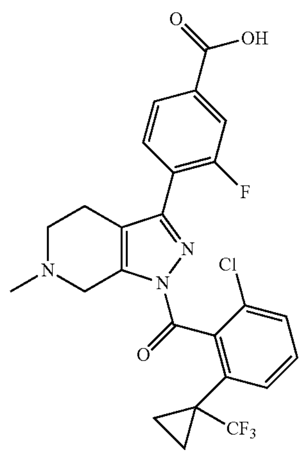 [SMILES: CN1CCc2c(-c3ccc(C(=O)O)cc3F)nn(C(=O)c3c(Cl)cccc3C3(C(F)(F)F)CC3)c2C1] | 4-(1-(2-chloro-6-(1-(trifluoromethyl)cyclopropyl)benzoyl)-6-methyl-4,5,6,7-tetrahydro-1H-pyrazolo[3,4-c]pyridin-3-yl)-3-fluorobenzoic acid | 522 |
| 19-B | 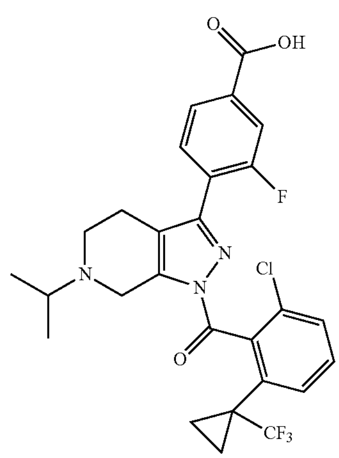 [SMILES: CC(C)N1CCc2c(-c3ccc(C(=O)O)cc3F)nn(C(=O)c3c(Cl)cccc3C3(C(F)(F)F)CC3)c2C1] | 4-(1-(2-chloro-6-(1-(trifluoromethyl)cyclopropyl)benzoyl)-6-isopropyl-4,5,6,7-tetrahydro-1H-pyrazolo[3,4-c]pyridin-3-yl)-3-fluorobenzoic acid | 550 |

TABLE 11-continued

| Example No. | Structure | Name | MS (M + 1) |
|---|---|---|---|
| 19-C | 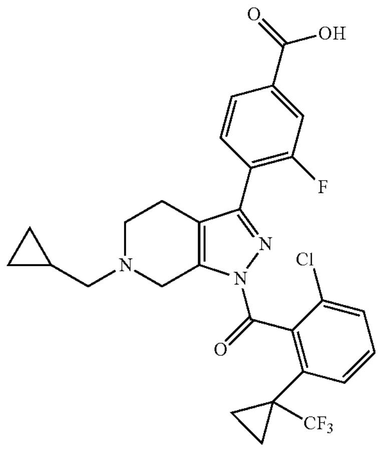 [SMILES: O=C(O)c1ccc(-c2nn(C(=O)c3c(Cl)cccc3C3(C(F)(F)F)CC3)c3c2CCN(CC2CC2)C3)c(F)c1] | 4-(1-(2-chloro-6-(1-(trifluoromethyl)cyclopropyl)benzoyl)-6-(cyclopropylmethyl)-4,5,6,7-tetrahydro-1H-pyrazolo[3,4-c]pyridin-3-yl)-3-fluorobenzoic acid | 562 |

Example 20A

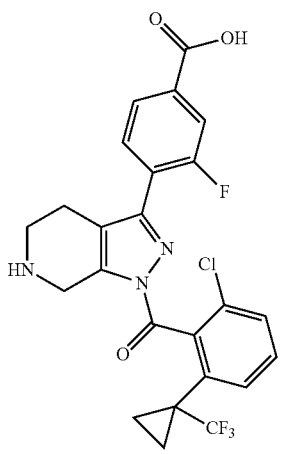

4-(1-(2-chloro-6-(1-(trifluoromethyl)cyclopropyl)benzoyl)-4,5,6,7-tetrahydro-1H-pyrazolo[3,4-c]pyridin-3-yl)-3-fluorobenzoic acid To a solution of 17A-2 (20 mg, 0.036 mmol) was added LiOH (4.29 mg, 0.179 mmol) in 1,4-Dioxane (0.7 mL) and Water (0.3 mL). The reaction mixture was stirred at room temperature for 1 h. Upon completion, the reaction was concentrated, dissolved in DMSO, filtered and purified by reverse phase HPLC (MeCN/water; TFA buffer) to afford the desired product as white solid. MS: 508 (M+1); $^1$H NMR (400 MHz, DMSO-$d_6$) δ 9.43 (br s, 1H), 7.85 (d, J=8.2 Hz, 1H), 7.80 (d, J=10.7 Hz, 1H), 7.67 (m, 3H), 7.53 (t, J=8.0 Hz, 1H), 4.84 (s, 2H), 3.45 (m, 2H), 2.85 (m, 2H), 1.40 (m, 1H), 1.26 (m, 2H), 0.82 (m, 1H).

The following example shown in Table 12 was prepared following similar procedures described for Example 20A which can be achieved by those of ordinary skill in the art of organic synthesis.

TABLE 12

| Example No. | Structure | IUPAC Name | Exact Mass [M + H]+ |
|---|---|---|---|
| 20B | 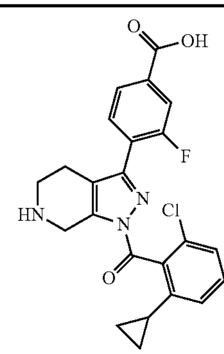 | 4-{1-[(2-chloro-6-cyclopropylphenyl)carbonyl]-4,5,6,7-tetrahydro-1H-pyrazolo[3,4-c]pyridin-3-yl}-3-fluorobenzoic acid | 440 |

Example 21A

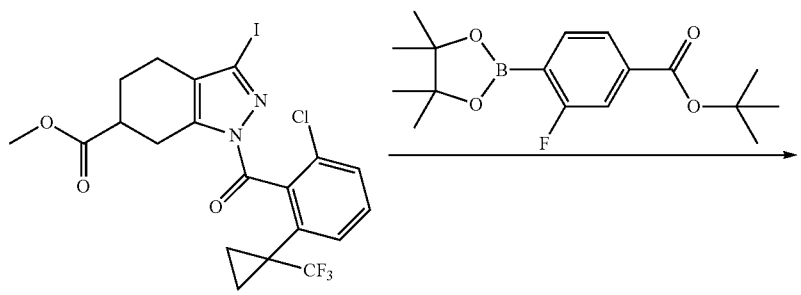

i-20A

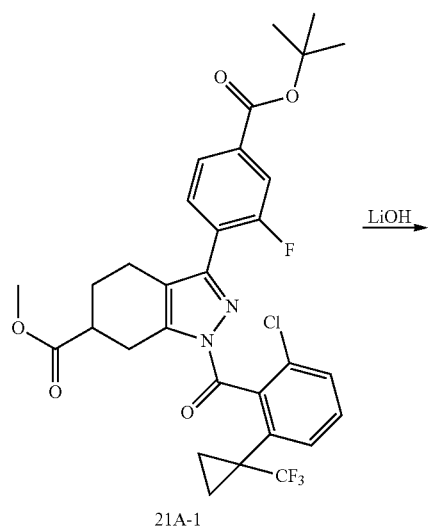

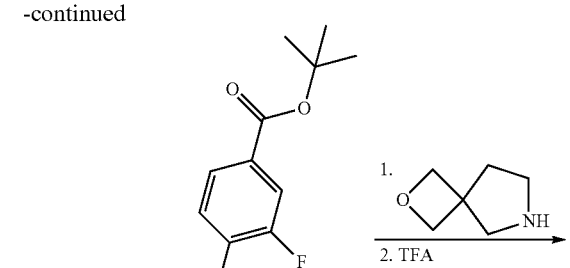

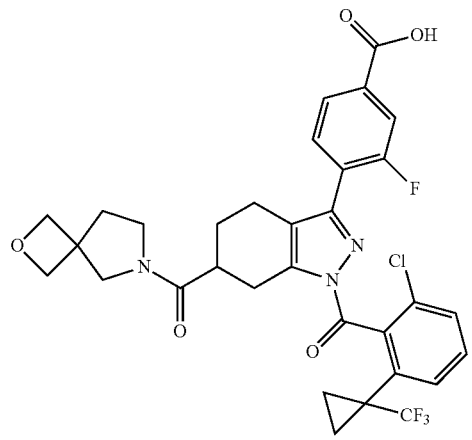

(R or S)-4-(1-(2-chloro-6-(1-(trifluoromethyl)cyclopropyl)benzoyl)-6-(2-oxa-6-azaspiro[3.4]octane-6-carbonyl)-4,5,6,7-tetrahydro-1H-indazol-3-yl)-3-fluorobenzoic acid Step 1: Preparation of methyl (R or S)-3-(4-(tert-butoxycarbonyl)-2-fluorophenyl)-1-(2-chloro-6-(1-(trifluoromethyl)cyclopropyl)benzoyl)-4,5,6,7-tetrahydro-1H-indazole-6-carboxylate (21A-1)

To a flask was added methyl (R or S)-1-(2-chloro-6-(1-(trifluoromethyl)cyclopropyl)benzoyl)-3-iodo-4,5,6,7-tetrahydro-1H-indazole-6-carboxylate (i-20A) (780 mg, 1.4 mmol), tert-butyl 3-fluoro-4-(4,4,5,5-tetramethyl-1,3,2-dioxaborolan-2-yl)benzoate (909 mg, 2.82 mmol), 1,1'-bis(diphenylphosphino)ferrocene-palladium(ii)dichloride dichloromethane complex (115 mg, 0.14 mmol), potassium acetate (416 mg, 4.23 mmol), and THF (3.76 mL) and the reaction was thoroughly degassed with Argon. Water (0.94 mL) was added and the reaction was heated to 80° C. overnight. The reaction was cooled and diluted with EtOAc. The organic layer was washed twice with aqueous NaHCO$_3$ and once with brine, dried with Na$_2$SO$_4$, filtered, and concentrated under reduced pressure. The residue was purified by silica gel chromatography (0-100% EtOAc/Hexane) to afford the title compound. MS: 621 (M+1).

Step 2: (R or S)-3-(4-(tert-butoxycarbonyl)-2-fluorophenyl)-1-(2-chloro-6-(1-(trifluoromethyl)cyclopropyl)benzoyl)-4,5,6,7-tetrahydro-1H-indazole-6-carboxylic acid (21A-2)

A mixture of methyl (R or S)-3-(4-(tert-butoxycarbonyl)-2-fluorophenyl)-1-(2-chloro-6-(1-(trifluoromethyl)cyclopropyl)benzoyl)-4,5,6,7-tetrahydro-1H-indazole-6-carboxylate (610 mg, 0.98 mmol) and LiOH (118 mg, 4.91 mmol) in THF (2.72 mL and Water (0.55 mL) was stirred overnight at room temperature. The reaction was diluted with EtOAc and the organic layer was washed twice with saturated ammonium chloride. The organic layer was dried with Na$_2$SO$_4$, filtered, and concentrated in vacuo. The crude product thus obtained was used in the next step without further purification. MS: 607 (M+1).

Step 3: (R or S)-4-(1-(2-chloro-6-(1-(trifluoromethyl)cyclopropyl)benzoyl)-6-(2-oxa-6-azaspiro[3.4]octane-6-carbonyl)-4,5,6,7-tetrahydro-1H-indazol-3-yl)-3-fluorobenzoic acid (21A)

To a mixture of (R or S)-3-(4-(tert-butoxycarbonyl)-2-fluorophenyl)-1-(2-chloro-6-(1-(trifluoromethyl)cyclopropyl)benzoyl)-4,5,6,7-tetrahydro-1H-indazole-6-carboxylic acid (212 mg, 0.35 mmol), HATU (199 mg, 0.52 mmol), Hunig's Base (244 µl, 1.4 mmol), and DMF (1164 µl) was added 2-oxa-6-azaspiro[3.4]octane hemioxalate (110 mg, 0.349 mmol) and the solution was allowed to stir overnight. The reaction was diluted with EtOAc. The organic layer was washed twice with aqueous $NaHCO_3$ and once with brine, dried with $Na_2SO_4$, filtered, and concentrated under reduced pressure. The residue was purified by silica gel chromatography (0-100% EtOAc/Hexane) to afford intermediate tert-butyl (R or S)-4-(1-(2-chloro-6-(1-(trifluoromethyl)cyclopropyl)benzoyl)-6-(2-oxa-6-azaspiro[3.4]octane-6-carbonyl)-4,5,6,7-tetrahydro-1H-indazol-3-yl)-3-fluorobenzoate. MS: 702 (M+1).

Intermediate tert-butyl 4-(1-(2-chloro-6-(1-(trifluoromethyl)cyclopropyl)benzoyl)-6-(2-oxa-6-azaspiro[3.4]octane-6-carbonyl)-4,5,6,7-tetrahydro-1H-indazol-3-yl)-3-fluorobenzoate was diluted with 2 mL of 3:1 DCM:TFA. The resulting solution was allowed to stir at room temperature overnight. The reaction was concentrated and the residue was brought up in dimethylsulfoxide. The mixture was filtered and purified by mass triggered reverse phase HPLC (ACN/water with 0.1% TFA modifier) to afford the title compound. MS: 646 (M+1). $^1$H NMR (DMSO-d6) δ (ppm): 13.41 (s, 1H), 7.86-7.69 (m, 2H), 7.68-7.55 (m, 3H), 7.48 (s, 1H), 4.56 (s, 2H), 4.49 (s, 2H), 3.89-3.82 (m, 1H), 3.70-3.52 (m, 2H), 3.33 (bs, 2H), 3.20 (bs, 1H), 3.04 (bs, 1H), 2.65 (bs, 1H), 2.22 (bs, 1H), 2.12 (bs, 1H), 2.00 (bs, 1H), 1.61 (bs, 1H), 1.37 (bs, 1H), 1.22 (m, 2H), 0.79 (bs, 1H).

The following examples shown in Table 13 were prepared following similar procedures described for Example 21A which can be achieved by those of ordinary skill in the art of organic synthesis.

TABLE 13

| Example No. | Structure | IUPAC Name | Exact Mass [M + H]+ |
|---|---|---|---|
| 21B | 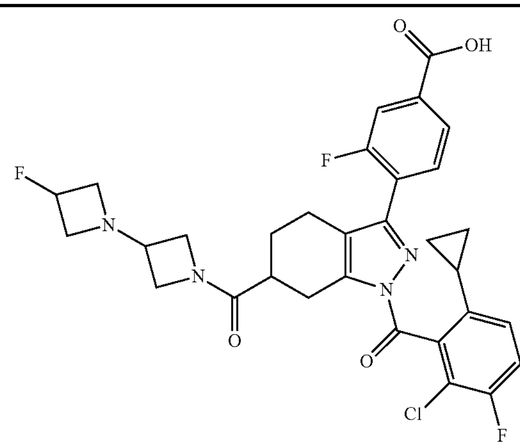 | (R or S)-4-(1-(2-chloro-6-cyclopropyl-3-fluorobenzoyl)-6-(3-fluoro-[1,3'-biazetidine]-1'-carbonyl)-4,5,6,7-tetrahydro-1H-indazol-3-yl)-3-fluorobenzoic acid | 613 |
| 21C | 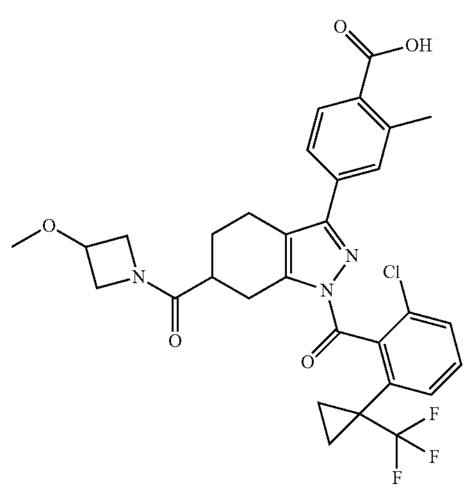 [SMILES: COC1CN(C(=O)C2CCc3c(-c4ccc(C(=O)O)c(C)c4)nn(C(=O)c4c(Cl)cccc4C4(C(F)(F)F)CC4)c3C2)C1] | 4-{(6R or S)-1-({2-chloro-6-[1-(trifluoromethyl)cyclopropyl]phenyl}carbonyl)-6-[(3-methoxyazetidin-1-yl)carbonyl]-4,5,6,7-tetrahydro-1H-indazol-3-yl}-2-methylbenzoic acid | 616 |

TABLE 13-continued

| Example No. | Structure | IUPAC Name | Exact Mass [M + H]+ |
|---|---|---|---|
| 21D | 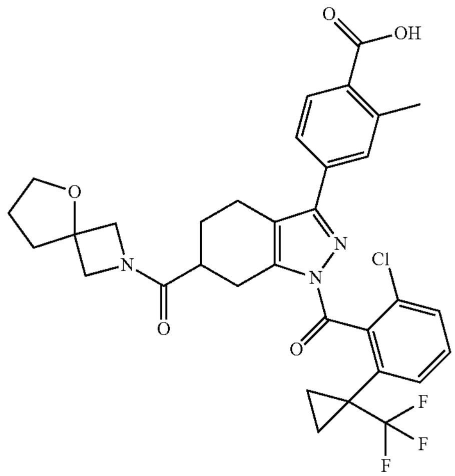 [SMILES: Cc1cc(-c2nn(C(=O)c3c(Cl)cccc3C3(C(F)(F)F)CC3)c3c2CCC(C(=O)N2CC4(CCCO4)C2)C3)ccc1C(=O)O] | 4-[(6R or S)-1-({2-chloro-6-[1-(trifluoromethyl)cyclopropyl]phenyl}carbonyl)-6-(5-oxa-2-azaspiro[3.4]oct-2-ylcarbonyl)-4,5,6,7-tetrahydro-1H-indazol-3-yl]-2-methylbenzoic acid | 642 |
| 21E | 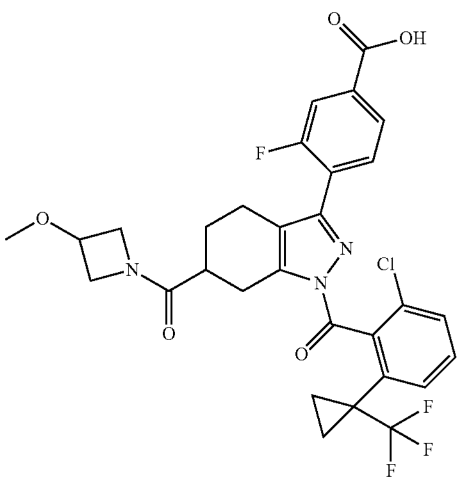 [SMILES: COC1CN(C(=O)C2CCc3c(-c4ccc(C(=O)O)cc4F)nn(C(=O)c4c(Cl)cccc4C4(C(F)(F)F)CC4)c3C2)C1] | 4-{(6R or S)-1-({2-chloro-6-[1-(trifluoromethyl)cyclopropyl]phenyl}carbonyl)-6-[(3-methoxyazetidin-1-yl)carbonyl]-4,5,6,7-tetrahydro-1H-indazol-3-yl}-3-fluorobenzoic acid | 620 |
| 21F | 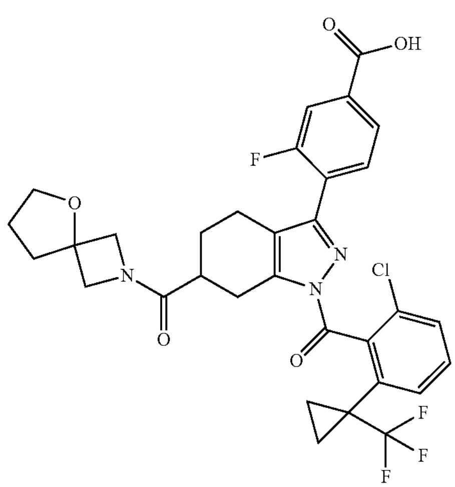 [SMILES: O=C(O)c1ccc(-c2nn(C(=O)c3c(Cl)cccc3C3(C(F)(F)F)CC3)c3c2CCC(C(=O)N2CC4(CCCO4)C2)C3)c(F)c1] | 4-[(6R or S)-1-({2-chloro-6-[1-(trifluoromethyl)cyclopropyl]phenyl}carbonyl)-6-(5-oxa-2-azaspiro[3.4]oct-2-ylcarbonyl)-4,5,6,7-tetrahydro-1H-indazol-3-yl]-3-fluorobenzoic acid | 646 |

TABLE 13-continued

| Example No. | Structure | IUPAC Name | Exact Mass [M + H]+ |
|---|---|---|---|
| 21G | 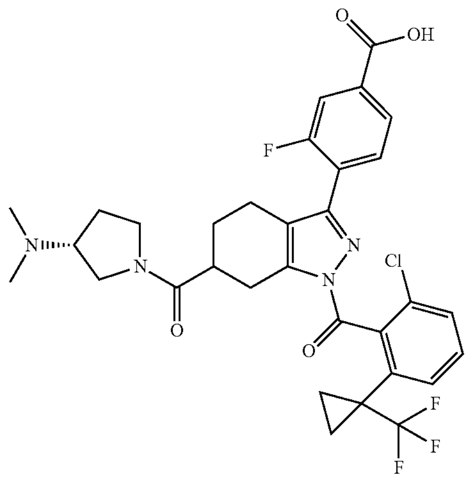 [SMILES: CN(C)[C@@H]1CCN(C(=O)C2CCc3c(-c4ccc(C(=O)O)cc4F)nn(C(=O)c4c(Cl)cccc4C4(C(F)(F)F)CC4)c3C2)C1] | 4-[(6R or S)-1-({2-chloro-6-[1-(trifluoromethyl)cyclopropyl]phenyl}carbonyl)-6-{[(3R)-3-(dimethylamino)pyrrolidin-1-yl]carbonyl}-4,5,6,7-tetrahydro-1H-indazol-3-yl]-3-fluorobenzoic acid | 647 |
| 21H | 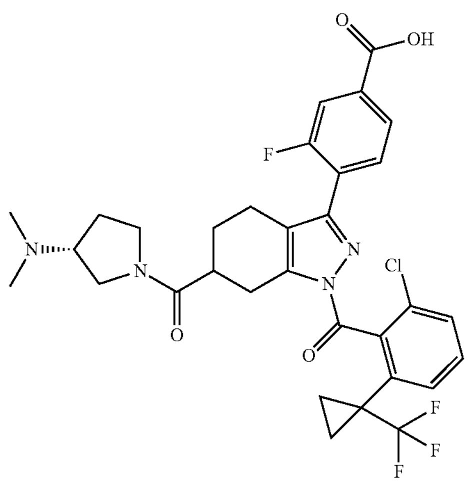 [SMILES: CN(C)[C@@H]1CCN(C(=O)C2CCc3c(-c4ccc(C(=O)O)cc4F)nn(C(=O)c4c(Cl)cccc4C4(C(F)(F)F)CC4)c3C2)C1] | 4-[(6R or S)-1-({2-chloro-6-[1-(trifluoromethyl)cyclopropyl]phenyl}carbonyl)-6-{[(3R)-3-(dimethylamino)pyrrolidin-1-yl]carbonyl}-4,5,6,7-tetrahydro-1H-indazol-3-yl]-3-fluorobenzoic acid | 647 |
| 21I | 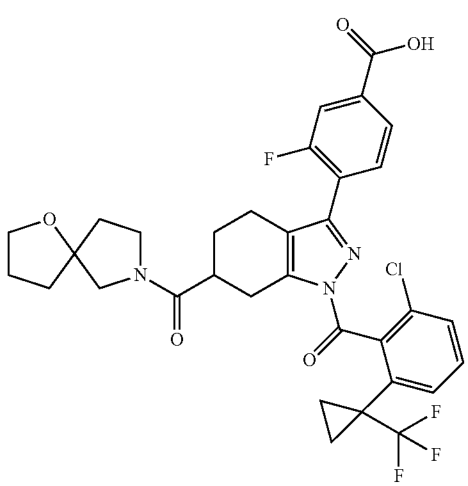 [SMILES: O=C(O)c1ccc(-c2nn(C(=O)c3c(Cl)cccc3C3(C(F)(F)F)CC3)c3c2CCC(C(=O)N2CCC4(CCCO4)C2)C3)c(F)c1] | 4-[(6R or S)-1-({2-chloro-6-[1-(trifluoromethyl)cyclopropyl]phenyl}carbonyl)-6-(1-oxa-7-azaspiro[4.4]non-7-ylcarbonyl)-4,5,6,7-tetrahydro-1H-indazol-3-yl]-3-fluorobenzoic acid | 660 |

TABLE 13-continued

| Example No. | Structure | IUPAC Name | Exact Mass [M + H]+ |
|---|---|---|---|
| 21J | 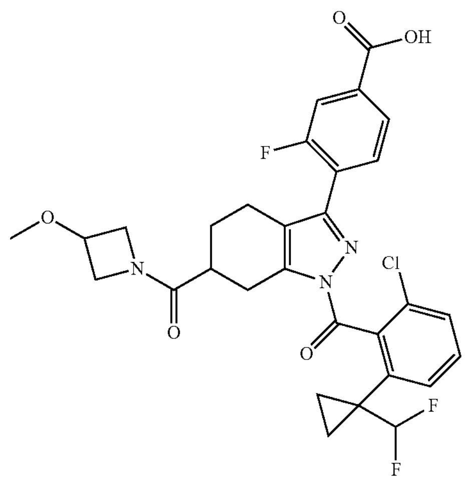 [SMILES: COC1CN(C(=O)C2CCc3c(-c4ccc(C(=O)O)cc4F)nn(C(=O)c4c(Cl)cccc4C4(C(F)F)CC4)c3C2)C1] | 4-{(6R or S)-1-({2-chloro-6-[1-(difluoromethyl)cyclopropyl]phenyl}carbonyl)-6-[(3-methoxyazetidin-1-yl)carbonyl]-4,5,6,7-tetrahydro-1H-indazol-3-yl}-3-fluorobenzoic acid | 602 |
| 21K | 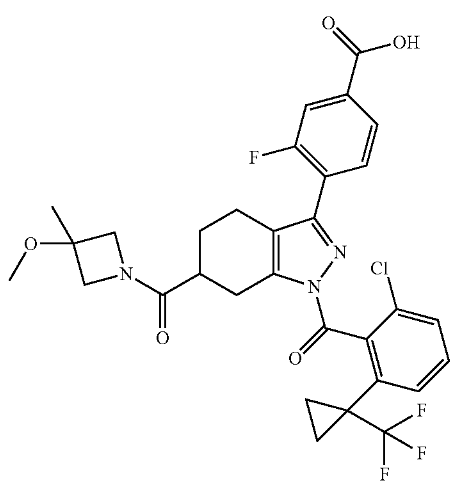 [SMILES: COC1(C)CN(C(=O)C2CCc3c(-c4ccc(C(=O)O)cc4F)nn(C(=O)c4c(Cl)cccc4C4(C(F)(F)F)CC4)c3C2)C1] | 4-{(6R or S)-1-({2-chloro-6-[1-(trifluoromethyl)cyclopropyl]phenyl}carbonyl)-6-[(3-methoxy-3-methylazetidin-1-yl)carbonyl]-4,5,6,7-tetrahydro-1H-indazol-3-yl}-3-fluorobenzoic acid | 634 |
| 21L | 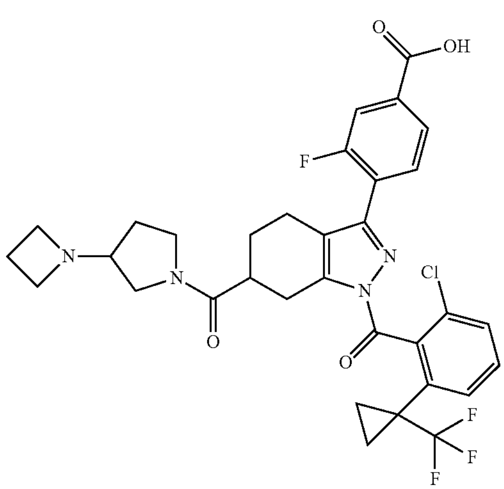 [SMILES: O=C(O)c1ccc(-c2nn(C(=O)c3c(Cl)cccc3C3(C(F)(F)F)CC3)c3c2CCC(C(=O)N2CCC(N4CCC4)C2)C3)c(F)c1] | 4-[(6R or S)-6-[(3-azetidin-1-yl)pyrrolidin-1-yl)carbonyl]-1-({2-chloro-6-[1-(trifluoromethyl)cyclopropyl]phenyl}carbonyl)-4,5,6,7-tetrahydro-1H-indazol-3-yl]-3-fluorobenzoic acid | 659 |

TABLE 13-continued

| Example No. | Structure | IUPAC Name | Exact Mass [M + H]+ |
|---|---|---|---|
| 21M | 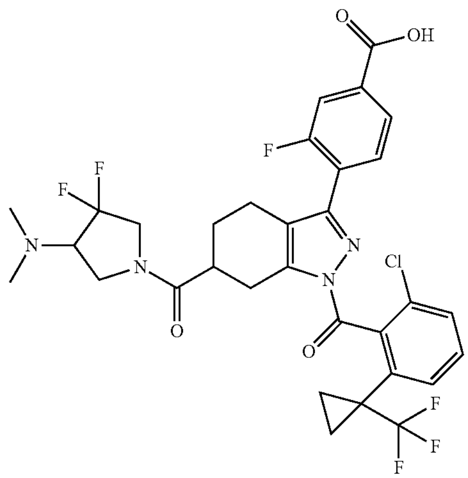 [SMILES: CN(C)C1CN(C(=O)C2CCc3c(-c4ccc(C(=O)O)cc4F)nn(C(=O)c4c(Cl)cccc4C4(C(F)(F)F)CC4)c3C2)CC1(F)F] | 4-[(6R or S)-1-({2-chloro-6-[1-(trifluoromethyl)cyclopropyl]phenyl}carbonyl)-6-{[4-(dimethylamino)-3,3-difluoropyrrolidin-1-yl]carbonyl}-4,5,6,7-tetrahydro-1H-indazol-3-yl]-3-fluorobenzoic acid | 683 |
| 21N | 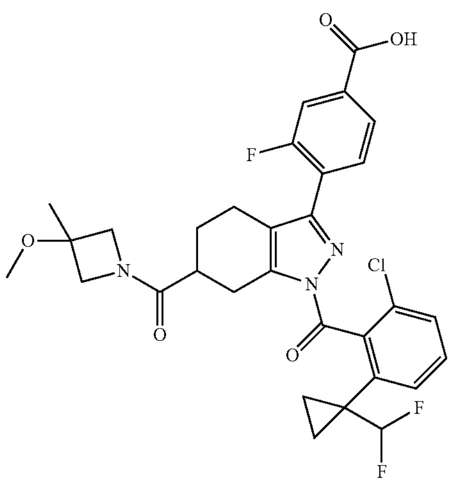 [SMILES: COC1(C)CN(C(=O)C2CCc3c(-c4ccc(C(=O)O)cc4F)nn(C(=O)c4c(Cl)cccc4C4(C(F)F)CC4)c3C2)C1] | 4-{(6R or S)-1-({2-chloro-6-[1-(difluoromethyl)cyclopropyl]phenyl}carbonyl)-6-[(3-methoxy-3-methylazetidin-1-yl)carbonyl]-4,5,6,7-tetrahydro-1H-indazol-3-yl}-3-fluorobenzoic acid | 616 |
| 21O | 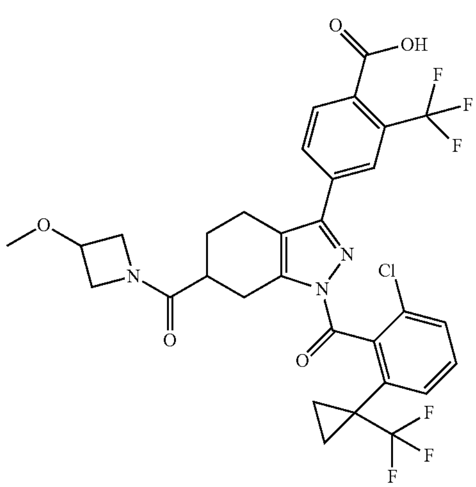 [SMILES: COC1CN(C(=O)C2CCc3c(-c4ccc(C(=O)O)c(C(F)(F)F)c4)nn(C(=O)c4c(Cl)cccc4C4(C(F)(F)F)CC4)c3C2)C1] | 4-{(6R or S)-1-({2-chloro-6-[1-(trifluoromethyl)cyclopropyl]phenyl}carbonyl)-6-[(3-methoxyazetidin-1-yl)carbonyl]-4,5,6,7-tetrahydro-1H-indazol-3-yl}-2-(trifluoromethyl)benzoic acid | 670 |

TABLE 13-continued

| Example No. | Structure | IUPAC Name | Exact Mass [M + H]+ |
|---|---|---|---|
| 21P | 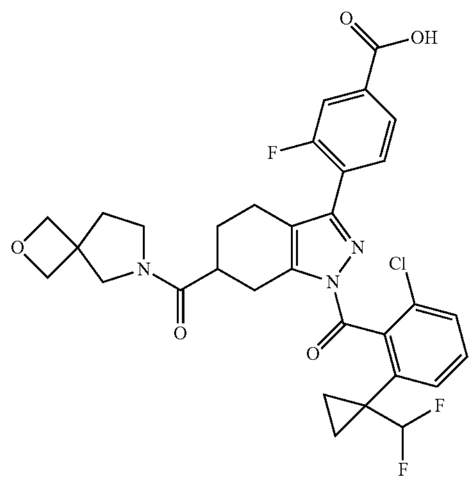 [SMILES: O=C(O)c1ccc(-c2nn(C(=O)c3c(Cl)cccc3C3(C(F)F)CC3)c3c2CCC(C(=O)N2CCC4(COC4)C2)C3)c(F)c1] | 4-[(6R or S)-1-({2-chloro-6-[1-(difluoromethyl)cyclopropyl]phenyl}carbonyl)-6-(2-oxa-6-azaspiro[3.4]oct-6-ylcarbonyl)-4,5,6,7-tetrahydro-1H-indazol-3-yl]-3-fluorobenzoic acid | 628 |
| 21Q | 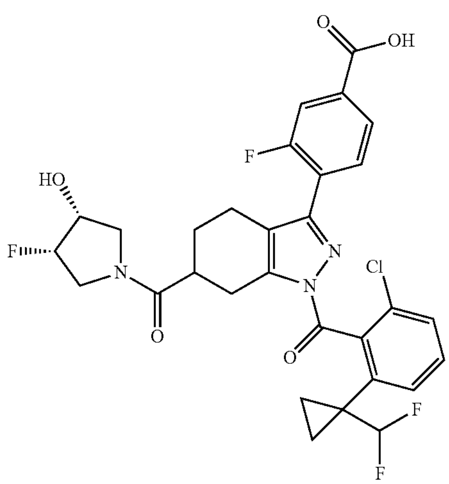 [SMILES: O=C(O)c1ccc(-c2nn(C(=O)c3c(Cl)cccc3C3(C(F)F)CC3)c3c2CCC(C(=O)N2C[C@@H](O)[C@@H](F)C2)C3)c(F)c1] | 4-[(6R or S)-1-({2-chloro-6-[1-(difluoromethyl)cyclopropyl]phenyl)carbonyl)-6-{[(3S,4R)-3-fluoro-4-hydroxypyrrolidin-1-yl]carbonyl}-4,5,6,7-tetrahydro-1H-indazol-3-yl]-3-fluorobenzoic acid | 620 |
| 21R | 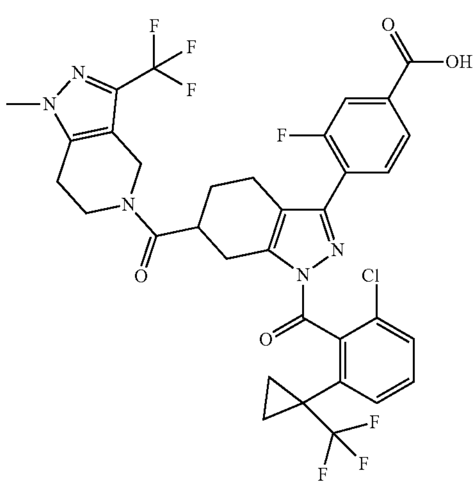 [SMILES: Cn1nc(C(F)(F)F)c2c1CCN(C(=O)C1CCc3c(-c4ccc(C(=O)O)cc4F)nn(C(=O)c4c(Cl)cccc4C4(C(F)(F)F)CC4)c3C1)C2] | (R or S)-4-(1-(2-chloro-6-(1-(trifluoromethyl)cyclopropyl)benzoyl)-6-(1-methyl-3-(trifluoromethyl)-4,5,6,7-tetrahydro-1H-pyrazolo[4,3-c]pyridine-5-carbonyl)-4,5,6,7-tetrahydro-1H-indazol-3-yl)-3-fluorobenzoic acid | 738 |

TABLE 13-continued

| Example No. | Structure | IUPAC Name | Exact Mass [M + H]+ |
|---|---|---|---|
| 21S | 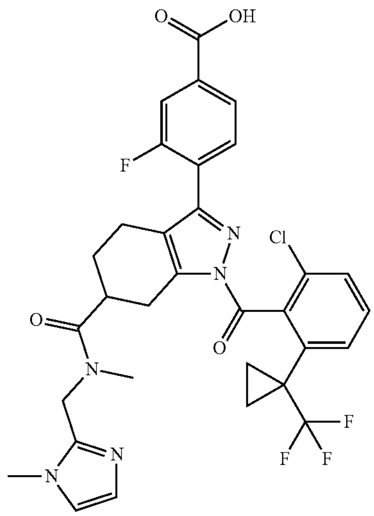 [SMILES: CN(Cc1nccn1C)C(=O)C1CCc2c(-c3ccc(C(=O)O)cc3F)nn(C(=O)c3c(Cl)cccc3C3(C(F)(F)F)CC3)c2C1] | (R or S)-4-(1-(2-chloro-6-(1-(trifluoromethyl)cyclopropyl)benzoyl)-6-(methyl((1-methyl-1H-imidazol-2-yl)methyl)carbamoyl)-4,5,6,7-tetrahydro-1H-indazol-3-yl)-3-fluorobenzoic acid | 658 |
| 21T | 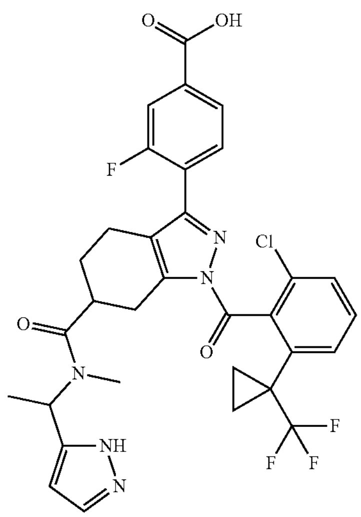 [SMILES: CC(c1ccn[nH]1)N(C)C(=O)C1CCc2c(-c3ccc(C(=O)O)cc3F)nn(C(=O)c3c(Cl)cccc3C3(C(F)(F)F)CC3)c2C1] | 4-((6R or S)-6-((1-(1H-pyrazol-5-yl)ethyl)(methyl)carbamoyl)-1-(2-chloro-6-(1-(trifluoromethyl)cyclopropyl)benzoyl)-4,5,6,7-tetrahydro-1H-indazol-3-yl)-3-fluorobenzoic acid | 658 |
| 21U | 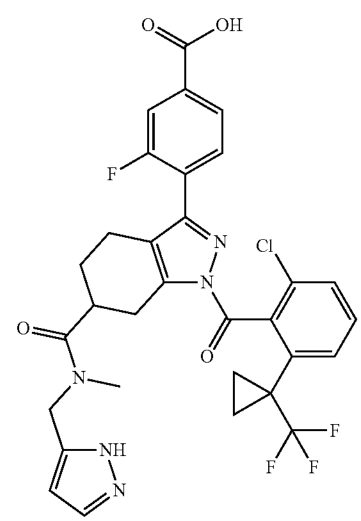 [SMILES: CN(Cc1ccn[nH]1)C(=O)C1CCc2c(-c3ccc(C(=O)O)cc3F)nn(C(=O)c3c(Cl)cccc3C3(C(F)(F)F)CC3)c2C1] | (R or S)-4-(6-(((1H-pyrazol-5-yl)methyl)(methyl)carbamoyl)-1-(2-chloro-6-(1-(trifluoromethyl)cyclopropyl)benzoyl)-4,5,6,7-tetrahydro-1H-indazol-3-yl)-3-fluorobenzoic acid | 644 |

TABLE 13-continued

| Example No. | Structure | IUPAC Name | Exact Mass [M + H]+ |
|---|---|---|---|
| 21V | 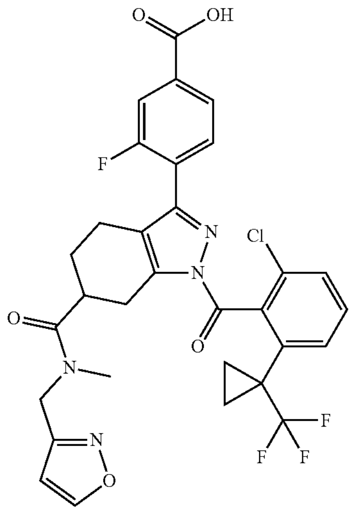 [SMILES: CN(Cc1ccon1)C(=O)C1CCc2c(-c3ccc(C(=O)O)cc3F)nn(C(=O)c3c(Cl)cccc3C3(C(F)(F)F)CC3)c2C1] | (R or S)-4-(1-(2-chloro-6-(1-(trifluoromethyl)cyclopropyl)benzoyl)-6-((isoxazol-3-ylmethyl)(methyl)carbamoyl)-4,5,6,7-tetrahydro-1H-indazol-3-yl)-3-fluorobenzoic acid | 645 |
| 21W | 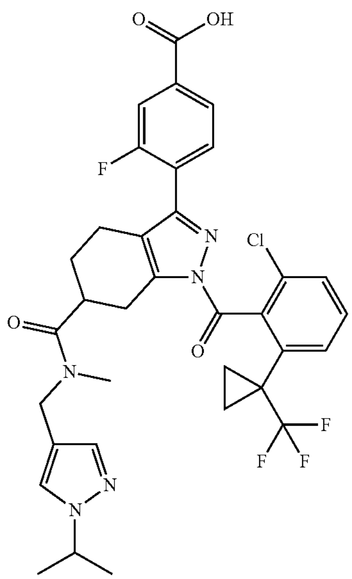 [SMILES: CC(C)n1cc(CN(C)C(=O)C2CCc3c(-c4ccc(C(=O)O)cc4F)nn(C(=O)c4c(Cl)cccc4C4(C(F)(F)F)CC4)c3C2)cn1] | (R or S)-4-(1-(2-chloro-6-(1-(trifluoromethyl)cyclopropyl)benzoyl)-6-(((1-isopropyl-1H-pyrazol-4-yl)methyl)(methyl)carbamoyl)-4,5,6,7-tetrahydro-1H-indazol-3-yl)-3-fluorobenzoic acid | 686 |
| 21X | 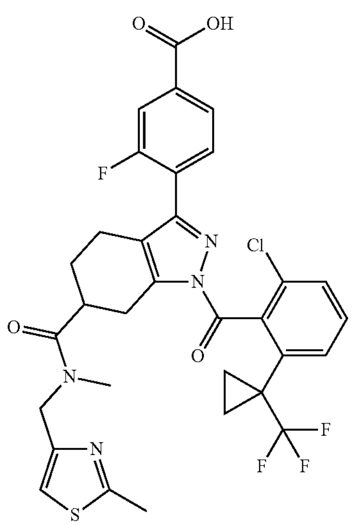 [SMILES: Cc1nc(CN(C)C(=O)C2CCc3c(-c4ccc(C(=O)O)cc4F)nn(C(=O)c4c(Cl)cccc4C4(C(F)(F)F)CC4)c3C2)cs1] | (R or S)-4-(1-(2-chloro-6-(1-(trifluoromethyl)cyclopropyl)benzoyl)-6-(methyl((2-methylthiazol-4-yl)methyl)carbamoyl)-4,5,6,7-tetrahydro-1H-indazol-3-yl)-3-fluorobenzoic acid | 675 |

TABLE 13-continued

| Example No. | Structure | IUPAC Name | Exact Mass [M + H]+ |
| --- | --- | --- | --- |
| 21Y | 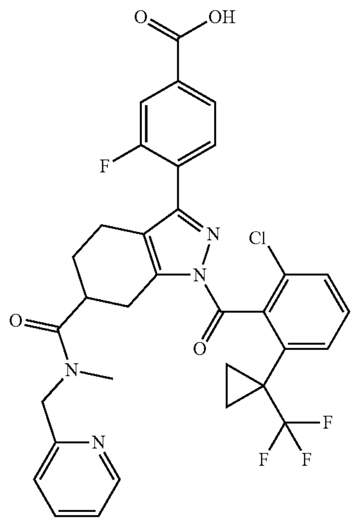 [SMILES: CN(Cc1ccccn1)C(=O)C1CCc2c(-c3ccc(C(=O)O)cc3F)nn(C(=O)c3c(Cl)cccc3C3(C(F)(F)F)CC3)c2C1] | (R or S)-4-(1-(2-chloro-6-(1-(trifluoromethyl)cyclopropyl)benzoyl)-6-(methyl(pyridin-2-ylmethyl)carbamoyl)-4,5,6,7-tetrahydro-1H-indazol-3-yl)-3-fluorobenzoic acid | 655 |
| 21Z | 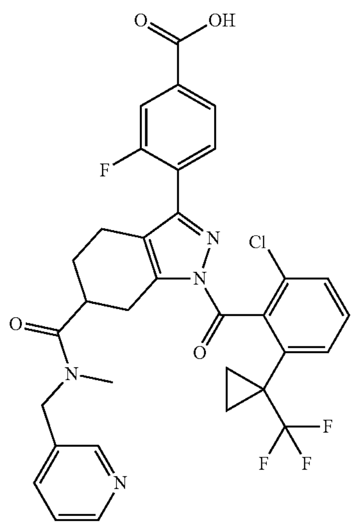 [SMILES: CN(Cc1cccnc1)C(=O)C1CCc2c(-c3ccc(C(=O)O)cc3F)nn(C(=O)c3c(Cl)cccc3C3(C(F)(F)F)CC3)c2C1] | (R or S)-4-(1-(2-chloro-6-(1-(trifluoromethyl)cyclopropyl)benzoyl)-6-(methyl(pyridin-3-ylmethyl)carbamoyl)-4,5,6,7-tetrahydro-1H-indazol-3-yl)-3-fluorobenzoic acid | 655 |
| 21AA | 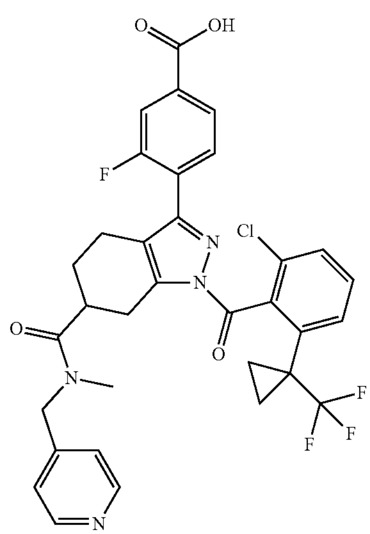 [SMILES: CN(Cc1ccncc1)C(=O)C1CCc2c(-c3ccc(C(=O)O)cc3F)nn(C(=O)c3c(Cl)cccc3C3(C(F)(F)F)CC3)c2C1] | (R or S)-4-(1-(2-chloro-6-(1-(trifluoromethyl)cyclopropyl)benzoyl)-6-(methyl(pyridin-4-ylmethyl)carbamoyl)-4,5,6,7-tetrahydro-1H-indazol-3-yl)-3-fluorobenzoic acid | 655 |

TABLE 13-continued

| Example No. | Structure | IUPAC Name | Exact Mass [M + H]+ |
|---|---|---|---|
| 21BB | 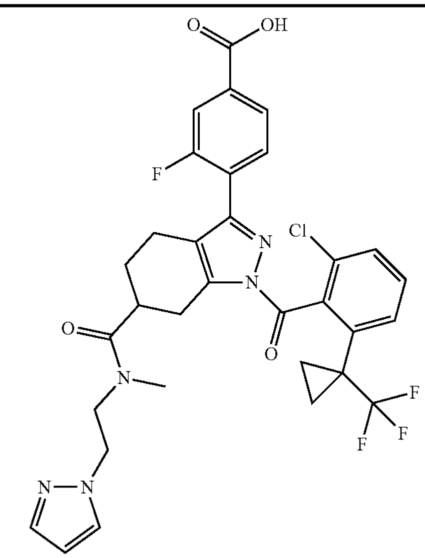 | (R or S)-4-(6-((2-(1H-pyrazol-1-yl)ethyl)(methyl)carbamoyl)-1-(2-chloro-6-(1-(trifluoromethyl)cyclopropyl)benzoyl)-4,5,6,7-tetrahydro-1H-indazol-3-yl)-3-fluorobenzoic acid | 658 |
| 21CC | 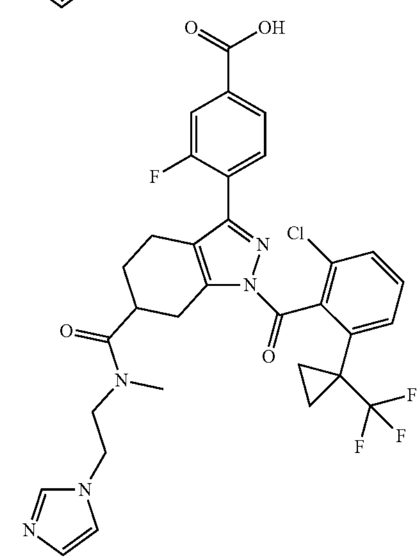 | (R or S)-4-(6-((2-(1H-imidazol-1-yl)ethyl)(methyl)carbamoyl)-1-(2-chloro-6-(1-(trifluoromethyl)cyclopropyl)benzoyl)-4,5,6,7-tetrahydro-1H-indazol-3-yl)-3-fluorobenzoic acid | 658 |
| 21DD | 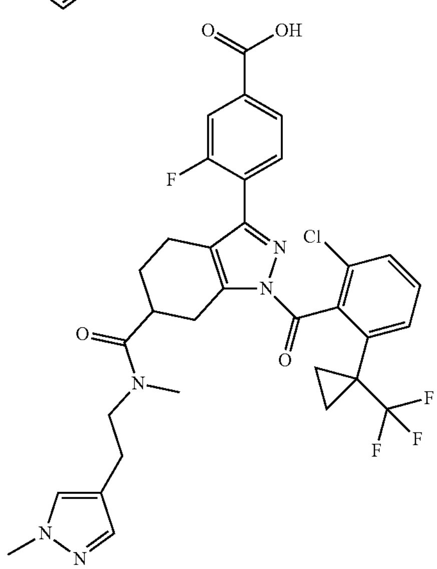 | (R or S)-4-(1-(2-chloro-6-(1-(trifluoromethyl)cyclopropyl)benzoyl)-6-(methyl(2-(1-methyl-1H-pyrazol-4-yl)ethyl)carbamoyl)-4,5,6,7-tetrahydro-1H-indazol-3-yl)-3-fluorobenzoic acid | 672 |

TABLE 13-continued

| Example No. | Structure | IUPAC Name | Exact Mass [M + H]+ |
|---|---|---|---|
| 21EE | 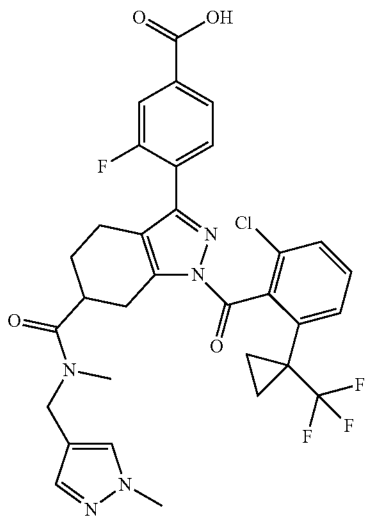 [SMILES: CN(Cc1cnn(C)c1)C(=O)C1CCc2c(-c3ccc(C(=O)O)cc3F)nn(C(=O)c3c(Cl)cccc3C3(C(F)(F)F)CC3)c2C1] | (R or S)-4-(1-(2-chloro-6-(1-(trifluoromethyl)cyclopropyl)benzoyl)-6-(methyl((1-methyl-1H-pyrazol-4-yl)methyl)carbamoyl)-4,5,6,7-tetrahydro-1H-indazol-3-yl)-3-fluorobenzoic acid | 658 |
| 21FF | 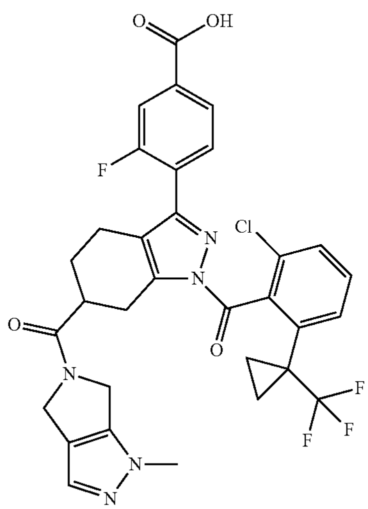 [SMILES: Cn1ncc2c1CN(C(=O)C1CCc3c(-c4ccc(C(=O)O)cc4F)nn(C(=O)c4c(Cl)cccc4C4(C(F)(F)F)CC4)c3C1)C2] | (R or S)-4-(1-(2-chloro-6-(1-(trifluoromethyl)cyclopropyl)benzoyl)-6-(1-methyl-1,4,5,6-tetrahydropyrrolo[3,4-c]pyrazole-5-carbonyl)-4,5,6,7-tetrahydro-1H-indazol-3-yl)-3-fluorobenzoic acid | 656 |
| 21GG | 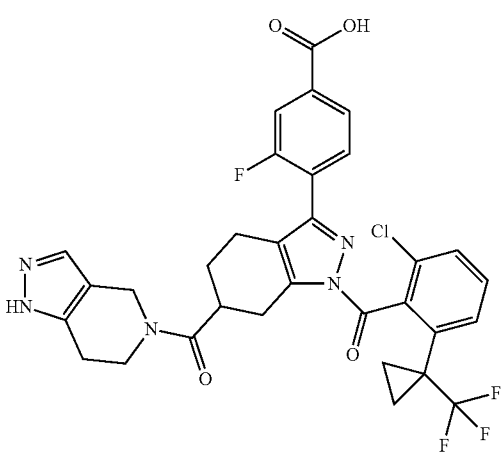 [SMILES: O=C(O)c1ccc(-c2nn(C(=O)c3c(Cl)cccc3C3(C(F)(F)F)CC3)c3c2CCC(C(=O)N2CCc4[nH]ncc4C2)C3)c(F)c1] | (R or S)-4-(1-(2-chloro-6-(1-(trifluoromethyl)cyclopropyl)benzoyl)-6-(4,5,6,7-tetrahydro-1H-pyrazolo[4,3-c]pyridine-5-carbonyl)-4,5,6,7-tetrahydro-1H-indazol-3-yl)-3-fluorobenzoic acid | 656 |

TABLE 13-continued

| Example No. | Structure | IUPAC Name | Exact Mass [M + H]+ |
|---|---|---|---|
| 21HH | 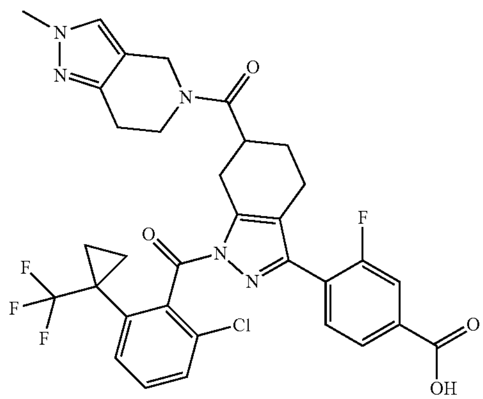 [SMILES: Cn1cc2c(n1)CCN(C(=O)C1CCc3c(-c4ccc(C(=O)O)cc4F)nn(C(=O)c4c(Cl)cccc4C4(C(F)(F)F)CC4)c3C1)C2] | (R or S)-4-(1-(2-chloro-6-(1-(trifluoromethyl)cyclopropyl)benzoyl)-6-(2-methyl-4,5,6,7-tetrahydro-2H-pyrazolo[4,3-c]pyridine-5-carbonyl)-4,5,6,7-tetrahydro-1H-indazol-3-yl)-3-fluorobenzoic acid | 670 |
| 21II | 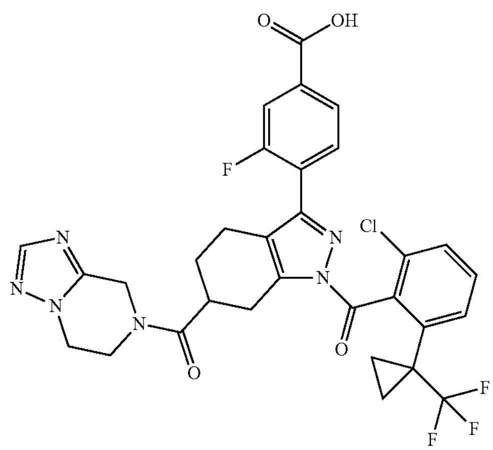 [SMILES: O=C(O)c1ccc(-c2nn(C(=O)c3c(Cl)cccc3C3(C(F)(F)F)CC3)c3c2CCC(C(=O)N2CCn4ncnc4C2)C3)c(F)c1] | (R or S)-4-(1-(2-chloro-6-(1-(trifluoromethyl)cyclopropyl)benzoyl)-6-(5,6,7,8-tetrahydro-[1,2,4]triazolo[1,5-a]pyrazine-7-carbonyl)-4,5,6,7-tetrahydro-1H-indazol-3-yl)-3-fluorobenzoic acid | 657 |
| 21JJ | 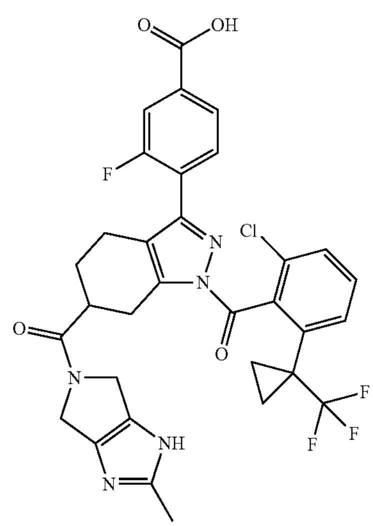 [SMILES: Cc1nc2c([nH]1)CN(C(=O)C1CCc3c(-c4ccc(C(=O)O)cc4F)nn(C(=O)c4c(Cl)cccc4C4(C(F)(F)F)CC4)c3C1)C2] | (R or S)-4-(1-(2-chloro-6-(1-(trifluoromethyl)cyclopropyl)benzoyl)-6-(2-methyl-1,4,5,6-tetrahydropyrrolo[3,4-d]imidazole-5-carbonyl)-4,5,6,7-tetrahydro-1H-indazol-3-yl)-3-fluorobenzoic acid | 656 |

TABLE 13-continued

| Example No. | Structure | IUPAC Name | Exact Mass [M + H]+ |
|---|---|---|---|
| 21KK | 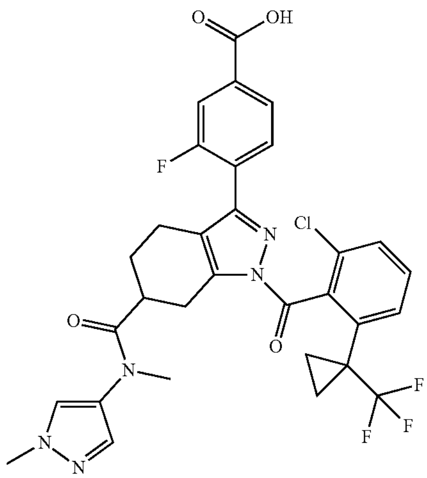 [SMILES: CN(C(=O)C1CCc2c(-c3ccc(C(=O)O)cc3F)nn(C(=O)c3c(Cl)cccc3C3(C(F)(F)F)CC3)c2C1)c1cnn(C)c1] | (R or S)-4-(1-(2-chloro-6-(1-(trifluoromethyl)cyclopropyl)benzoyl)-6-(methyl(1-methyl-1H-pyrazol-4-yl)carbamoyl)-4,5,6,7-tetrahydro-1H-indazol-3-yl)-3-fluorobenzoic acid | 644 |
| 21LL | 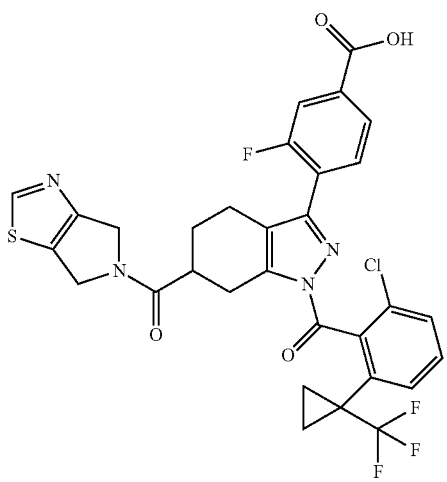 [SMILES: O=C(O)c1ccc(-c2nn(C(=O)c3c(Cl)cccc3C3(C(F)(F)F)CC3)c3c2CCC(C(=O)N2Cc4ncsc4C2)C3)c(F)c1] | (R or S)-4-(1-(2-chloro-6-(1-(trifluoromethyl)cyclopropyl)benzoyl)-6-(5,6-dihydro-4H-pyrrolo[3,4-d]thiazole-5-carbonyl)-4,5,6,7-tetrahydro-1H-indazol-3-yl)-3-fluorobenzoic acid | 659 |
| 21MM | 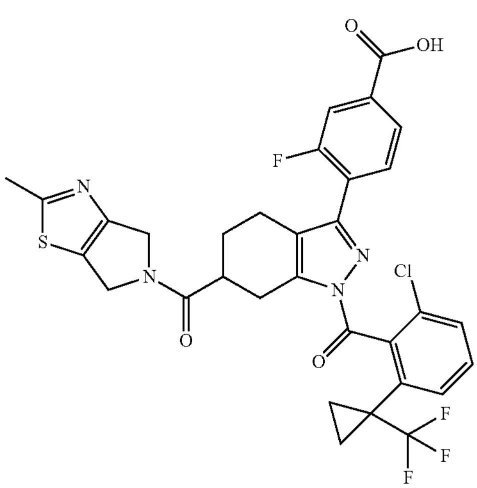 [SMILES: Cc1nc2c(s1)CN(C(=O)C1CCc3c(-c4ccc(C(=O)O)cc4F)nn(C(=O)c4c(Cl)cccc4C4(C(F)(F)F)CC4)c3C1)C2] | (R or S)-4-(1-(2-chloro-6-(1-(trifluoromethyl)cyclopropyl)benzoyl)-6-(2-methyl-5,6-dihydro-4H-pyrrolo[3,4-d]thiazole-5-carbonyl)-4,5,6,7-tetrahydro-1H-indazol-3-yl)-3-fluorobenzoic acid | 673 |

TABLE 13-continued

| Example No. | Structure | IUPAC Name | Exact Mass [M + H]+ |
|---|---|---|---|
| 21NN | 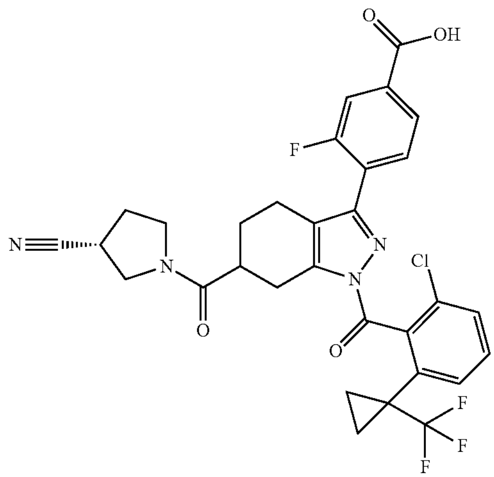 [SMILES: N#C[C@@H]1CCN(C(=O)C2CCc3c(-c4ccc(C(=O)O)cc4F)nn(C(=O)c4c(Cl)cccc4C4(C(F)(F)F)CC4)c3C2)C1] | 4-[(6R or S)-1-({2-chloro-6-[1-(trifluoromethyl)cyclopropyl]phenyl}carbonyl)-6-{[(3R)-3-cyanopyrrolidin-1-yl]carbonyl}-4,5,6,7-tetrahydro-1H-indazol-3-yl]-3-fluorobenzoic acid | 629 |
| 21PP | 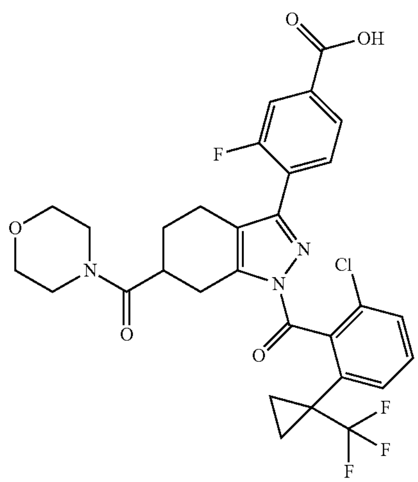 [SMILES: O=C(O)c1ccc(-c2nn(C(=O)c3c(Cl)cccc3C3(C(F)(F)F)CC3)c3c2CCC(C(=O)N2CCOCC2)C3)c(F)c1] | 4-[(6R or S)-1-({2-chloro-6-[1-(trifluoromethyl)cyclopropyl]phenyl}carbonyl)-6-(morpholin-4-ylcarbonyl)-4,5,6,7-tetrahydro-1H-indazol-3-yl]-3-fluorobenzoic acid | 620 |
| 21QQ | 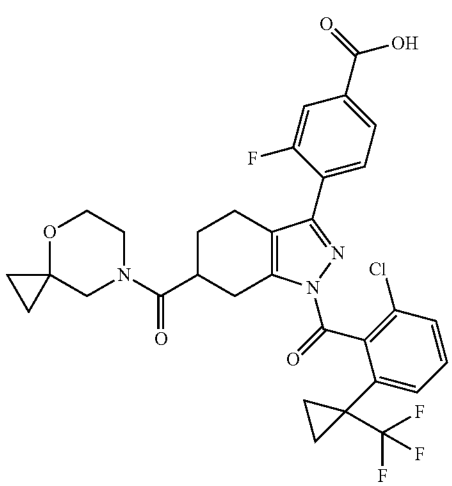 [SMILES: O=C(O)c1ccc(-c2nn(C(=O)c3c(Cl)cccc3C3(C(F)(F)F)CC3)c3c2CCC(C(=O)N2CCOC4(CC4)C2)C3)c(F)c1] | 4-[(6R or S)-1-({2-chloro-6-[1-(trifluoromethyl)cyclopropyl]phenyl}carbonyl)-6-(4-oxa-7-azaspiro[2.5]oct-7-ylcarbonyl)-4,5,6,7-tetrahydro-1H-indazol-3-yl]-3-fluorobenzoic acid | 646 |

TABLE 13-continued

| Example No. | Structure | IUPAC Name | Exact Mass [M + H]+ |
|---|---|---|---|
| 21RR | 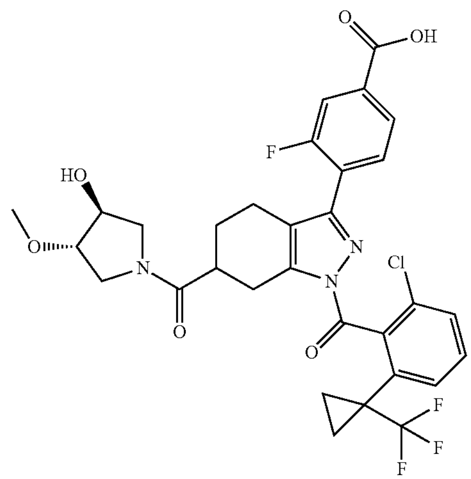 [SMILES: CO[C@H]1CN(C(=O)C2CCc3c(-c4ccc(C(=O)O)cc4F)nn(C(=O)c4c(Cl)cccc4C4(C(F)(F)F)CC4)c3C2)C[C@@H]1O] | 4-[(6R or S)-1-({2-chloro-6-[1-(trifluoromethyl)cyclopropyl]phenyl}carbonyl)-6-{[(3S,4S)-3-hydroxy-4-methoxypyrrolidin-1-yl]carbonyl}-4,5,6,7-tetrahydro-1H-indazol-3-yl]-3-fluorobenzoic acid | 650 |
| 21SS | 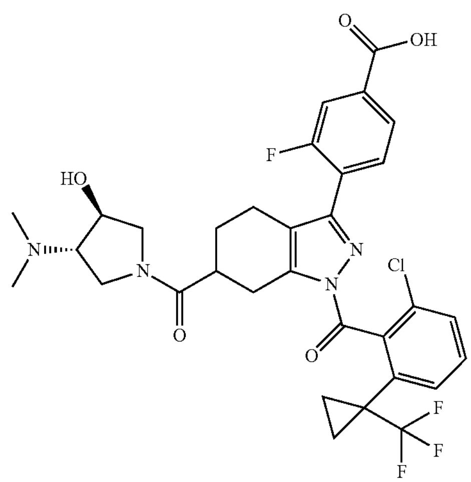 [SMILES: CN(C)[C@H]1CN(C(=O)C2CCc3c(-c4ccc(C(=O)O)cc4F)nn(C(=O)c4c(Cl)cccc4C4(C(F)(F)F)CC4)c3C2)C[C@@H]1O] | 4-[(6R or S)-1-({2-chloro-6-[1-(trifluoromethyl)cyclopropyl]phenyl}carbonyl)-6-{[(3S,4S)-3-(dimethylamino)-4-hydroxypyrrolidin-1-yl]carbonyl}-4,5,6,7-tetrahydro-1H-indazol-3-yl]-3-fluorobenzoic acid | 663 |
| 21TT | 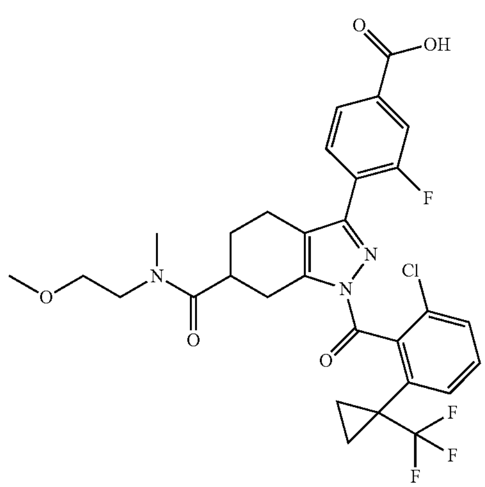 [SMILES: COCCN(C)C(=O)C1CCc2c(-c3ccc(C(=O)O)cc3F)nn(C(=O)c3c(Cl)cccc3C3(C(F)(F)F)CC3)c2C1] | (R or S)-4-(1-(2-chloro-6-(1-(trifluoromethyl)cyclopropyl)benzoyl)-6-((2-methoxyethyl)(methyl)carbamoyl)-4,5,6,7-tetrahydro-1H-indazol-3-yl)-3-fluorobenzoic acid | 622 |

TABLE 13-continued

| Example No. | Structure | IUPAC Name | Exact Mass [M + H]+ |
|---|---|---|---|
| 21UU | 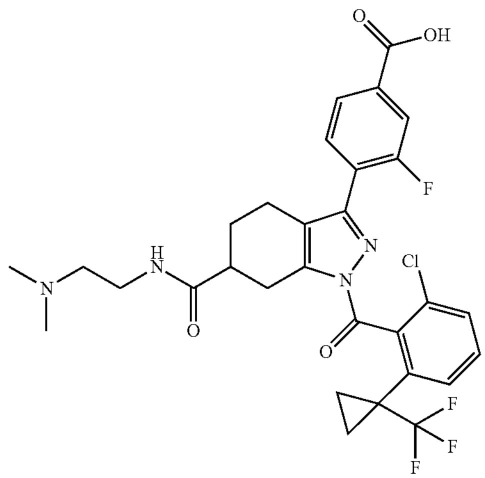 [SMILES: CN(C)CCNC(=O)C1CCc2c(-c3ccc(C(=O)O)cc3F)nn(C(=O)c3c(Cl)cccc3C3(C(F)(F)F)CC3)c2C1] | (R or S)-4-(1-(2-chloro-6-(1-(trifluoromethyl)cyclopropyl)benzoyl)-6-((2-(dimethylamino)ethyl)carbamoyl)-4,5,6,7-tetrahydro-1H-indazol-3-yl)-3-fluorobenzoic acid | 621 |
| 21VV | 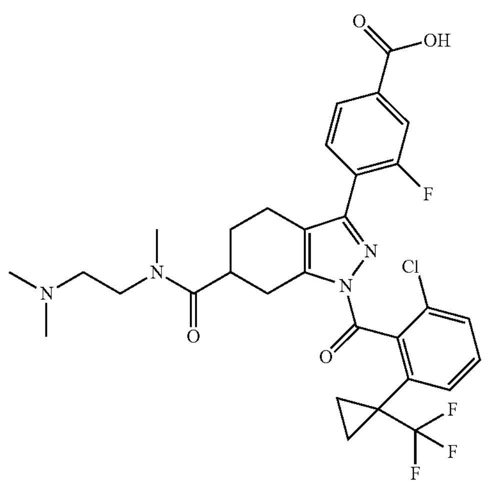 [SMILES: CN(C)CCN(C)C(=O)C1CCc2c(-c3ccc(C(=O)O)cc3F)nn(C(=O)c3c(Cl)cccc3C3(C(F)(F)F)CC3)c2C1] | (R or S)-4-(1-(2-chloro-6-(1-(trifluoromethyl)cyclopropyl)benzoyl)-6-((2-(dimethylamino)ethyl)(methyl)carbamoyl)-4,5,6,7-tetrahydro-1H-indazol-3-yl)-3-fluorobenzoic acid | 635 |
| 21WW | 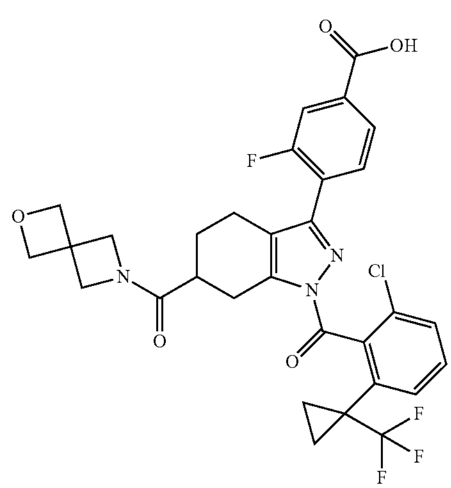 [SMILES: O=C(O)c1ccc(-c2nn(C(=O)c3c(Cl)cccc3C3(C(F)(F)F)CC3)c3c2CCC(C(=O)N2CC4(COC4)C2)C3)c(F)c1] | (R or S)-4-(1-(2-chloro-6-(1-(trifluoromethyl)cyclopropyl)benzoyl)-6-(2-oxa-6-azaspiro[3.3]heptane-6-carbonyl)-4,5,6,7-tetrahydro-1H-indazol-3-yl)-3-fluorobenzoic acid | 632 |

TABLE 13-continued

| Example No. | Structure | IUPAC Name | Exact Mass [M + H]+ |
|---|---|---|---|
| 21XX | 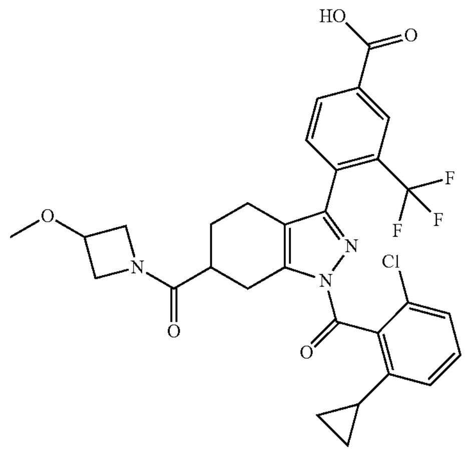 [SMILES: COC1CN(C(=O)C2CCc3c(-c4ccc(C(=O)O)cc4C(F)(F)F)nn(C(=O)c4c(Cl)cccc4C4CC4)c3C2)C1] | (R or S)-4-(1-(2-chloro-6-cyclopropylbenzoyl)-6-(3-methoxyazetidine-1-carbonyl)-4,5,6,7-tetrahydro-1H-indazol-3-yl)-3-(trifluoromethyl)benzoic acid | 602 |
| 21YY | 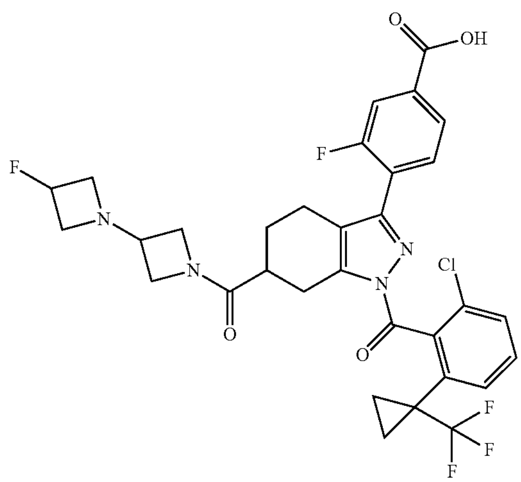 [SMILES: O=C(O)c1ccc(-c2nn(C(=O)c3c(Cl)cccc3C3(C(F)(F)F)CC3)c3c2CCC(C(=O)N2CC(N4CC(F)C4)C2)C3)c(F)c1] | (R or S)-4-(1-(2-chloro-6-(1-(trifluoromethyl)cyclopropyl)benzoyl)-6-(3-fluoro-[1,3'-biazetidine]-1'-carbonyl)-4,5,6,7-tetrahydro-1H-indazol-3-yl)-3-fluorobenzoic acid | 663 |
| 21ZZ | 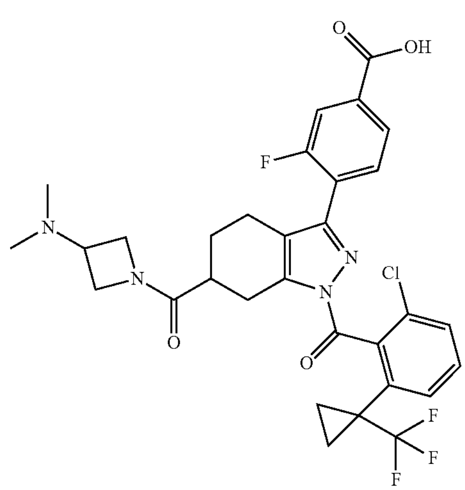 [SMILES: CN(C)C1CN(C(=O)C2CCc3c(-c4ccc(C(=O)O)cc4F)nn(C(=O)c4c(Cl)cccc4C4(C(F)(F)F)CC4)c3C2)C1] | (R or S)-4-(1-(2-chloro-6-(1-(trifluoromethyl)cyclopropyl)benzoyl)-6-(3-(dimethylamino)azetidine-1-carbonyl)-4,5,6,7-tetrahydro-1H-indazol-3-yl)-3-fluorobenzoic acid | 633 |

TABLE 13-continued

| Example No. | Structure | IUPAC Name | Exact Mass [M + H]+ |
|---|---|---|---|
| 21AAA | 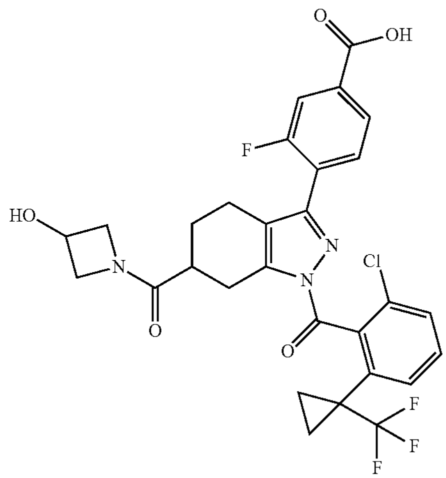 [SMILES: O=C(O)c1ccc(-c2nn(C(=O)c3c(Cl)cccc3C3(C(F)(F)F)CC3)c3c2CCC(C(=O)N2CC(O)C2)C3)c(F)c1] | 4-{(6R or S)-1-({2-chloro-6-[1-(trifluoromethyl)cyclopropyl]phenyl}carbonyl)-6-[(3-hydroxyazetidin-1-yl)carbonyl]-4,5,6,7-tetrahydro-1H-indazol-3-yl}-3-fluorobenzoic acid | 606 |
| 21BBB | 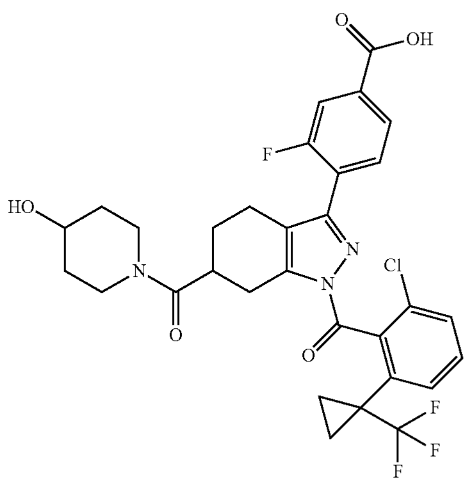 [SMILES: O=C(O)c1ccc(-c2nn(C(=O)c3c(Cl)cccc3C3(C(F)(F)F)CC3)c3c2CCC(C(=O)N2CCC(O)CC2)C3)c(F)c1] | (R or S)-4-(1-(2-chloro-6-(1-(trifluoromethyl)cyclopropyl)benzoyl)-6-(4-hydroxypiperidine-1-carbonyl)-4,5,6,7-tetrahydro-1H-indazol-3-yl)-3-fluorobenzoic acid | 634 |
| 21CCC | 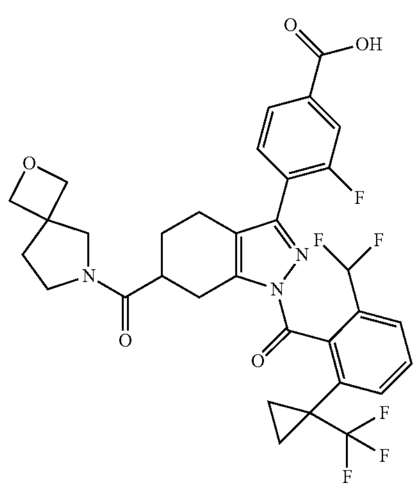 [SMILES: O=C(O)c1ccc(-c2nn(C(=O)c3c(C(F)F)cccc3C3(C(F)(F)F)CC3)c3c2CCC(C(=O)N2CCC4(COC4)C2)C3)c(F)c1] | (R or S)-4-(1-(2-(difluoromethyl)-6-(1-(trifluoromethyl)cyclopropyl)benzoyl)-6-(2-oxa-6-azaspiro[3.4]octane-6-carbonyl)-4,5,6,7-tetrahydro-1H-indazol-3-yl)-3-fluorobenzoic acid | 662 |

Example 22A

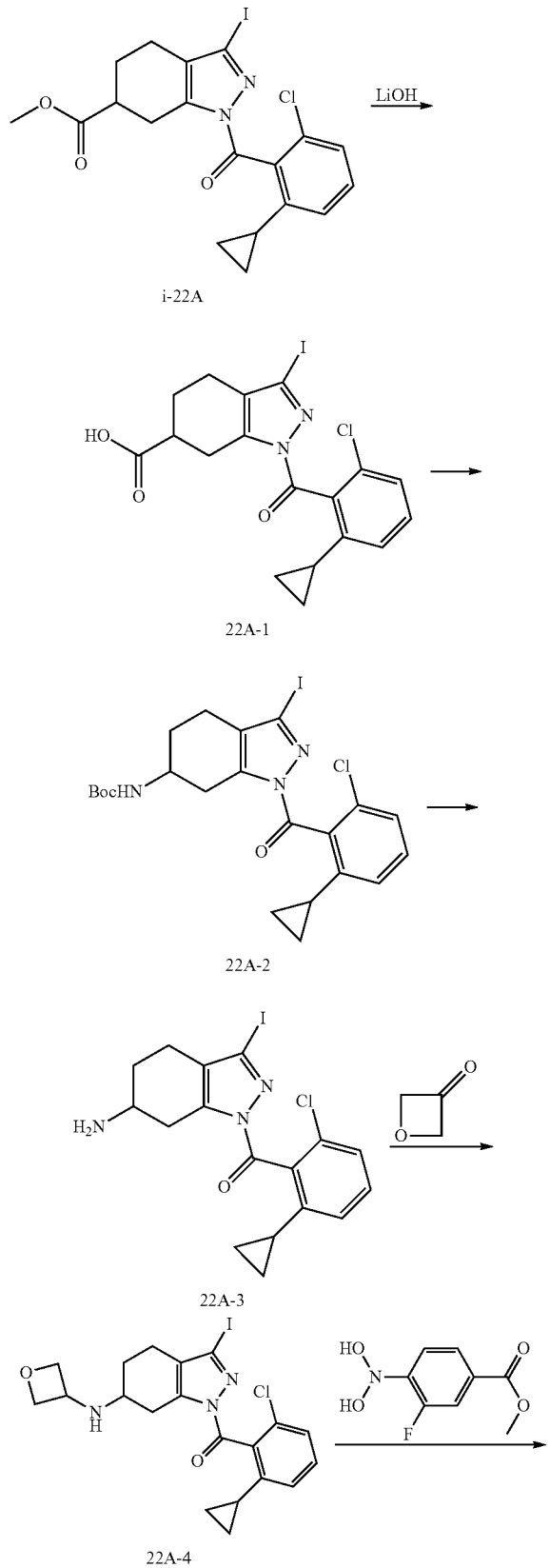

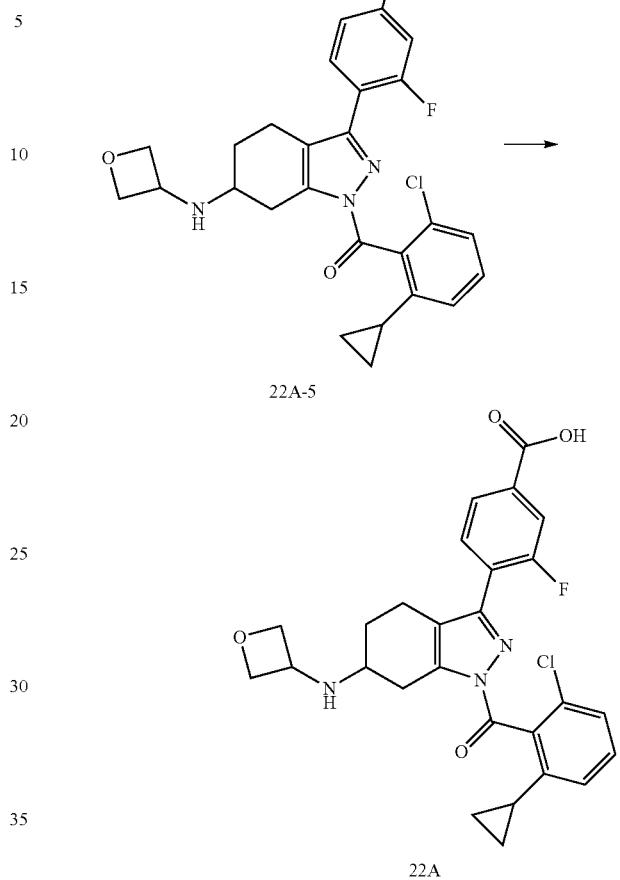

(R or S)-4-(1-(2-chloro-6-cyclopropylbenzoyl)-6-(oxetan-3-ylamino)-4,5,6,7-tetrahydro-1H-indazol-3-yl)-3-fluorobenzoic acid Step 1: Preparation of (R or S)-1-(2-chloro-6-cyclopropylbenzoyl)-3-iodo-4,5,6,7-tetrahydro-1H-indazole-6-carboxylic acid (22A-1)

A mixture of methyl (R or S)-1-(2-chloro-6-cyclopropylbenzoyl)-3-iodo-4,5,6,7-tetrahydro-1H-indazole-6-carboxylate (i-23A) (2.4 g, 4.95 mmol), LiOH (0.593 g, 24.76 mmol), THF (8.25 ml), and water (8.25 ml) was stirred overnight at room temperature. The reaction was diluted with EtOAc and the organic layer was washed twice with saturated ammonium chloride. The organic layer was dried with $Na_2SO_4$, filtered, and concentrated in vacuo. The crude product thus obtained was used in the next step without further purification. MS: 471 (M+1).

Step 2: Preparation of tert-butyl (R or S)-(1-(2-chloro-6-cyclopropylbenzoyl)-3-iodo-4,5,6,7-tetrahydro-1H-indazol-6-yl)carbamate (22A-2)

To a mixture of (R or S)-1-(2-chloro-6-cyclopropylbenzoyl)-3-iodo-4,5,6,7-tetrahydro-1H-indazole-6-carboxylic acid (1.5 g, 3.19 mmol) in Toluene (15.93 ml) was added triethylamine (0.489 ml, 3.51 mmol) and diphenylphosphoryl azide (0.725 ml, 3.35 mmol). The resulting reaction mixture was heated to 110° C. for 2 hours. Tert-butanol (6.10 ml, 63.7 mmol) was then added and the reaction was heated at 85° C. overnight. The reaction was cooled and diluted with EtOAc. The organic layer was separated and washed twice with aqueous sodium hydroxide (0.1M) and once with brine. The combined organic layers were dried with $Na_2SO_4$, filtered, and concentrated in vacuo. The residue was purified by silica gel chromatography (0-100% EtOAc/Hexane) to afford the title compound. MS: 542 (M+1).

Step 3: Preparation of (R or S)-(6-amino-3-iodo-4,5,6,7-tetrahydro-1H-indazol-1-yl)(2-chloro-6-cyclopropylphenyl)methanone (22A-3)

To a flask was added tert-butyl (R or 5)-(1-(2-chloro-6-cyclopropylbenzoyl)-3-iodo-4,5,6,7-tetrahydro-1H-indazol-6-yl)carbamate (776 mg, 1.432 mmol), HCl (4M in Dioxane) (1790 µl, 7.16 mmol), and DCM (5729 µl) and the solution was allowed to stir at room temperature for 3 hours at room temperature. Reaction concentrated to give HCl salt of product. MS: 442 (M+1).

Step 4: Preparation of (R or S)-(2-chloro-6-cyclopropylphenyl)(3-iodo-6-(oxetan-3-ylamino)-4,5,6,7-tetrahydro-1H-indazol-1-yl)methanone (22A-4)

To a mixture of (R or S)-(6-amino-3-iodo-4,5,6,7-tetrahydro-1H-indazol-1-yl)(2-chloro-6-cyclopropylphenyl)methanone (150 mg, 0.340 mmol), oxetan-3-one (48.9 mg, 0.679 mmol), and triethylamine (237 µl, 1.698 mmol) in THF (1698 µl) and methanol (1698 µl) was added sodium cyanoborohydride (32.0 mg, 0.509 mmol) and acetic acid (38.9 µl, 0.679 mmol). The reaction was allowed to stir at room temperature overnight. The reaction was diluted with EtOAc. The organic layer was separated and washed twice with aqueous $NaHCO_3$ and once with brine. The combined organic layers were dried with $Na_2SO_4$, filtered, and concentrated in vacuo. The residue was purified by silica gel chromatography (0-100% EtOAc/Hexane) to afford the title compound. MS: 498 (M+1).

Step 5: Preparation of methyl (R or S)-4-(1-(2-chloro-6-cyclopropylbenzoyl)-6-(oxetan-3-ylamino)-4,5,6,7-tetrahydro-1H-indazol-3-yl)-3-fluorobenzoate (22A-5)

To a flask was added (R or S)-(2-chloro-6-cyclopropylphenyl)(3-iodo-6-(oxetan-3-ylamino)-4,5,6,7-tetrahydro-1H-indazol-1-yl)methanone (80 mg, 0.161 mmol), (2-fluoro-4-(methoxycarbonyl)phenyl)boronic acid (63.6 mg, 0.321 mmol), $PdCl_2$(dppf)-$CH_2Cl_2$ Adduct (26.3 mg, 0.032 mmol), potassium acetate (47.3 mg, 0.482 mmol), and THF (643 µl) and the reaction was thoroughly purged with Argon for 5 minutes. Water (161 µl) was then added and the solution was heated to 80° C. overnight. The reaction was cooled and diluted with EtOAc. The organic layer was separated and washed twice with aqueous $NaHCO_3$ and once with brine. The combined organic layers were dried with $Na_2SO_4$, filtered, and concentrated in vacuo. The residue was purified by silica gel chromatography (0-100% EtOAc/Hexane) to afford the title compound. MS: 524 (M+1).

Step 6: Preparation of (R or S)-4-(1-(2-chloro-6-cyclopropylbenzoyl)-6-(oxetan-3-ylamino)-4,5,6,7-tetrahydro-1H-indazol-3-yl)-3-fluorobenzoic acid (22A)

A mixture of methyl (R or S)-4-(1-(2-chloro-6-cyclopropylbenzoyl)-6-(oxetan-3-ylamino)-4,5,6,7-tetrahydro-1H-indazol-3-yl)-3-fluorobenzoate (22 mg, 0.042 mmol) and LiOH (1.005 mg, 0.042 mmol) in THF (336 µl), and Water (84 µl) was allowed to stir at room temperature overnight. Reaction concentrated and residue was purified using mass directed reverse phase chromatography to afford desired product. MS: 510 (M+1). $^1$H NMR (DMSO-d6) δ (ppm): 9.58 (s, 2H), 7.86-7.69 (m, 2H), 7.52-7.31 (m, 3H), 7.09-6.99 (m, 1H), 4.84-4.75 (m, 2H), 4.71-4.60 (m, 2H), 3.69 (d, J=14.9 Hz, 2H), 3.25-3.09 (m, 1H), 2.15-2.05 (m, 1H), 1.88-1.58 (m, 3H), 0.92-0.58 (m, 4H).

Example 23A

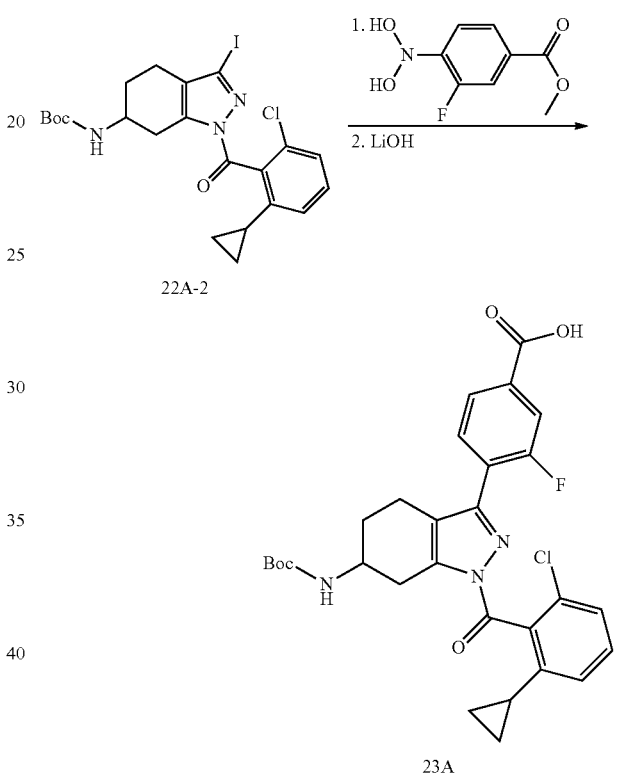

23A (R or S)-4-(6-((tert-butoxycarbonyl)amino)-1-(2-chloro-6-cyclopropylbenzoyl)-4,5,6,7-tetrahydro-1H-indazol-3-yl)-3-fluorobenzoic acid Step 1: Preparation of (S)-4-(6-((tert-butoxycarbonyl)amino)-1-(2-chloro-6-cyclopropylbenzoyl)-4,5,6,7-tetrahydro-1H-indazol-3-yl)-3-fluorobenzoic acid A mixture of tert-butyl (R or S)-(1-(2-chloro-6-cyclopropylbenzoyl)-3-iodo-4,5,6,7-tetrahydro-1H-indazol-6-yl)carbamate (22A-2) (67 mg, 0.124 mmol), (2-fluoro-4-(methoxycarbonyl)phenyl)boronic acid (49.0 mg, 0.247 mmol), $PdCl_2$(dppf)-$CH_2Cl_2$ adduct (20.20 mg, 0.025 mmol), potassium acetate (36.4 mg, 0.371 mmol) and THF (495 µl) was thoroughly degassed with Argon for 5 minutes. Water (124 µl) was then added and the solution was heated to 80° C. overnight. The reaction was cooled and diluted with EtOAc. The organic layer was separated and washed twice with aqueous $NaHCO_3$ and once with brine. The combined organic layers were dried with Na₂SO₄, filtered, and concentrated in vacuo. The residue was purified by silica gel chromatography (0-100% EtOAc/Hexane) to afford the intermediate methyl (R or S)-4-(6-((tert-butoxycarbonyl)amino)-1-(2-chloro-6-cyclopropylbenzoyl)-4,5,6,7-tetrahydro-1H-indazol-3-yl)-3-fluorobenzoate. MS: 568 (M+1).

To a mixture of methyl (R or S)-4-(6-((tert-butoxycarbonyl)amino)-1-(2-chloro-6-cyclopropylbenzoyl)-4,5,6,7-tetrahydro-1H-indazol-3-yl)-3-fluorobenzoate in 1:1 THF:Water (2 mL) was added LiOH (59.2 mg, 2.473 mmol). The resulting reaction mixture was allowed to stir at room temperature overnight. Reaction concentrated and residue was purified using mass directed reverse phase chromatography to afford desired product. MS: 554 (M+1). ¹H NMR (DMSO-d6) δ (ppm): 7.75 (dd, J=39.2, 9.3 Hz, 2H), 7.53-7.30 (m, 2H), 7.15-6.97 (m, 2H), 3.83 (bs, 1H), 3.53-3.37 (m, 1H), 3.00-2.90 (m, 1H), 2.60-2.48 (m, 2H), 1.86 (bs, 1H), 1.74-1.60 (m, 2H), 1.38 (s, 9H), 0.91-0.53 (m, 4H).

Example 24A

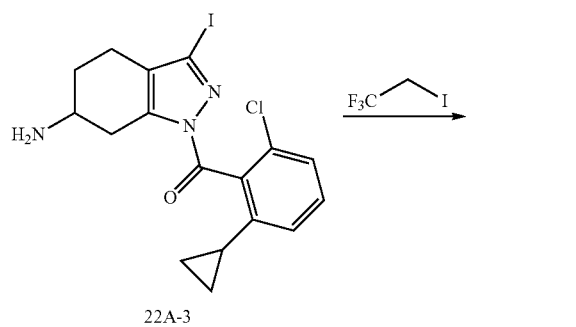

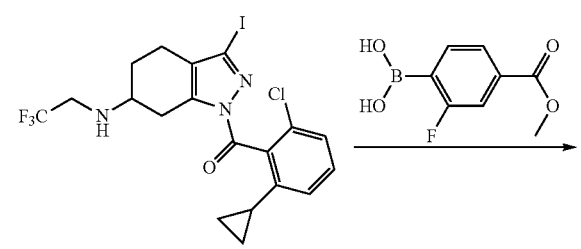

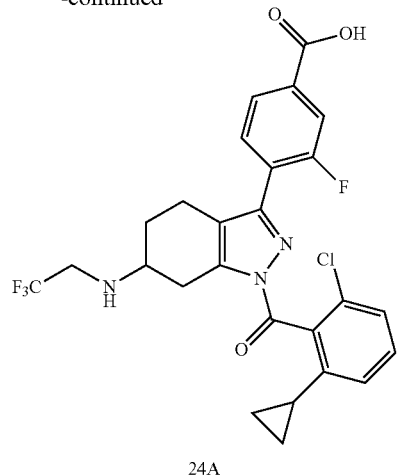

24A (R or S)-4-(1-(2-chloro-6-cyclopropylbenzoyl)-6-((2,2,2-trifluoroethyl)amino)-4,5,6,7-tetrahydro-1H-indazol-3-yl)-3-fluorobenzoic acid Step 1: Preparation of (R or S)-(2-chloro-6-cyclopropylphenyl)(3-iodo-6-((2,2,2-trifluoroethyl)amino)-4,5,6,7-tetrahydro-1H-indazol-1-yl)methanone (24A-1)

A mixture of (R or S)-(6-amino-3-iodo-4,5,6,7-tetrahydro-1H-indazol-1-yl)(2-chloro-6-cyclopropylphenyl)methanone (22A-3) (100 mg, 0.209 mmol), 2-iodo-1,1,1-trifluoroethane (351 mg, 1.673 mmol), potassium carbonate (173 mg, 1.255 mmol), and acetonitrile (697 µl) was heated to 130° C. for 72 hours. The reaction was cooled and diluted with EtOAc. The organic layer was separated and washed twice with aqueous NaHCO₃ and once with brine. The combined organic layers were dried with Na₂SO₄, filtered, and concentrated in vacuo. The residue was purified by silica gel chromatography (0-100% EtOAc/Hexane) to afford desired product. MS: 524 (M+1).

Step 2: Preparation of methyl (R or S)-4-(1-(2-chloro-6-cyclopropylbenzoyl)-6-((2,2,2-trifluoroethyl)amino)-4,5,6,7-tetrahydro-1H-indazol-3-yl)-3-fluorobenzoate (24A-2)

A mixture of (R or S)-(2-chloro-6-cyclopropylphenyl)(3-iodo-6-((2,2,2-trifluoroethyl)amino)-4,5,6,7-tetrahydro-1H-indazol-1-yl)methanone (20 mg, 0.038 mmol), (2-fluoro-4-(methoxycarbonyl)phenyl)boronic acid (15.12 mg, 0.076 mmol), PdCl₂(dppf)-CH₂Cl₂ adduct (6.24 mg, 7.64 µmol), potassium acetate (11.24 mg, 0.115 mmol), and THF (306 µl) was degassed with Argon for 5 minutes. Water (76 µl) was then added and the reaction was heated to 80° C. overnight. The reaction was cooled and diluted with EtOAc. The organic layer was separated and washed twice with aqueous NaHCO₃ and once with brine. The combined organic layers were dried with Na₂SO₄, filtered, and concentrated in vacuo. The residue was purified by silica gel chromatography (0-100% EtOAc/Hexane) to afford desired product. MS: 550 (M+1).

Step 3: Preparation of (R or S)-4-(1-(2-chloro-6-cyclopropylbenzoyl)-6-((2,2,2-trifluoroethyl)amino)-4,5,6,7-tetrahydro-1H-indazol-3-yl)-3-fluorobenzoic acid (24A)

A mixture of methyl (R or S)-4-(1-(2-chloro-6-cyclopropylbenzoyl)-6-((2,2,2-trifluoroethyl)amino)-4,5,6,7-tetrahydro-1H-indazol-3-yl)-3-fluorobenzoate (12 mg, 0.022 mmol) and LiOH (0.523 mg, 0.022 mmol) in THF (349 µl) and Water (87 µl) was allowed to stir at room temperature overnight. Reaction concentrated and residue was purified using mass directed reverse phase chromatography to afford desired product. MS: 536 (M+1). $^1$H NMR (DMSO-d6) δ (ppm): 7.76 (dd, J=37.5, 9.3 Hz, 2H), 7.54-7.29 (m, 3H), 7.03 (dd, J=16.8, 7.7 Hz, 1H), 3.60 (bs, 2H), 3.00 (bs, 1H), 2.86-2.49 (m, 4H), 2.04 (bs, 1H), 1.75-1.57 (m, 2H), 0.90-0.55 (m, 4H).

Example 25A

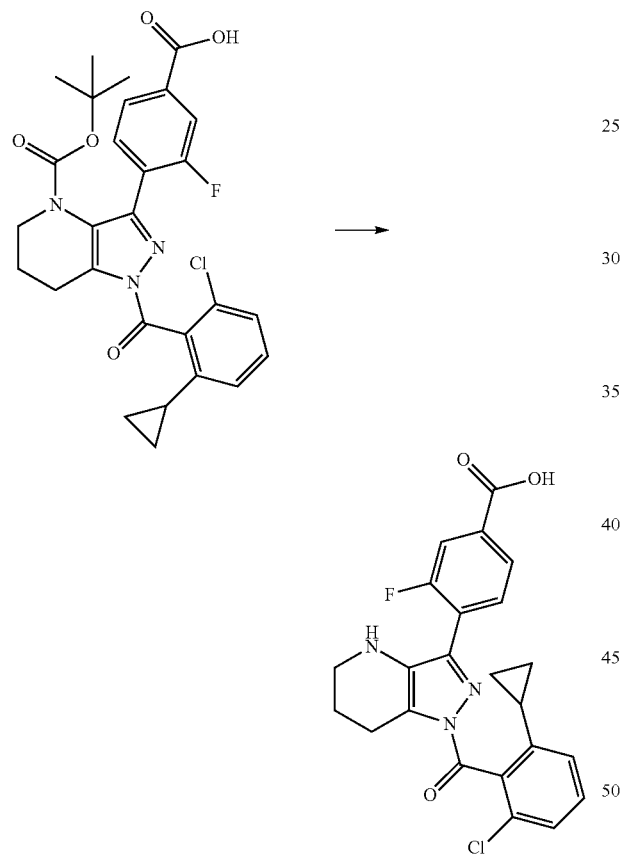

4-(1-(2-chloro-6-cyclopropylbenzoyl)-4,5,6,7-tetrahydro-1H-pyrazolo[4,3-b]pyridin-3-yl)-3-fluorobenzoic acid

Step 1: Preparation of 4-(1-(2-chloro-6-cyclopropylbenzoyl)-4,5,6,7-tetrahydro-1H-pyrazolo[4,3-b]pyridin-3-yl)-3-fluorobenzoic acid A mixture of Example 7A (15.5 mg, 0.024 mmol), DCM (379 µl), and TFA (95 µl) was allowed to stir at room temperature for 3 hours. Reaction concentrated and residue was purified using mass directed reverse phase chromatography to afford desired product. MS: 440 (M+1). $^1$H NMR (DMSO-d6) δ (ppm): 7.77 (dd, J=8.0, 1.6 Hz, 1H), 7.68 (dd, J=10.7, 1.6 Hz, 1H), 7.57 (t, J=7.6 Hz, 1H), 7.38-7.28 (m, 2H), 6.99 (d, J=7.7 Hz, 1H), 3.18-3.02 (m, 4H), 1.91-1.80 (m, 2H), 1.72-1.59 (m, 1H), 0.89-0.55 (m, 4H).

The following example shown in Table 14 was prepared following similar procedures described for Example 25A which can be achieved by those of ordinary skill in the art of organic synthesis.

TABLE 14

| Example No. | Structure | IUPAC Name | Exact Mass [M + H]+ |
|---|---|---|---|
| 25B | 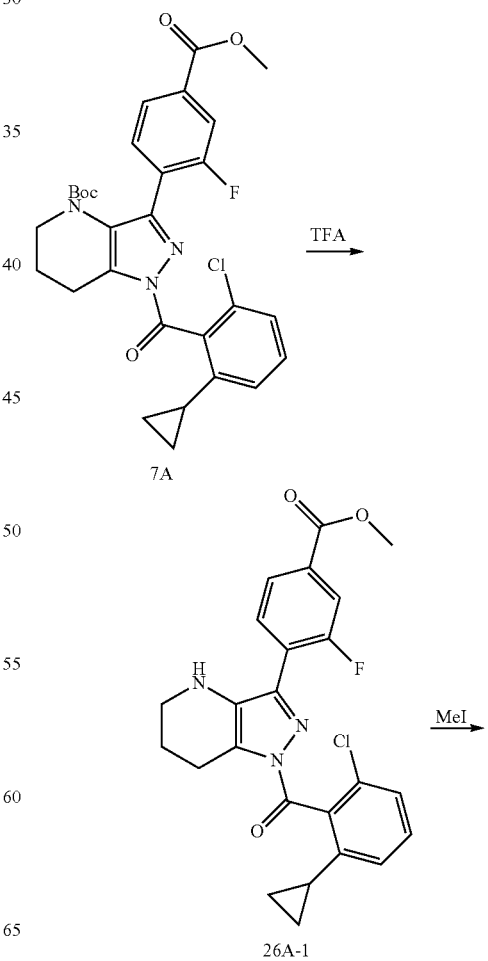 | 4-[1-({2-chloro-6-[1-(trifluoromethyl)cyclopropyl]phenyl}carbonyl)-4,5,6,7-tetrahydro-1H-pyrazolo[4,3-b]pyridin-3-yl]-3-fluorobenzoic acid | 508 |

Example 26A

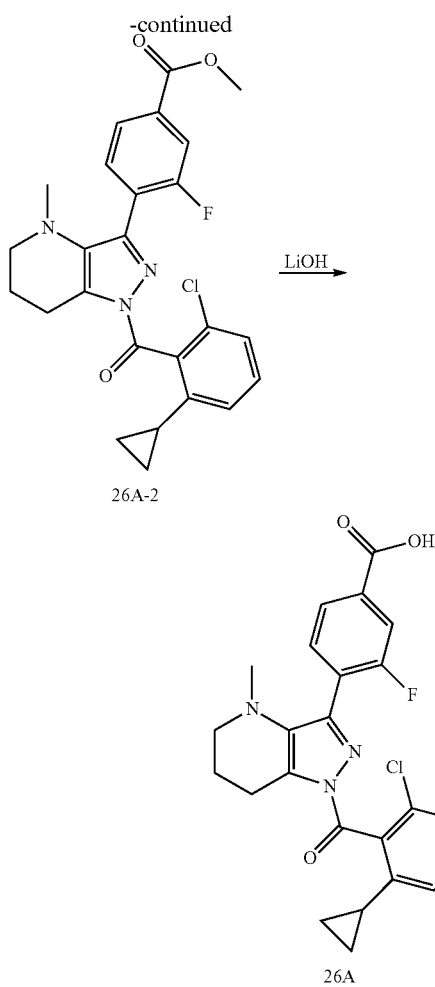

4-(1-(2-chloro-6-cyclopropylbenzoyl)-4-methyl-4,5,6,7-tetrahydro-1H-pyrazolo[4,3-b]pyridin-3-yl)-3-fluorobenzoic acid Step 1: Preparation of methyl 4-(1-(2-chloro-6-cyclopropylbenzoyl)-4,5,6,7-tetrahydro-1H-pyrazolo[4,3-b]pyridin-3-yl)-3-fluorobenzoate (26A-1)

A mixture of tert-butyl 1-(2-chloro-6-cyclopropylbenzoyl)-3-(2-fluoro-4-(methoxycarbonyl)phenyl)-1,5,6,7-tetrahydro-4H-pyrazolo[4,3-b]pyridine-4-carboxylate (7A) (105 mg, 0.190 mmol), DCM (1516 µl), and TFA (379 µl) was allowed to stir at RT for 3 hours.

The reaction concentrated and dried on high vacuum to afford crude product. MS: 454 (M+1).

Step 2: Preparation of methyl 4-(1-(2-chloro-6-cyclopropylbenzoyl)-4-methyl-4,5,6,7-tetrahydro-1H-pyrazolo[4,3-b]pyridin-3-yl)-3-fluorobenzoate (26A-2)

A mixture of methyl 4-(1-(2-chloro-6-cyclopropylbenzoyl)-4,5,6,7-tetrahydro-1H-pyrazolo[4,3-b]pyridin-3-yl)-3-fluorobenzoate (85 mg, 0.19 mmol), DMF (1873 µl) and NaH (22.47 mg, 0.56 mmol) was allowed to stir at room temperature for 10 minutes. Methyl iodide (17.56 µl, 0.28 mmol) was then added and the solution was allowed to stir at room temperature overnight. The reaction was diluted with EtOAc. The organic layer was separated and washed twice with aqueous NaHCO₃ and once with brine. The combined organic layers were dried with Na₂SO₄, filtered, and concentrated in vacuo. The residue was purified by silica gel chromatography (0-100% EtOAc/Hexane) to afford desired product. MS: 468 (M+1).

Step 3: Preparation of 4-(1-(2-chloro-6-cyclopropylbenzoyl)-4-methyl-4,5,6,7-tetrahydro-1H-pyrazolo[4,3-b]pyridin-3-yl)-3-fluorobenzoic acid (26A)

A mixture of methyl 4-(1-(2-chloro-6-cyclopropylbenzoyl)-4-methyl-4,5,6,7-tetrahydro-1H-pyrazolo[4,3-b]pyridin-3-yl)-3-fluorobenzoate (28 mg, 0.060 mmol) and LiOH (14.33 mg, 0.598 mmol) in THF (479 µl) and Water (120 µl) was allowed to stir at room temperature overnight. Reaction concentrated and residue was purified using mass directed reverse phase chromatography to afford desired product. MS: 454 (M+1). $^1$H NMR (DMSO-d6) δ (ppm): 7.86-7.69 (m, 2H), 7.58 (t, J=7.5 Hz, 1H), 7.42-7.29 (m, 2H), 7.01 (d, J=7.6 Hz, 1H), 3.19-3.09 (m, 2H), 3.04-2.92 (m, 2H), 2.33 (s, 3H), 1.92 (s, 2H), 1.72-1.58 (m, 1H), 0.94-0.55 (m, 4H).

Example 27A

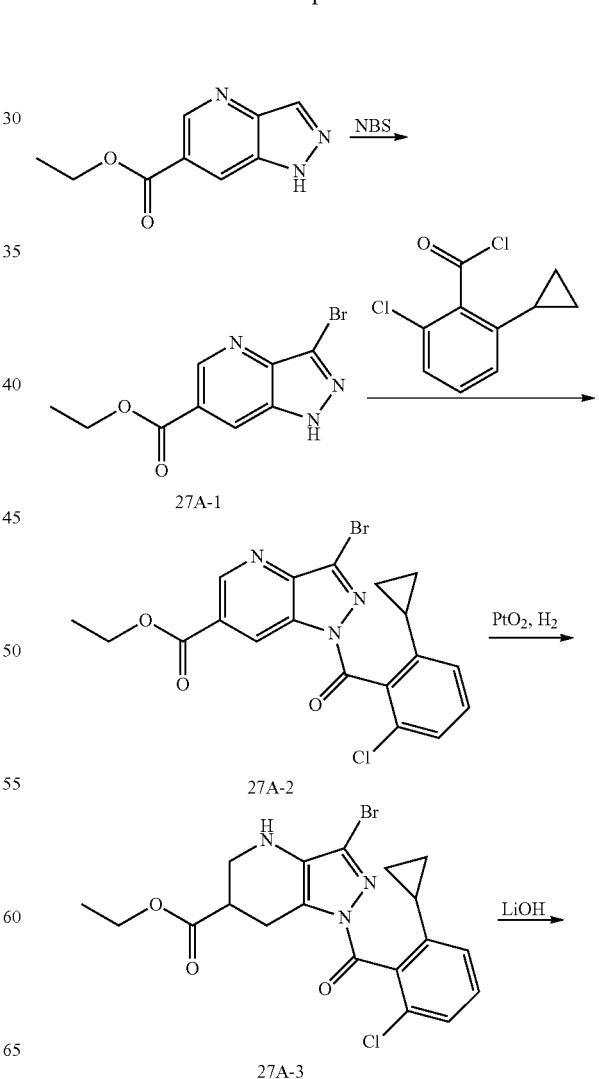

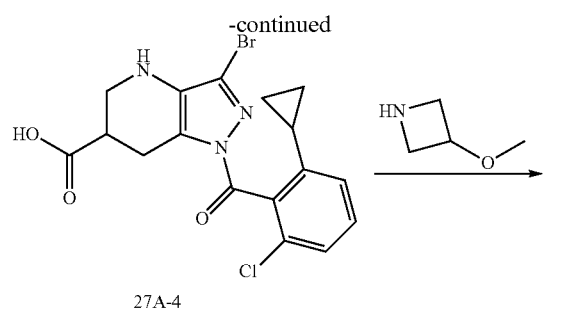

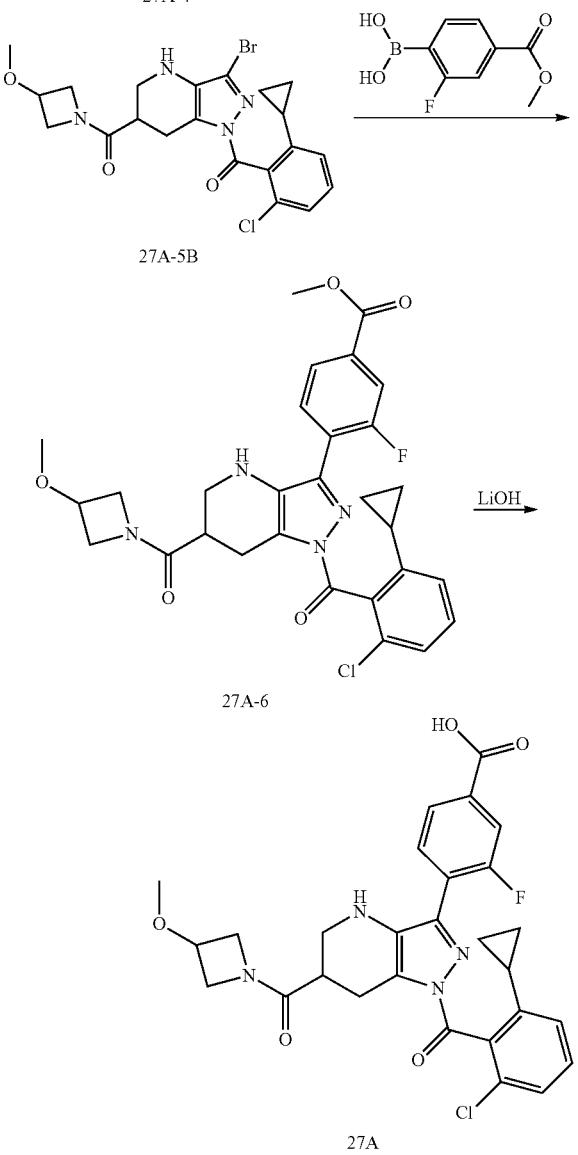

27A (R or S)-4-(1-(2-chloro-6-cyclopropylbenzoyl)-6-(3-methoxyazetidine-1-carbonyl)-4,5,6,7-tetrahydro-1H-pyrazolo[4,3-b]pyridin-3-yl)-3-fluorobenzoic acid Step 1: Preparation of ethyl 3-bromo-1H-pyrazolo[4,3-b]pyridine-6-carboxylate (27A-1)

A mixture of ethyl 1H-pyrazolo[4,3-b]pyridine-6-carboxylate (100 mg, 0.523 mmol), DMF (1743 µl), and NBS (112 mg, 0.628 mmol) was allowed to stir at room temperature overnight. The reaction was diluted with EtOAc. The organic layer was separated and washed twice with saturated sodium thiosulfate and once with brine. The combined organic layers were dried with $Na_2SO_4$, filtered, and concentrated in vacuo to afford crude product. MS: 270 (M+1).

Step 2: Preparation of ethyl 3-bromo-1-(2-chloro-6-cyclopropylbenzoyl)-1H-pyrazolo[4,3-b]pyridine-6-carboxylate (27A-2)

A mixture of ethyl 3-bromo-1H-pyrazolo[4,3-b]pyridine-6-carboxylate (140 mg, 0.518 mmol), TEA (217 µl, 1.555 mmol), DMAP (12.67 mg, 0.104 mmol), DMF (1728 µl), and 2-chloro-6-cyclopropylbenzoyl chloride (223 mg, 1.037 mmol) was allowed to stir at room temperature overnight. The reaction was diluted with EtOAc. The organic layer was separated and washed twice with aqueous $NaHCO_3$ and once with brine. The combined organic layers were dried with $Na_2SO_4$, filtered, and concentrated in vacuo. The residue was purified by silica gel chromatography (0-100% EtOAc/Hexane) to afford desired product. MS: 448 (M+1).

Step 3: Preparation of ethyl 3-bromo-1-(2-chloro-6-cyclopropylbenzoyl)-4,5,6,7-tetrahydro-1H-pyrazolo[4,3-b]pyridine-6-carboxylate (27A-3)

To a parr shaker flask was added ethyl 3-bromo-1-(2-chloro-6-cyclopropylbenzoyl)-1H-pyrazolo[4,3-b]pyridine-6-carboxylate (4 g, 8.91 mmol), HCl (4M in dioxane, 4.46 ml, 17.83 mmol), ethanol (44.6 ml), and platinum(IV) oxide (0.405 g, 1.783 mmol) and the resulting mixture was allowed to react under an hydrogen (55 psi) overnight in the parr shaker. The reaction was filtered through activated celite and concentrated in vacuo. The residue was purified by silica gel chromatography (0-100% EtOAc/Hexane) to afford desired product. MS: 452 (M+1).

Step 4: Preparation of 3-bromo-1-(2-chloro-6-cyclopropylbenzoyl)-4,5,6,7-tetrahydro-1H-pyrazolo[4,3-b]pyridine-6-carboxylic acid (27A-4)

A mixture of ethyl 3-bromo-1-(2-chloro-6-cyclopropylbenzoyl)-4,5,6,7-tetrahydro-1H-pyrazolo[4,3-b]pyridine-6-carboxylate (200 mg, 0.442 mmol) and LiOH (52.9 mg, 2.209 mmol) in THF (1767 µl) and Water (442 µl) was allowed to stir at room temperature overnight. The reaction was diluted with EtOAc. The organic layer was separated and washed twice with aqueous ammonium chloride and once with brine. The combined organic layers were dried with $Na_2SO_4$, filtered, and concentrated in vacuo to give crude product. MS: 424 (M+1).

Step 5: Preparation of (R or S)-(3-bromo-1-(2-chloro-6-cyclopropylbenzoyl)-4,5,6,7-tetrahydro-1H-pyrazolo[4,3-b]pyridin-6-yl)(3-methoxyazetidin-1-yl)methanone (27A-5B)

A mixture of 3-bromo-1-(2-chloro-6-cyclopropylbenzoyl)-4,5,6,7-tetrahydro-1H-pyrazolo[4,3-b]pyridine-6-carboxylic acid (150 mg, 0.353 mmol), 3-methoxyazetidine hydrochloride (87 mg, 0.706 mmol), TEA (148 µl, 1.060 mmol), HATU (201 mg, 0.530 mmol) and DCM (1766 µl) was allowed to stir at room temperature overnight. The reaction was diluted with EtOAc. The organic layer was separated and washed twice with aqueous NaHCO$_3$ and once with brine. The combined organic layers were dried with Na$_2$SO$_4$, filtered, and concentrated in vacuo. The residue was purified by silica gel chromatography (0-100% EtOAc/Hexane) to afford racemic product. MS: 493 (M+1).

The mixture of the two stereoisomers was purified by chiral SFC (Phenomenex-Lux-4 column, 35%/65% Methanol with 0.25% Dimethyl Ethyl Amine/CO$_2$) to afford 27A-5A (faster eluting): MS: 493 (M+1). 27A-5B (slower eluting): MS: 493 (M+1).

Step 6: Preparation of methyl (R or S)-4-(1-(2-chloro-6-cyclopropylbenzoyl)-6-(3-methoxyazetidine-1-carbonyl)-4,5,6,7-tetrahydro-1H-pyrazolo[4,3-b]pyridin-3-yl)-3-fluorobenzoate (27A-6)

A mixture of (R or S)-(3-bromo-1-(2-chloro-6-cyclopropylbenzoyl)-4,5,6,7-tetrahydro-1H-pyrazolo[4,3-b]pyridin-6-yl)(3-methoxyazetidin-1-yl)methanone 27A-5B (40 mg, Step 7: Preparation of (R or S)-4-(1-(2-chloro-6-cyclopropylbenzoyl)-6-(3-methoxyazetidine-1-carbonyl)-4,5,6,7-tetrahydro-1H-pyrazolo[4,3-b]pyridin-3-yl)-3-fluorobenzoic acid (27A)

A mixture of methyl (R or S)-4-(1-(2-chloro-6-cyclopropylbenzoyl)-6-(3-methoxyazetidine-1-carbonyl)-4,5,6,7-tetrahydro-1H-pyrazolo[4,3-b]pyridin-3-yl)-3-fluorobenzoate (20.5 mg, 0.036 mmol) and LiOH (0.866 mg, 0.036 mmol) in THF (289 µl) and Water (72.3 µl) was allowed to stir at room temperature for 3 hours. Reaction concentrated and residue was purified using mass directed reverse phase chromatography to afford desired product. MS: 553 (M+1). $^1$H NMR (DMSO-d6) δ (ppm): 7.81-7.66 (m, 2H), 7.57 (q, J=7.3 Hz, 1H), 7.39-7.26 (m, 2H), 7.00 (dd, J=16.9, 7.6 Hz, 1H), 4.49-4.40 (m, 1H), 4.39-4.32 (m, 1H), 4.24-4.15 (m, 1H), 4.14-3.96 (m, 2H), 3.73-3.59 (m, 1H), 3.34-3.23 (m, 2H), 3.23-3.05 (m, 4H), 2.87-2.76 (m, 1H), 2.75-2.61 (m, 1H), 1.73-1.58 (m, 1H), 0.93-0.53 (m, 4H).

The following example shown in Table 15 was prepared following similar procedures described for Example 27A using 27A-5A which can be achieved by those of ordinary skill in the art of organic synthesis.

TABLE 15

| Example No. | Structure | IUPAC Name | Exact Mass [M + H]+ |
|---|---|---|---|
| 27B | 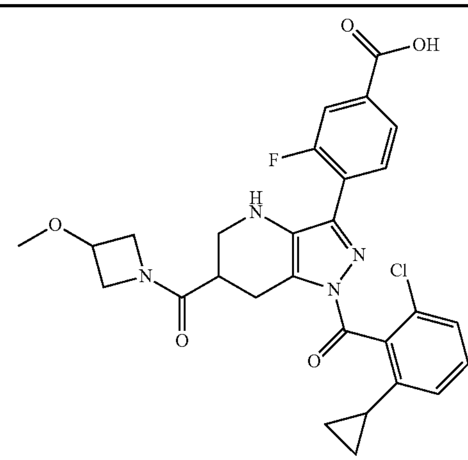 | (R or S)-4-(1-(2-chloro-6-cyclopropylbenzoyl)-6-(3-methoxyazetidine-1-carbonyl)-4,5,6,7-tetrahydro-1H-pyrazolo[4,3-b]pyridin-3-yl)-3-fluorobenzoic acid | 553 |

0.081 mmol), (2-fluoro-4-(methoxycarbonyl)phenyl)boronic acid (32.1 mg, 0.162 mmol), PdCl$_2$(dppf)-CH$_2$Cl$_2$ adduct (13.23 mg, 0.016 mmol), potassium acetate (23.85 mg, 0.243 mmol), and THF (648 µl) was thoroughly degassed with Argon for 5 minutes. Water (162 µl) was then added and the solution was heated to 80° C. overnight. The reaction was cooled and diluted with EtOAc. The organic layer was separated and washed twice with aqueous NaHCO$_3$ and once with brine. The combined organic layers were dried with Na$_2$SO$_4$, filtered, and concentrated in vacuo. The residue was purified by silica gel chromatography (0-100% EtOAc/Hexane) to afford desired product. MS: 567 (M+1).

Example 28A

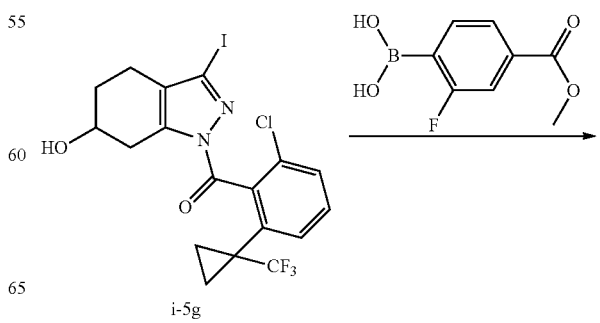

i-5g

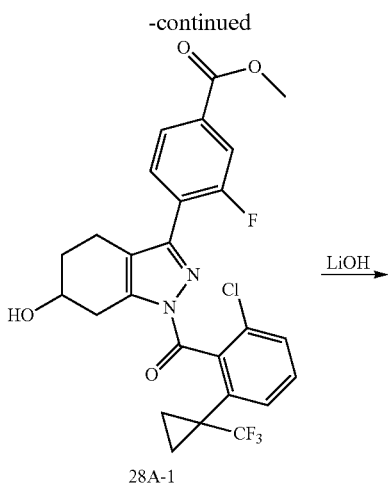

28A-1

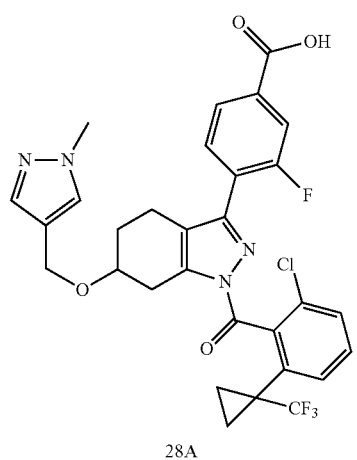

28A 4-(1-(2-Chloro-6-(1-(trifluoromethyl)cyclopropyl)
benzoyl)-6-(((1-methyl-1H-pyrazol-4-yl)methoxy)-4,
5,6,7-tetrahydro-1H-indazol-3-yl)-3-fluorobenzoic
acid Step 1: Preparation of Methyl 4-(1-(2-chloro-6-(1-
(trifluoromethyl)cyclopropyl)benzoyl)-6-hydroxy-4,
5,6,7-tetrahydro-1H-indazol-3-yl)-3-fluorobenzoate
(28A-1)

To a vial was added (2-chloro-6-(1-(trifluoromethyl)cyclopropyl)phenyl)(6-hydroxy-3-iodo-4,5,6,7-tetrahydro-1H-indazol-1-yl)methanone (120.0 mg, 0.23 mmol), (2-fluoro-4-(methoxycarbonyl)phenyl)boronic acid (93.0 mg, 0.47 mmol), PdCl$_2$(dppf)-CH$_2$Cl$_2$ Adduct (38.4 mg, 0.047 mmol), potassium acetate (69.2 mg, 0.70 mmol), THF (940 µl), and Water (235 µl). The reaction was thoroughly degassed with Argon and heated to 80° C. overnight. The reaction mixture was cooled to rt, diluted with ethyl acetate, washed with aqueous sodium hydrogen carbonate (×2) and brine. The combined aqueous layers were extracted with ethyl acetate. The combined organic layers were dried over sodium sulfate, filtered, and concentrated in vacuo while loading onto silica gel. The residue was purified by column chromatography on silica (5-60% EtOAc/hexanes) to afford methyl 4-(1-(2-chloro-6-(1-(trifluoromethyl)cyclopropyl) benzoyl)-6-hydroxy-4,5,6,7-tetrahydro-1H-indazol-3-yl)-3-fluorobenzoate. MS: 537 (M+1)

Step 2: Preparation of 4-(1-(2-Chloro-6-(1-(trifluoromethyl)cyclopropyl)benzoyl)-6-((1-methyl-1H-pyrazol-4-yl)methoxy)-4,5,6,7-tetrahydro-1H-indazol-3-yl)-3-fluorobenzoic acid (28A)

Methyl 4-(1-(2-chloro-6-(1-(trifluoromethyl)cyclopropyl)benzoyl)-6-hydroxy-4,5,6,7-tetrahydro-1H-indazol-3-yl)-3-fluorobenzoate (30.0 mg, 0.06 mmol) was dissolved in DMF (0.5 mL) and cooled to 0° C. NaH (3.3 mg, 0.08 mmol) was then added. The reaction mixture was stirred at 0° C. for 15 min. 4-(Chloromethyl)-1-methyl-1H-pyrazole, HCl (18.67 mg, 0.11 mmol) and DIEA (0.1 mL, 0.6 mmol) was added and the reaction mixture was stirred at 50° C. for one hour. The reaction mixture was diluted with ethyl acetate and washed with brine. The organic layer was dried over sodium sulfate, filtered, and concentrated in vacuo. The residue was purified by mass triggered reverse phase HPLC (C-18; acetonitrile/water containing 0.1% TFA) to afford 4-(1-(2-chloro-6-(1-(trifluoromethyl)cyclopropyl)benzoyl)-6-((1-methyl-1H-pyrazol-4-yl)methoxy)-4,5,6,7-tetrahydro-1H-indazol-3-yl)-3-fluorobenzoic acid as a TFA salt. MS: 617 (M+1). $^1$H NMR (500 MHz, d-DMSO) δ 7.83-7.78 (m, 2H), 7.75 (dd, J=10.5, 1.6 Hz, 1H), 7.64-7.55 (m, 3H), 7.52-7.47 (m, 2H), 5.21 (s, 2H), 4.20-4.14 (m, 1H), 3.80 (s, 3H), 3.35 (dd, J=18.0, 4.7 Hz, 1H), 3.03 (dt, J=18.1, 5.9 Hz, 1H), 2.58-2.42 (m, 2H), 1.83-1.71 (m, 2H), 1.38-1.34 (m, 1H), 1.23-1.18 (m, 2H), 0.76 (s, 1H).

Example 29A

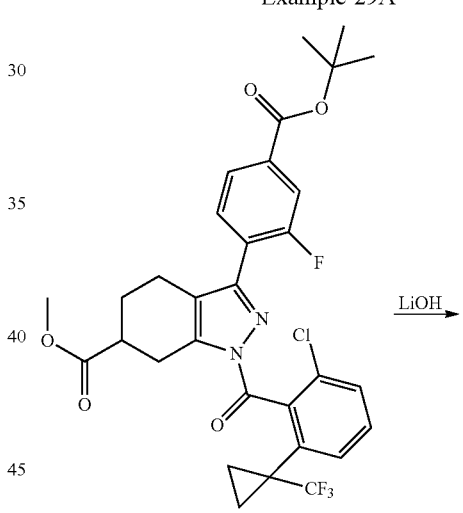

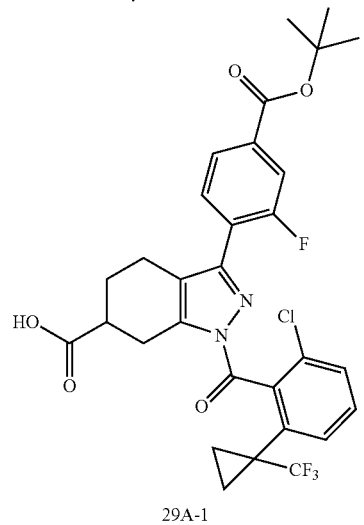

29A-1

-continued

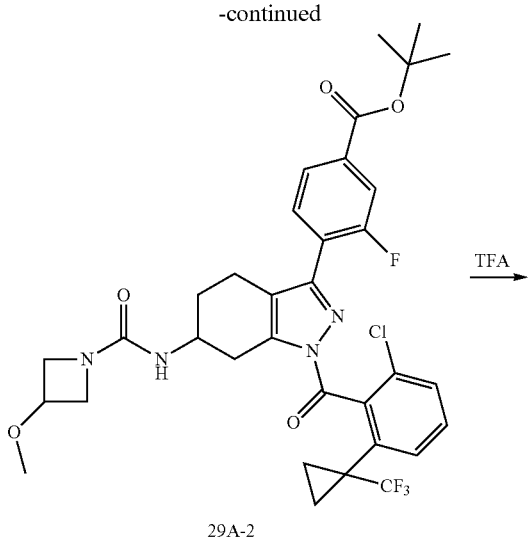

29A-2

↓ TFA

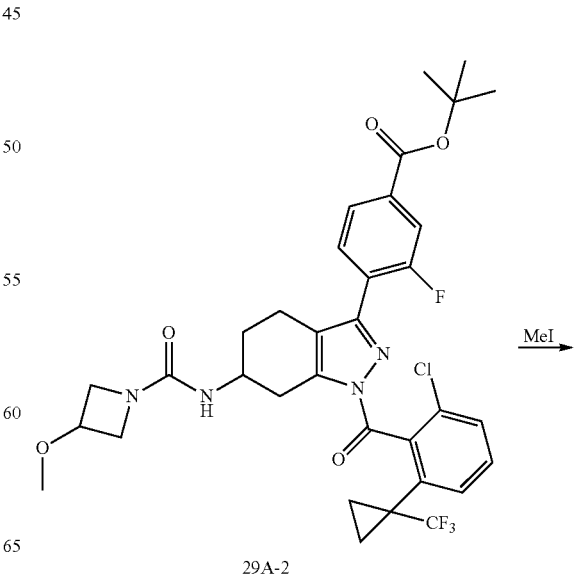

29A 4-(1-(2-Chloro-6-(1-(trifluoromethyl)cyclopropyl)
benzoyl)-6-(3-methoxyazetidine-1-carboxamido)-4,
5,6,7-tetrahydro-1H-indazol-3-yl)-3-fluorobenzoic
acid Step 1: Preparation of 3-(4-(tert-Butoxycarbonyl)-2-fluorophenyl)-1-(2-chloro-6-(1-(trifluoromethyl)cyclopropyl)benzoyl)-4,5,6,7-tetrahydro-1H-indazole-6-carboxylic acid (29A-1)

To a vial was added methyl 3-(4-(tert-butoxycarbonyl)-2-fluorophenyl)-1-(2-chloro-6-(1-(trifluoromethyl)cyclopropyl)benzoyl)-4,5,6,7-tetrahydro-1H-indazole-6-carboxylate (1.08 g, 1.74 mmol), LiOH (0.21 g, 8.70 mmol), THF (4.83 mL), and Water (0.97 mL). The reaction mixture was stirred at room temperature overnight. The reaction mixture was diluted with ethyl acetate, washed with aqueous ammonium chloride (×2), and brine. The combined organic layers were dried over sodium sulfate, filtered, and concentrated in vacuo to afford 3-(4-(tert-Butoxycarbonyl)-2-fluorophenyl)-1-(2-chloro-6-(1-(trifluoromethyl)cyclopropyl)benzoyl)-4,5,6,7-tetrahydro-1H-indazole-6-carboxylic acid. MS: 608 (M+1)

Step 2: Preparation of tert-Butyl 4-(1-(2-chloro-6-(1-(trifluoromethyl)cyclopropyl)benzoyl)-6-(3-methoxyazetidine-1-carboxamido)-4,5,6,7-tetrahydro-1H-indazol-3-yl)-3-fluorobenzoate (29A-2)

3-(4-(tert-Butoxycarbonyl)-2-fluorophenyl)-1-(2-chloro-6-(1-(trifluoromethyl)cyclopropyl)benzoyl)-4,5,6,7-tetrahydro-1H-indazole-6-carboxylic acid (100.0 mg, 0.16 mmol) was dissolved in THF (1.0 mL) and under nitrogen diphenylphosphoryl azide (0.054 mL, 0.247 mmol) and triethylamine (0.034 mL, 0.247 mmol) were added. The reaction mixture was heated to 85° C. and stirred for two hours. 3-Methoxyazetidine hydrochloride (61.1 mg, 0.49 mmol) and Hunig's Base (0.086 mL, 0.494 mmol) were added. The reaction mixture was stirred at 85° C. for 30 min. The reaction mixture was diluted with ethyl acetate and washed with brine. The organic layer was dried over sodium sulfate, filtered, and concentrated in vacuo while loading onto silica gel. The residue was purified by column chromatography on silica (10-100% EtOAc/hexanes) to afford tert-butyl 4-(1-(2-chloro-6-(1-(trifluoromethyl)cyclopropyl)benzoyl)-6-(3-methoxyazetidine-1-carboxamido)-4,5,6,7-tetrahydro-1H-indazol-3-yl)-3-fluorobenzoate. MS: 692 (M+1)

Step 3: Preparation of 4-(1-(2-Chloro-6-(1-(trifluoromethyl)cyclopropyl)benzoyl)-6-(3-methoxyazetidine-1-carboxamido)-4,5,6,7-tetrahydro-1H-indazol-3-yl)-3-fluorobenzoic acid (29A)

tert-Butyl 4-(1-(2-chloro-6-(1-(trifluoromethyl)cyclopropyl)benzoyl)-6-(3-methoxyazetidine-1-carboxamido)-4,5,6,7-tetrahydro-1H-indazol-3-yl)-3-fluorobenzoate (13.0 mg, 0.02 mmol) was dissolved in DCM (0.25 mL) then TFA (0.25 mL) was added. The reaction mixture was stirred at rt for one hour. The reaction mixture was concentrated in vacuo. The residue was purified by mass triggered reverse phase HPLC (C-18; acetonitrile/water containing 0.1% TFA) to afford 4-(1-(2-chloro-6-(1-(trifluoromethyl)cyclopropyl)benzoyl)-6-(3-methoxyazetidine-1-carboxamido)-4,5,6,7-tetrahydro-1H-indazol-3-yl)-3-fluorobenzoic acid as a TFA salt. MS: 635 (M+1). $^1$H NMR (500 MHz, d-DMSO) δ 13.43 (s, 1H), 7.80-7.74 (m, 2H), 7.67-7.56 (m, 3H), 7.51 (dt, J=9.1, 7.6, 1H), 6.49 (dd, J=10.3, 7.7 Hz, 1H), 4.16-4.13 (m, 1H), 4.02-3.99 (m, 2H), 3.96 (d, J=11.2 Hz, 1H), 3.64 (dd, J=9.0, 3.8 Hz, 2H), 3.37-3.34 (m, 1H), 3.19 (s, 3H), 2.97 (dt, J=16.4, 7.4 Hz, 1H), 2.54 (d, J=5.5 Hz, 1H), 1.96 (dd, J=19.9, 11.6 Hz, 1H), 1.72-1.58 (m, 1H), 1.35-1.32 (m, 1H), 1.28-1.16 (m, 2H), 0.82-0.75 (m, 1H).

Example 30A

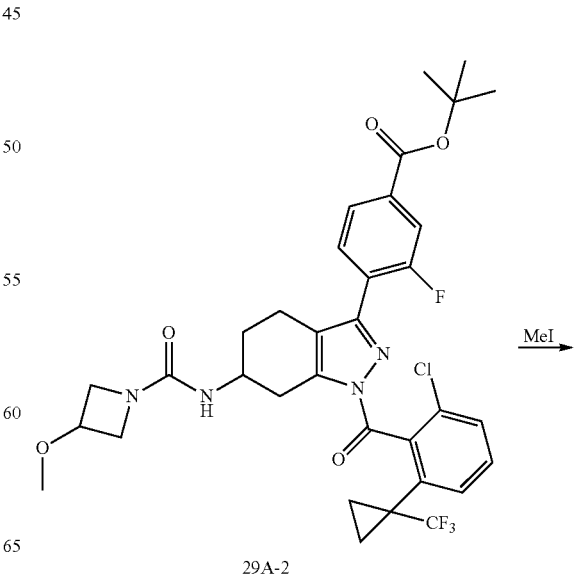

29A-2

→ MeI

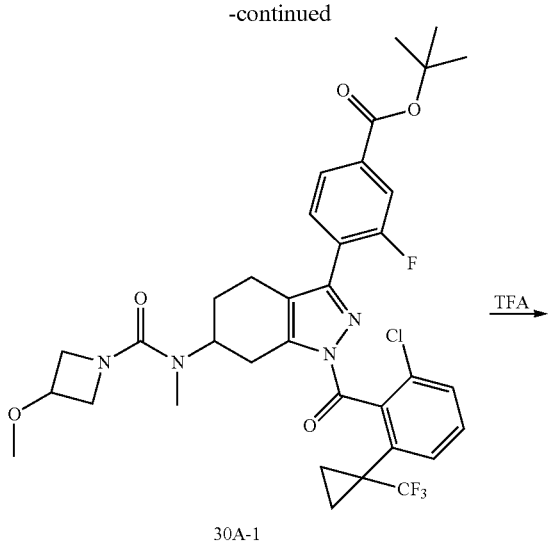

30A-1

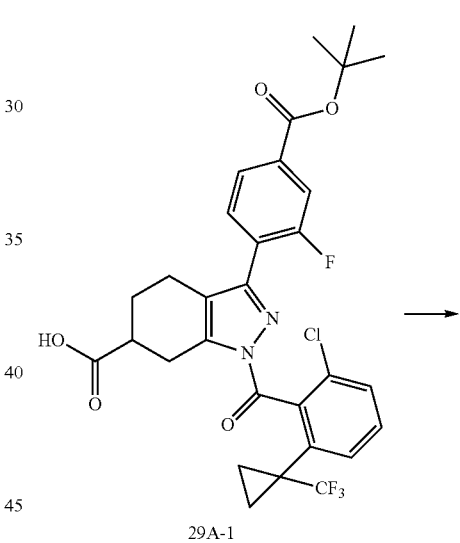

30A 4-(1-(2-Chloro-6-(1-(trifluoromethyl)cyclopropyl)
benzoyl)-6-(3-methoxy-N-methylazetidine-1-carboxamido)-4,5,6,7-tetrahydro-1H-indazol-3-yl)-3-fluorobenzoic acid Step 1: Preparation of tert-Butyl 4-(1-(2-chloro-6-(1-(trifluoromethyl)cyclopropyl)benzoyl)-6-(3-methoxy-N-methylazetidine-1-carboxamido)-4,5,6,7-tetrahydro-1H-indazol-3-yl)-3-fluorobenzoate (30A-1)

tert-Butyl 4-(1-(2-chloro-6-(1-(trifluoromethyl)cyclopropyl)benzoyl)-6-(3-methoxyazetidine-1-carboxamido)-4,5,6,7-tetrahydro-1H-indazol-3-yl)-3-fluorobenzoate (29A-2; 32.0 mg, 0.05 mmol) was dissolved in DMF (0.5 mL) and NaH (2.2 mg, 0.06 mmol) was added. The reaction mixture was stirred at rt for 20 min. MeI (4.34 µl, 0.07 mmol) was then added and the reaction mixture was stirred at rt overnight. The reaction mixture was diluted with ethyl acetate and washed with brine. The organic layer was dried over sodium sulfate, filtered, and concentrated in vacuo while loading onto silica gel. The residue was purified by column chromatography on silica (10-100% EtOAc/hexanes) to afford tert-butyl 4-(1-(2-chloro-6-(1-(trifluoromethyl)cyclopropyl)benzoyl)-6-(3-methoxy-N-methylazetidine-1-carboxamido)-4,5,6,7-tetrahydro-1H-indazol-3-yl)-3-fluorobenzoate. MS: 705 (M+1)

Step 2: Preparation of 4-(1-(2-Chloro-6-(1-(trifluoromethyl)cyclopropyl)benzoyl)-6-(3-methoxy-N-methylazetidine-1-carboxamido)-4,5,6,7-tetrahydro-1H-indazol-3-yl)-3-fluorobenzoic acid (30A)

tert-Butyl 4-(1-(2-chloro-6-(1-(trifluoromethyl)cyclopropyl)benzoyl)-6-(3-methoxy-N-methylazetidine-1-carboxamido)-4,5,6,7-tetrahydro-1H-indazol-3-yl)-3-fluorobenzoate (4.0 mg, 5.67 µmol) was dissolved in DCM (0.1 mL) then TFA (0.1 mL) was added. The reaction mixture was stirred at rt for one hour. The reaction mixture was concentrated in vacuo. The residue was purified by mass triggered reverse phase HPLC (C-18; acetonitrile/water containing 0.1% TFA) to afford 4-(1-(2-chloro-6-(1-(trifluoromethyl)cyclopropyl)benzoyl)-6-(3-methoxy-N-methylazetidine-1-carboxamido)-4,5,6,7-tetrahydro-1H-indazol-3-yl)-3-fluorobenzoic acid as a TFA salt. MS: 649 (M+1). $^1$H NMR (500 MHz, d-DMSO) δ 13.44 (s, 1H), 7.81 (dd, J=8.3, 4.7 Hz, 1H), 7.75 (dd, J=10.8, 3.5 Hz, 1H), 7.68-7.57 (m, 3H), 7.51 (q, J=7.4 Hz, 1H), 4.32-4.22 (m, 1H), 4.16-4.09 (m, 2H), 4.08-4.02 (m, 1H), 3.80-3.76 (m, 1H), 3.73-3.69 (m, 1H), 3.31 (td, J=20.7, 19.5, 5.7 Hz, 2H), 3.20 (s, 3H), 3.17-3.11 (m, 1H), 2.78 (d, J=4.6 Hz, 3H), 2.74-2.62 (m, 1H), 1.99-1.89 (m, 1H), 1.86-1.78 (m, 1H), 1.42-1.32 (m, 1H), 1.28-1.15 (m, 2H), 0.93-0.82 (m, 1H).

Example 31A

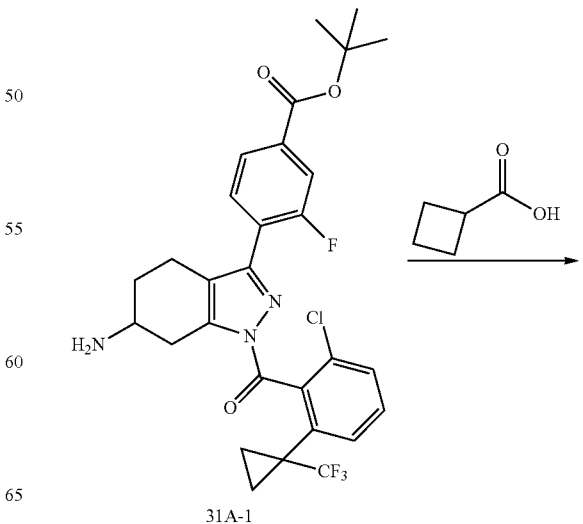

29A-1

31A-1

-continued

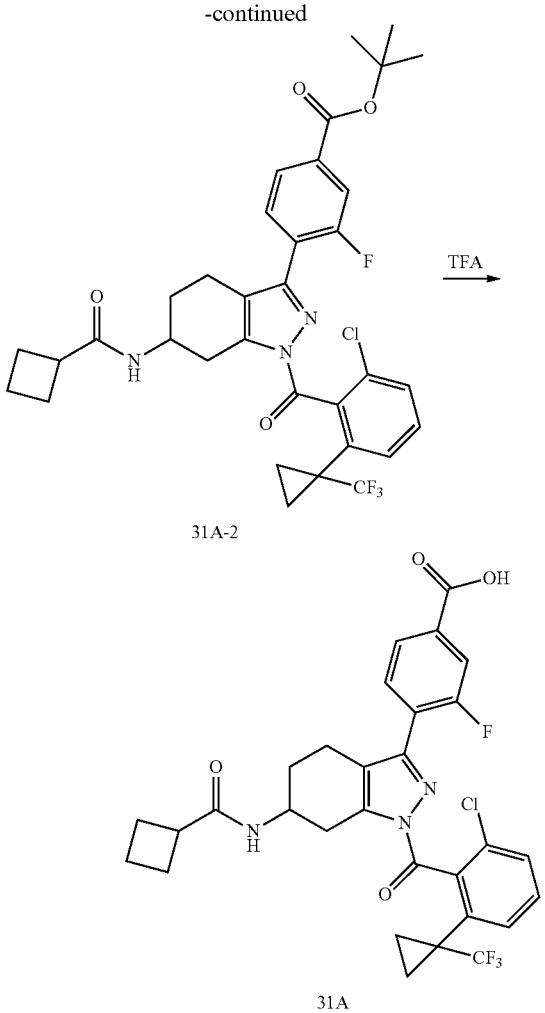

4-(1-(2-Chloro-6-(1-(trifluoromethyl)cyclopropyl)
benzoyl)-6-(cyclobutanecarboxamido)-4,5,6,7-tetra-
hydro-1H-indazol-3-yl)-3-fluorobenzoic acid Step 1: Preparation of tert-Butyl 4-(6-amino-1-(2-
chloro-6-(1-(trifluoromethyl)cyclopropyl)benzoyl)-
4,5,6,7-tetrahydro-1H-indazol-3-yl)-3-fluorobenzo-
ate (31A-1)

3-(4-(tert-Butoxycarbonyl)-2-fluorophenyl)-1-(2-chloro-6-(1-(trifluoromethyl)cyclopropyl)benzoyl)-4,5,6,7-tetrahydro-1H-indazole-6-carboxylic acid (29A-1; 200.0 mg, 0.329 mmol) was dissolved in Toluene (2.0 mL) and under nitrogen diphenylphosphoryl azide (0.107 mL, 0.494 mmol) and triethylamine (0.069 mL, 0.494 mmol) was added. The reaction mixture was heated to 85° C. and stirred for two hours. The reaction mixture was concentrated in vacuo and cooled to 0° C. then HCl (1.5 mL, 6 N) was added. The reaction mixture was stirred at rt for two hours. The reaction mixture was extracted with dichloromethane. The organic layer was dried over sodium sulfate, filtered, concentrated in vacuo while loading onto silica gel. The residue was purified by column chromatography on silica (0-100% 3:1 EtOAc: Ethanol/hexanes) to afford tert-butyl 4-(6-amino-1-(2-chloro-6-(1-(trifluoromethyl)cyclopropyl)benzoyl)-4,5,6,7-tetrahydro-1H-indazol-3-yl)-3-fluorobenzoate. MS: 578 (M+1)

Step 2: Preparation of tert-Butyl 4-(1-(2-chloro-6-
(1-(trifluoromethyl)cyclopropyl)benzoyl)-6-(cy-
clobutanecarboxamido)-4,5,6,7-tetrahydro-1H-inda-
zol-3-yl)-3-fluorobenzoate (31A-2)

tert-Butyl 4-(6-amino-1-(2-chloro-6-(1-(trifluoromethyl)cyclopropyl)benzoyl)-4,5,6,7-tetrahydro-1H-indazol-3-yl)-3-fluorobenzoate (111.33 mg, 0.193 mmol), cyclobutanecarboxylic acid (28.9 mg, 0.29 mmol), HATU (110 mg, 0.29 mmol), and Hunig's Base (135 µL, 0.77 mmol) was dissolved in DMF (1.9 mL) and stirred at rt overnight. The reaction mixture was diluted with ethyl acetate and washed with brine. The organic layer was dried over sodium sulfate, filtered, concentrated in vacuo while loading onto silica gel. The residue was purified by column chromatography on silica (0-60% EtOAc/hexanes) to afford tert-butyl 4-(1-(2-chloro-6-(1-(trifluoromethyl)cyclopropyl)benzoyl)-6-(cy-clobutanecarboxamido)-4,5,6,7-tetrahydro-1H-indazol-3-yl)-3-fluorobenzoate. MS: 660 (M+1)

Step 3: Preparation of 4-(1-(2-Chloro-6-(1-(trifluo-
romethyl)cyclopropyl)benzoyl)-6-(cyclobutanecar-
boxamido)-4,5,6,7-tetrahydro-1H-indazol-3-yl)-3-
fluorobenzoic acid (31A)

tert-Butyl 4-(1-(2-chloro-6-(1-(trifluoromethyl)cyclopro-pyl)benzoyl)-6-(cyclobutanecarboxamido)-4,5,6,7-tetra-hydro-1H-indazol-3-yl)-3-fluorobenzoate (14.5 mg, 0.02 mmol) was dissolved in DCM (0.25 mL) then TFA (0.25 mL) was added. The reaction mixture was stirred at rt for one hour. The reaction mixture was concentrated in vacuo. The residue was purified by mass triggered reverse phase HPLC (C-18; acetonitrile/water containing 0.1% TFA) to afford 4-(1-(2-chloro-6-(1-(trifluoromethyl)cyclopropyl)benzoyl)-6-(cyclobutanecarboxamido)-4,5,6,7-tetrahydro-1H-indazol-3-yl)-3-fluorobenzoic acid as a TFA salt. MS: 604 (M+1). $^1$H NMR (500 MHz, d-DMSO) δ 13.43 (s, 1H), 7.88 (dd, J=13.2, 7.4 Hz, 1H), 7.81 (ddd, J=8.1, 2.9, 1.5 Hz, 1H), 7.75 (dd, J=10.6, 1.5 Hz, 1H), 7.67-7.56 (m, 2H), 7.51 (td, J=7.6, 3.7 Hz, 1H), 4.19-4.08 (m, 1H), 3.04 (qd, J=8.4, 2.6 Hz, 1H), 2.95 (dt, J=16.9, 7.7 Hz, 1H), 2.67-2.60 (m, 1H), 2.56 (t, J=6.4 Hz, 1H), 2.22-2.11 (m, 2H), 2.08-1.98 (m, 2H), 1.95-1.84 (m, 2H), 1.80-1.61 (m, 2H), 1.39-1.32 (m, 1H), 1.25 (dt, J=9.8, 5.7 Hz, 1H), 1.18 (tt, J=7.7, 4.7 Hz, 2H), 0.86-0.73 (m, 1H).

Example 32A

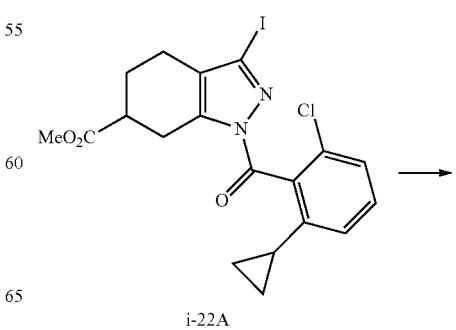

i-22A

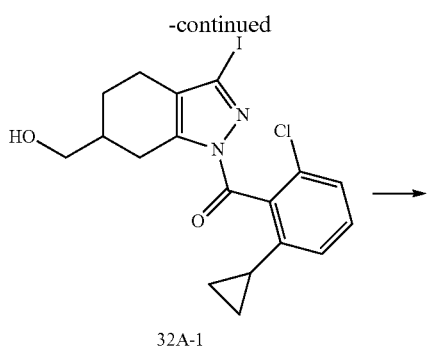

32A-1

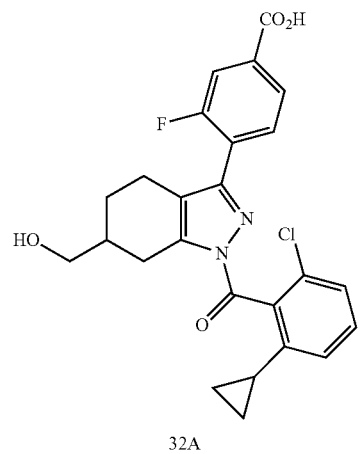

32A (R or S)-4-(1-(2-chloro-6-cyclopropylbenzoyl)-6-(hydroxymethyl)-4,5,6,7-tetrahydro-1H-indazol-3-yl)-3-fluorobenzoic acid Step 1: Preparation of (R or S)-(2-chloro-6-cyclopropylphenyl)(6-(hydroxymethyl)-3-iodo-4,5,6,7-tetrahydro-1H-indazol-1-yl)methanone (32A-1)

To an oven dried microwave vial equipped with magnetic stir bar under an atmosphere of $N_2$, methyl (R or S)-1-(2-chloro-6-cyclopropylbenzoyl)-3-iodo-4,5,6,7-tetrahydro-1H-indazole-6-carboxylate (i-22A) (250 mg, 0.52 mmol, 1 equiv) and DCM (1.79 mL, 0.3 M) were added. The reaction mixture was cooled to −78° C., and diisobutylaluminum hydride (1.547 mL, 1 M in THF, 3 equiv) was added. The reaction mixture was warmed to 0° C. over 1 h, and then quenched with 1 HCl (5 mL), and diluted with EtOAc (20 mL). The mixture was stirred vigorously for 1 h at room temperature. The layers were separated, the aqeuous layer was extracted with EtOAc (3×25 mL), the combined organic layers were washed with brine, filtered through celite, and then concentrated in vacuo. The residue was purified by silica gel chromatography (0-100% EtOAc/Hexane) to afford desired product. MS: 457 (M+1).

Step 2: Preparation of (R or S)-4-(1-(2-chloro-6-cyclopropylbenzoyl)-6-(hydroxymethyl)-4,5,6,7-tetrahydro-1H-indazol-3-yl)-3-fluorobenzoic acid (32A)

To an oven dried microwave vial equipped with magnetic stir bar under an atmosphere of $N_2$, (R or S)-(2-chloro-6-cyclopropylphenyl)(6-(hydroxymethyl)-3-iodo-4,5,6,7-tetrahydro-1H-indazol-1-yl)methanone (90 mg, 0.2 mmol, 1 equiv), $2^{nd}$ Gen Sphos Precatalyst (14.2 mg, 0.02 mmol, 0.1 equiv), tert-butyl 3-fluoro-4-(4,4,5,5-tetramethyl-1,3,2-dioxaborolan-2-yl)benzoate (190 mg, 0.6 mmol, 3 equiv), and dioxane (985 μL, 0.2 M) were added, followed by potassium phosphate tribasic (591 μL, 1M, 3 equiv). The reaction mixture was heated to 80° C. for 24 h, and then cooled to room temperature. The crude reaction mixture was diluted with EtOAc (50 mL), filtered through celite, and concentrated in vacuo. The resulting oil was taken up in DCM (1 mL), and trifluoroacetic acid (1 mL). After stirring for 3 h at room temperature, the solution was concentrated in vacuo, and purified using mass directed reverse phase chromatography to afford desired product. MS: 469 (M+1). $^1$H NMR (DMSO-d6) δ (ppm): 13.36 (s, 1H), 7.78 (d, J=8 Hz, 1H), 7.71 (d, J=8 Hz, 1H), 7.50 (m, 1H), 7.38-7.31 (m, 2H), 7.04 (d, J=8 Hz, 1H), 7.02 (d, J=8 Hz, 1H), 4.69 (bs, 1H), 3.48-3.45 (m, 2H), 3.34 (m, 1H), 2.71 (m, 1H), 1.95 (m, 1H), 1.89 (m, 1H), 1.65 (m, 1H), 1.35 (m, 1H), 0.85 (m, 1H), 0.74 (m, 1H), 0.68-0.53 (m, 3H).

Example 33A

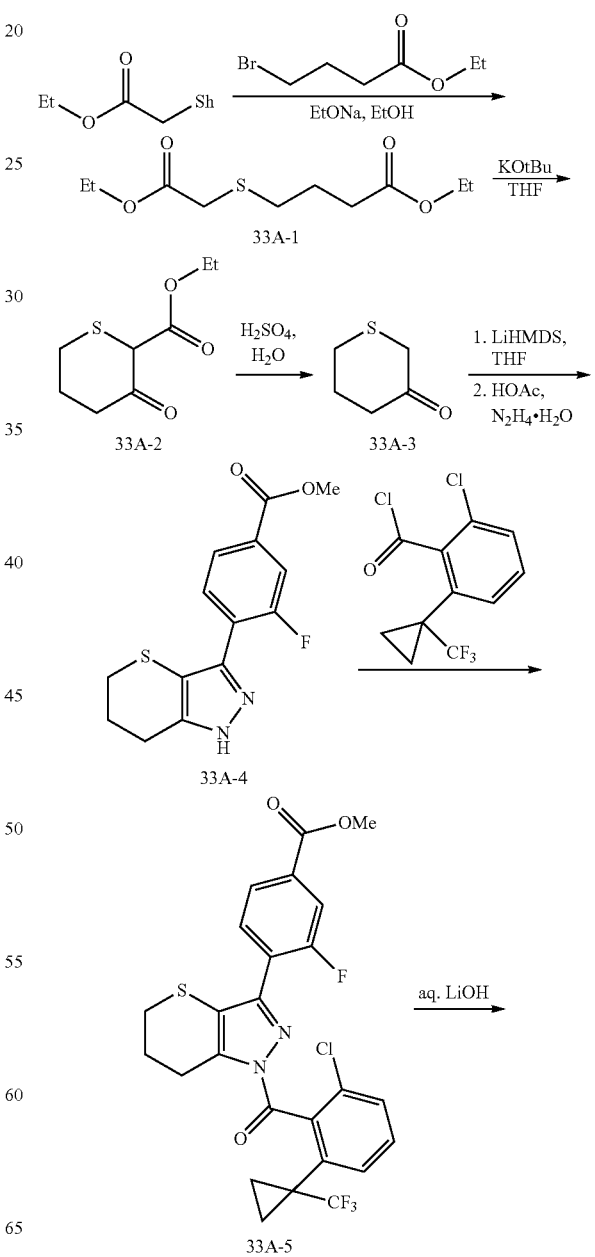

-continued

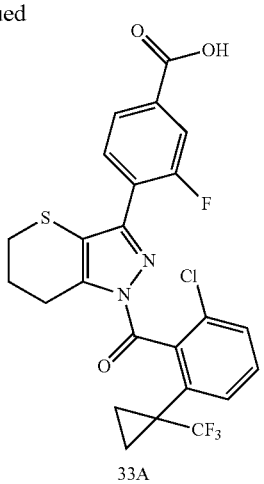

33A 4-(1-(2-chloro-6-(1-(trifluoromethyl)cyclopropyl)
benzoyl)-1,5,6,7-tetrahydrothiopyrano[3,2-c]pyra-
zol-3-yl)-3-fluorobenzoic acid Step 1: Preparation of ethyl 4-((2-ethoxy-2-oxo-
ethyl)thio)butanoate (33A-1)

To a mixture of sodium ethanolate (13.96 g, 205 mmol) in Ethanol (150 mL) at 0° C. was added ethyl 2-mercaptoacetate (24.64 g, 205 mmol) and ethyl 4-bromobutanoate (40 g, 205 mmol) dropwise. The resulting mixture was stirred at 20° C. for 16 h. TLC showed no starting material remained and one major new spot formed. The solvent was removed under vacuum and the residue was diluted with water (200 mL), then extracted with EtOAc (3×100 mL). The combined organic phase was washed with brine, dried over $Na_2SO_4$ and concentrated to give ethyl 4-((2-ethoxy-2-oxoethyl)thio) butanoate, which was used for the next reaction directly without further purification.

Step 2: Preparation of ethyl
3-oxotetrahydro-2H-thiopyran-2-carboxylate
(33A-2)

To a mixture of potassium tert-butoxide (9.58 g, 85 mmol) in THF (100 mL) was added ethyl 4-((2-ethoxy-2-oxoethyl)thio)butanoate (10 g, 42.7 mmol) dropwise. The mixture was stirred at 60° C. for 2 hours. TLC showed no starting material remained and one major new spot formed. Then the mixture was concentrated in vacuum. The residue was diluted with water (100 mL) and adjusted to pH=5 with 2M HCl. The mixture was extracted with EtOAc (3×50 mL). The combined organic phase was washed with brine, dried over $Na_2SO_4$, filtered and concentrated to give ethyl 3-oxotetrahydro-2H-thiopyran-2-carboxylate. Crude material moved forward without further purification. $^1$H-NMR ($CDCl_3$, 400 MHz) δ 12.27 (s, 1H), 4.24-4.28 (m, 2H), 2.79-2.82 (m, 2H), 2.40-2.44 (m, 2H), 2.13-2.15 (m, 2H), 1.31-1.34 (m, 3H)

Step 3: Preparation of
dihydro-2H-thiopyran-3(4H)-one (33A-3)

A mixture of ethyl 3-oxotetrahydro-2H-thiopyran-2-carboxylate (2.5 g, 13.28 mmol) in $H_2SO_4$ (2.167 mL, 39.8 mmol) and Water (21.0 mL) was stirred at 90° C. for 14 hours. TLC showed no starting material remained and one major new spot formed. A 10% NaOH solution in water was added dropwise to reach pH=6. The mixture was extracted with EtOAc (3×10 mL). The combined organic phase was washed with brine, dried over $Na_2SO_4$, filtered and concentrated to give dihydro-2H-thiopyran-3(4H)-one. Crude material moved forward without further purification.

Step 4: Preparation of methyl 3-fluoro-4-(1,5,6,7-
tetrahydrothiopyrano[3,2-c]pyrazol-3-yl)benzoate
(33A-4)

To a mixture of dihydro-2H-thiopyran-3(4H)-one (500 mg, 4.30 mmol) in anhydrous THF (8 mL) was added LiHMDS (5.16 mL, 5.16 mmol) at 0° C. The mixture was stirred at 0° C. for 10 min, methyl 4-(chlorocarbonyl)-3-fluorobenzoate (i-9) (932 mg, 4.30 mmol) was added to the mixture, which was stirred at 0° C. for 1 h. The reaction mixture was quenched with AcOH (1 ml, 17.47 mmol), then hydrazine (1724 mg, 43.0 mmol) was added to this mixture. The mixture was stirred at 20° C. for 3 h. LCMS showed the starting material was consumed, and the desired product was formed. The reaction was completed. The mixture was diluted with water (10 mL), extracted with EtOAc (3×20 mL). The organic layer was dried over $Na_2SO_4$, filtered and the filtrate was concentrated in vacuum. The residue was purified by column chromatography ($SiO_2$, PE:EtOAc=1:1) to give methyl 3-fluoro-4-(1,5,6,7-tetrahydrothiopyrano[3,2-c]pyrazol-3-yl)benzoate. MS: 293 (M+1)

Step 5: Preparation of methyl 4-(1-(2-chloro-6-(1-
(trifluoromethyl)cyclopropyl)benzoyl)-1,5,6,7-tetra-
hydrothiopyrano[3,2-c]pyrazol-3-yl)-3-fluorobenzo-
ate (33A-5)

To a mixture of methyl 3-fluoro-4-(1,5,6,7-tetrahydrothiopyrano[3,2-c]pyrazol-3-yl)benzoate (600 mg, 2.052 mmol) in anhydrous THF (15 mL) was added $Et_3N$ (0.858 mL, 6.16 mmol), DMAP (301 mg, 2.463 mmol) and 2-chloro-6-(1-(trifluoromethyl)cyclopropyl)benzoyl chloride (581 mg, 2.052 mmol), then it was stirred at 60° C. for 16 h. LCMS showed the starting material was consumed, and the desired product was formed. The reaction was completed. The mixture was concentrated in vacuum. The residue was purified by column chromatography ($SiO_2$, PE:EtOAc=3:1) to give methyl 4-(1-(2-chloro-6-(1-(trifluoromethyl)cyclopropyl)benzoyl)-1,5,6,7-tetrahydrothiopyrano[3,2-c]pyrazol-3-yl)-3-fluorobenzoate. MS: 539 (M+1)

Step 6: Preparation of 4-(1-(2-chloro-6-(1-(trifluo-
romethyl)cyclopropyl)benzoyl)-1,5,6,7-tetrahydroth-
iopyrano[3,2-c]pyrazol-3-yl)-3-fluorobenzoic acid
(33A)

To a mixture of methyl 4-(1-(2-chloro-6-(1-(trifluoromethyl)cyclopropyl)benzoyl)-1,5,6,7-tetrahydrothiopyrano[3,2-c]pyrazol-3-yl)-3-fluorobenzoate (50 mg, 0.093 mmol) in THF (2 mL) and Water (0.5 mL) was added LiOH (6.67 mg, 0.278 mmol). The mixture was stirred at 20° C. for 3 h. LCMS showed the starting material was consumed, and the desired product was formed. The mixture was concentrated in vacuum to remove THF and the mixture was purified by prep-HPLC (TFA) to give 4-(1-(2-chloro-6-(1-(trifluoromethyl)cyclopropyl)benzoyl)-1,5,6,7-tetrahydrothiopyrano[3,2-c]pyrazol-3-yl)-3-fluorobenzoic. LCMS (ESI) calc'd for $C_{24}H_{17}ClF_4N_2O_3S$ [M+H]$^+$: 539.1, found: 525.1. $^1$H-NMR ($CDCl_3$, 400 MHz) δ 7.87 (d, J=7.94 Hz, 1H), 7.80 (d, J=10.14 Hz, 1H), 7.51-7.58 (m, 2H), 7.37-7.46 (m, 2H), 3.42 (t, J=6.17 Hz, 2H), 3.00 (t, J=5.18 Hz, 2H), 2.35 (d, J=5.51 Hz, 2H), 1.33-1.42 (m, 1H), 1.21-1.29 (m, 1H), 1.16 (s, 1H), 0.93 (s, 1H).

Example 34A

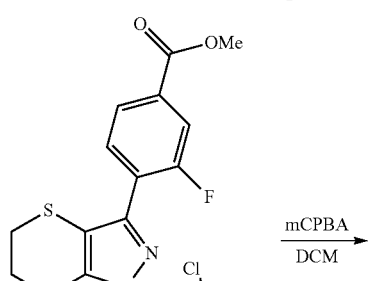

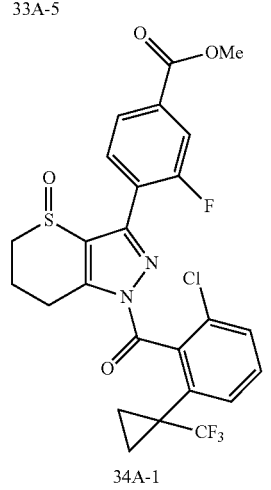

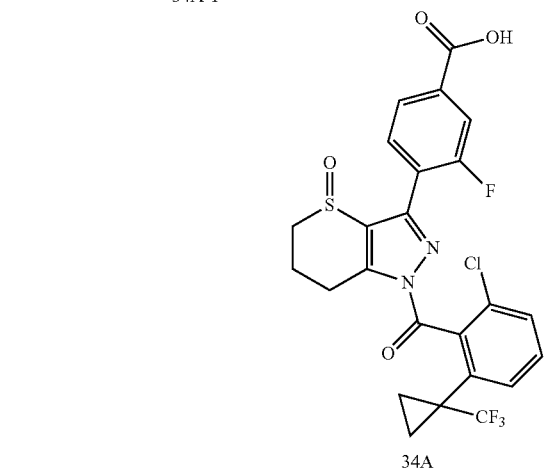

4-(1-(2-chloro-6-(1-(trifluoromethyl)cyclopropyl)
benzoyl)-4-oxido-1,5,6,7-tetrahydrothiopyrano[3,2-
c]pyrazol-3-yl)-3-fluorobenzoic acid Step 1: Preparation of methyl 4-(1-(2-chloro-6-(1-
(trifluoromethyl)cyclopropyl)benzoyl)-4-oxido-1,5,
6,7-tetrahydrothiopyrano[3,2-c]pyrazol-3-yl)-3-fluo-
robenzoate (34A-1)

To a mixture of methyl 4-(1-(2-chloro-6-(1-(trifluoromethyl)cyclopropyl)benzoyl)-1,5,6,7-tetrahydrothiopyrano[3,2-c]pyrazol-3-yl)-3-fluorobenzoate (100 mg, 0.186 mmol) in CH₂Cl₂ (3 mL) was added mCPBA (28.0 mg, 0.130 mmol) (80%), then it was stirred at 20° C. for 16 h. LCMS showed the desired product was formed. The mixture was concentrated in vacuum to give crude methyl 4-(1-(2-chloro-6-(1-(trifluoromethyl)cyclopropyl)benzoyl)-4-oxido-1,5,6,7-tetrahydrothiopyrano[3,2-c]pyrazol-3-yl)-3-fluorobenzoate, which was used directly to next step without further purification. MS: 555 (M+1)

Step 2: Preparation of 4-(1-(2-chloro-6-(1-(trifluoromethyl)cyclopropyl)benzoyl)-4-oxido-1,5,6,7-tetrahydrothiopyrano[3,2-c]pyrazol-3-yl)-3-fluorobenzoic acid (34A)

To a mixture of methyl 4-(1-(2-chloro-6-(1-(trifluoromethyl)cyclopropyl)benzoyl)-4-oxido-1,5,6,7-tetrahydrothiopyrano[3,2-c]pyrazol-3-yl)-3-fluorobenzoate (50 mg, 0.090 mmol) in THF (2 mL) and Water (0.5 mL) was added LiOH (6.47 mg, 0.270 mmol). The mixture was stirred at 20° C. for 3 hours. LCMS showed the starting material was consumed, and the desired product was formed. The mixture was concentrated in vacuum. The residue was purified by prep-HPLC (TFA) to give 4-(1-(2-chloro-6-(1-(trifluoromethyl)cyclopropyl)benzoyl)-4-oxido-1,5,6,7-tetrahydrothiopyrano[3,2-c]pyrazol-3-yl)-3-fluorobenzoic acid. MS: 541 (M+1). (CDCl₃, 400 MHz) δ 7.89 (s, 1H), 7.78 (s, 1H), 7.53 (s, 4H), 2.97-3.11 (m, 2H), 2.68 (s, 2H), 2.39 (s, 1H), 1.19-1.31 (m, 3H), 0.88 (s, 2H)

Example 35A

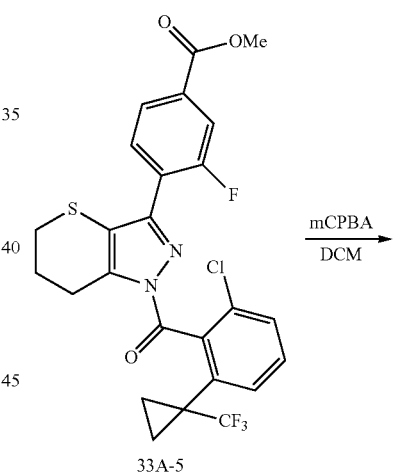

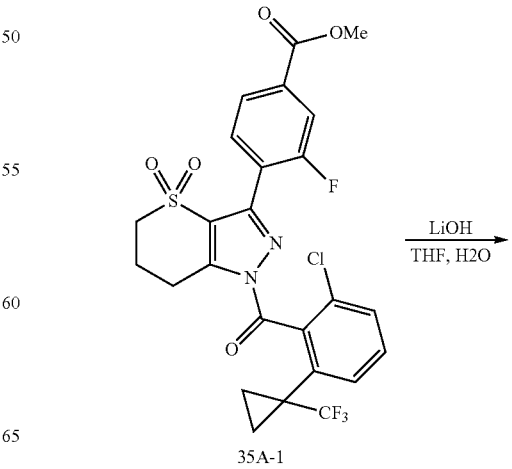

175
-continued

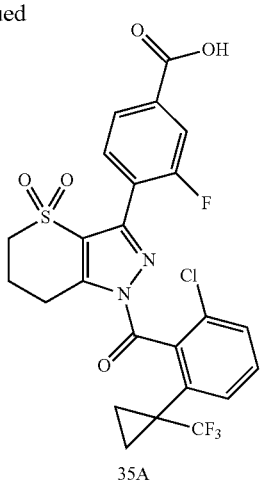

35A 4-(1-(2-chloro-6-(1-(trifluoromethyl)cyclopropyl)
benzoyl)-4,4-dioxido-1,5,6,7-tetrahydrothiopyrano
[3,2-c]pyrazol-3-yl)-3-fluorobenzoic acid Step 1: Preparation of methyl 4-(1-(2-chloro-6-(1-(trifluoromethyl)cyclopropyl)benzoyl)-4,4-dioxido-1,5,6,7-tetrahydrothiopyrano[3,2-c]pyrazol-3-yl)-3-fluorobenzoate (35A-1)

To a mixture of methyl 4-(1-(2-chloro-6-(1-(trifluoromethyl)cyclopropyl)benzoyl)-1,5,6,7-tetrahydrothiopyrano[3,2-c]pyrazol-3-yl)-3-fluorobenzoate (100 mg, 0.186 mmol) in CH$_2$Cl$_2$ (3 mL) was added mCPBA (80 mg, 0.371 mmol) (80%). The mixture was stirred at 20° C. for 14 h. LCMS showed the starting material was consumed, and the desired product was formed. The mixture was concentrated in vacuum to give crude methyl 4-(1-(2-chloro-6-(1-(trifluoromethyl)cyclopropyl)benzoyl)-4,4-dioxido-1,5,6,7-tetrahydrothiopyrano[3,2-c]pyrazol-3-yl)-3-fluorobenzoate, which was used directly to next step without further purification. MS: 571 (M+1)

Step 2: Preparation of 4-(1-(2-chloro-6-(1-(trifluoromethyl)cyclopropyl)benzoyl)-4,4-dioxido-1,5,6,7-tetrahydrothiopyrano[3,2-c]pyrazol-3-yl)-3-fluorobenzoic acid (35A)

To a mixture of methyl 4-(1-(2-chloro-6-(1-(trifluoromethyl)cyclopropyl)benzoyl)-4,4-dioxido-1,5,6,7-tetrahydrothiopyrano[3,2-c]pyrazol-3-yl)-3-fluorobenzoate (106 mg, 0.186 mmol) in THF (2 ml) and Water (0.4 ml) was added LiOH (13.34 mg, 0.557 mmol), then it was stirred at 20° C. for 16 h. LCMS showed the starting material was consumed, and the desired product was formed. The mixture was concentrated in vacuum. The residue was purified by prep-HPLC (TFA) to give 4-(1-(2-chloro-6-(1-(trifluoromethyl)cyclopropyl)benzoyl)-4,4-dioxido-1,5,6,7-tetrahydrothiopyrano[3,2-c]pyrazol-3-yl)-3-fluorobenzoic acid. MS: 557 (M+1). $^1$H NMR (MeOD, 400 MHz) δ 7.86 (d, J=7.94 Hz, 1H), 7.70-7.77 (m, 2H), 7.61-7.67 (m, 1H), 7.51-7.57 (m, 2H), 3.56 (d, J=4.19 Hz, 2H), 3.40-3.47 (m, 2H), 2.65 (s, 2H), 1.36-1.47 (m, 1H), 1.26-1.35 (m, 1H), 1.21 (s, 1H), 0.95 (s, 1H).

176
Example 36A

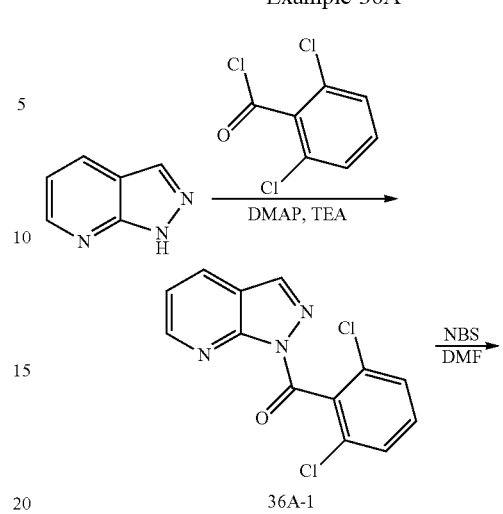

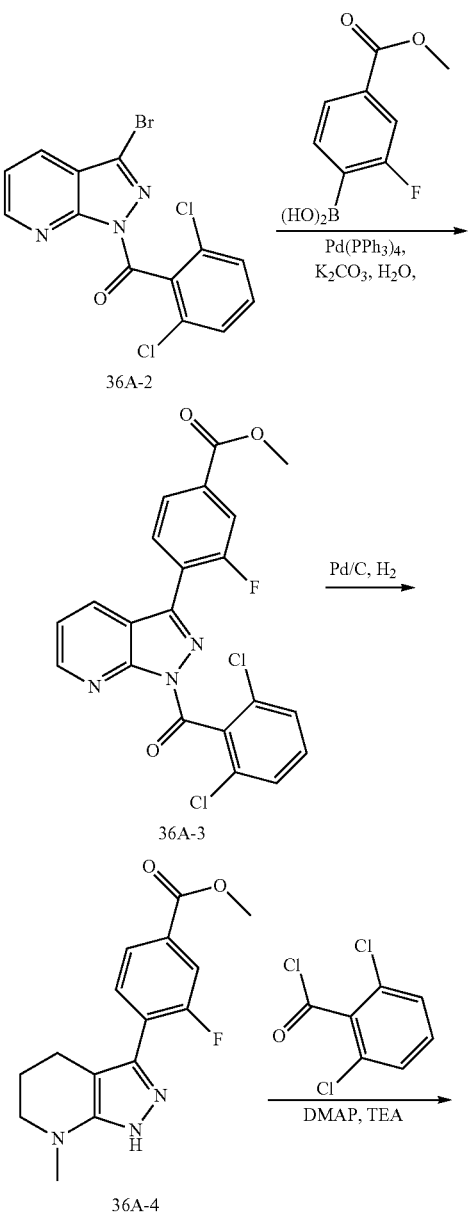

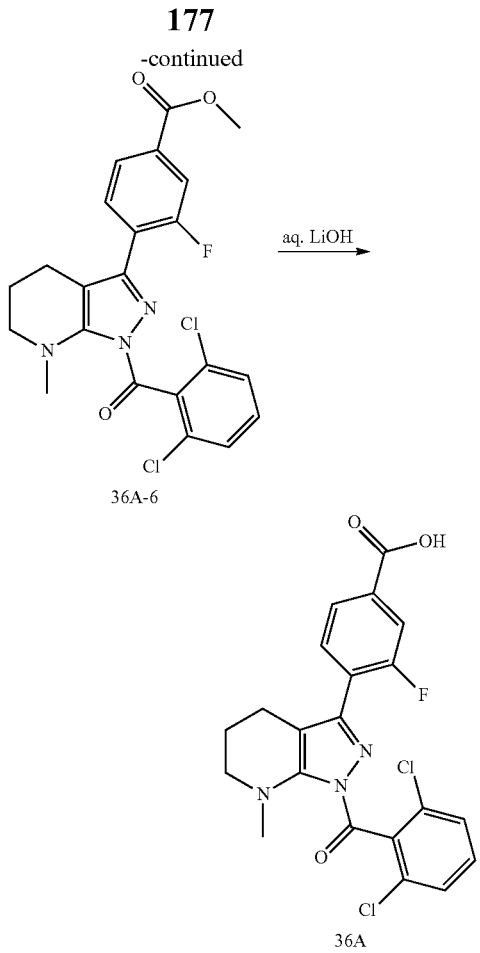

4-(1-(2,6-dichlorobenzoyl)-7-methyl-4,5,6,7-tetrahydro-1H-pyrazolo[3,4-b]pyridin-3-yl)-3-fluorobenzoic acid Step 1: Preparation of (2,6-dichlorophenyl)(1H-pyrazolo[3,4-b]pyridin-1-yl)methanone (36A-1)

To a solution of 1H-pyrazolo[3,4-b]pyridine (500 mg, 4.20 mmol) in THF (8 mL) was added 2,6-dichlorobenzoyl chloride (879 mg, 4.20 mmol), TEA (1.755 mL, 12.59 mmol) and DMAP (256 mg, 2.099 mmol). The reaction was stirred at 90° C. for 4 hours. LCMS show no starting material and the desired product formed. The reaction mixture was concentrated and purified by silica gel column chromatography (SiO₂, EtOAc/PE=0% to 50%) to give (2,6-dichlorophenyl)(1H-pyrazolo[3,4-b]pyridin-1-yl)methanone. MS: 292 (M+1)

Step 2: Preparation of (3-bromo-1H-pyrazolo[3,4-b]pyridin-1-yl)(2,6-dichlorophenyl)methanone (36A-2)

To a solution of (2,6-dichlorophenyl)(1H-pyrazolo[3,4-b]pyridin-1-yl)methanone (900 mg, 3.08 mmol) in DMF (10 mL) was added 1-bromopyrrolidine-2,5-dione (1645 mg, 9.24 mmol). The reaction was stirred at 20° C. for 2 hours. LCMS show the desired product formed. The reaction mixture was concentrated and purified by column chromatography (SiO₂,PE:EA=3:1) to give (3-bromo-1H-pyrazolo[3,4-b]pyridin-1-yl)(2,6-dichlorophenyl)methanone. LCMS (ESI) calc'd for $C_{13}H_6BrCl_2N_3O$ [M+2H]+: 369.9, found: 371.7.

Step 3: Preparation of methyl 4-(1-(2,6-dichlorobenzoyl)-1H-pyrazolo[3,4-b]pyridin-3-yl)-3-fluorobenzoate (36A-3)

To a solution of (3-bromo-1H-pyrazolo[3,4-b]pyridin-1-yl)(2,6-dichlorophenyl)methanone (180 mg, 0.485 mmol) in Dioxane (6 mL) and Water (1.5 mL) was added (2-fluoro-4-(methoxycarbonyl)phenyl)boronic acid (144 mg, 0.728 mmol), Pd(Ph3P)4 (56.1 mg, 0.049 mmol) and K2CO3 (201 mg, 1.455 mmol). The reaction was stirred at 110° C. for 4.5 hours. LCMS show most of starting material was consumed and the desired product formed. The reaction mixture was filtered and purified by column chromatography (SiO₂, petroleum ether:ethyl acetate=100:1 to 4:1) to give methyl 4-(1-(2,6-dichlorobenzoyl)-1H-pyrazolo[3,4-b]pyridin-3-yl)-3-fluorobenzoate. MS: 444 (M+1)

Step 4: Preparation of methyl 3-fluoro-4-(7-methyl-4,5,6,7-tetrahydro-1H-pyrazolo[3,4-b]pyridin-3-yl)benzoate (36A-4)

To a solution of methyl 4-(1-(2,6-dichlorobenzoyl)-1H-pyrazolo[3,4-b]pyridin-3-yl)-3-fluorobenzoate (20 mg, 0.045 mmol) in MeOH (10 mL) was added 10% Pd/C (4.79 mg, 4.50 µmol). Then the reaction was flushed with a nitrogen (50 psi) stream and stirred at 25° C. for 18 h. LCMS show no starting material and desired product formed. The reaction mixture was filtered and concentrated to give crude methyl 3-fluoro-4-(7-methyl-4,5,6,7-tetrahydro-1H-pyrazolo[3,4-b]pyridin-3-yl)benzoate, which was used directly without further purification. LCMS (ESI) calc'd for $C_{15}H_{16}FN_3O_2$ [M+H]+: 290.1, found: 290.1.

Step 5: Preparation of methyl 4-(1-(2,6-dichlorobenzoyl)-7-methyl-4,5,6,7-tetrahydro-1H-pyrazolo[3,4-b]pyridin-3-yl)-3-fluorobenzoate (36A-5)

To a solution of methyl 3-fluoro-4-(7-methyl-4,5,6,7-tetrahydro-1H-pyrazolo[3,4-b]pyridin-3-yl)benzoate (20 mg, 0.069 mmol) in THF (8 mL) was added 2,6-dichlorobenzoyl chloride (14.48 mg, 0.069 mmol), TEA (0.029 mL, 0.207 mmol) and DMAP (4.22 mg, 0.035 mmol). The reaction was stirred at 90° C. for 4 hours. LCMS show no starting material and the desired product formed. The reaction mixture was concentrated to give methyl 4-(1-(2,6-dichlorobenzoyl)-7-methyl-4,5,6,7-tetrahydro-1H-pyrazolo[3,4-b]pyridin-3-yl)-3-fluorobenzoate, which was used directly without further purification. MS: 462 (M+1)

Step 6: Preparation of 4-(1-(2,6-dichlorobenzoyl)-7-methyl-4,5,6,7-tetrahydro-1H-pyrazolo[3,4-b]pyridin-3-yl)-3-fluorobenzoic acid (36A)

To a solution of methyl 4-(1-(2,6-dichlorobenzoyl)-7-methyl-4,5,6,7-tetrahydro-1H-pyrazolo[3,4-b]pyridin-3-yl)-3-fluorobenzoate (20 mg, 0.043 mmol) in ACN (2 mL) and Water (0.5 mL) was added LiOH (10.36 mg, 0.433 mmol). The reaction was stirred at 25° C. for 4 hours. LCMS show no starting material and the desired product formed. The reaction mixture was concentrated and purified by pre-HPLC(TFA) to give 4-(1-(2,6-dichlorobenzoyl)-7-methyl-4,5,6,7-tetrahydro-1H-pyrazolo[3,4-b]pyridin-3-yl)-3-fluorobenzoic acid. MS: 448 (M+1); (CDCl₃, 400 MHz) δ 7.83-7.85 (H, m), δ 7.74-7.77 (H, m), δ 7.38 (H, s), δ 7.29-7.33 (3H, m), 3.61-3.65 (2H, m), 3.42-3.48 (1H, m), 3.32-3.34 (1H, m), 3.25-3.26 (1H, m), 2.98-2.99 (1H, m), 2.85-2.89 (1H, m) 2.82 (3H, s).

Example 37A

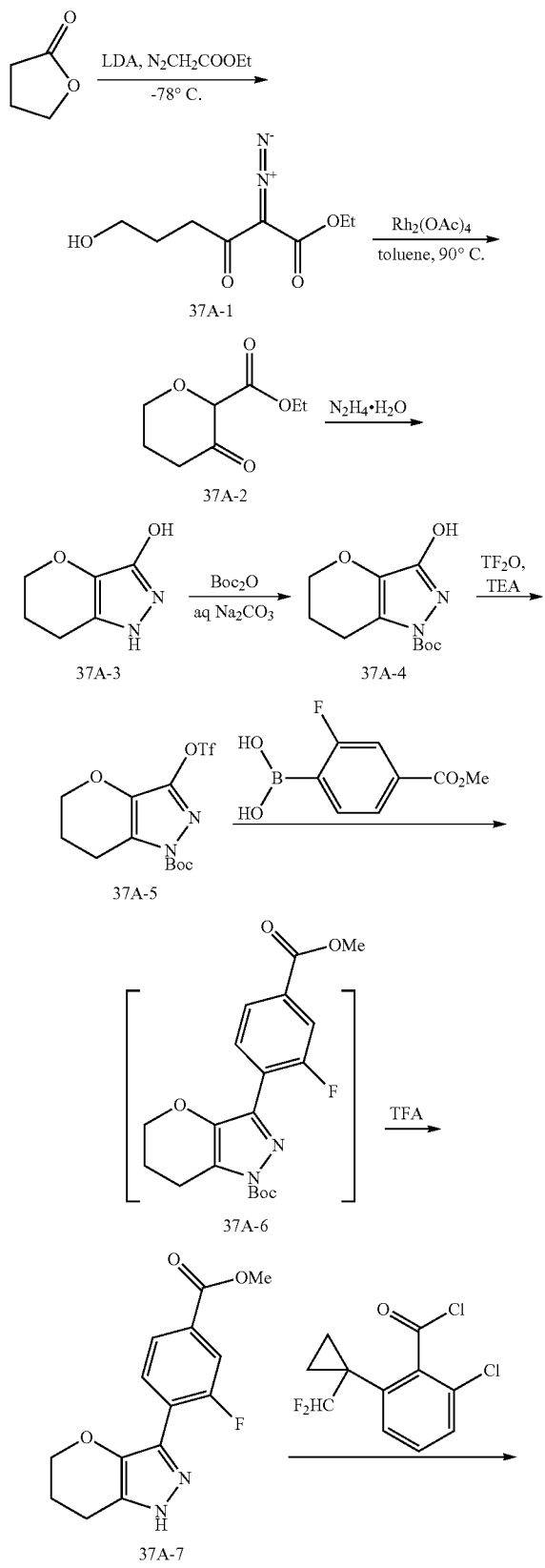

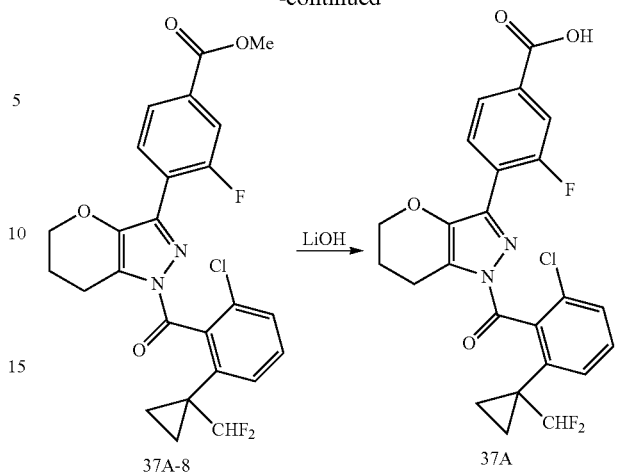

4-(1-(2-chloro-6-(1-(difluoromethyl)cyclopropyl)benzoyl)-1,5,6,7-tetrahydropyrano[3,2-c]pyrazol-3-yl)-3-fluorobenzoic acid Step 1: Preparation of ethyl 2-diazo-6-hydroxy-3-oxohexanoate (37A-1)

Ethyl diazoacetate (21.87 g, 192 mmol) was added drop wise over 5 min to a cold solution of LDA (100 mL, 200 mmol) in THF (600 mL) under an atmosphere of nitrogen, the temperature being maintained at −78° C. The orange-brown solution was stirred at −78° C. for 15 min and this was followed by drop wise addition of dihydrofuran-2(3H)-one (15.0 g, 174 mmol) at −78° C. The solution was stirred at −78° C. for 2 h, before dropwise addition of acetic acid (40 mL). The reaction mixture was allowed to warm to 0° C., water (100 mL) was added, and then the mixture extracted with DCM (300 mL×3). The combined organic extracts were washed brine (50 mL), dried (MgSO$_4$), and evaporated. The crude product was purified by flash chromatography on silica gel (petroleum ether:EtOAc=10:1-2:1) to give the title compound. $^1$H NMR (400 MHz, CDCl$_3$) δ 4.26-4.33 (m, 2H), 3.60-3.70 (m, 2H), 2.97 (t, J=6.9 Hz, 2H), 1.88-1.93 (m, 2H), 1.30-1.34 (m, 3H).

Step 2: Preparation of ethyl 3-oxotetrahydro-2H-pyran-2-carboxylate (37A-2)

Solution of ethyl 2-diazo-6-hydroxy-3-oxohexanoate (2.00 g, 9.99 mmol) in toluene (100 mL) was added over 35 min to a suspension of rhodium(ii) acetate dimer (0.088 g, 0.200 mmol) in toluene (100 mL) at 90° C. The mixture was then stirred at 90° C. for 1 h. The reaction mixture was concentrated to give the title compound. $^1$H NMR (400 MHz, CDCl$_3$) δ 10.37 (s, 1H), 4.29-4.40 (m, 2H), 3.93-4.01 (m, 1H), 2.34-2.43 (m, 1H), 1.93-2.02 (m, 1H), 1.33-1.44 (m, 3H).

Step 3: Preparation of 1,5,6,7-tetrahydropyrano[3,2-c]pyrazol-3-ol (37A-3)

Hydrazine hydrate (0.324 mL, 10.34 mmol) was added to a stirred mixture of methyl 3-oxotetrahydro-2H-pyran-2-carboxylate (1.09 g, 6.89 mmol) in EtOH (15 mL), and the mixture was stirred at room temperature for 1 h. The mixture was concentrated to give the title compound. MS: 141 (M+1).

Step 4: Preparation of tert-butyl 3-hydroxy-6,7-dihydropyrano[3,2-c]pyrazole-1(5H)-carboxylate (37A-4)

(BOC)₂O (2.36 mL, 10.17 mmol) was added to a stirred mixture of 1,5,6,7-tetrahydropyrano[3,2-c]pyrazol-3-ol (950 mg, 6.78 mmol) and Na₂CO₃ (1.08 g, 10.17 mmol) in MeOH (15 mL) and water (3 mL) at 10° C. and the mixture was stirred at room temperature for 12 h. The mixture was filtered and the filter cake was washed with ethanol (50 mL). The filtrate was concentrated to dryness. The residue was purified by silica gel flash chromatography, eluting with CH₂Cl₂/MeOH=100:1-20:1 to give the title compound. ¹H NMR (400 MHz, DMSO-d₆) δ 3.97-4.06 (m, 2H), 2.81 (t, J=6.3 Hz, 2H), 1.83-1.93 (m, 2H), 1.49 (s, 9H).

Step 5: Preparation of tert-butyl 3-(((trifluoromethyl)sulfonyl)oxy)-6,7-dihydropyrano[3,2-c]pyrazole-1(5H)-carboxylate (37A-5)

Tf₂O (0.387 mL, 2.289 mmol) was added to the mixture of TEA (0.319 mL, 2.289 mmol) and tert-butyl 3-hydroxy-6,7-dihydropyrano[3,2-c]pyrazole-1(5H)-carboxylate (500 mg, 2.081 mmol) in DCM (5 mL), the resultant mixture was stirred at room temperature for 1.5 h. The mixture was concentrated and the residue was purified by silica gel flash chromatography, eluting with petroleum ether/EtOAc=25:1-15:1 to give the title compound. MS: 373 (M+1). ¹H NMR (400 MHz, CDCl₃) δ 4.10-4.25 (m, 2H), 3.00 (t, J=6.4 Hz, 2H), 1.96-2.13 (m, 2H), 1.63 (s, 9H).

Step 6: Preparation of tert-butyl 3-(2-fluoro-4-(methoxycarbonyl)phenyl)-6,7-dihydropyrano[3,2-c]pyrazole-1(5H)-carboxylate (37A-6)

To a microwave reaction vial was added tert-butyl 3-(((trifluoromethyl) sulfonyl)oxy)-6,7-dihydropyrano[3,2-c]pyrazole-1(5H)-carboxylate (160 mg, 0.43 mmol), 2-fluoro-4-methoxycarbonylphenylboronic acid (170 mg, 0.86 mmol), Na₂CO₃ (645 μl, 1.29 mmol), and dioxane (2.1 ml). The mixture was degassed for 5 min by bubbling argon, followed by the addition of PdCl₂(dppf) (63 mg, 0.086 mmol). The vial was sealed and heated at 90° C. for 14 h. The mixture was cooled down, diluted with EtOAc and H₂O. The organic layer was separated, washed with brine, dried over MgSO₄, and concentrated. The crude residue was used for next step without purification. MS: 377 (M+1)

Step 7: Preparation of methyl 3-fluoro-4-(1,5,6,7-tetrahydropyrano[3,2-c]pyrazol-3-yl)benzoate (37A-7)

The crude material containing tert-butyl 3-(2-fluoro-4-(methoxycarbonyl) phenyl)-6,7-dihydropyrano[3,2-c]pyrazole-1(5H)-carboxylate from previous step was dissolved in CH₂Cl₂ (1 ml), followed by the addition of TFA (0.3 ml). The mixture was stirred at rt for 2 h, neutralized with sat. NaHCO₃, and extracted with EtOAc. The organic layer was washed with brine, concentrated. The residue was purified by flash chromatography (0-80% EtOAc/hexanes) to give the final product. MS: 277 (M+1).

Step 8: Preparation of methyl 4-(1-(2-chloro-6-(1-(difluoromethyl)cyclopropyl)benzoyl)-1,5,6,7-tetrahydropyrano[3,2-c]pyrazol-3-yl)-3-fluorobenzoate (37A-8)

To a solution of 2-chloro-6-(1-(difluoromethyl)cyclopropyl)benzoic acid (98 mg, 0.40 mmol) in 1,2-dichloroethane (1 ml) was added one drop DMF and oxalyl chloride (0.087 ml, 0.995 mmol). The mixture was stirred at rt for 1 h, concentrated to give 2-chloro-6-(1-(difluoromethyl)cyclopropyl)benzoyl chloride. This crude material was used for next step directly.

To a solution of methyl 3-fluoro-4-(1,5,6,7-tetrahydropyrano[3,2-c]pyrazol-3-yl)benzoate (55 mg, 0.199 mmol) in THF (1.0 ml)/1,2-dichloroethane (1.0 ml) at rt was added DMAP (12 mg, 0.10 mmol), Et₃N (0.28 ml, 2.0 mmol), and 2-chloro-6-(1-(difluoromethyl)cyclopropyl)benzoyl chloride from previous step (dissolved in 0.5 ml THF). The mixture was heated at 60° C. for 14 h. The reaction mixture was cooled down, diluted with H₂O, and extracted with EtOAc. The organic layer was separated, washed with brine, dried over MgSO₄, and concentrated. The residue was purified by flash chromatography (0-80% EtOAc/hexanes) to give the final compound. MS: 505 (M+1).

Step 9: Preparation of 4-(1-(2-chloro-6-(1-(difluoromethyl)cyclopropyl)benzoyl)-1,5,6,7-tetrahydropyrano[3,2-c]pyrazol-3-yl)-3-fluorobenzoic acid (37A)

To a solution of methyl 4-(1-(2-chloro-6-(1-(difluoromethyl)cyclopropyl) benzoyl)-1,5,6,7-tetrahydropyrano[3,2-c]pyrazol-3-yl)-3-fluorobenzoate (68 mg, 0.135 mmol) in THF (0.67 ml)/MeOH (0.67 ml) was added LiOH (0.67 ml, 1.34 mmol). The mixture was stirred at rt for 2 h, then acidified with 2N HCl, and extracted with EtOAc. The organic layer was separated, washed with brine, dried over MgSO₄, and concentrated. The residue was submitted to singleton purification (reverse HPLC H₂O/CH₃CN containing 0.1% TFA) to give the final product. MS: 491 (M+1). ¹H NMR (600 MHz, DMSO-d6) δ 7.76 (d, J=7.8 Hz, 1H), 7.60-7.66 (m, 2H), 7.45-7.56 (m, 2H), 7.44 (d, J=7.2 Hz, 1H), 5.91 (t, J=57.6 Hz, 1H), 4.18-4.22 (m, 2H), 3.12-3.14 (m, 2H), 1.98-2.02 (m, 2H), 1.10-1.14 (m, 1H), 0.87-0.96 (m, 2H), 0.51-0.53 (m, 1H).

The following example shown in Table 16 was prepared following similar procedures described for Example 37A which can be achieved by those of ordinary skill in the art of organic synthesis.

TABLE 16

| Example No. | Structure | IUPAC Name | Exact Mass [M + H]+ |
|---|---|---|---|
| 37B | (structure shown) | 4-[1-({2-chloro-6-[1-(trifluoromethyl)cyclopropyl]phenyl}carbonyl)-1,5,6,7-tetrahydropyrano[3,2-c]pyrazol-3-yl]-3-fluorobenzoic acid | 509 |

Biological Assay

The compounds of the invention inhibit RORgammaT activity. Activation of RORgammaT activity can be measured using, e.g., biochemical TR-FRET assay. In such an assay, interaction of cofactor-derived peptides with human RORgammaT-Ligand Binding Domain (LBD) can be measured. The TR-FRET technique is a sensitive biochemical proximity assay that will give information concerning the interaction of a ligand with the LBD, in the presence of cofactor-derived peptides (Zhou et al., Methods 25:54-61, 2001).

To identify novel antagonists of RORgammaT, an assay was developed which employs the interaction of RORgammaT with its co-activator peptide SRC1_2. This peptide mimics the recruitment of co-activators to RORgammaT through its interaction with the LXXLL (e.g., NR box) motifs (Xie et al., J. Immunol. 175: 3800-09, 2005; Kurebayashi et al., Biochem. Biophys. Res. Commun. 315: 919-27, 2004; Jin et al., Mol. Endocrinology 24:923-29, 2010). The RORγ-Ligand Binding Domain TR-FRET Assay was run according to the following protocol.

HIS-tagged RORγ-LBD protein was recombinantly expressed in *Escherichia coli*. The RORγ-LBD protein was purified by $Ni^{2+}$-affinity resin. Purified protein was then diluted in assay buffer (50 mM Tris pH 7.0, 50 mM KCl, 1 mM EDTA, 0.1 mM DTT, 100 mg/ml bovine serum albumin, delipidated) to obtain a RORγ-LBD final concentration of 3 nM. Europium tagged anti-HIS antibody was also added to this solution (1.25 nM). Separately, SF9 cells not expressing any recombinant protein were lysed (32,000 cells per ml in 25 mM Tris, 50 mM NaCl) and the previously frozen lysate was added to the diluted RORγ-LBD solution at a ratio of 0.75 ml SF9 lysate per 15 ml of diluted RORγ-LBD.

Compounds to be tested were injected to the 384-well assay plate using Acoustic Droplet Ejection technology by Echo 550 liquid handler (Labcyte, CA).

A stock of biotinylated-LXXLL peptide from coactivator SRC1 (Biotin-SPSSHSSLTERHKILHRLLQEGSP) (SEQ ID NO:1) and APC-conjugated streptavidin (final concentrations 100 nM and 8 nM respectively) were also added to each well.

The final assay mixture was incubated overnight at 4° C., warmed to room temperature and the fluorescence signal was measured on an Envision plate reader: (Excitation filter=340 nm; APC emission=665 nm; Europium emission=615 nm; dichroic mirror=D400/D630; delay time=100 μs, integration time=200 μs). IC50 values for test compounds were calculated from the quotient of the fluorescence signal at 665 nm divided by the fluorescence signal at 615 nm.

The $IC_{50}$ value for representative compounds of the invention are set forth below in Table 17.

TABLE 17

| Example No. | Fret $IC_{50}$ (nM) |
|---|---|
| 1A | 3.9 |
| 1B | 21.3 |
| 1C | 7932 |
| 1D | 1.7 |
| 1E | 2.1 |
| 1F | 3.5 |
| 1G | 6733 |
| 1H | 12.4 |
| 1I | 17.4 |
| 1J | 9.2 |
| 1K | 21.6 |
| 1L | 2.5 |
| 1M | 13.9 |
| 2A | 2.1 |
| 3A | 728 |
| 4A | 56.7 |
| 5A | 141 |
| 6A | 1.7 |
| 6B | 2.4 |
| 6C | 5.3 |
| 7A | 2925 |
| 8A | 93 |
| 9A | 1.6 |
| 9B | 3.5 |
| 10A | 622 |
| 11A | 187 |
| 12A-A | 94 |
| 12A-B | 1 |
| 13A-A | 642 |
| 13A-B | 3.6 |
| 14A-A | 294 |
| 14A-B | 7.5 |
| 15A-A | 625 |
| 15A-B | 4.4 |
| 16A-B | 5.2 |
| 17A | 185 |
| 17B | 1222 |
| 17C | 642 |
| 17D | 235 |
| 18A | 14 |
| 18B | 48 |
| 18C | 606 |
| 18D | 23 |
| 18E | 91 |
| 18F | 158 |
| 18G | 814 |
| 19A | 223 |
| 19B | 773 |
| 19C | 95 |
| 20A | 21 |
| 20B | 28 |
| 21A | 0.7 |
| 21B | 1.5 |
| 21C | 1.2 |
| 21D | 1.2 |
| 21E | 0.8 |
| 21F | 0.7 |
| 21G | 0.9 |
| 21H | 0.9 |
| 21I | 0.6 |
| 21J | 0.5 |
| 21K | 0.6 |
| 21L | 1.3 |
| 21M | 0.7 |
| 21N | 0.6 |
| 21O | 2.9 |
| 21P | 0.8 |
| 21Q | 0.8 |
| 21R | 0.9 |
| 21S | 7 |
| 21T | 1.7 |
| 21U | 0.9 |
| 21V | 1 |
| 21W | 1 |
| 21X | 1.1 |
| 21Y | 1 |
| 21Z | 1.4 |
| 21AA | 1.7 |

TABLE 17-continued

| Example No. | Fret IC$_{50}$ (nM) |
| --- | --- |
| 21BB | 1.6 |
| 21CC | 1.4 |
| 21DD | 0.9 |
| 21EE | 0.8 |
| 21FF | 0.5 |
| 21GG | 0.6 |
| 21HH | 0.5 |
| 21II | 0.5 |
| 21JJ | 0.6 |
| 21KK | 0.6 |
| 21LL | 1.1 |
| 21MM | 1.1 |
| 21NN | 0.9 |
| 21PP | 1.4 |
| 21QQ | 1.2 |
| 21RR | 0.7 |
| 21SS | 0.8 |
| 21TT | 1.0 |
| 21UU | 4.8 |
| 21VV | 3.4 |
| 21WW | 0.7 |
| 21XX | 29 |
| 21YY | 0.9 |
| 21ZZ | 1.1 |
| 21AAA | 0.8 |
| 21BBB | 1.1 |
| 21CCC | 1.3 |
| 22A | 332 |
| 23A | 78 |
| 24A | 159 |
| 25A | 13 |
| 25B | 21 |
| 26A | 67 |
| 27A | 121 |
| 27B | 6.9 |
| 28A | 166 |
| 29A | 5 |
| 30A | 83 |
| 31A | 2.3 |
| 32A | 1.2 |
| 33A | 2.1 |
| 34A | 81 |
| 35A | 4.5 |
| 36A | 5225 |
| 37A | 3.1 |
| 37B | 1.9 |

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

What is claimed is:

1. A compound according to Formula I-1:

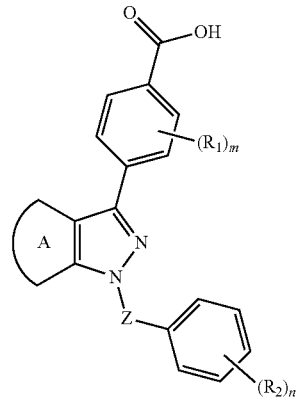

(I-1)

wherein:

Ring A is a monocyclic ring formed by an alkylene group taken together with the C=C of the pyrazolyl to which Ring A is fused, wherein 1, 2, or 3 carbon atoms of the alkylene group are optionally replaced with a heteroatom selected from O, N or S, and Ring A is optionally substituted with one to three substituents independently selected from $R_3$, wherein $R_3$ is selected from the group consisting of OH, oxo, $(C_{1-4})$alkyl, —$(C_{1-4})$alkylene-$N(R_a)_2$, —$(C_{1-4})$alkylene-$(C_{3-6}$ cycloalkyl), $(C_{1-4})$ alkoxy, $N(R_a)_2$, $N(R_6)CO_2R_7$, $N(R_6)C(O)R_8$, $C(O)R_8$, $C(O)N(R)_2$,

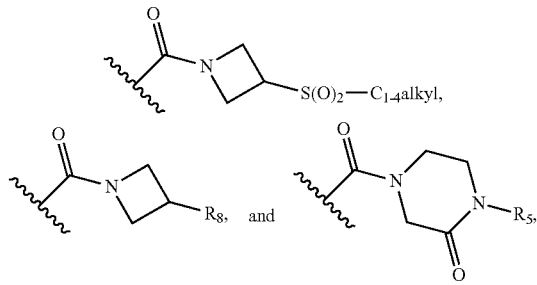

wherein said alkyl is optionally substituted with one or more halogen or hydroxyl;

Z is C(O) or CH$_2$;

m is 0, 1, or 2;

n is 1, 2 or 3;

$R_1$ is independently OH, halogen, $(C_{1-4})$alkyl, CN, CF$_3$, or CHF$_2$, wherein said alkyl is optionally substituted with one or more halogen;

$R_2$ is independently halogen, $(C_{1-4})$alkyl, CF$_3$, CHF$_2$, or $(C_{3-4})$cycloalkyl, wherein said alkyl and cycloalkyl are optionally substituted with one or more substituents independently selected from the group consisting of CN, $(C_{1-4})$haloalkyl, and halogen;

$R_5$ is independently OH, $(C_{0-4})$alkyl, or $S(O)_2R_b$;

$R_6$ is independently $(C_{0-4})$alkyl;

$R_7$ is independently $(C_{1-6})$alkyl;

$R_8$ is independently OH, $(C_{0-4})$alkyl, 2-8 membered heteroalkyl, or one of the following:

a heterocyclyl-containing group selected from 3-10 membered heterocyclyl, —$C_{1-6}$ alkylene-(5-6 membered heteroaryl), —O—$(C_{1-6}$ alkylene)-(5-6 membered heteroaryl), or -(3-10 membered heterocycloalkylene)-(3-10 membered heterocycloalkyl), each optionally substituted by one or more $R_9$;

a carbocyclyl-containing group selected from $C_{3-7}$ carbocyclyl, —$C_{1-6}$ alkylene-($C_{3-7}$ carbocyclyl), —O—$C_{3-7}$ carbocyclyl, or —O—($C_{1-6}$ alkylene)-$C_{3-7}$ carbocyclyl, each optionally substituted by one or more $R_9$;

$R_9$ is independently halogen, hydroxyl, ($C_{1-4}$)alkyl, ($C_{1-4}$)haloalkyl, ($C_{1-6}$)alkoxyl, $N(R_a)_2$, ($C_{3-4}$)cycloalkyl, or cyano, wherein said cycloalkyl is optionally substituted with one or more substituents independently selected from the group consisting of CN, ($C_{1-4}$)haloalkyl, and halogen;

$R_a$ is independently ($C_{0-4}$)alkyl, ($C_{1-4}$) haloalkyl, or 3-7 membered heterocycloalkyl; and $R_b$ is ($C_1$-4)alkyl;

or a pharmaceutically acceptable salt thereof.

2. A compound of claim 1, wherein Z is C(O).

3. A compound of claim 2, wherein $R_1$ is independently OH or halogen.

4. A compound of claim 2, wherein $R_1$ is independently OH, chloro, or fluoro.

5. A compound of claim 2, wherein $R_1$ is OH.

6. A compound of claim 2, wherein $R_1$ is fluoro.

7. A compound of claim 3, wherein m is 1.

8. A compound of claim 6, wherein $R_1$ is located meta to the —$CO_2H$ group.

9. A compound of claim 2, wherein $R_2$ is independently halogen, ($C_{3-4}$)cycloalkyl, or ($C_{3-4}$)cycloalkyl substituted by ($C_{1-4}$)haloalkyl.

10. A compound of claim 7, wherein $R_2$ is independently chloro, cyclopropyl, or cyclopropyl substituted by trifluoromethyl.

11. A compound of claim 7, wherein a first occurrence of $R_2$ is chloro, and a second occurrence of $R^2$ is cyclopropyl.

12. A compound of claim 7, wherein a first occurrence of $R_2$ is chloro, and a second occurrence of $R^2$ is cyclopropyl substituted by trifluoromethyl.

13. A compound of claim 7, wherein a first occurrence of $R_2$ is chloro, and a second occurrence of $R^2$ is

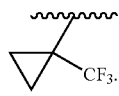

14. A compound of claim 12, wherein any $R_2$ is located at an ortho-position on the phenyl group to which $R_2$ is attached.

15. A compound of claim 12, wherein n is 2.

16. A compound of claim 2, wherein Ring A is a 6-membered monocyclic ring formed by an alkylene group taken together with the C=C of the pyrazolyl to which Ring A is fused, and Ring A is substituted with one $R_3$ group selected from $C(O)R_8$, $C(O)N(R_8)_2$, and

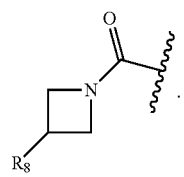

17. A compound of claim 12, wherein Ring A is

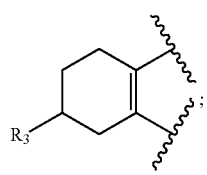

and $R_3$ is $C(O)R_8$, $C(O)N(R_8)_2$, or

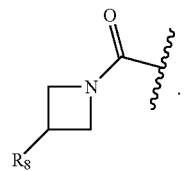

18. A compound of claim 17, wherein $R_8$ is independently ($C_{0-4}$)alkyl, 2-8 membered heteroalkyl, or -(3-10 membered heterocyclyl optionally substituted by one or more $R_9$).

19. A compound of claim 1, wherein the compound is represented by Formula I-1A:

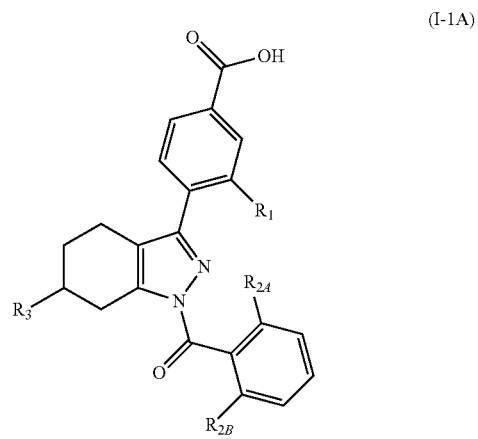

(I-1A)

wherein:

$R_1$ is halogen;

$R_{2A}$ is halogen;

$R_{2B}$ is independently halogen, ($C_{1-4}$)alkyl, $CF_3$, $CHF_2$, or ($C_{3-4}$)cycloalkyl, wherein said alkyl and cycloalkyl are optionally substituted with one or more substituents independently selected from the group consisting of CN, ($C_{1-4}$)haloalkyl, and halogen;

$R_3$ is $N(R_a)_2$, $N(R_6)CO_2R_7$, $N(R_6)C(O)R$, $C(O)R_8$, $C(O)N(R_8)_2$, or

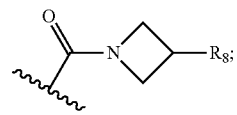

$R_6$ is independently ($C_{0-4}$)alkyl;

$R_7$ is independently ($C_{1-6}$)alkyl;

$R_8$ is independently ($C_{0-4}$)alkyl, 2-8 membered heteroalkyl, or -(3-10 membered heterocyclyl optionally substituted by one or more $R_9$);

$R_9$ is independently halogen, hydroxyl, ($C_{1-4}$)alkyl, or ($C_{1-4}$)haloalkyl; and $R_a$ is independently ($C_{0-4}$)alkyl;

or a pharmaceutically acceptable salt thereof.

20. A compound according to Formula I-2, II, or III, wherein Formula I-2 is represented by:

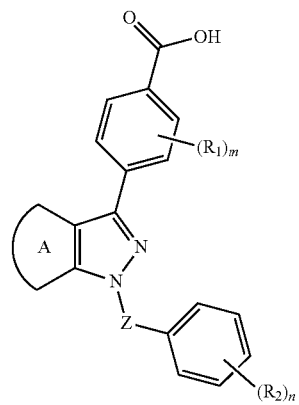

(I-2)

wherein:

Ring A is a saturated monocyclic ring optionally containing 1, 2, or 3 heteroatoms selected from O, N or S and optionally substituted with one to three substituents independently selected from $R_3$, wherein $R_3$ is selected from the group consisting of OH, oxo, $(C_{1-4})$alkyl, $(C_{1-4})$alkyl-$N(R_a)_2$, $(C_{1-4})$alkoxy, $N(R_a)_2$, $C(O)R_5$, $C(O)N(R_5)_2$,

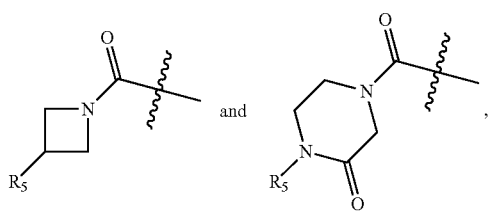

wherein said alkyl is optionally substituted with one or more halogen;

Z is C(O) or $CH_2$;

m is 0, 1, or 2;

n is 1, 2 or 3;

$R_1$ is independently OH, $(C_{1-4})$alkyl, CN, $CF_3$, $CHF_2$ or halogen, wherein said alkyl is optionally substituted with one or more halogen;

$R_2$ is independently selected from halogen, $(C_{1-4})$alkyl, $CF_3$, $CHF_2$ and $(C_{3-4})$cycloalkyl, wherein said alkyl may optionally be substituted with CN and one to three halogen;

$R_5$ is independently selected from OH, $(C_{0-4})$alkyl, $(C_{1-4})$alkoxy and $S(O)_2R_b$;

$R_a$ is independently selected from $(C_{0-4})$alkyl; and $R_b$ is $(C_{0-4})$alkyl;

or a pharmaceutically acceptable salt thereof;

Formula II is represented by:

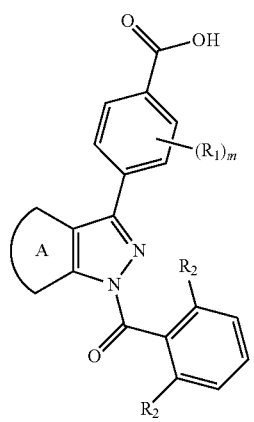

(II)

wherein:

Ring A is a saturated monocyclic ring optionally containing 1, 2, or 3 heteroatoms selected from O, N or S and optionally substituted with one to three substituents independently selected from $R_3$, wherein $R_3$ is selected from the group consisting of OH, oxo, $(C_{1-4})$alkyl, $(C_{1-4})$alkyl-$N(R_a)_2$, $(C_{1-4})$alkoxy, $N(R_a)_2$, $C(O)R_5$, $C(O)N(R_5)_2$,

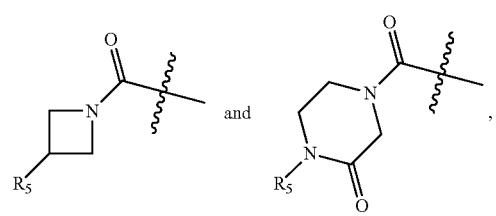

wherein said alkyl is optionally substituted with one or more halogen;

m is 0, 1, or 2;

$R_1$ is independently OH, $(C_{1-4})$alkyl, CN, $CF_3$, $CHF_2$ or halogen, wherein said alkyl is optionally substituted with one or more halogen;

$R_2$ is independently selected from halogen, $(C_{1-4})$alkyl, $CF_3$, $CHF_2$ and $(C_{3-4})$cycloalkyl, wherein said alkyl may optionally be substituted with CN and one to three halogen;

$R_5$ is independently selected from OH, $(C_{0-4})$alkyl, $(C_{1-4})$alkoxy and $S(O)_2R_b$;

$R_a$ is independently selected from $(C_{0-4})$alkyl; and $R_b$ is $(C_{0-4})$alkyl;

or a pharmaceutically acceptable salt thereof; and

Formula III is represented by:

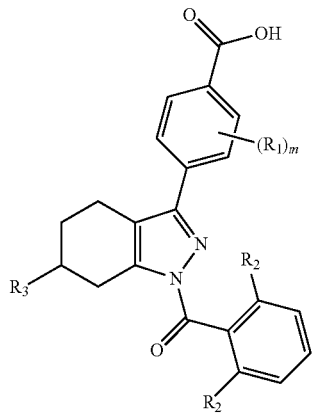

(III)

wherein:

m is 0, 1, or 2;

R₁ is independently OH, methyl or F;

R₂ is independently selected from Cl, CF₃ and (C₃₋₄) cycloalkyl, wherein the cycloalkyl may optionally be substituted with CN; and R₃ is selected from the group consisting of OH, oxo, (C₁₋₄)alkoxy, C(O)R₅, C(O)N(R₅)₂,

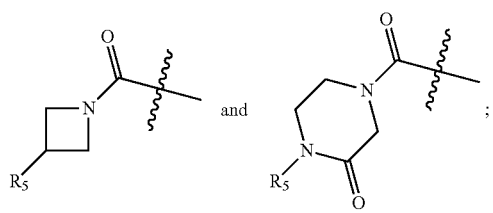

R₅ is independently selected from OH, (C₀₋₄)alkyl, (C₁₋₄)alkoxy and S(O)₂R_b; and R_b is methyl;

or a pharmaceutically acceptable salt thereof.

21. A compound of claim 20, wherein the compound is according to Formula III:

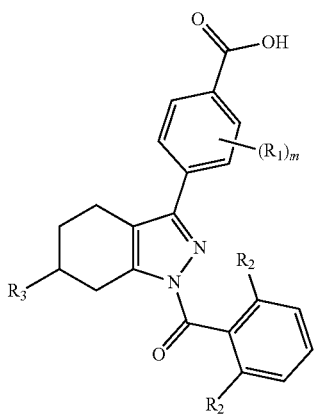

(III)

wherein:

m is 0, 1, or 2;

R₁ is independently OH, methyl or F;

R₂ is independently selected from Cl, CF₃ and (C₃₋₄) cycloalkyl, wherein the cycloalkyl may optionally be substituted with CN; and R₃ is selected from the group consisting of OH, oxo, (C₁₋₄)alkoxy, C(O)R₅, C(O)N(R₅)₂,

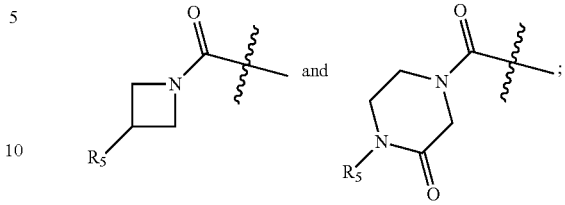

R₅ is independently selected from OH, (C₀₋₄)alkyl, (C₁₋₄)alkoxy and S(O)₂R_b; and R_b is methyl;

or a pharmaceutically acceptable salt thereof.

22. A compound according to claim 1 selected from:
4-(1-(2-chloro-6-(trifluoromethyl)benzoyl)-4,5,6,7-tetrahydro-1H-indazol-3-yl)-3-fluorobenzoic acid;
4-(1-(2-chloro-6-(trifluoromethyl)benzoyl)-1,4,5,6-tetrahydrocyclopenta[c]pyrazol-3-yl)-3-fluorobenzoic acid;
4-(6-(tert-butoxycarbonyl)-1-(2-chloro-6-(trifluoromethyl)benzoyl)-1,4,5,6,7,8-hexahydropyrazolo[3,4-d]azepin-3-yl)-3-fluorobenzoic acid;
4-(1-(2-chloro-6-cyclopropylbenzoyl)-4,5,6,7-tetrahydro-1H-indazol-3-yl)-2-hydroxybenzoic acid;
4-(1-(2-chloro-6-cyclopropylbenzoyl)-4,5,6,7-tetrahydro-1H-indazol-3-yl)-3-fluorobenzoic acid;
4-(1-(2-chloro-6-cyclopropylbenzoyl)-6-hydroxy-4,5,6,7-tetrahydro-1H-indazol-3-yl)-3-fluorobenzoic acid;
4-(6-(tert-butoxycarbonyl)-1-(2-chloro-6-cyclopropylbenzoyl)-4,5,6,7-tetrahydro-1H-pyrazolo[3,4-c]pyridin-3-yl)-3-fluorobenzoic acid;
4-(1-(2-chloro-6-cyclopropylbenzoyl)-4-oxo-4,5,6,7-tetrahydro-1H-indazol-3-yl)-3-fluorobenzoic acid;
4-(1-(2-chloro-6-cyclopropylbenzoyl)-6-methoxy-4,5,6,7-tetrahydro-1H-indazol-3-yl)-3-fluorobenzoic acid;
4-(1-(2-chloro-6-cyclopropylbenzoyl)-6-oxo-4,5,6,7-tetrahydro-1H-indazol-3-yl)-3-fluorobenzoic acid;
4-(1-(2-chloro-6-cyclopropylbenzoyl)-1,4,5,6,7,8-hexahydrocyclohepta[c]pyrazol-3-yl)-3-fluorobenzoic acid;
4-(1-(2-chloro-6-cyclobutylbenzoyl)-4,5,6,7-tetrahydro-1H-indazol-3-yl)-3-fluorobenzoic acid;
4-(1-(2,6-dichlorobenzoyl)-4,5,6,7-tetrahydro-1H-indazol-3-yl)benzoic acid;
4-(1-(2-chloro-6-cyclopropylbenzoyl)-4,5,6,7-tetrahydro-1H-indazol-3-yl)-5-fluoro-2-hydroxybenzoic acid;
4-(1-(2-chloro-6-(trifluoromethyl)benzoyl)-1,4,5,6,7,8-hexahydropyrazolo[3,4-d]azepin-3-yl)-3-fluorobenzoic acid;
4-(1-(2-chloro-6-(trifluoromethyl)benzyl)-4,5,6,7-tetrahydro-1H-indazol-3-yl)-3-fluorobenzoic acid;
3-(4-carboxy-2-fluorophenyl)-1-(2-chloro-6-cyclopropylbenzoyl)-4,5,6,7-tetrahydro-1H-indazole-6-carboxylic acid;
4-(1-(2-chloro-6-cyclopropylbenzoyl)-6-(dimethylcarbamoyl)-4,5,6,7-tetrahydro-1H-indazol-3-yl)-3-fluorobenzoic acid;
4-(6-(azetidine-1-carbonyl)-1-(2-chloro-6-cyclopropylbenzoyl)-4,5,6,7-tetrahydro-1H-indazol-3-yl)-3-fluorobenzoic acid;
4-(1-(2-chloro-6-cyclopropylbenzoyl)-6-(methylcarbamoyl)-4,5,6,7-tetrahydro-1H-indazol-3-yl)-3-fluorobenzoic acid;

4-(4-(tert-butoxycarbonyl)-1-(2-chloro-6-cyclopropyl-benzoyl)-4,5,6,7-tetrahydro-1H-pyrazolo[4,3-b]pyridin-3-yl)-3-fluorobenzoic acid;
4-(1-(2-chloro-6-cyclopropylbenzoyl)-1,4,6,7-tetrahydropyrano[4,3-c]pyrazol-3-yl)benzoic acid;
4-(1-(2-chloro-6-cyclopropylbenzoyl)-1,4,5,7-tetrahydropyrano[3,4-c]pyrazol-3-yl)-3-fluorobenzoic acid;
4-(6-acetyl-1-(2-chloro-6-cyclopropylbenzoyl)-4,5,6,7-tetrahydro-1H-pyrazolo[3,4-c]pyridin-3-yl)-3-fluorobenzoic acid;
4-(1-(2-chloro-6-cyclopropylbenzoyl)-6-(methoxycarbonyl)-4,5,6,7-tetrahydro-1H-pyrazolo[3,4-c]pyridin-3-yl)-3-fluorobenzoic acid;
4-(1-(2-chloro-6-cyclopropylbenzoyl)-6-(3-methoxyazetidine-1-carbonyl)-4,5,6,7-tetrahydro-1H-indazol-3-yl)-3-fluorobenzoic acid;
4-(1-(2-chloro-6-cyclopropylbenzoyl)-6-(3-methoxyazetidine-1-carbonyl)-4,5,6,7-tetrahydro-1H-indazol-3-yl)-3-fluorobenzoic acid;
4-(1-(2-chloro-6-(1-cyanocyclopropyl)benzoyl)-6-(3-methoxyazetidine-1-carbonyl)-4,5,6,7-tetrahydro-1H-indazol-3-yl)-3-fluorobenzoic acid;
4-(1-(2-chloro-6-(1-cyanocyclopropyl)benzoyl)-6-(3-methoxyazetidine-1-carbonyl)-4,5,6,7-tetrahydro-1H-indazol-3-yl)-3-fluorobenzoic acid;
4-(1-(2-chloro-6-(1-cyanocyclobutyl)benzoyl)-6-(3-(methylsulfonyl)azetidine-1-carbonyl)-4,5,6,7-tetrahydro-1H-indazol-3-yl)-3-fluorobenzoic acid;
4-(1-(2-chloro-6-(1-cyanocyclobutyl)benzoyl)-6-(3-(methylsulfonyl)azetidine-1-carbonyl)-4,5,6,7-tetrahydro-1H-indazol-3-yl)-3-fluorobenzoic acid;
4-(1-(2-chloro-6-(1-cyanocyclobutyl)benzoyl)-6-(4-methyl-3-oxopiperazine-1-carbonyl)-4,5,6,7-tetrahydro-1H-indazol-3-yl)-3-fluorobenzoic acid;
4-(1-(2-chloro-6-(1-cyanocyclobutyl)benzoyl)-6-(4-methyl-3-oxopiperazine-1-carbonyl)-4,5,6,7-tetrahydro-1H-indazol-3-yl)-3-fluorobenzoic acid; and
4-(1-(2-chloro-6-cyclopropylbenzoyl)-6-(3-methoxyazetidine-1-carbonyl)-4,5,6,7-tetrahydro-1H-indazol-3-yl)-2-methylbenzoic acid;
or a pharmaceutically acceptable salt thereof.

23. A compound in Table 17 or a pharmaceutically acceptable salt thereof:

TABLE 17

| Example No. | Chemical Structure |
|---|---|
| 1A | |
| 1B | 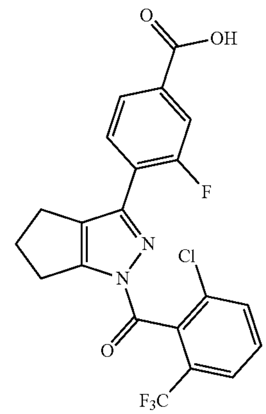 [SMILES: O=C(O)c1ccc(-c2nn(C(=O)c3c(Cl)cccc3C(F)(F)F)c3c2CCC3)c(F)c1] |
| 1C | 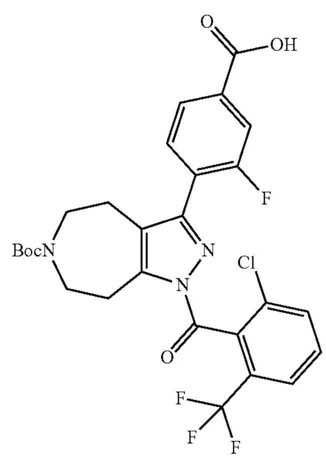 [SMILES: CC(C)(C)OC(=O)N1CCc2c(-c3ccc(C(=O)O)cc3F)nn(C(=O)c3c(Cl)cccc3C(F)(F)F)c2CC1] |
| 1D | 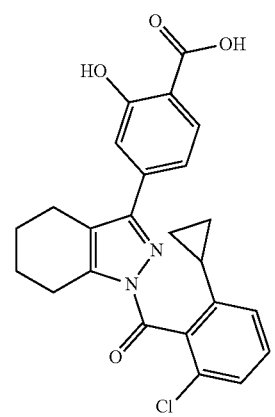 [SMILES: O=C(O)c1ccc(-c2nn(C(=O)c3c(Cl)cccc3C3CC3)c3c2CCCC3)cc1O] |

TABLE 17-continued

| Example No. | Chemical Structure |
|---|---|
| 1E | 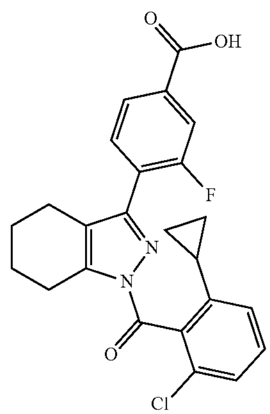 [SMILES: O=C(O)c1ccc(-c2nn(C(=O)c3c(Cl)cccc3C3CC3)c3c2CCCC3)c(F)c1] |
| 1F | 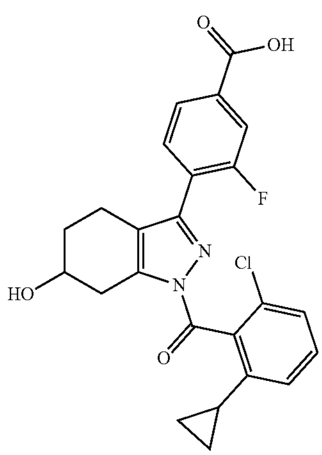 [SMILES: O=C(O)c1ccc(-c2nn(C(=O)c3c(Cl)cccc3C3CC3)c3c2CCC(O)C3)c(F)c1] |
| 1G | 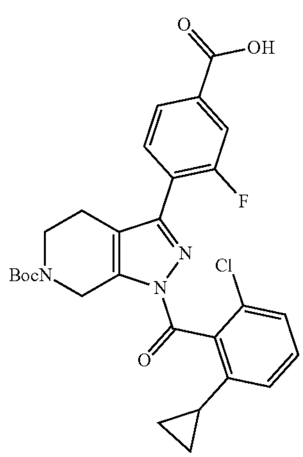 [SMILES: CC(C)(C)OC(=O)N1CCc2c(-c3ccc(C(=O)O)cc3F)nn(C(=O)c3c(Cl)cccc3C3CC3)c2C1] |
| 1H | 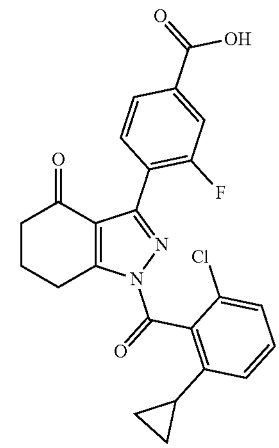 [SMILES: O=C(O)c1ccc(-c2nn(C(=O)c3c(Cl)cccc3C3CC3)c3c2C(=O)CCC3)c(F)c1] |
| 1I | 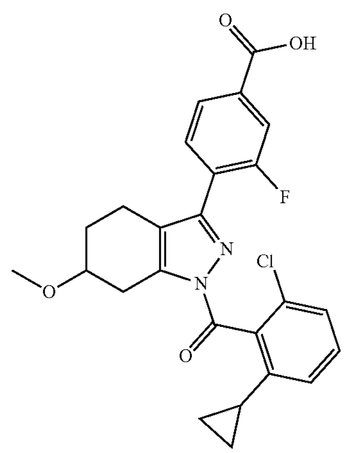 [SMILES: COC1CCc2c(-c3ccc(C(=O)O)cc3F)nn(C(=O)c3c(Cl)cccc3C3CC3)c2C1] |
| 1J | 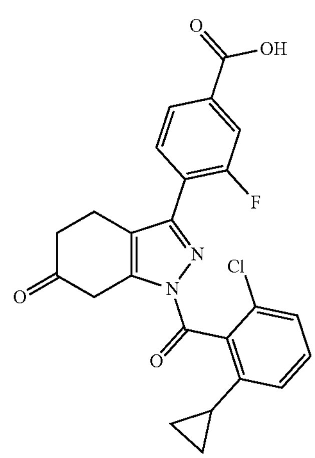 [SMILES: O=C1CCc2c(-c3ccc(C(=O)O)cc3F)nn(C(=O)c3c(Cl)cccc3C3CC3)c2C1] |

TABLE 17-continued
| Example No. | Chemical Structure |
|---|---|
| 1K | 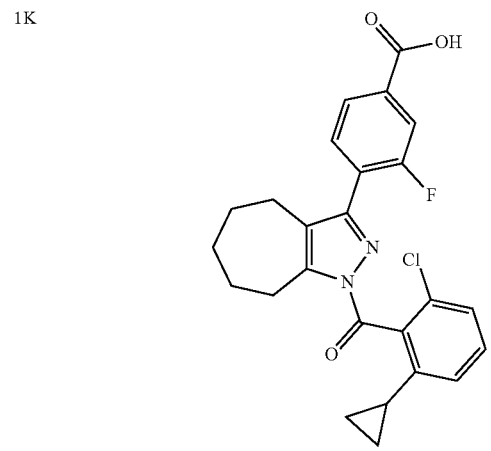 |
| 1L | 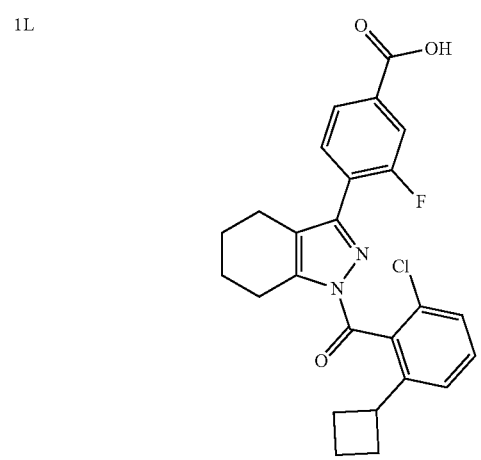 |
| 1M | 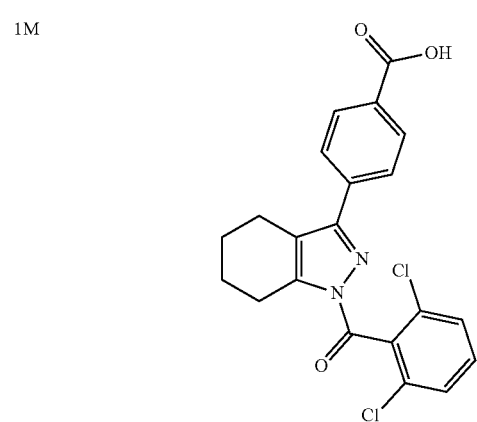 |
TABLE 17-continued
| Example No. | Chemical Structure |
|---|---|
| 2A | 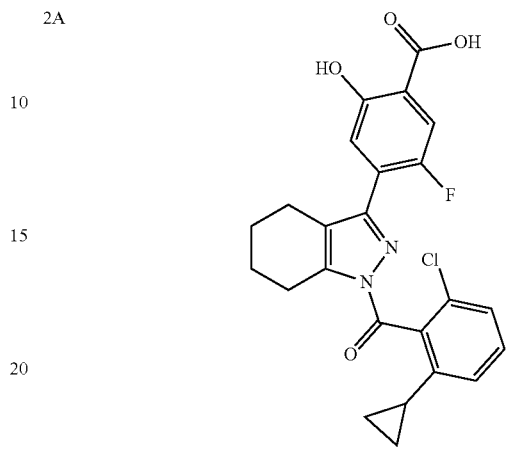 |
| 3A | 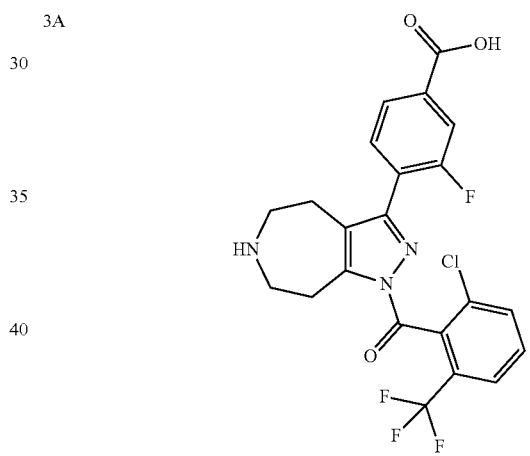 |
| 4A | 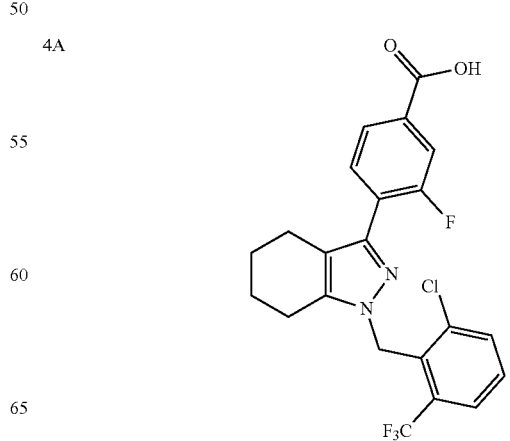 |

TABLE 17-continued
| Example No. | Chemical Structure |
|---|---|
| 5A | 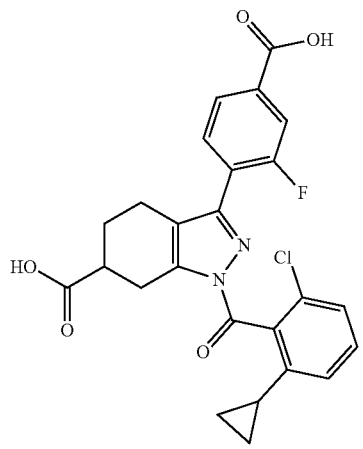 [SMILES: O=C(O)c1ccc(-c2nn(C(=O)c3c(Cl)cccc3C3CC3)c3c2CCC(C(=O)O)C3)c(F)c1] |
| 6A | 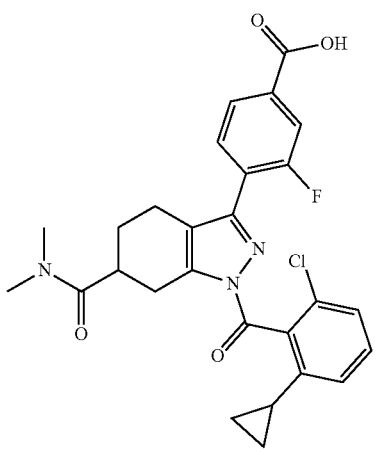 [SMILES: CN(C)C(=O)C1CCc2c(-c3ccc(C(=O)O)cc3F)nn(C(=O)c3c(Cl)cccc3C3CC3)c2C1] |
| 6B | 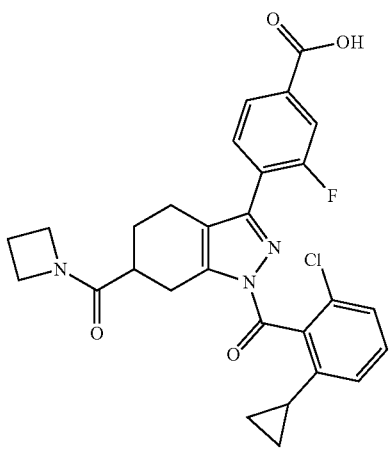 [SMILES: O=C(O)c1ccc(-c2nn(C(=O)c3c(Cl)cccc3C3CC3)c3c2CCC(C(=O)N2CCC2)C3)c(F)c1] |
TABLE 17-continued
| Example No. | Chemical Structure |
|---|---|
| 6C | 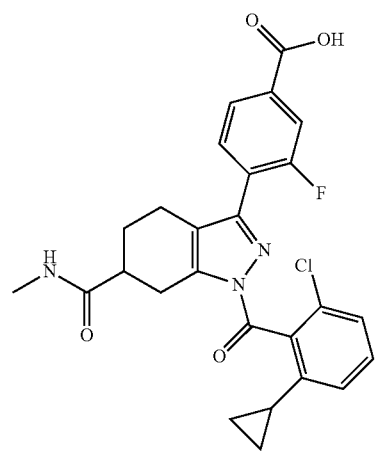 [SMILES: CNC(=O)C1CCc2c(-c3ccc(C(=O)O)cc3F)nn(C(=O)c3c(Cl)cccc3C3CC3)c2C1] |
| 7A | 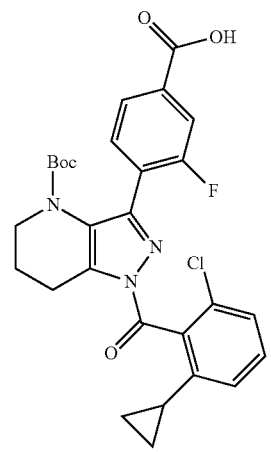 [SMILES: CC(C)(C)OC(=O)N1CCCc2c1c(-c1ccc(C(=O)O)cc1F)nn2C(=O)c1c(Cl)cccc1C1CC1] |
| 8A | 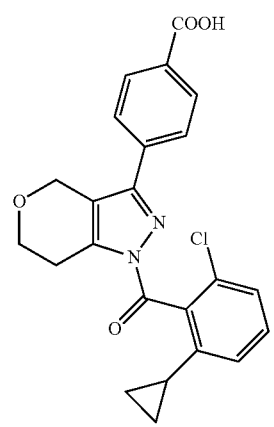 [SMILES: O=C(O)c1ccc(-c2nn(C(=O)c3c(Cl)cccc3C3CC3)c3c2COCC3)cc1] |

TABLE 17-continued
| Example No. | Chemical Structure |
|---|---|
| 9A | 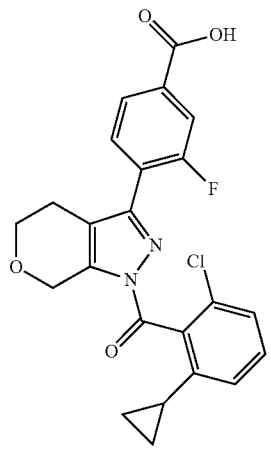 [SMILES: O=C(O)c1ccc(-c2nn(C(=O)c3c(Cl)cccc3C3CC3)c3c2CCOC3)c(F)c1] |
| 9B | 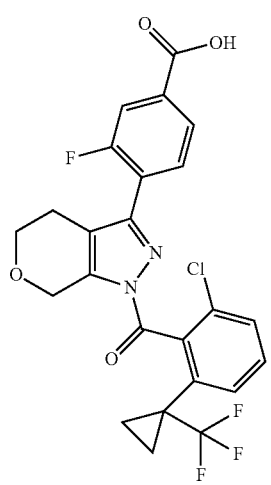 [SMILES: O=C(O)c1ccc(-c2nn(C(=O)c3c(Cl)cccc3C3(C(F)(F)F)CC3)c3c2CCOC3)c(F)c1] |
| 10A | 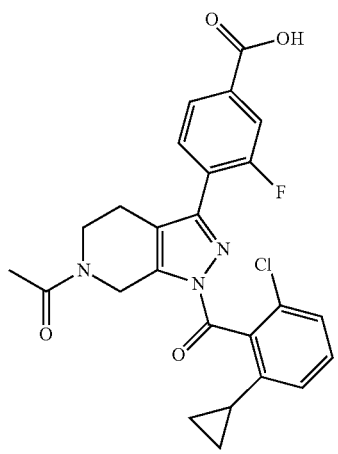 [SMILES: CC(=O)N1CCc2c(-c3ccc(C(=O)O)cc3F)nn(C(=O)c3c(Cl)cccc3C3CC3)c2C1] |
TABLE 17-continued
| Example No. | Chemical Structure |
|---|---|
| 11A | 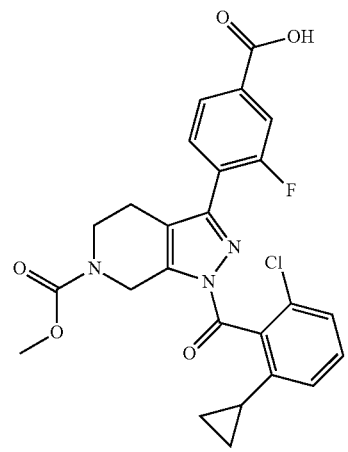 [SMILES: COC(=O)N1CCc2c(-c3ccc(C(=O)O)cc3F)nn(C(=O)c3c(Cl)cccc3C3CC3)c2C1] |
| 12A-A | 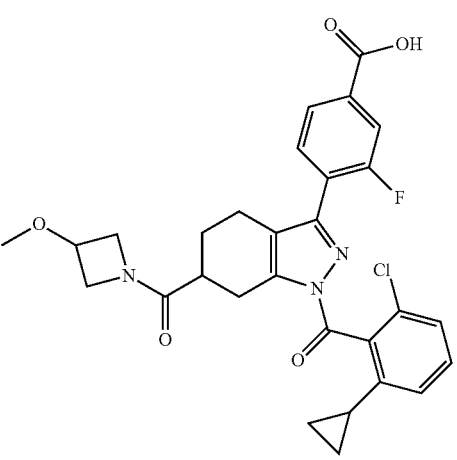 [SMILES: COC1CN(C(=O)C2CCc3c(-c4ccc(C(=O)O)cc4F)nn(C(=O)c4c(Cl)cccc4C4CC4)c3C2)C1] |
| 12A-B | 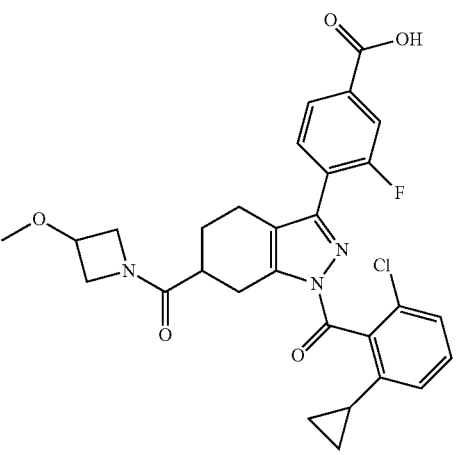 [SMILES: COC1CN(C(=O)C2CCc3c(-c4ccc(C(=O)O)cc4F)nn(C(=O)c4c(Cl)cccc4C4CC4)c3C2)C1] |

TABLE 17-continued
| Example No. | Chemical Structure |
|---|---|
| 13A-A | 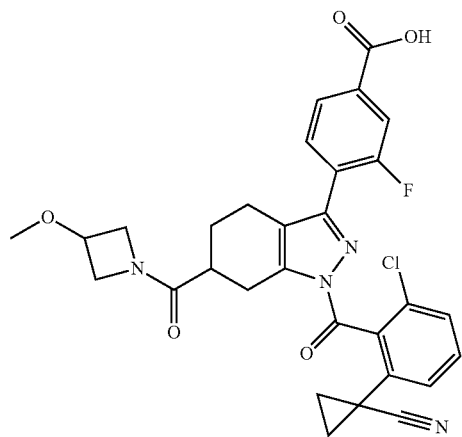 [SMILES: COC1CN(C(=O)C2CCc3c(-c4ccc(C(=O)O)cc4F)nn(C(=O)c4c(Cl)cccc4C4(C#N)CC4)c3C2)C1] |
| 13A-B | 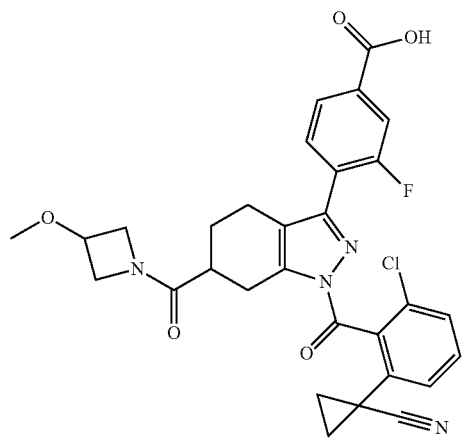 [SMILES: COC1CN(C(=O)C2CCc3c(-c4ccc(C(=O)O)cc4F)nn(C(=O)c4c(Cl)cccc4C4(C#N)CC4)c3C2)C1] |
| 14A-A | 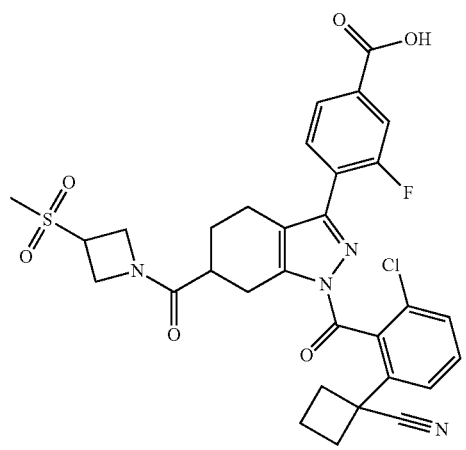 [SMILES: CS(=O)(=O)C1CN(C(=O)C2CCc3c(-c4ccc(C(=O)O)cc4F)nn(C(=O)c4c(Cl)cccc4C4(C#N)CCC4)c3C2)C1] |
| 14A-B | 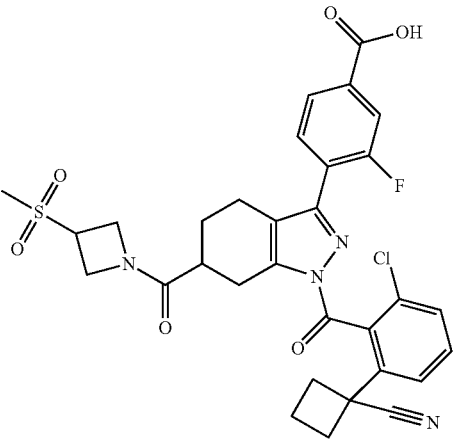 [SMILES: CS(=O)(=O)C1CN(C(=O)C2CCc3c(-c4ccc(C(=O)O)cc4F)nn(C(=O)c4c(Cl)cccc4C4(C#N)CCC4)c3C2)C1] |
| 15A-A | 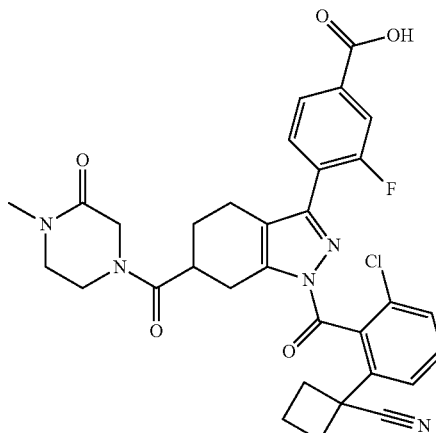 |
| 15A-B | 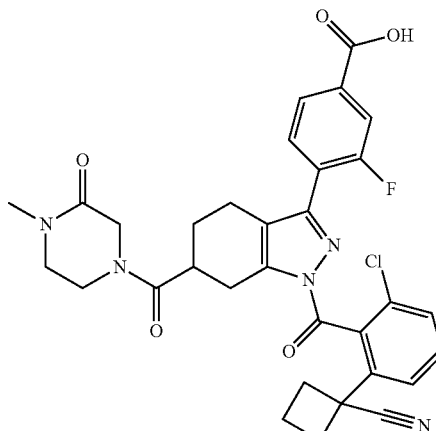 |

TABLE 17-continued
| Example No. | Chemical Structure |
|---|---|
| 16A-B | 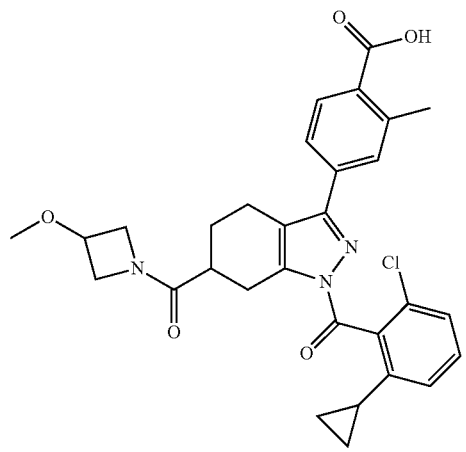 [SMILES: COC1CN(C(=O)C2CCc3c(-c4ccc(C(=O)O)c(C)c4)nn(C(=O)c4c(Cl)cccc4C4CC4)c3C2)C1] |
| 17A | 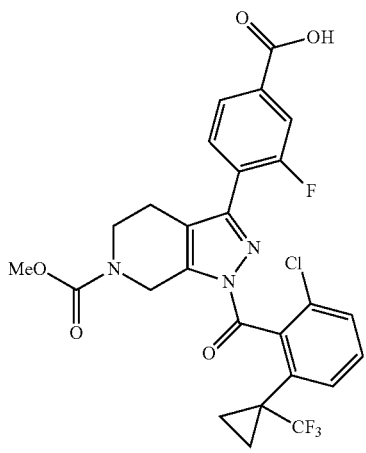 [SMILES: COC(=O)N1CCc2c(-c3ccc(C(=O)O)cc3F)nn(C(=O)c3c(Cl)cccc3C3(C(F)(F)F)CC3)c2C1] |
| 17B | 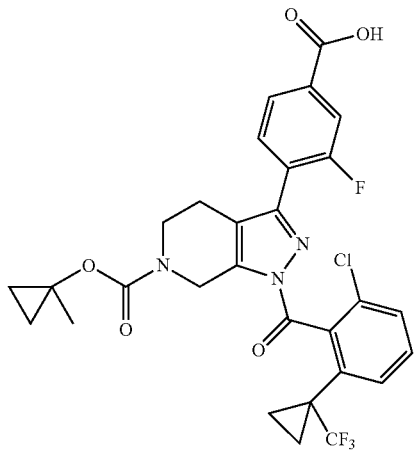 [SMILES: CC1(OC(=O)N2CCc3c(-c4ccc(C(=O)O)cc4F)nn(C(=O)c4c(Cl)cccc4C4(C(F)(F)F)CC4)c3C2)CC1] |
| 17C | 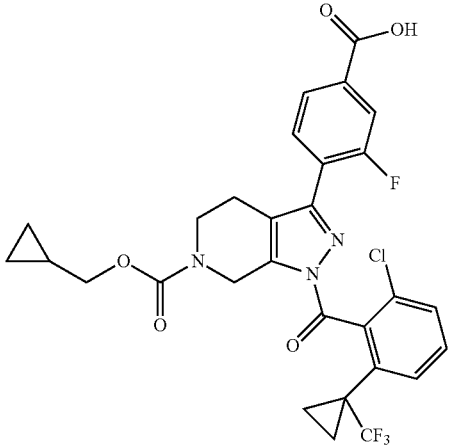 [SMILES: O=C(O)c1ccc(-c2nn(C(=O)c3c(Cl)cccc3C3(C(F)(F)F)CC3)c3c2CCN(C(=O)OCC2CC2)C3)c(F)c1] |
| 17D | 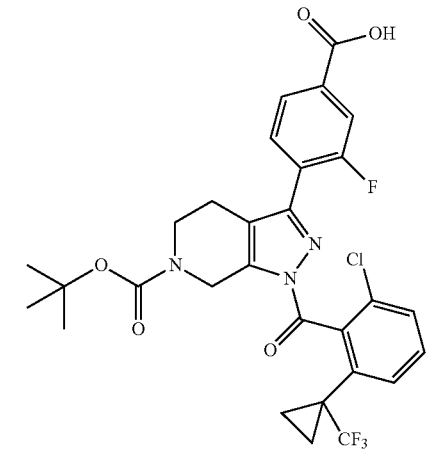 [SMILES: CC(C)(C)OC(=O)N1CCc2c(-c3ccc(C(=O)O)cc3F)nn(C(=O)c3c(Cl)cccc3C3(C(F)(F)F)CC3)c2C1] |
| 18A | 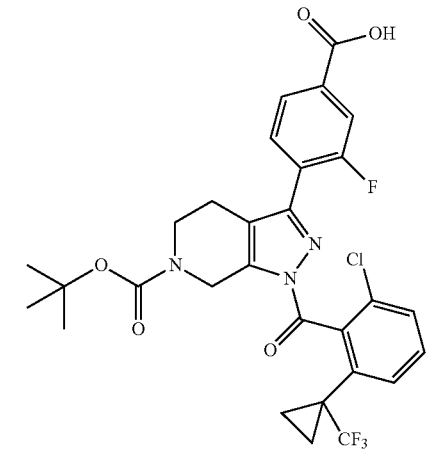 [SMILES: CC(C)(C)OC(=O)N1CCc2c(-c3ccc(C(=O)O)cc3F)nn(C(=O)c3c(Cl)cccc3C3(C(F)(F)F)CC3)c2C1] |

TABLE 17-continued
| Example No. | Chemical Structure |
|---|---|
| 18B | 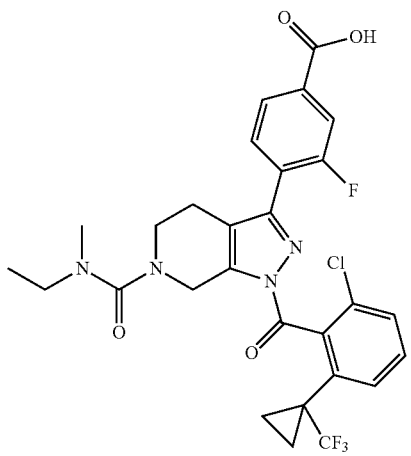 [SMILES: CCN(C)C(=O)N1CCc2c(-c3ccc(C(=O)O)cc3F)nn(C(=O)c3c(Cl)cccc3C3(C(F)(F)F)CC3)c2C1] |
| 18C | 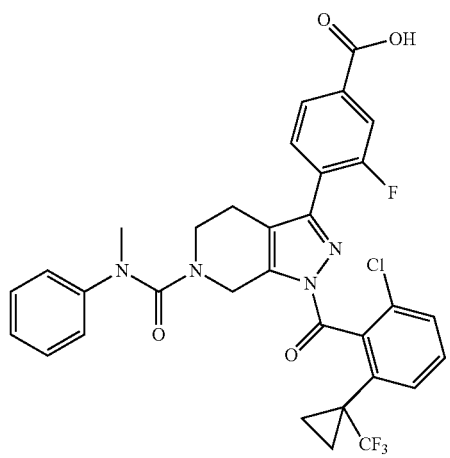 [SMILES: CN(C(=O)N1CCc2c(-c3ccc(C(=O)O)cc3F)nn(C(=O)c3c(Cl)cccc3C3(C(F)(F)F)CC3)c2C1)c1ccccc1] |
| 18D | 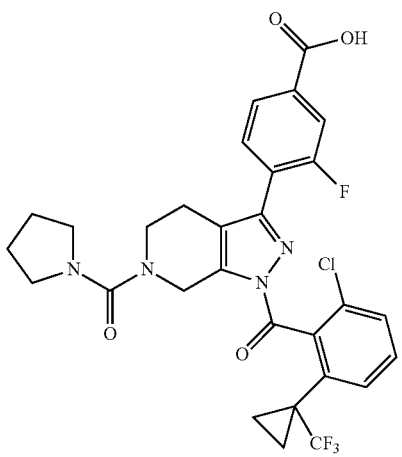 [SMILES: O=C(O)c1ccc(-c2nn(C(=O)c3c(Cl)cccc3C3(C(F)(F)F)CC3)c3c2CCN(C(=O)N2CCCC2)C3)c(F)c1] |
| 18E | 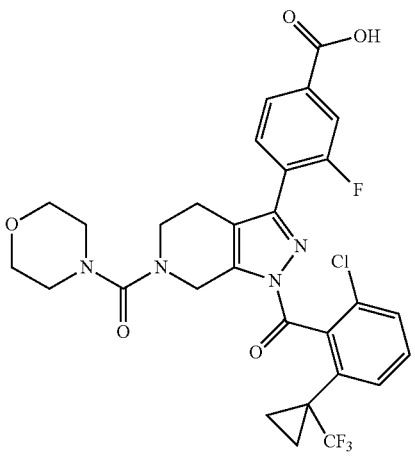 [SMILES: O=C(O)c1ccc(-c2nn(C(=O)c3c(Cl)cccc3C3(C(F)(F)F)CC3)c3c2CCN(C(=O)N2CCOCC2)C3)c(F)c1] |
| 18F | 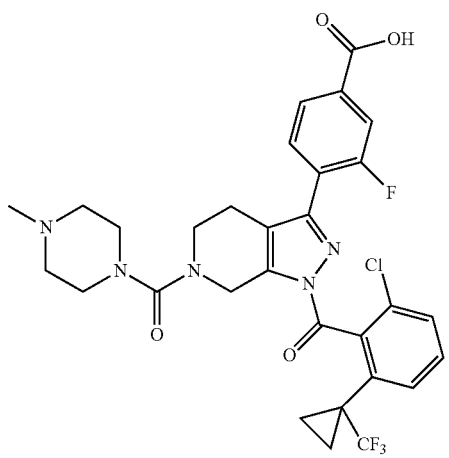 [SMILES: CN1CCN(C(=O)N2CCc3c(-c4ccc(C(=O)O)cc4F)nn(C(=O)c4c(Cl)cccc4C4(C(F)(F)F)CC4)c3C2)CC1] |
| 18G | 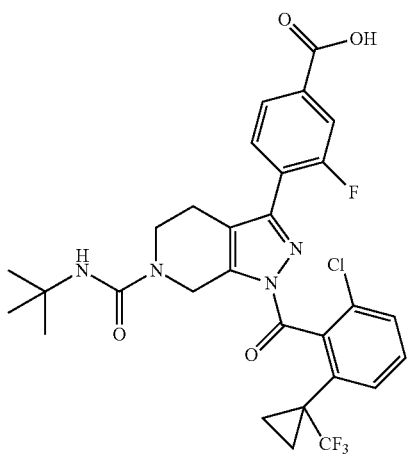 [SMILES: CC(C)(C)NC(=O)N1CCc2c(-c3ccc(C(=O)O)cc3F)nn(C(=O)c3c(Cl)cccc3C3(C(F)(F)F)CC3)c2C1] |

TABLE 17-continued
| Example No. | Chemical Structure |
|---|---|
| 19A | 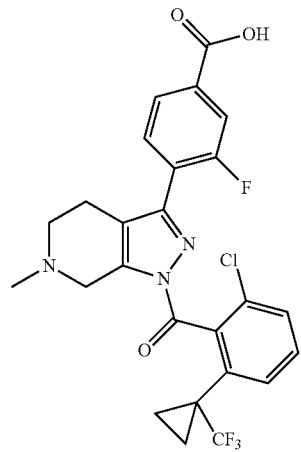 [SMILES: CN1CCc2c(-c3ccc(C(=O)O)cc3F)nn(C(=O)c3c(Cl)cccc3C3(C(F)(F)F)CC3)c2C1] |
| 19B | 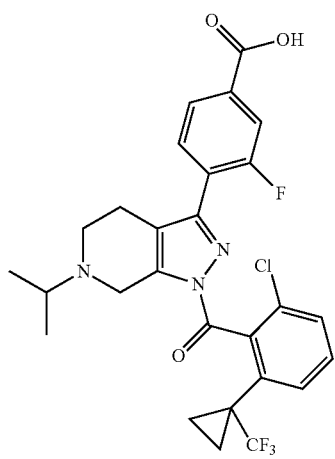 [SMILES: CC(C)N1CCc2c(-c3ccc(C(=O)O)cc3F)nn(C(=O)c3c(Cl)cccc3C3(C(F)(F)F)CC3)c2C1] |
| 19C | 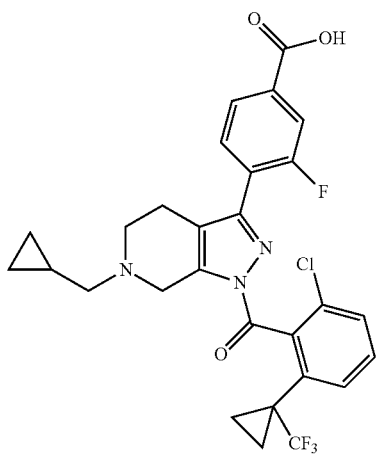 [SMILES: O=C(O)c1ccc(-c2nn(C(=O)c3c(Cl)cccc3C3(C(F)(F)F)CC3)c3c2CCN(CC2CC2)C3)c(F)c1] |
TABLE 17-continued
| Example No. | Chemical Structure |
|---|---|
| 20A | 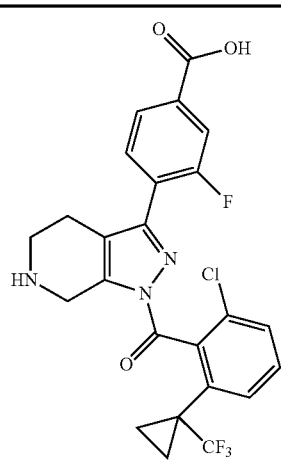 |
| 20B | 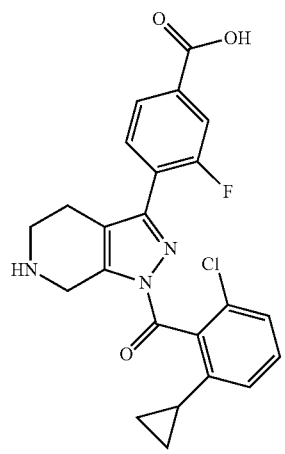 [SMILES: O=C(O)c1ccc(-c2nn(C(=O)c3c(Cl)cccc3C3CC3)c3c2CCNC3)c(F)c1] |
| 21A | 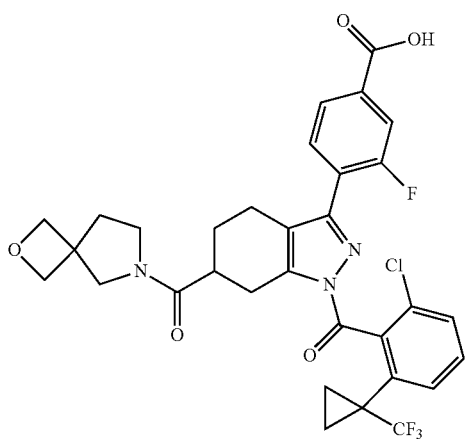 [SMILES: O=C(O)c1ccc(-c2nn(C(=O)c3c(Cl)cccc3C3(C(F)(F)F)CC3)c3c2CCC(C(=O)N2CCC4(COC4)C2)C3)c(F)c1] |

TABLE 17-continued
| Example No. | Chemical Structure |
|---|---|
| 21B | 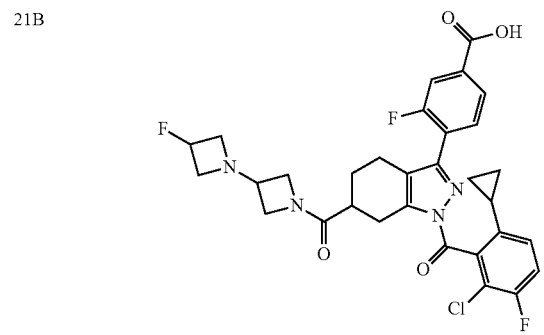 |
| 21C | 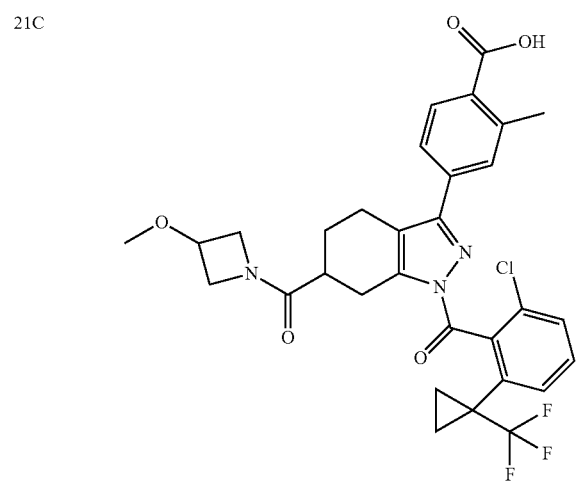 |
| 21D | 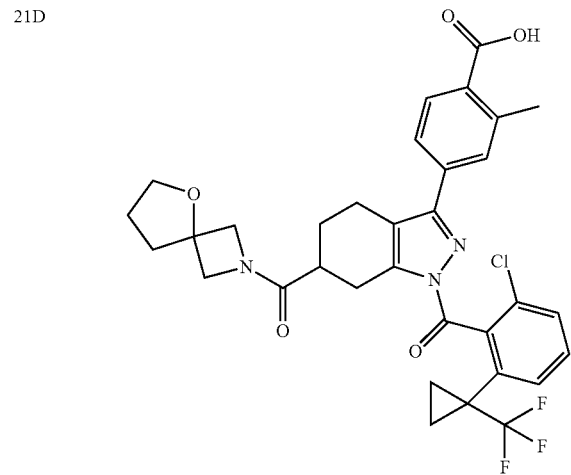 |
| 21E | 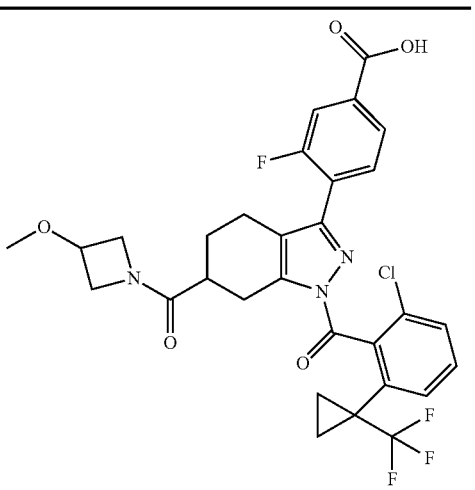 |
| 21F | 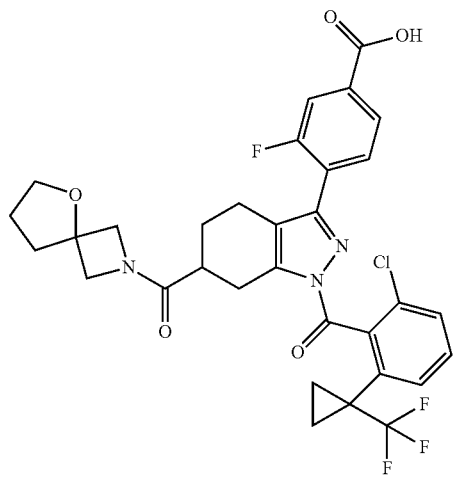 [SMILES: O=C(O)c1ccc(-c2nn(C(=O)c3c(Cl)cccc3C3(C(F)(F)F)CC3)c3c2CCC(C(=O)N2CC4(CCCO4)C2)C3)c(F)c1] |
| 21G | 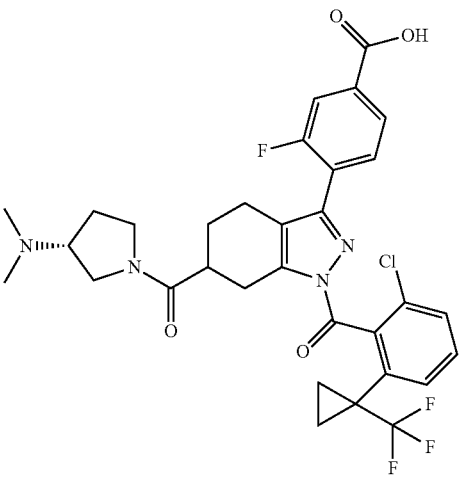 [SMILES: CN(C)[C@@H]1CCN(C(=O)C2CCc3c(-c4ccc(C(=O)O)cc4F)nn(C(=O)c4c(Cl)cccc4C4(C(F)(F)F)CC4)c3C2)C1] |

TABLE 17-continued
| Example No. | Chemical Structure |
|---|---|
| 21H | 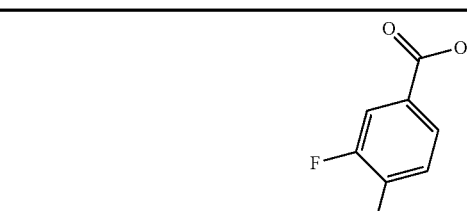 |
| 21I | 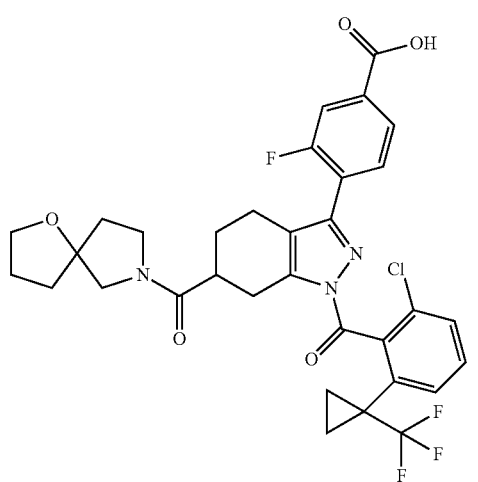 [SMILES: O=C(O)c1ccc(-c2nn(C(=O)c3c(Cl)cccc3C3(C(F)(F)F)CC3)c3c2CCC(C(=O)N2CCC4(CCCO4)C2)C3)c(F)c1] |
| 21J | 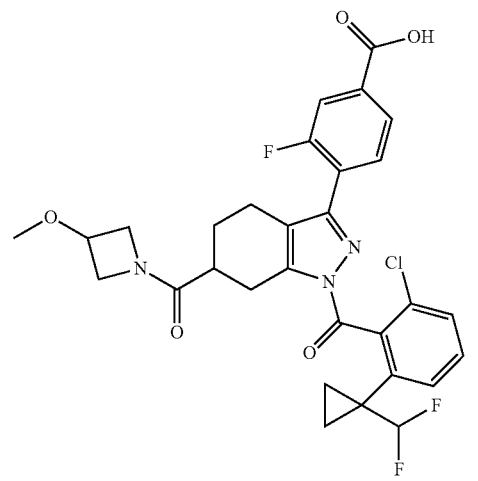 [SMILES: COC1CN(C(=O)C2CCc3c(-c4ccc(C(=O)O)cc4F)nn(C(=O)c4c(Cl)cccc4C4(C(F)F)CC4)c3C2)C1] |
| 21K | 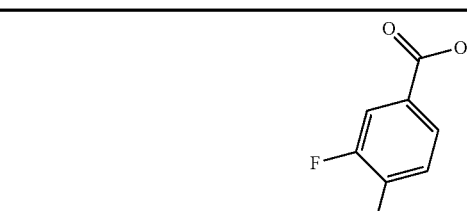 |
| 21L | 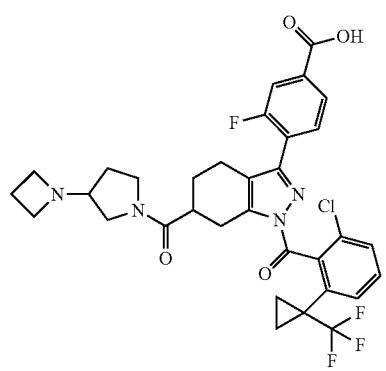 [SMILES: O=C(O)c1ccc(-c2nn(C(=O)c3c(Cl)cccc3C3(C(F)(F)F)CC3)c3c2CCC(C(=O)N2CCC(N4CCC4)C2)C3)c(F)c1] |
| 21M | 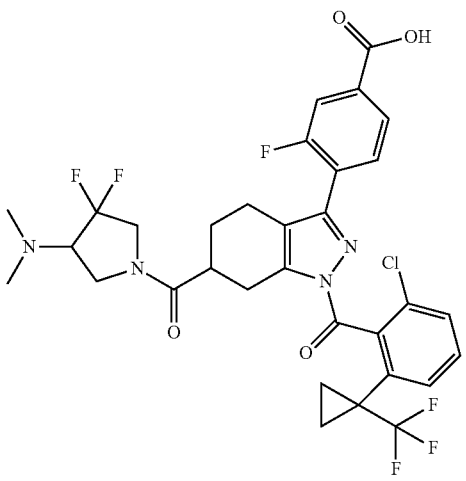 [SMILES: CN(C)C1CN(C(=O)C2CCc3c(-c4ccc(C(=O)O)cc4F)nn(C(=O)c4c(Cl)cccc4C4(C(F)(F)F)CC4)c3C2)CC1(F)F] |

TABLE 17-continued

| Example No. | Chemical Structure |
|---|---|
| 21N | 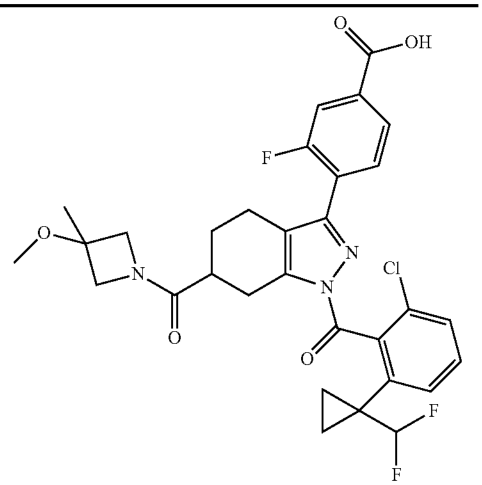 |
| 21O | 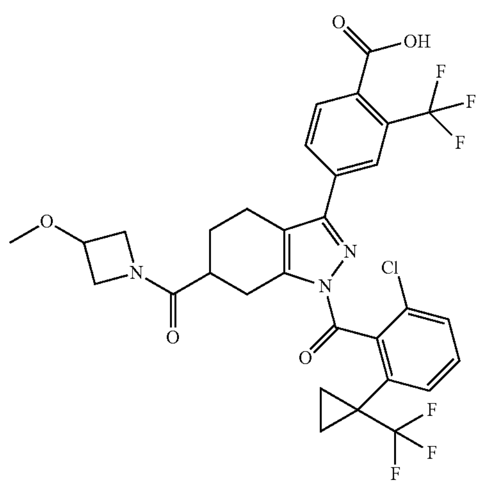 [SMILES: COC1CN(C(=O)C2CCc3c(-c4ccc(C(=O)O)c(C(F)(F)F)c4)nn(C(=O)c4c(Cl)cccc4C4(C(F)(F)F)CC4)c3C2)C1] |
| 21P | 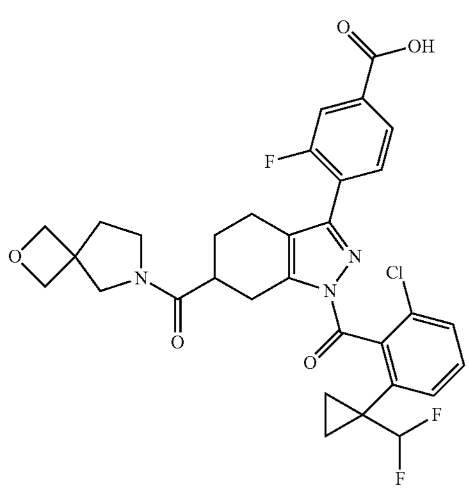 [SMILES: O=C(O)c1ccc(-c2nn(C(=O)c3c(Cl)cccc3C3(C(F)F)CC3)c3c2CCC(C(=O)N2CCC4(COC4)C2)C3)c(F)c1] |
| 21Q | |
| 21R | |
| 21S | |

TABLE 17-continued
| Example No. | Chemical Structure |
|---|---|
| 21T | 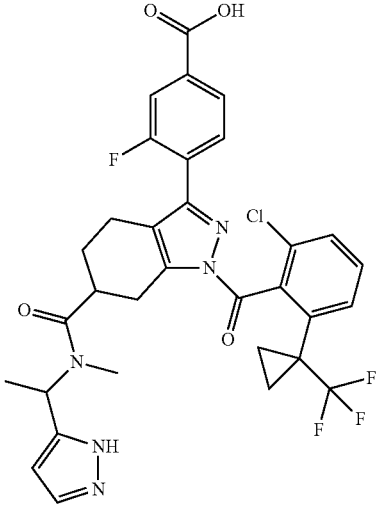 [SMILES: CC(c1ccn[nH]1)N(C)C(=O)C1CCc2c(-c3ccc(C(=O)O)cc3F)nn(C(=O)c3c(Cl)cccc3C3(C(F)(F)F)CC3)c2C1] |
| 21U | 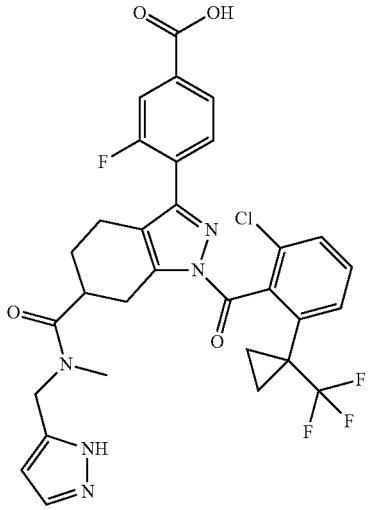 [SMILES: CN(Cc1ccn[nH]1)C(=O)C1CCc2c(-c3ccc(C(=O)O)cc3F)nn(C(=O)c3c(Cl)cccc3C3(C(F)(F)F)CC3)c2C1] |
| 21V | 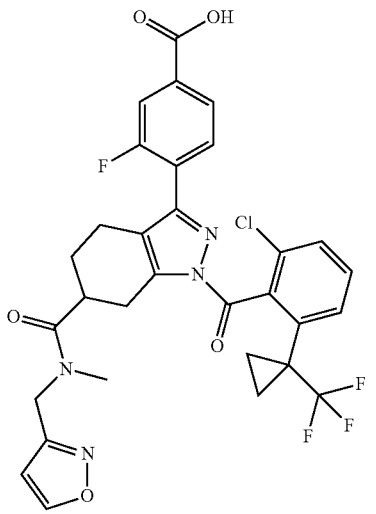 [SMILES: CN(Cc1ccon1)C(=O)C1CCc2c(-c3ccc(C(=O)O)cc3F)nn(C(=O)c3c(Cl)cccc3C3(C(F)(F)F)CC3)c2C1] |
| 21W | 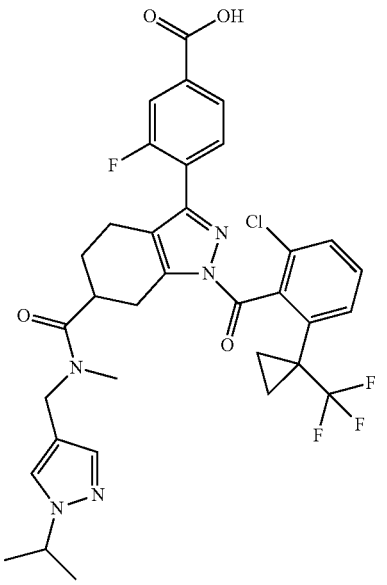 [SMILES: CC(C)n1cc(CN(C)C(=O)C2CCc3c(-c4ccc(C(=O)O)cc4F)nn(C(=O)c4c(Cl)cccc4C4(C(F)(F)F)CC4)c3C2)cn1] |
| 21X | 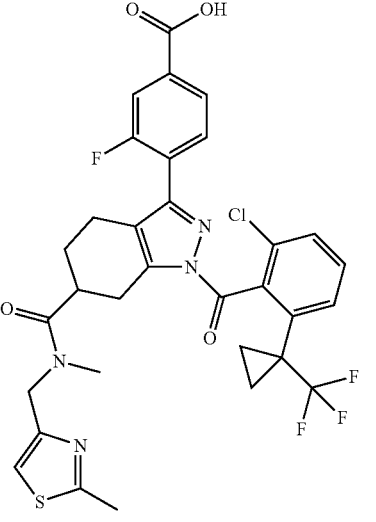 [SMILES: Cc1nc(CN(C)C(=O)C2CCc3c(-c4ccc(C(=O)O)cc4F)nn(C(=O)c4c(Cl)cccc4C4(C(F)(F)F)CC4)c3C2)cs1] |

TABLE 17-continued

| Example No. | Chemical Structure |
|---|---|
| 21Y | (structure) |
| 21Z | (structure) |
| 21AA | (structure) |
| 21BB | (structure) |
| 21CC | (structure) |

TABLE 17-continued
| Example No. | Chemical Structure |
|---|---|
| 21DD | 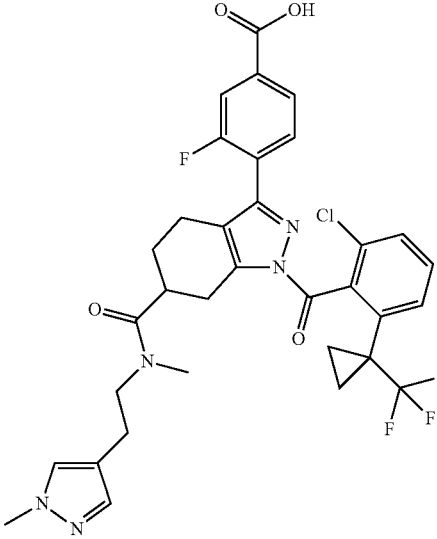 |
| 21EE | 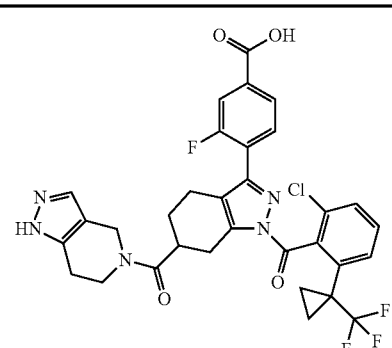 |
| 21FF | 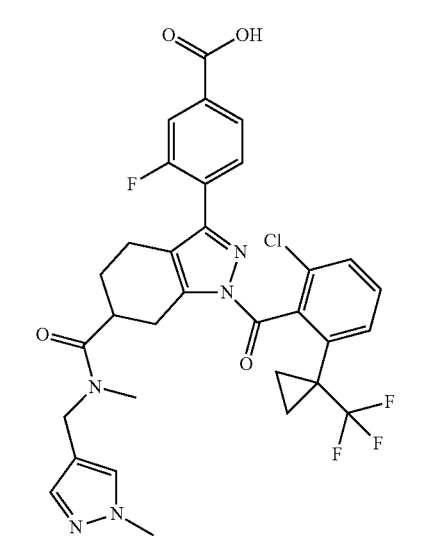 [SMILES: CN(Cc1cnn(C)c1)C(=O)C1CCc2c(-c3ccc(C(=O)O)cc3F)nn(C(=O)c3c(Cl)cccc3C3(C(F)(F)F)CC3)c2C1] |
| 21GG | 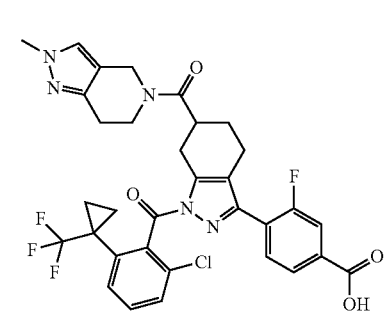 |
| 21HH | 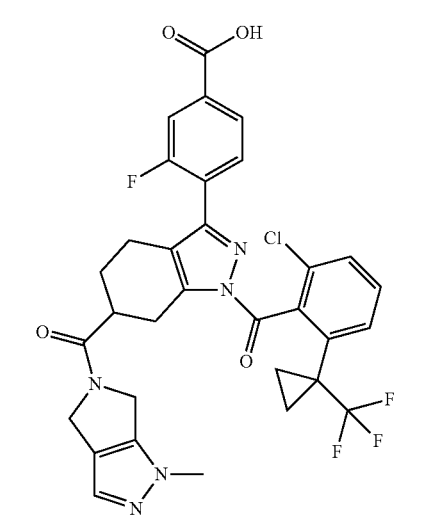 [SMILES: Cn1ncc2c1CN(C(=O)C1CCc3c(-c4ccc(C(=O)O)cc4F)nn(C(=O)c4c(Cl)cccc4C4(C(F)(F)F)CC4)c3C1)C2] |
| 21II | 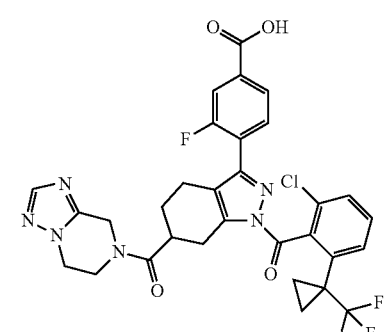 |
| 21JJ | 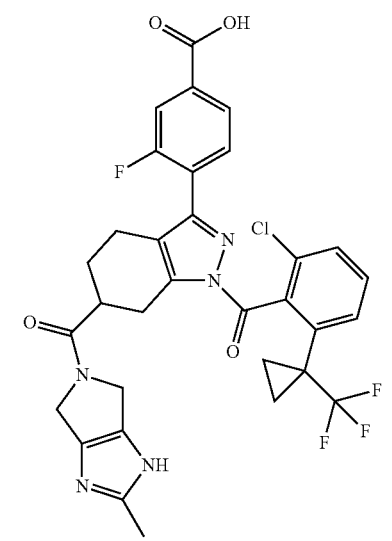 [SMILES: Cc1nc2c([nH]1)CN(C(=O)C1CCc3c(-c4ccc(C(=O)O)cc4F)nn(C(=O)c4c(Cl)cccc4C4(C(F)(F)F)CC4)c3C1)C2] |

TABLE 17-continued
| Example No. | Chemical Structure |
|---|---|
| 21KK | 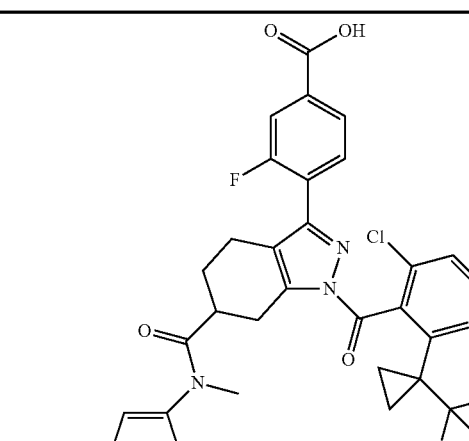 |
| 21LL | 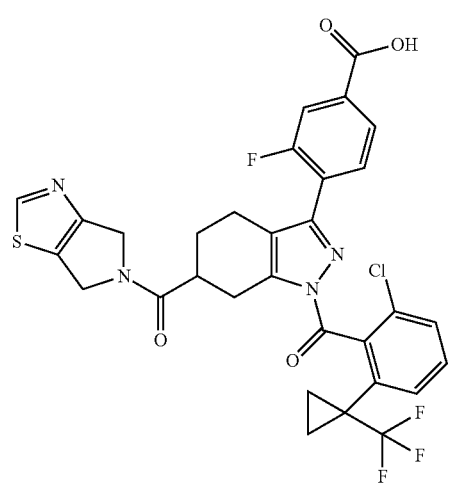 [SMILES: O=C(O)c1ccc(-c2nn(C(=O)c3c(Cl)cccc3C3(C(F)(F)F)CC3)c3c2CCC(C(=O)N2Cc4ncsc4C2)C3)c(F)c1] |
| 21MM | 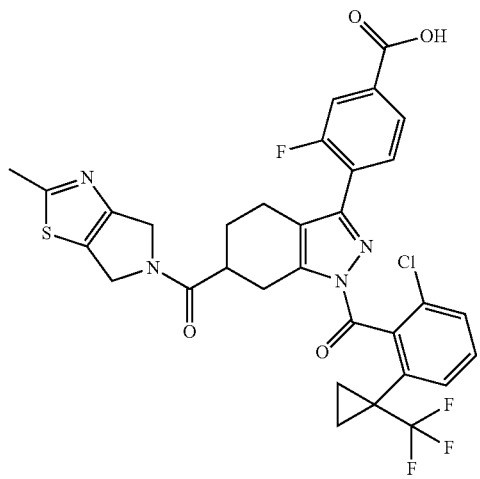 [SMILES: Cc1nc2c(s1)CN(C(=O)C1CCc3c(-c4ccc(C(=O)O)cc4F)nn(C(=O)c4c(Cl)cccc4C4(C(F)(F)F)CC4)c3C1)C2] |
| 21NN | 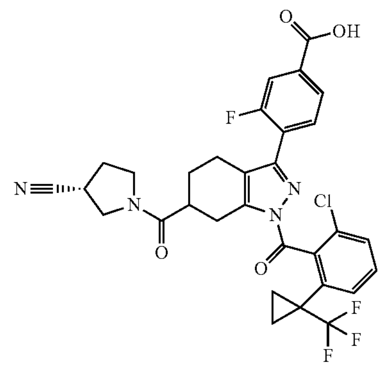 [SMILES: N#C[C@@H]1CCN(C(=O)C2CCc3c(-c4ccc(C(=O)O)cc4F)nn(C(=O)c4c(Cl)cccc4C4(C(F)(F)F)CC4)c3C2)C1] |
| 21PP | 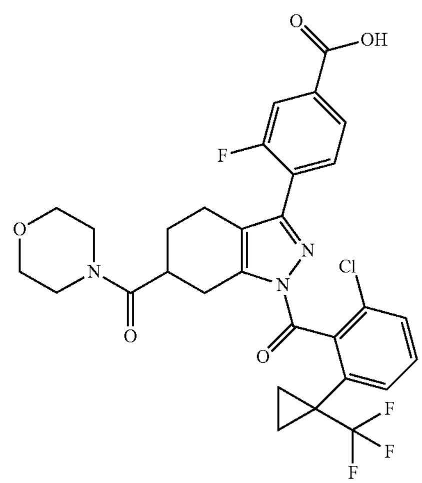 [SMILES: O=C(O)c1ccc(-c2nn(C(=O)c3c(Cl)cccc3C3(C(F)(F)F)CC3)c3c2CCC(C(=O)N2CCOCC2)C3)c(F)c1] |
| 21QQ | 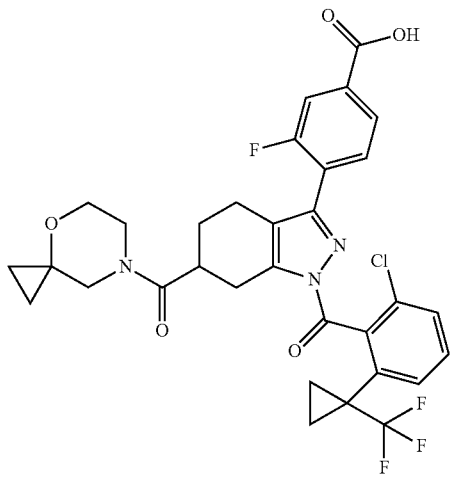 [SMILES: O=C(O)c1ccc(-c2nn(C(=O)c3c(Cl)cccc3C3(C(F)(F)F)CC3)c3c2CCC(C(=O)N2CCOC4(CC4)C2)C3)c(F)c1] |

TABLE 17-continued
| Example No. | Chemical Structure |
|---|---|
| 21RR | 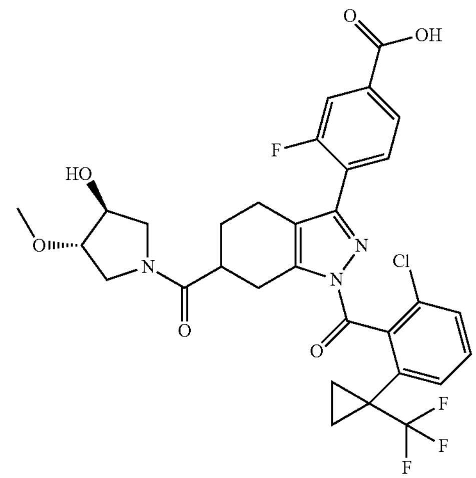 [SMILES: CO[C@H]1CN(C(=O)C2CCc3c(-c4ccc(C(=O)O)cc4F)nn(C(=O)c4c(Cl)cccc4C4(C(F)(F)F)CC4)c3C2)C[C@@H]1O] |
| 21SS | 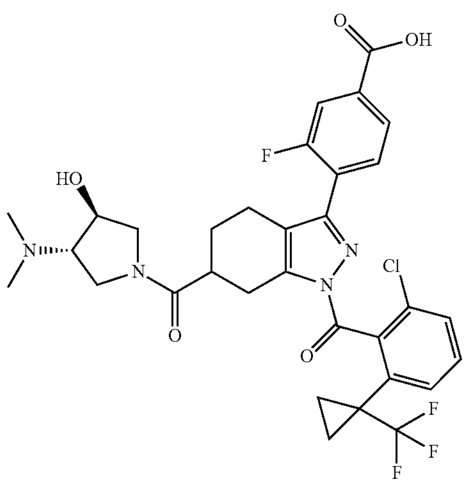 [SMILES: CN(C)[C@H]1CN(C(=O)C2CCc3c(-c4ccc(C(=O)O)cc4F)nn(C(=O)c4c(Cl)cccc4C4(C(F)(F)F)CC4)c3C2)C[C@@H]1O] |
| 21TT | 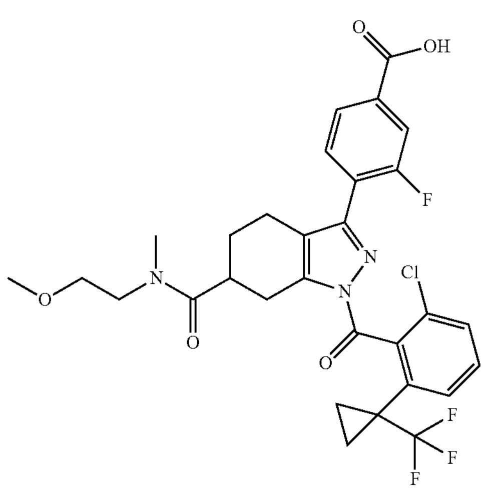 [SMILES: COCCN(C)C(=O)C1CCc2c(-c3ccc(C(=O)O)cc3F)nn(C(=O)c3c(Cl)cccc3C3(C(F)(F)F)CC3)c2C1] |
| 21UU | |
| 21VV | |
| 21WW | |
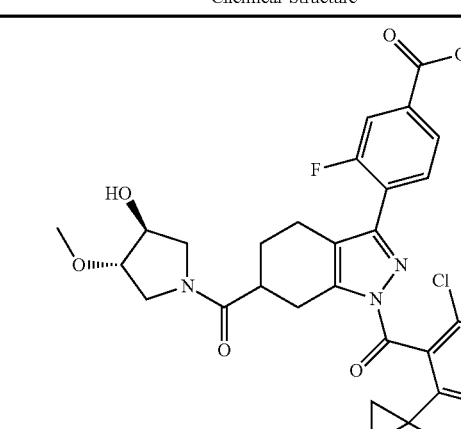
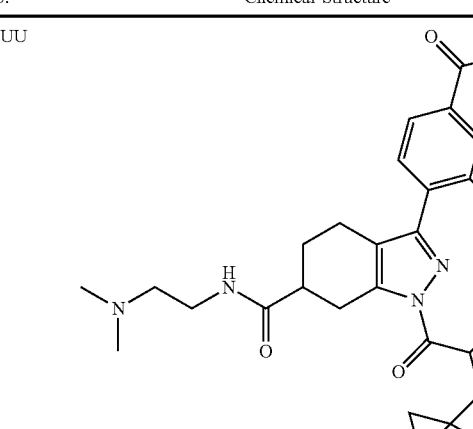

TABLE 17-continued

| Example No. | Chemical Structure |
|---|---|
| 21XX | 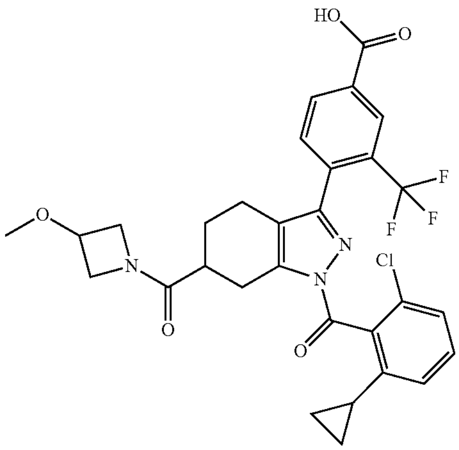 [SMILES: COC1CN(C(=O)C2CCc3c(-c4ccc(C(=O)O)cc4C(F)(F)F)nn(C(=O)c4c(Cl)cccc4C4CC4)c3C2)C1] |
| 21YY | 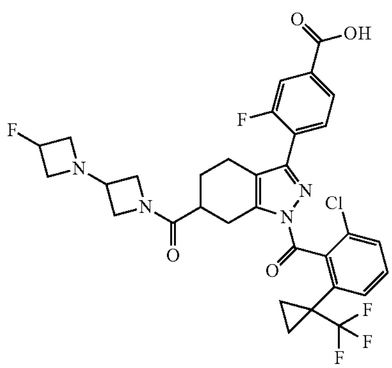 [SMILES: O=C(O)c1ccc(-c2nn(C(=O)c3c(Cl)cccc3C3(C(F)(F)F)CC3)c3c2CCC(C(=O)N2CC(N4CC(F)C4)C2)C3)c(F)c1] |
| 21ZZ | 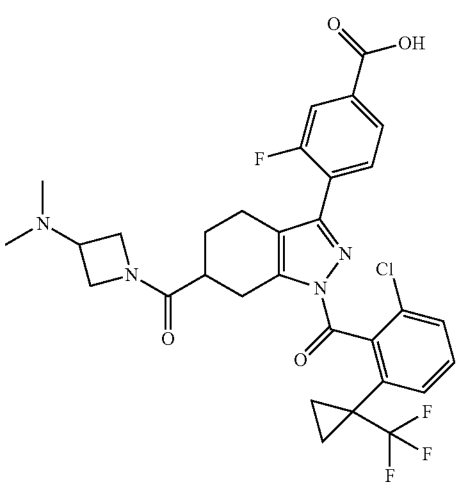 [SMILES: CN(C)C1CN(C(=O)C2CCc3c(-c4ccc(C(=O)O)cc4F)nn(C(=O)c4c(Cl)cccc4C4(C(F)(F)F)CC4)c3C2)C1] |
| 21AAA | |
| 21BBB | |
| 21CCC | |

TABLE 17-continued
| Example No. | Chemical Structure |
|---|---|
| 22A | 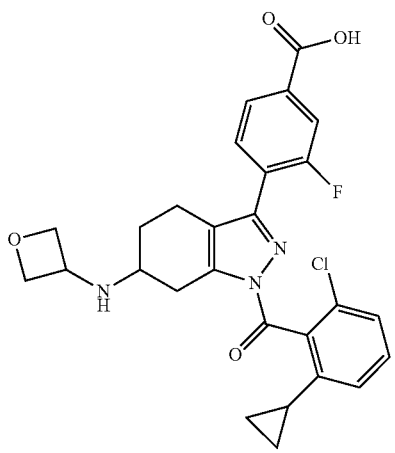 [SMILES: O=C(O)c1ccc(-c2nn(C(=O)c3c(Cl)cccc3C3CC3)c3c2CCC(NC2COC2)C3)c(F)c1] |
| 23A | 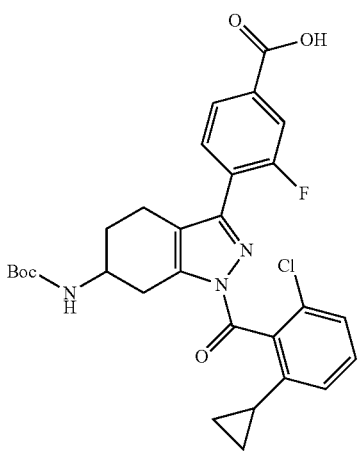 [SMILES: CC(C)(C)OC(=O)NC1CCc2c(-c3ccc(C(=O)O)cc3F)nn(C(=O)c3c(Cl)cccc3C3CC3)c2C1] |
| 24A | 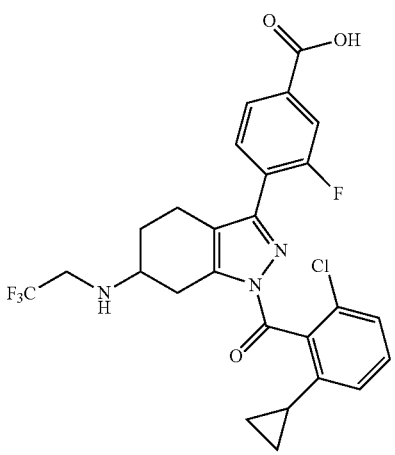 [SMILES: O=C(O)c1ccc(-c2nn(C(=O)c3c(Cl)cccc3C3CC3)c3c2CCC(NCC(F)(F)F)C3)c(F)c1] |
TABLE 17-continued
| Example No. | Chemical Structure |
|---|---|
| 25A | 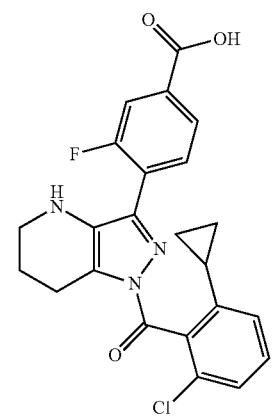 [SMILES: O=C(O)c1ccc(-c2nn(C(=O)c3c(Cl)cccc3C3CC3)c3c2NCCC3)c(F)c1] |
| 25B | 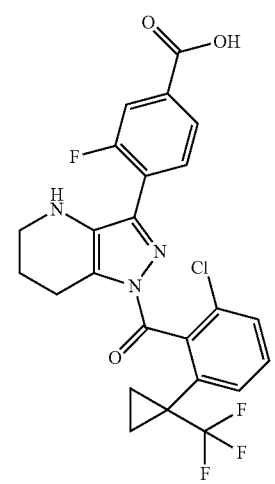 [SMILES: O=C(O)c1ccc(-c2nn(C(=O)c3c(Cl)cccc3C3(C(F)(F)F)CC3)c3c2NCCC3)c(F)c1] |
| 26A | 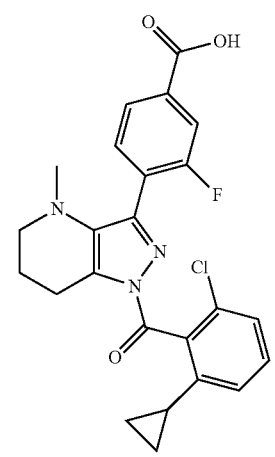 [SMILES: CN1CCCc2c1c(-c1ccc(C(=O)O)cc1F)nn2C(=O)c1c(Cl)cccc1C1CC1] |

TABLE 17-continued
| Example No. | Chemical Structure |
|---|---|
| 27A | 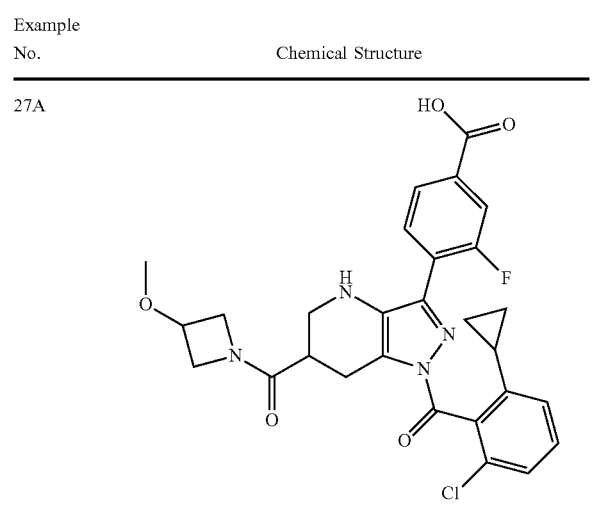 |
| 27B | 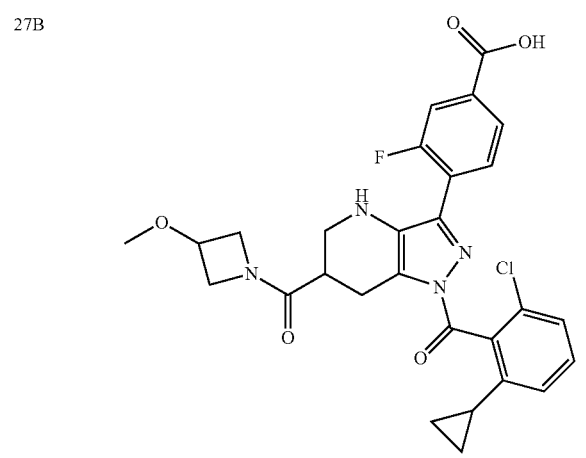 |
| 28A | 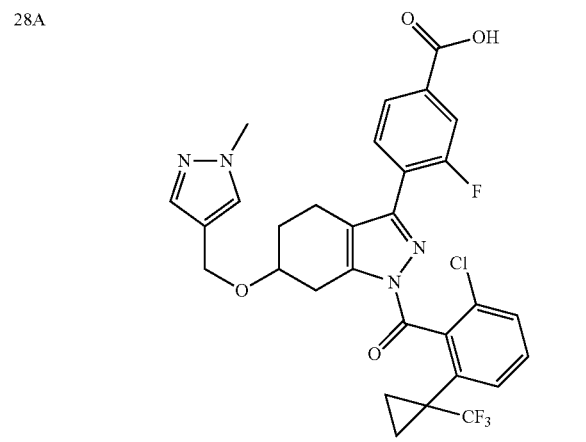 |
| 29A | 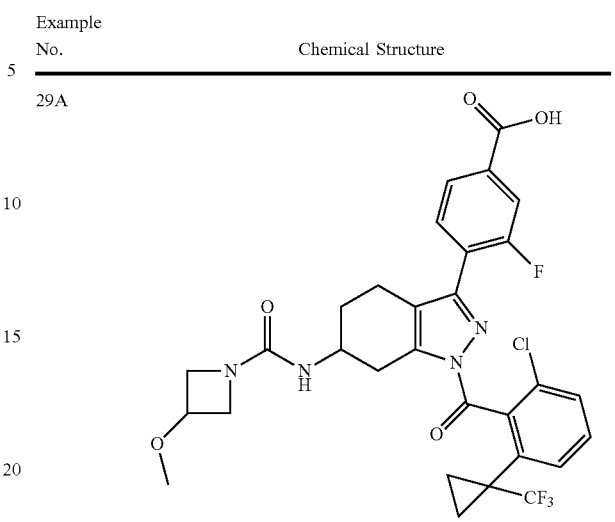 |
| 30A | 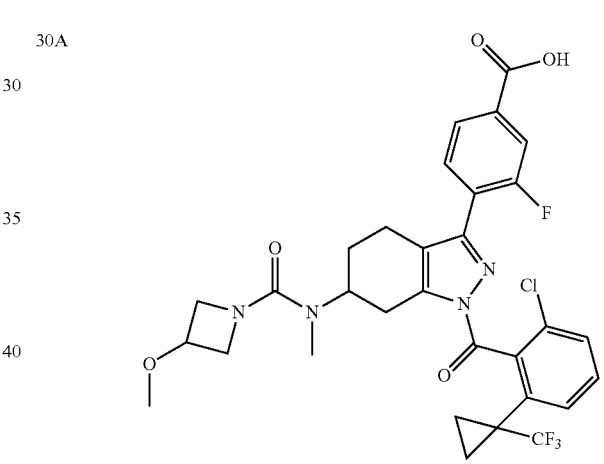 |
| 31A | 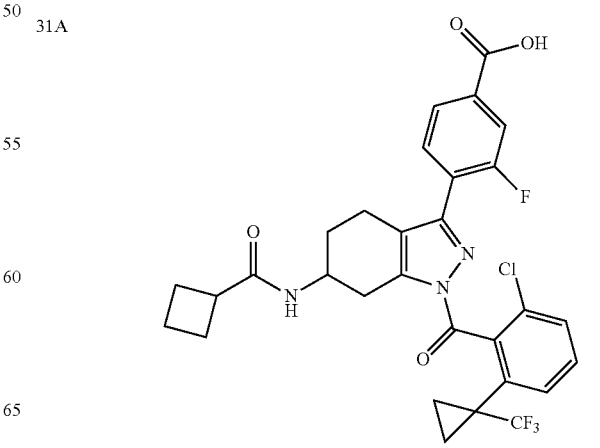 |

TABLE 17-continued
| Example No. | Chemical Structure |
|---|---|
| 32A | 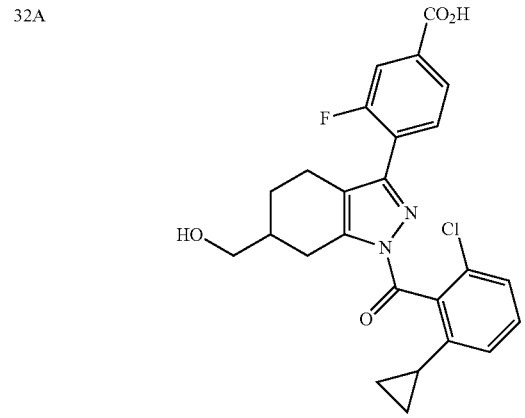 |
| 33A | 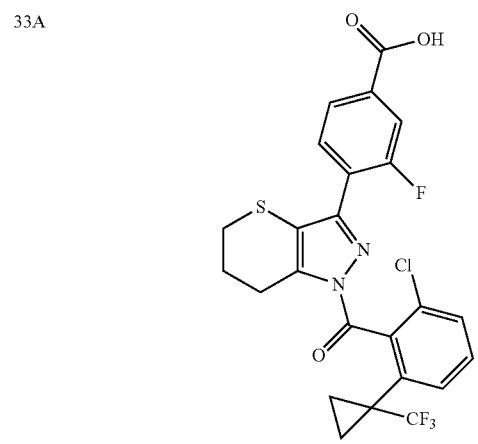 |
| 34A | 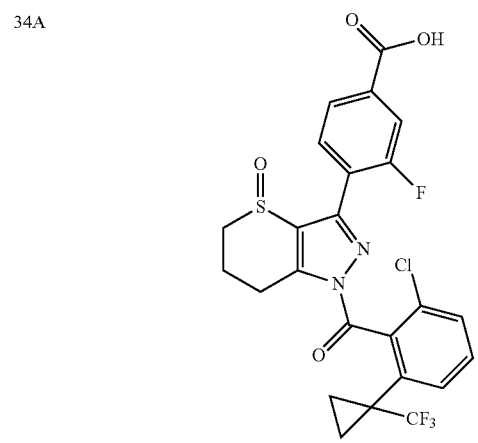 |
TABLE 17-continued
| Example No. | Chemical Structure |
|---|---|
| 35A | 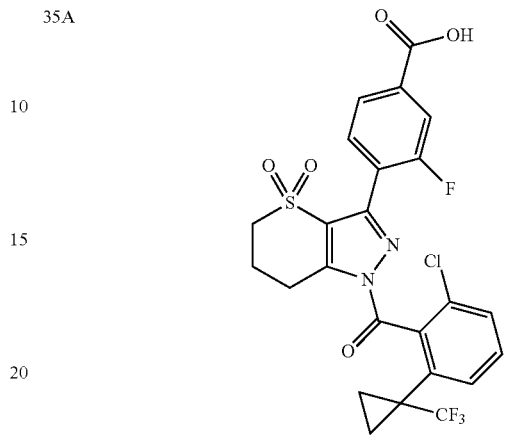 |
| 36A | 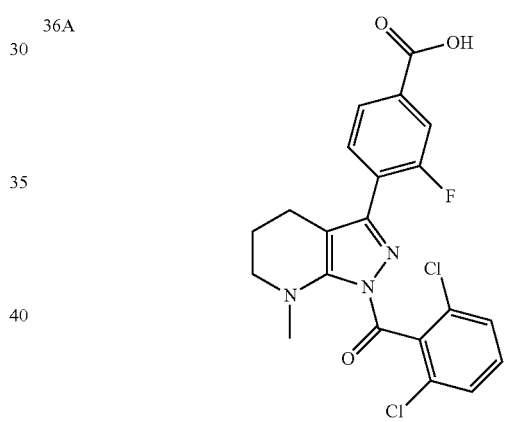 |
| 37A | 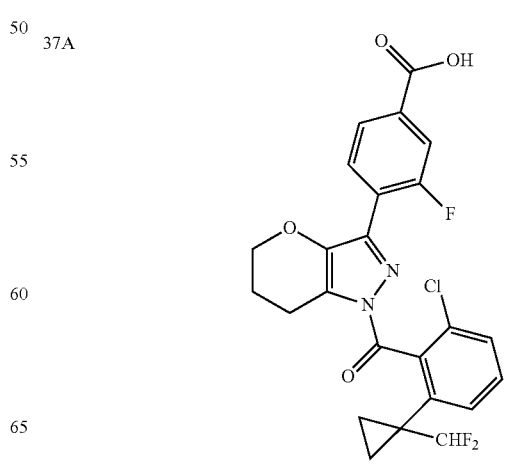 |

TABLE 17-continued

| Example No. | Chemical Structure |
|---|---|
| 37B | 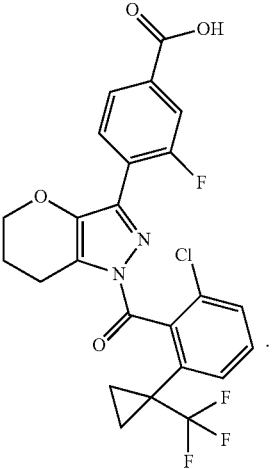 [SMILES: O=C(O)c1ccc(-c2nn(C(=O)c3c(Cl)cccc3C3(C(F)(F)F)CC3)c3c2OCCC3)c(F)c1] |

24. A pharmaceutical composition comprising a compound of claim 1 and one or more pharmaceutically acceptable carriers.

25. A method for treating a disease or condition mediated by Retinoic acid receptor-related Orphan Receptor gamma T (RORgammaT) in a subject, comprising administering to the subject an amount of a compound of claim 1 that is effective for treating the disease or condition mediated by RORgammaT in the subject.

26. The method of claim 25, wherein the disease or condition is multiple sclerosis, inflammatory bowel disease, Crohn's disease, ankylosing spondylitis, psoriasis, rheumatoid arthritis, asthma, osteoarthritis, Kawasaki disease, Hashimoto's thyroiditis, or mucosal leishmaniasis.

27. The method of claim 25, wherein the disease or condition is a cancer selected from the group consisting of breast cancer, colon cancer, small-cell lung cancer, non-small cell lung cancer, prostate cancer, renal cancer, ovarian cancer, leukemia, melanoma, and cancer of the central nervous system tissue.

28. A pharmaceutical composition comprising a compound of claim 19 and one or more pharmaceutically acceptable carriers.

29. A pharmaceutical composition comprising a compound of claim 20 and one or more pharmaceutically acceptable carriers.

* * * * *